United States Patent
Silva et al.

(10) Patent No.: US 10,738,289 B2
(45) Date of Patent: Aug. 11, 2020

(54) TEVI CHIMERIC ENDONUCLEASE AND THEIR PREFERENTIAL CLEAVAGE SITES

(71) Applicant: CELLECTIS S.A., Paris (FR)

(72) Inventors: George Silva, Le Plessis-Trevise (FR); Marine Beurdeley, Paris (FR)

(73) Assignee: CELLECTIS, Paris (FR)

( * ) Notice: Subject to any disclaimer, the term of this patent is extended or adjusted under 35 U.S.C. 154(b) by 0 days.

(21) Appl. No.: 15/466,714

(22) Filed: Mar. 22, 2017

(65) Prior Publication Data
US 2017/0260513 A1  Sep. 14, 2017

Related U.S. Application Data

(62) Division of application No. 14/764,933, filed as application No. PCT/IB2014/058646 on Jan. 29, 2014, now abandoned.

(60) Provisional application No. 61/759,728, filed on Feb. 1, 2013.

(51) Int. Cl.
| | |
|---|---|
| *C12N 9/22* | (2006.01) |
| *C07K 14/47* | (2006.01) |
| *C12N 9/16* | (2006.01) |
| *C12N 15/90* | (2006.01) |
| *C12N 15/82* | (2006.01) |
| *C07K 14/195* | (2006.01) |

(52) U.S. Cl.
CPC .............. *C12N 9/22* (2013.01); *C07K 14/195* (2013.01); *C12N 15/8213* (2013.01); *C12N 15/907* (2013.01); *C07K 2319/80* (2013.01)

(58) Field of Classification Search
None
See application file for complete search history.

(56) References Cited

U.S. PATENT DOCUMENTS

| 8,673,557 B2 * | 3/2014 | Scharenberg .......... A61K 38/45 435/24 |
| 2003/0073623 A1 | 4/2003 | Drmanac et al. |
| 2012/0324603 A1 | 12/2012 | Hlubek et al. |
| 2013/0210151 A1 | 8/2013 | Edgell et al. |

FOREIGN PATENT DOCUMENTS

| WO | 2007-123636 A2 | 11/2007 |
| WO | 2012-138901 A1 | 10/2012 |
| WO | 2012-138927 A2 | 10/2012 |
| WO | 2012-138939 A1 | 10/2012 |
| WO | 2013-009525 A1 | 1/2013 |
| WO | 2013-043638 A1 | 3/2013 |
| WO | 2013-068845 A2 | 5/2016 |

OTHER PUBLICATIONS

Arimondo, P. B. et al., "Exploring the cellular activity of camptothecin-triple-helix-forming oligonucleotide conjugates"; Mol. Cell. Biol. (2006); vol. 26(1); pp. 324-333.
Arnould, S. et al., "Engineering of large numbers of highly specific homing endonucleases that induce recombination on novel DNA targets"; J. Mol. Biol. (2006); vol. 355(3); pp. 443-458.
Arnould, S. et al., "The I-CreI meganuclease and its engineered derivatives: applications from cell modification to gene therapy"; Protein Eng. Des. Sel. (2011); vol. 24(1-2); pp. 27-31.
Arnould, S. et al., "Engineered I-CreI derivatives cleaving sequences from the human XPC gene can induce highly efficient gene correction in mammalian cells"; J. Mol. Biol. (2007); vol. 371(1); pp. 49-65.
Beurdeley, M. et al, "Compact designer TALENs for efficient genome engineering"; Nature Communications (2013); vol. 4, pp. 1-8.
Boch, J. et al., "Breaking the code of DNA binding specificity of TAL-type III effectors"; Science (2009); vol. 326(5959): 1509-12.
Chames, P., et al., "In vivo selection of engineered homing endonucleases using double-strand break induced homologous recombination"; Nucleic Acids Res (2005); vol. 33(20); pp. e178 (10 pgs).
Choulika, A. et al. "Induction of homologous recombination in mammalian chromosomes by using the I-SceI system of *Saccharomyces cerevisiae*"; Mol Cell Biol (1995); vol. 15(4); pp. 1968-1973.
Christian, M. et al. "Targeting DNA double-strand breaks with TAL effector nucleases"; Genetics (2010); vol. 186(2); pp. 757-761.
Daboussi, F. et al., "Chromosomal context and epigenetic mechanisms control the efficacy of genome editing by rare-cutting designer endonucleases." Nucleic Acids Res (2012); vol. 40(13); pp. 6367-6379.
Edgell, D. R. et al., "Coincidence of cleavage sites of intron endonuclease I-TevI and critical sequences of the host hymidylate synthase gene"; J Mol Biol (2004); vol. 343(5); pp. 1231-1241.
Eisenschmidt, K et al., "Developing a programmed restriction endonuclease for highly specific DNA cleavage" Nucleic Acids Res (2005 ); vol. 33(22); pp. 7039-7047.
Epinat, J. C. et al., "A novel engineered meganuclease induces homologous recombination in yeast and mammalian mils." Nucleic Acids Res (2003); vol. 31(11); pp. 2952-2962.
Kalish, J. M. et al., "Targeted genome modification via triple helix formation"; Ann N Y Acad Sci (2005); vol. 1058; pp. 151-161.

(Continued)

*Primary Examiner* — Maria G Leavitt
(74) *Attorney, Agent, or Firm* — Arrigo, Lee, Guttman & Mouta-Bellum LLP

(57) ABSTRACT

The present invention relates to a method to cleave target nucleic acid sequence by the catalytic domain of a GIY-YIG homing endonucleases I-TevI. More precisely, the invention relates to the deciphering of new preferential I-TevI cleavage sites for efficient and specific cleavage activity. The invention concerns a method for the generation of TevI specific chimeric endonucleases to target nucleic acid sequence including such cleavage sites and methods of using same for gene editing.

17 Claims, 8 Drawing Sheets

Specification includes a Sequence Listing.

(56) References Cited

OTHER PUBLICATIONS

Kim, Y. et al., "Hybrid restriction enzymes: zinc finger fusions to Fok I cleavage domain"; Proc Natl Acad Sci U S A (1996); vol. 93(3); pp. 1156-1160.

Kleinstiver, B. P.et al., "Monomeric site-specific nucleases for genome editing"; Proc Natl Acad Sci U S A (2012); vol. 109(21); pp. 8061-8066.

Li, T. et al., "TAL nucleases (TALNs): hybrid proteins composed of TAL effectors and FokI DNA-cleavage domain"; Nucleic Acids Res (2011); vol. 39(1); pp. 359-372.

Li et al., "Modularly assembled designer TAL effector nucleases for targeted gene knockout and gene replacement in eukaryotes"; Nucleic Acids Res (2011); vol. 39(14): 6315-25.

Liu, Q. et al., "Role of the Interdomain Linker in Distance Determination for Remote Cleavage by Homing ndonuclease I-TevI"; J. Mol. Bio. Acd. (2008); vol. 379(5); pp. 1094-1106.

Marcaida, M. J. et al., "Homing endonucleases: from basics to therapeutic applications"; Cell Mol Life Sci (2010); vol. 67(5); pp. 727-748.

Moscou, M. J. et al., "A simple cipher governs DNA recognition by TAL effectors"; Science (2009); vol. 326(5959); p. 1501.

Pabo, C. O. et al., "Design and selection of novel Cys2His2 zinc finger proteins"; Annu Rev Biochem (2001); vol. 70; pp. 313-340.

Paques, F. et al., "Meganucleases and DNA double-strand break-induced recombination: perspectives for gene therapy." Curr Gene Ther (2007); vol. 7(1); pp. 49-66.

Pingoud, A. et al., "Precision genome surgery" Nat Biotechnol (2007); vol. 25(7); pp. 743-744.

Porteus, et al., "Gene targeting using zinc finger nucleases" Nat Biotechnol (2005); vol. 23(8); pp. 967-973.

Reyon, D. et al., "Flash assembly of TALENs for high-throughput genome editing"; Nat Biotechnol (2012); vol. 30 (5); pp. 460-465.

Rouet, P. et al., "Expression of a site-specific endonuclease stimulates homologous recombination in mammalian cells"; Proc Natl Acad Sci U S A (1994); vol. 91(13); pp. 6064-6068.

Rouet, P. et al., "Introduction of double-strand breaks into the genome of mouse cells by expression of a rare-cutting endonuclease"; Mol Cell Biol (1994); vol. 14(12); pp. 8096-8106.

Simon, P. et al., "Sequence-specific DNA cleavage mediated by bipyridine polyamide conjugates"; Nucleic Acids Res (2008); vol. 36(11); pp. 3531-3538.

Smith, J. et al., "A detailed study of the substrate specificity of a chimeric restriction enzyme"; Nucleic Acids Res (1999); vol. 27(2); pp. 674-681.

Smith, J. et al., "Requirements for double-strand cleavage by chimeric restriction enzymes with zinc finger DNA-recognition domains"; Nucleic Acids Res (2000); vol. 28(17); pp. 3361-3369.

Smith, J. et al., "A combinatorial approach to create artificial homing endonucleases cleaving chosen sequences"; Nucleic Acids Res (2006); vol. 34(22); e149 (12 pgs.).

Stoddard, B. L. "Homing endonuclease structure and function"; Q Rev Biophys (2005); vol. 38(1); pp. 49-95.

Stoddard, B. L. et al., "Advances in Engineering Homing Endonucleases for Gene Targeting:Ten Years After Structures", Progress in Gene Therapy: Autologous and Cancer Stem Cell Gene Therapy. R. Bertolotti and K. Ozawa, World Scientific Publishing Co. Pte. Ltd, (2007); vol. 3, pp. 135-168.

Zhao, L. et al., "The restriction fold turns to the dark side: a bacterial homing endonuclease with a PD-(D/E)-XK motif"; Embo J (2007); vol. 26(9); pp. 2432-2442.

Streubel et al ., "TAL effector RVD specificities and efficiencies", Nature Biotechnology 30, 593-595 (2012).

Kleinstiver et al., "The monomeric GIY-YIG homing endonuclease I-Bmol uses a molecular anchor and a flexible tether to sequentially nick DNA" Nucleic Acids Research, 2013, vol. 41, No. 10, pp. 5413-5427.

Roy et al., "Perpetuating the homing endonuclease life cycle: identification of mutations that modulate and change 1-TevI cleavage preference", Nucleic Acids Research, 2016, vol. 44, No. 15, pp. 7350-7359.

* cited by examiner

SEQUENCE LISTING

```
<160> NUMBER OF SEQ ID NOS: 459

<210> SEQ ID NO 1
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 1 caacgc                                                                     6

<210> SEQ ID NO 2
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 2 caaagg                                                                     6

<210> SEQ ID NO 3
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 3 caacgg                                                                     6

<210> SEQ ID NO 4
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 4
```

```
caatgg                                                                  6

<210> SEQ ID NO 5
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 5 cacagg                                                                  6

<210> SEQ ID NO 6
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 6 caccgg                                                                  6

<210> SEQ ID NO 7
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 7 cagagg                                                                  6

<210> SEQ ID NO 8
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 8 cagcgc                                                                  6

<210> SEQ ID NO 9
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 9 cagcgg                                                                  6

<210> SEQ ID NO 10
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 10 cagtgg                                                                  6

<210> SEQ ID NO 11
<211> LENGTH: 6
<212> TYPE: DNA
```

```
<213> ORGANISM: artificial sequence
<220> FEATURE:
<223> OTHER INFORMATION: I-TevI motif(high activity)

<400> SEQUENCE: 11 catagc                                                                      6

<210> SEQ ID NO 12
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 12 catagg                                                                      6

<210> SEQ ID NO 13
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 13 catcgg                                                                      6

<210> SEQ ID NO 14
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 14 catggg                                                                      6

<210> SEQ ID NO 15
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 15 cattgg                                                                      6

<210> SEQ ID NO 16
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 16 ccacgg                                                                      6

<210> SEQ ID NO 17
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 17 cgacgg                                                                      6
```

<210> SEQ ID NO 18
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 18 ctacgg                                                                     6

<210> SEQ ID NO 19
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 19 ctatgg                                                                     6

<210> SEQ ID NO 20
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 20 ctgagg                                                                     6

<210> SEQ ID NO 21
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 21 ctgcgg                                                                     6

<210> SEQ ID NO 22
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 22 cttagg                                                                     6

<210> SEQ ID NO 23
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 23 caacgt                                                                     6

<210> SEQ ID NO 24
<211> LENGTH: 6
<212> TYPE: DNA
<213> ORGANISM: artificial sequence
<220> FEATURE:

```
<223> OTHER INFORMATION: I-TevI motif(high activity)

<400> SEQUENCE: 24 caaggg                                                                    6

<210> SEQ ID NO 25
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 25 caatgc                                                                    6

<210> SEQ ID NO 26
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 26 caatgt                                                                    6

<210> SEQ ID NO 27
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 27 cactgg                                                                    6

<210> SEQ ID NO 28
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 28 cagagc                                                                    6

<210> SEQ ID NO 29
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 29 cagcga                                                                    6

<210> SEQ ID NO 30
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 30 cagggg                                                                    6
```

```
<210> SEQ ID NO 31
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 31 cagtgt                                                                     6

<210> SEQ ID NO 32
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 32 cataga                                                                     6

<210> SEQ ID NO 33
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 33 catagt                                                                     6

<210> SEQ ID NO 34
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 34 catcgc                                                                     6

<210> SEQ ID NO 35
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 35 cattgc                                                                     6

<210> SEQ ID NO 36
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 36 ccaagg                                                                     6

<210> SEQ ID NO 37
<211> LENGTH: 6
<212> TYPE: DNA
<213> ORGANISM: artificial sequence
<220> FEATURE:
<223> OTHER INFORMATION: I-TevI motif(high activity)
```

```
<400> SEQUENCE: 37 ccatgg                                                              6

<210> SEQ ID NO 38
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 38 ccgcgg                                                              6

<210> SEQ ID NO 39
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 39 cctagg                                                              6

<210> SEQ ID NO 40
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 40 cctcgg                                                              6

<210> SEQ ID NO 41
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 41 cgaagg                                                              6

<210> SEQ ID NO 42
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 42 cgatgg                                                              6

<210> SEQ ID NO 43
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 43 ctaagg                                                              6

<210> SEQ ID NO 44
<211> LENGTH: 6
```

```
<212> TYPE: DNA
<213> ORGANISM: artificial sequence
<220> FEATURE:
<223> OTHER INFORMATION: I-TevI motif(high activity)

<400> SEQUENCE: 44 ctacga                                                                      6

<210> SEQ ID NO 45
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 45 ctacgc                                                                      6

<210> SEQ ID NO 46
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 46 ctacgt                                                                      6

<210> SEQ ID NO 47
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 47 ctatgc                                                                      6

<210> SEQ ID NO 48
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 48 ctcagg                                                                      6

<210> SEQ ID NO 49
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 49 ctgtgg                                                                      6

<210> SEQ ID NO 50
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 50
``` cttcgg                                                              6

<210> SEQ ID NO 51
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 51 ctttgg                                                              6

<210> SEQ ID NO 52
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 52 ctgcgc                                                              6

<210> SEQ ID NO 53
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 53 cagtgc                                                              6

<210> SEQ ID NO 54
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 54 cgtagg                                                              6

<210> SEQ ID NO 55
<211> LENGTH: 6
<212> TYPE: DNA
<213> ORGANISM: artificial sequence
<220> FEATURE:
<223> OTHER INFORMATION: I-TevI motif(high activity)

<400> SEQUENCE: 55 cacggg                                                              6

<210> SEQ ID NO 56
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 56 caatga                                                              6

<210> SEQ ID NO 57
<211> LENGTH: 6
<212> TYPE: DNA
<213> ORGANISM: artificial sequence

```
<220> FEATURE:
<223> OTHER INFORMATION: I-TevI motif(medium activity)

<400> SEQUENCE: 57 cagagt                                                                      6

<210> SEQ ID NO 58
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 58 cattga                                                                      6

<210> SEQ ID NO 59
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 59 cattgt                                                                      6

<210> SEQ ID NO 60
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 60 ccacgt                                                                      6

<210> SEQ ID NO 61
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 61 ccgagg                                                                      6

<210> SEQ ID NO 62
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 62 ccgtgg                                                                      6

<210> SEQ ID NO 63
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 63 ccttgg                                                                      6
```

```
<210> SEQ ID NO 64
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 64 cgacgc                                                                    6

<210> SEQ ID NO 65
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 65 cgtcgg                                                                    6

<210> SEQ ID NO 66
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 66 ctatgt                                                                    6

<210> SEQ ID NO 67
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 67 ctccgg                                                                    6

<210> SEQ ID NO 68
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 68 cttcgc                                                                    6

<210> SEQ ID NO 69
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 69 caaagc                                                                    6

<210> SEQ ID NO 70
<211> LENGTH: 6
<212> TYPE: DNA
<213> ORGANISM: artificial sequence
<220> FEATURE:
<223> OTHER INFORMATION: I-TevI motif(medium activity)
```

<400> SEQUENCE: 70 catggc                                                                6

<210> SEQ ID NO 71
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 71 caccgt                                                                6

<210> SEQ ID NO 72
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 72 cagcgt                                                                6

<210> SEQ ID NO 73
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 73 cagtga                                                                6

<210> SEQ ID NO 74
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 74 ccacgc                                                                6

<210> SEQ ID NO 75
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 75 cggagg                                                                6

<210> SEQ ID NO 76
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 76 cgttgg                                                                6

<210> SEQ ID NO 77

```
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 77 ctctgg                                                              6

<210> SEQ ID NO 78
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 78 ctgtgt                                                              6

<210> SEQ ID NO 79
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 79 cttcgt                                                              6

<210> SEQ ID NO 80
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 80 cttggg                                                              6

<210> SEQ ID NO 81
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 81 caaaga                                                              6

<210> SEQ ID NO 82
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 82 caacga                                                              6

<210> SEQ ID NO 83
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 83
``` cacagc                                                              6

<210> SEQ ID NO 84
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 84 cacagt                                                              6

<210> SEQ ID NO 85
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 85 caccgc                                                              6

<210> SEQ ID NO 86
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 86 cagaga                                                              6

<210> SEQ ID NO 87
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 87 catcga                                                              6

<210> SEQ ID NO 88
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 88 ccaggg                                                              6

<210> SEQ ID NO 89
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 89 ccatgc                                                              6

<210> SEQ ID NO 90
<211> LENGTH: 6
<212> TYPE: DNA

```
<213> ORGANISM: artificial sequence
<220> FEATURE:
<223> OTHER INFORMATION: I-TevI motif(medium activity)

<400> SEQUENCE: 90 ccatgt                                                                       6

<210> SEQ ID NO 91
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 91 cccagg                                                                       6

<210> SEQ ID NO 92
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 92 ccccgg                                                                       6

<210> SEQ ID NO 93
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 93 ccctgg                                                                       6

<210> SEQ ID NO 94
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 94 cctggg                                                                       6

<210> SEQ ID NO 95
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 95 cgacga                                                                       6

<210> SEQ ID NO 96
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 96 cgacgt                                                                       6
```

```
<210> SEQ ID NO 97
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 97 cgcagg                                                                6

<210> SEQ ID NO 98
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 98 cgccgg                                                                6

<210> SEQ ID NO 99
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 99 cgctgg                                                                6

<210> SEQ ID NO 100
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 100 cggcgg                                                                6

<210> SEQ ID NO 101
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 101 cggtgg                                                                6

<210> SEQ ID NO 102
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 102 cgtggg                                                                6

<210> SEQ ID NO 103
<211> LENGTH: 6
<212> TYPE: DNA
<213> ORGANISM: artificial sequence
<220> FEATURE:
```

```
<223> OTHER INFORMATION: I-TevI motif(medium activity)

<400> SEQUENCE: 103 ctaagc                                                                     6

<210> SEQ ID NO 104
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 104 ctaggg                                                                     6

<210> SEQ ID NO 105
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 105 ctatga                                                                     6

<210> SEQ ID NO 106
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 106 ctgagc                                                                     6

<210> SEQ ID NO 107
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 107 ctgcga                                                                     6

<210> SEQ ID NO 108
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 108 ctgcgt                                                                     6

<210> SEQ ID NO 109
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 109 ctgggg                                                                     6
```

-continued

```
<210> SEQ ID NO 110
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 110 ctgtgc                                                                    6

<210> SEQ ID NO 111
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 111 cttagc                                                                    6

<210> SEQ ID NO 112
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 112 ctttgc                                                                    6

<210> SEQ ID NO 113
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 113 cactgc                                                                    6

<210> SEQ ID NO 114
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 114 catgga                                                                    6

<210> SEQ ID NO 115
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 115 cgaggg                                                                    6

<210> SEQ ID NO 116
<211> LENGTH: 6
<212> TYPE: DNA
<213> ORGANISM: artificial sequence
<220> FEATURE:
<223> OTHER INFORMATION: I-TevI motif(medium activity)
```

```
<400> SEQUENCE: 116 cgtagc                                                                    6

<210> SEQ ID NO 117
<211> LENGTH: 6
<212> TYPE: DNA
<213> ORGANISM: artificial sequence
<220> FEATURE:
<223> OTHER INFORMATION: I-TevI motif(medium activity)

<400> SEQUENCE: 117 catcgt                                                                    6

<210> SEQ ID NO 118
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 118 caaagt                                                                    6

<210> SEQ ID NO 119
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 119 cactgt                                                                    6

<210> SEQ ID NO 120
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 120 ccttgt                                                                    6

<210> SEQ ID NO 121
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 121 cgatgt                                                                    6

<210> SEQ ID NO 122
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 122 cgttgt                                                                    6

<210> SEQ ID NO 123
<211> LENGTH: 6
```

```
<212> TYPE: DNA
<213> ORGANISM: artificial sequence
<220> FEATURE:
<223> OTHER INFORMATION: I-TevI motif(low/no activity)

<400> SEQUENCE: 123 ctaagt                                                                      6

<210> SEQ ID NO 124
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 124 ctgtga                                                                      6

<210> SEQ ID NO 125
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 125 cttagt                                                                      6

<210> SEQ ID NO 126
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 126 ctttgt                                                                      6

<210> SEQ ID NO 127
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 127 caaggt                                                                      6

<210> SEQ ID NO 128
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 128 cagggc                                                                      6

<210> SEQ ID NO 129
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 129
``` catggt 6

<210> SEQ ID NO 130
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 130 ccaagc 6

<210> SEQ ID NO 131
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 131 ccatga 6

<210> SEQ ID NO 132
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 132 ccgcgc 6

<210> SEQ ID NO 133
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 133 ccgcgt 6

<210> SEQ ID NO 134
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 134 ccgtgc 6

<210> SEQ ID NO 135
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 135 ccgtgt 6

<210> SEQ ID NO 136
<211> LENGTH: 6
<212> TYPE: DNA
<213> ORGANISM: artificial sequence

```
<220> FEATURE:
<223> OTHER INFORMATION: I-TevI motif(low/no activity)

<400> SEQUENCE: 136 cctagc                                                                          6

<210> SEQ ID NO 137
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 137 cctcgc                                                                          6

<210> SEQ ID NO 138
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 138 cctcgt                                                                          6

<210> SEQ ID NO 139
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 139 ccttgc                                                                          6

<210> SEQ ID NO 140
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 140 cgaagc                                                                          6

<210> SEQ ID NO 141
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 141 cgatgc                                                                          6

<210> SEQ ID NO 142
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 142 cggtgc                                                                          6
```

```
<210> SEQ ID NO 143
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 143 cggtgt                                                                     6

<210> SEQ ID NO 144
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 144 cgtagt                                                                     6

<210> SEQ ID NO 145
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 145 cgtcgc                                                                     6

<210> SEQ ID NO 146
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 146 cgttgc                                                                     6

<210> SEQ ID NO 147
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 147 ctccgc                                                                     6

<210> SEQ ID NO 148
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 148 ctcggg                                                                     6

<210> SEQ ID NO 149
<211> LENGTH: 6
<212> TYPE: DNA
<213> ORGANISM: artificial sequence
<220> FEATURE:
<223> OTHER INFORMATION: I-TevI motif(low/no activity)
```

```
<400> SEQUENCE: 149 ctctgc                                                                          6

<210> SEQ ID NO 150
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 150 ctgagt                                                                          6

<210> SEQ ID NO 151
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 151 ctttga                                                                          6

<210> SEQ ID NO 152
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 152 cacggc                                                                          6

<210> SEQ ID NO 153
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 153 cgctgc                                                                          6

<210> SEQ ID NO 154
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 154 cttaga                                                                          6

<210> SEQ ID NO 155
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 155 caccga                                                                          6

<210> SEQ ID NO 156
```

```
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 156 cacggt                                                                     6

<210> SEQ ID NO 157
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 157 cactga                                                                     6

<210> SEQ ID NO 158
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 158 cagggt                                                                     6

<210> SEQ ID NO 159
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 159 ccaagt                                                                     6

<210> SEQ ID NO 160
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 160 ccacga                                                                     6

<210> SEQ ID NO 161
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 161 ccgggg                                                                     6

<210> SEQ ID NO 162
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 162
```

```
cctagt                                                                      6

<210> SEQ ID NO 163
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 163 ccttga                                                                      6

<210> SEQ ID NO 164
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 164 cgaaga                                                                      6

<210> SEQ ID NO 165
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 165 cgatga                                                                      6

<210> SEQ ID NO 166
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 166 cggagc                                                                      6

<210> SEQ ID NO 167
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 167 cggcgt                                                                      6

<210> SEQ ID NO 168
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 168 cggtga                                                                      6

<210> SEQ ID NO 169
<211> LENGTH: 6
<212> TYPE: DNA
```

```
<213> ORGANISM: artificial sequence
<220> FEATURE:
<223> OTHER INFORMATION: I-TevI motif(low/no activity)

<400> SEQUENCE: 169 cgtaga                                                                      6

<210> SEQ ID NO 170
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 170 cgtcga                                                                      6

<210> SEQ ID NO 171
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 171 cgtcgt                                                                      6

<210> SEQ ID NO 172
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 172 cgttga                                                                      6

<210> SEQ ID NO 173
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 173 ctaaga                                                                      6

<210> SEQ ID NO 174
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 174 ctcagc                                                                      6

<210> SEQ ID NO 175
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 175 ctcagt                                                                      6
```

```
<210> SEQ ID NO 176
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 176 ctccgt                                                                    6

<210> SEQ ID NO 177
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 177 ctctgt                                                                    6

<210> SEQ ID NO 178
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 178 ctgaga                                                                    6

<210> SEQ ID NO 179
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 179 cttcga                                                                    6

<210> SEQ ID NO 180
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 180 cttggc                                                                    6

<210> SEQ ID NO 181
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 181 caaggc                                                                    6

<210> SEQ ID NO 182
<211> LENGTH: 6
<212> TYPE: DNA
<213> ORGANISM: artificial sequence
<220> FEATURE:
```

<223> OTHER INFORMATION: I-TevI motif(low/no activity)

<400> SEQUENCE: 182 cggcgc                                                                          6

<210> SEQ ID NO 183
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 183 cacgga                                                                          6

<210> SEQ ID NO 184
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 184 ccaaga                                                                          6

<210> SEQ ID NO 185
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 185 cccggg                                                                          6

<210> SEQ ID NO 186
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 186 cccggt                                                                          6

<210> SEQ ID NO 187
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 187 ccgagc                                                                          6

<210> SEQ ID NO 188
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 188 cgcagc                                                                          6

```
<210> SEQ ID NO 189
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 189 cgcggg                                                                     6

<210> SEQ ID NO 190
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 190 cggaga                                                                     6

<210> SEQ ID NO 191
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 191 cggagt                                                                     6

<210> SEQ ID NO 192
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 192 ctaggc                                                                     6

<210> SEQ ID NO 193
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 193 ctcaga                                                                     6

<210> SEQ ID NO 194
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 194 caggga                                                                     6

<210> SEQ ID NO 195
<211> LENGTH: 6
<212> TYPE: DNA
<213> ORGANISM: artificial sequence
<220> FEATURE:
<223> OTHER INFORMATION: I-TevI motif(low/no activity)
```

```
<400> SEQUENCE: 195 ccaggt                                                              6

<210> SEQ ID NO 196
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 196 ccccgc                                                              6

<210> SEQ ID NO 197
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 197 ccctgc                                                              6

<210> SEQ ID NO 198
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 198 cgcagt                                                              6

<210> SEQ ID NO 199
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 199 cacaga                                                              6

<210> SEQ ID NO 200
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 200 ccgtga                                                              6

<210> SEQ ID NO 201
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 201 cctcga                                                              6

<210> SEQ ID NO 202
<211> LENGTH: 6
```

```
<212> TYPE: DNA
<213> ORGANISM: artificial sequence
<220> FEATURE:
<223> OTHER INFORMATION: I-TevI motif(low/no activity)

<400> SEQUENCE: 202 caagga                                                                     6

<210> SEQ ID NO 203
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 203 ccagga                                                                     6

<210> SEQ ID NO 204
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 204 ccaggc                                                                     6

<210> SEQ ID NO 205
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 205 cccaga                                                                     6

<210> SEQ ID NO 206
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 206 cccagc                                                                     6

<210> SEQ ID NO 207
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 207 cccagt                                                                     6

<210> SEQ ID NO 208
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 208
``` ccccga                                                                      6

<210> SEQ ID NO 209
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 209 ccccgt                                                                      6

<210> SEQ ID NO 210
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 210 cccgga                                                                      6

<210> SEQ ID NO 211
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 211 cccggc                                                                      6

<210> SEQ ID NO 212
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 212 ccctga                                                                      6

<210> SEQ ID NO 213
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 213 ccctgt                                                                      6

<210> SEQ ID NO 214
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 214 ccgaga                                                                      6

<210> SEQ ID NO 215
<211> LENGTH: 6
<212> TYPE: DNA
<213> ORGANISM: artificial sequence

```
<220> FEATURE:
<223> OTHER INFORMATION: I-TevI motif(low/no activity)

<400> SEQUENCE: 215 ccgagt                                                                   6

<210> SEQ ID NO 216
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 216 ccgcga                                                                   6

<210> SEQ ID NO 217
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 217 ccggga                                                                   6

<210> SEQ ID NO 218
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 218 ccgggc                                                                   6

<210> SEQ ID NO 219
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 219 ccgggt                                                                   6

<210> SEQ ID NO 220
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 220 cctaga                                                                   6

<210> SEQ ID NO 221
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 221 cctgga                                                                   6
```

```
<210> SEQ ID NO 222
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 222 cctggc                                                                    6

<210> SEQ ID NO 223
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 223 cctggt                                                                    6

<210> SEQ ID NO 224
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 224 cgaagt                                                                    6

<210> SEQ ID NO 225
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 225 cgagga                                                                    6

<210> SEQ ID NO 226
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 226 cgaggc                                                                    6

<210> SEQ ID NO 227
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 227 cgaggt                                                                    6

<210> SEQ ID NO 228
<211> LENGTH: 6
<212> TYPE: DNA
<213> ORGANISM: artificial sequence
<220> FEATURE:
<223> OTHER INFORMATION: I-TevI motif(low/no activity)
```

```
<400> SEQUENCE: 228 cgcaga                                                              6

<210> SEQ ID NO 229
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 229 cgccga                                                              6

<210> SEQ ID NO 230
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 230 cgccgc                                                              6

<210> SEQ ID NO 231
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 231 cgccgt                                                              6

<210> SEQ ID NO 232
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 232 cgcgga                                                              6

<210> SEQ ID NO 233
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 233 cgcggc                                                              6

<210> SEQ ID NO 234
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 234 cgcggt                                                              6

<210> SEQ ID NO 235
```

```
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 235 cgctga                                                                    6

<210> SEQ ID NO 236
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 236 cgctgt                                                                    6

<210> SEQ ID NO 237
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 237 cggcga                                                                    6

<210> SEQ ID NO 238
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 238 cgggga                                                                    6

<210> SEQ ID NO 239
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 239 cggggc                                                                    6

<210> SEQ ID NO 240
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 240 cggggg                                                                    6

<210> SEQ ID NO 241
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 241
``` cggggt 6

<210> SEQ ID NO 242
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 242 cgtgga 6

<210> SEQ ID NO 243
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 243 cgtggc 6

<210> SEQ ID NO 244
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 244 cgtggt 6

<210> SEQ ID NO 245
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 245 ctagga 6

<210> SEQ ID NO 246
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 246 ctaggt 6

<210> SEQ ID NO 247
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 247 ctccga 6

<210> SEQ ID NO 248
<211> LENGTH: 6
<212> TYPE: DNA

```
<213> ORGANISM: artificial sequence
<220> FEATURE:
<223> OTHER INFORMATION: I-TevI motif(low/no activity)

<400> SEQUENCE: 248 ctcgga                                                                6

<210> SEQ ID NO 249
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 249 ctcggc                                                                6

<210> SEQ ID NO 250
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 250 ctcggt                                                                6

<210> SEQ ID NO 251
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 251 ctctga                                                                6

<210> SEQ ID NO 252
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 252 ctggga                                                                6

<210> SEQ ID NO 253
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 253 ctgggc                                                                6

<210> SEQ ID NO 254
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 254 ctgggt                                                                6
```

<210> SEQ ID NO 255
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 255 cttgga                                                                   6

<210> SEQ ID NO 256
<211> LENGTH: 6
<212> TYPE: DNA
<213> ORGANISM: artificial sequence
<220> FEATURE:
<223> OTHER INFORMATION: I-TevI motif(low/no activity)

<400> SEQUENCE: 256 cttggt                                                                   6

<210> SEQ ID NO 257
<211> LENGTH: 246
<212> TYPE: PRT
<213> ORGANISM: artificial sequence
<220> FEATURE:
<223> OTHER INFORMATION: I-TevI catalytic domain

<400> SEQUENCE: 257

Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
        35                  40                  45

Ser Phe Asn Lys His Gly Asn Val Phe Glu Cys Ser Ile Leu Glu Glu
    50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ser Lys Asn Gly Arg Trp
    130                 135                 140

Asn Pro Glu Thr His Lys Phe Cys Lys Cys Gly Val Arg Ile Gln Thr
145                 150                 155                 160

Ser Ala Tyr Thr Cys Ser Lys Cys Arg Asn Arg Ser Gly Glu Asn Asn
                165                 170                 175

Ser Phe Phe Asn His Lys His Ser Asp Ile Thr Lys Ser Lys Ile Ser
            180                 185                 190

Glu Lys Met Lys Gly Lys Lys Pro Ser Asn Ile Lys Lys Ile Ser Cys
        195                 200                 205

Asp Gly Val Ile Phe Asp Cys Ala Ala Asp Ala Ala Arg His Phe Lys
    210                 215                 220

Ile Ser Ser Gly Leu Val Thr Tyr Arg Val Lys Ser Asp Lys Trp Asn
225                 230                 235                 240

Trp Phe Tyr Ile Asn Ala
            245

<210> SEQ ID NO 258
<211> LENGTH: 518
<212> TYPE: PRT
<213> ORGANISM: artificial sequence
<220> FEATURE:
<223> OTHER INFORMATION: TALE scaffold: st1

<400> SEQUENCE: 258

Asp Pro Ile Arg Ser Arg Thr Pro Ser Pro Ala Arg Glu Leu Leu Pro
1               5                   10                  15

Gly Pro Gln Pro Asp Gly Val Gln Pro Thr Ala Asp Arg Gly Val Ser
            20                  25                  30

Pro Pro Ala Gly Gly Pro Leu Asp Gly Leu Pro Ala Arg Arg Thr Met
        35                  40                  45

Ser Arg Thr Arg Leu Pro Ser Pro Pro Ala Pro Ser Pro Ala Phe Ser
50                  55                  60

Ala Gly Ser Phe Ser Asp Leu Leu Arg Gln Phe Asp Pro Ser Leu Phe
65                  70                  75                  80

Asn Thr Ser Leu Phe Asp Ser Leu Pro Pro Phe Gly Ala His His Thr
                85                  90                  95

Glu Ala Ala Thr Gly Glu Trp Asp Glu Val Gln Ser Gly Leu Arg Ala
            100                 105                 110

Ala Asp Ala Pro Pro Pro Thr Met Arg Val Ala Val Thr Ala Ala Arg
        115                 120                 125

Pro Pro Arg Ala Lys Pro Ala Pro Arg Arg Arg Ala Ala Gln Pro Ser
    130                 135                 140

Asp Ala Ser Pro Ala Ala Gln Val Asp Leu Arg Thr Leu Gly Tyr Ser
145                 150                 155                 160

Gln Gln Gln Gln Glu Lys Ile Lys Pro Lys Val Arg Ser Thr Val Ala
                165                 170                 175

Gln His His Glu Ala Leu Val Gly His Gly Phe Thr His Ala His Ile
            180                 185                 190

Val Ala Leu Ser Gln His Pro Ala Ala Leu Gly Thr Val Ala Val Lys
        195                 200                 205

Tyr Gln Asp Met Ile Ala Ala Leu Pro Glu Ala Thr His Glu Ala Ile
    210                 215                 220

Val Gly Val Gly Lys Gln Trp Ser Gly Ala Arg Ala Leu Glu Ala Leu
225                 230                 235                 240

Leu Thr Val Ala Gly Glu Leu Arg Gly Pro Pro Leu Gln Leu Asp Thr
                245                 250                 255

Gly Gln Leu Leu Lys Ile Ala Lys Arg Gly Gly Val Thr Ala Val Glu
            260                 265                 270

Ala Val His Ala Trp Arg Asn Ala Leu Thr Gly Ala Pro Leu Asn Ser
        275                 280                 285

Ile Val Ala Gln Leu Ser Arg Pro Asp Pro Ala Leu Ala Ala Leu Thr
    290                 295                 300

Asn Asp His Leu Val Ala Leu Ala Cys Leu Gly Gly Arg Pro Ala Leu
305                 310                 315                 320

Asp Ala Val Lys Lys Gly Leu Pro His Ala Pro Ala Leu Ile Lys Arg
                325                 330                 335

Thr Asn Arg Arg Ile Pro Glu Arg Thr Ser His Arg Val Ala Asp His
            340                 345                 350

```
Ala Gln Val Val Arg Val Leu Gly Phe Phe Gln Cys His Ser His Pro
        355                 360                 365

Ala Gln Ala Phe Asp Asp Ala Met Thr Gln Phe Gly Met Ser Arg His
        370                 375                 380

Gly Leu Leu Gln Leu Phe Arg Arg Val Gly Val Thr Glu Leu Glu Ala
385                 390                 395                 400

Arg Ser Gly Thr Leu Pro Pro Ala Ser Gln Arg Trp Asp Arg Ile Leu
                405                 410                 415

Gln Ala Ser Gly Met Lys Arg Ala Lys Pro Ser Pro Thr Ser Thr Gln
                420                 425                 430

Thr Pro Asp Gln Ala Ser Leu His Ala Phe Ala Asp Ser Leu Glu Arg
        435                 440                 445

Asp Leu Asp Ala Pro Ser Pro Met His Glu Gly Asp Gln Thr Arg Ala
        450                 455                 460

Ser Ser Arg Lys Arg Ser Arg Ser Asp Arg Ala Val Thr Gly Pro Ser
465                 470                 475                 480

Ala Gln Gln Ser Phe Glu Val Arg Val Pro Glu Gln Arg Asp Ala Leu
                485                 490                 495

His Leu Pro Leu Ser Trp Arg Val Lys Arg Pro Arg Thr Ser Ile Gly
                500                 505                 510

Gly Gly Leu Pro Asp Pro
        515
```

<210> SEQ ID NO 259
<211> LENGTH: 147
<212> TYPE: PRT
<213> ORGANISM: artificial sequence
<220> FEATURE:
<223> OTHER INFORMATION: TALE scaffold:st2

<400> SEQUENCE: 259

```
Val Asp Leu Arg Thr Leu Gly Tyr Ser Gln Gln Gln Gln Glu Lys Ile
1               5                   10                  15

Lys Pro Lys Val Arg Ser Thr Val Ala Gln His His Glu Ala Leu Val
                20                  25                  30

Gly His Gly Phe Thr His Ala His Ile Val Ala Leu Ser Gln His Pro
        35                  40                  45

Ala Ala Leu Gly Thr Val Ala Val Lys Tyr Gln Asp Met Ile Ala Ala
        50                  55                  60

Leu Pro Glu Ala Thr His Glu Ala Ile Val Gly Val Gly Lys Gln Trp
65                  70                  75                  80

Ser Gly Ala Arg Ala Leu Glu Ala Leu Leu Thr Val Ala Gly Glu Leu
                85                  90                  95

Arg Gly Pro Pro Leu Gln Leu Asp Thr Gly Gln Leu Leu Lys Ile Ala
                100                 105                 110

Lys Arg Gly Gly Val Thr Ala Val Glu Ala Val His Ala Trp Arg Asn
        115                 120                 125

Ala Leu Thr Gly Ala Pro Leu Asn Ser Ile Val Ala Gln Leu Ser Arg
        130                 135                 140

Pro Asp Pro
145
```

<210> SEQ ID NO 260
<211> LENGTH: 1116
<212> TYPE: PRT
<213> ORGANISM: artificial sequence
<220> FEATURE:
<223> OTHER INFORMATION: TALE scaffold:bT1-Avr

<400> SEQUENCE: 260

```
Asp Pro Ile Arg Ser Arg Thr Pro Ser Pro Ala Arg Glu Leu Leu Pro
1               5                   10                  15

Gly Pro Gln Pro Asp Gly Val Gln Pro Thr Ala Asp Arg Gly Val Ser
            20                  25                  30

Pro Pro Ala Gly Gly Pro Leu Asp Gly Leu Pro Ala Arg Arg Thr Met
        35                  40                  45

Ser Arg Thr Arg Leu Pro Ser Pro Pro Ala Pro Ser Pro Ala Phe Ser
50                  55                  60

Ala Gly Ser Phe Ser Asp Leu Leu Arg Gln Phe Asp Pro Ser Leu Phe
65                  70                  75                  80

Asn Thr Ser Leu Phe Asp Ser Leu Pro Pro Phe Gly Ala His His Thr
                85                  90                  95

Glu Ala Ala Thr Gly Glu Trp Asp Glu Val Gln Ser Gly Leu Arg Ala
            100                 105                 110

Ala Asp Ala Pro Pro Pro Thr Met Arg Val Ala Val Thr Ala Ala Arg
        115                 120                 125

Pro Pro Arg Ala Lys Pro Ala Pro Arg Arg Arg Ala Ala Gln Pro Ser
130                 135                 140

Asp Ala Ser Pro Ala Ala Gln Val Asp Leu Arg Thr Leu Gly Tyr Ser
145                 150                 155                 160

Gln Gln Gln Gln Glu Lys Ile Lys Pro Lys Val Arg Ser Thr Val Ala
                165                 170                 175

Gln His His Glu Ala Leu Val Gly His Gly Phe Thr His Ala His Ile
            180                 185                 190

Val Ala Leu Ser Gln His Pro Ala Ala Leu Gly Thr Val Ala Val Lys
        195                 200                 205

Tyr Gln Asp Met Ile Ala Ala Leu Pro Glu Ala Thr His Glu Ala Ile
210                 215                 220

Val Gly Val Gly Lys Gln Trp Ser Gly Ala Arg Ala Leu Glu Ala Leu
225                 230                 235                 240

Leu Thr Val Ala Gly Glu Leu Arg Gly Pro Pro Leu Gln Leu Asp Thr
                245                 250                 255

Gly Gln Leu Leu Lys Ile Ala Lys Arg Gly Gly Val Thr Ala Val Glu
            260                 265                 270

Ala Val His Ala Trp Arg Asn Ala Leu Thr Gly Ala Pro Leu Asn Leu
        275                 280                 285

Thr Pro Glu Gln Val Val Ala Ile Ala Ser Asn Ile Gly Gly Lys Gln
290                 295                 300

Ala Leu Glu Thr Val Gln Ala Leu Leu Pro Val Leu Cys Gln Ala His
305                 310                 315                 320

Gly Leu Thr Pro Gln Gln Val Val Ala Ile Ala Ser Asn Gly Gly Gly
                325                 330                 335

Lys Gln Ala Leu Glu Thr Val Gln Arg Leu Leu Pro Val Leu Cys Gln
            340                 345                 350

Ala His Gly Leu Thr Pro Glu Gln Val Val Ala Ile Ala Ser Asn Ile
        355                 360                 365

Gly Gly Lys Gln Ala Leu Glu Thr Val Gln Ala Leu Leu Pro Val Leu
370                 375                 380

Cys Gln Ala His Gly Leu Thr Pro Gln Gln Val Val Ala Ile Ala Ser
385                 390                 395                 400
```

```
Asn Gly Gly Gly Lys Gln Ala Leu Glu Thr Val Gln Arg Leu Leu Pro
            405                 410                 415

Val Leu Cys Gln Ala His Gly Leu Thr Pro Glu Gln Val Val Ala Ile
            420                 425                 430

Ala Ser Asn Ile Gly Gly Lys Gln Ala Leu Glu Thr Val Gln Ala Leu
            435                 440                 445

Leu Pro Val Leu Cys Gln Ala His Gly Leu Thr Pro Glu Gln Val Val
450                 455                 460

Ala Ile Ala Ser Asn Ile Gly Gly Lys Gln Ala Leu Glu Thr Val Gln
465                 470                 475                 480

Ala Leu Leu Pro Val Leu Cys Gln Ala His Gly Leu Thr Pro Glu Gln
            485                 490                 495

Val Val Ala Ile Ala Ser Asn Ile Gly Gly Lys Gln Ala Leu Glu Thr
            500                 505                 510

Val Gln Ala Leu Leu Pro Val Leu Cys Gln Ala His Gly Leu Thr Pro
            515                 520                 525

Glu Gln Val Val Ala Ile Ala Ser His Asp Gly Gly Lys Gln Ala Leu
            530                 535                 540

Glu Thr Val Gln Arg Leu Leu Pro Val Leu Cys Gln Ala His Gly Leu
545                 550                 555                 560

Thr Pro Glu Gln Val Val Ala Ile Ala Ser His Asp Gly Gly Lys Gln
            565                 570                 575

Ala Leu Glu Thr Val Gln Arg Leu Leu Pro Val Leu Cys Gln Ala His
            580                 585                 590

Gly Leu Thr Pro Gln Gln Val Val Ala Ile Ala Ser Asn Gly Gly Gly
            595                 600                 605

Lys Gln Ala Leu Glu Thr Val Gln Arg Leu Leu Pro Val Leu Cys Gln
            610                 615                 620

Ala His Gly Leu Thr Pro Glu Gln Val Val Ala Ile Ala Ser Asn Ile
625                 630                 635                 640

Gly Gly Lys Gln Ala Leu Glu Thr Val Gln Ala Leu Leu Pro Val Leu
            645                 650                 655

Cys Gln Ala His Gly Leu Thr Pro Glu Gln Val Val Ala Ile Ala Ser
            660                 665                 670

Asn Ile Gly Gly Lys Gln Ala Leu Glu Thr Val Gln Ala Leu Leu Pro
            675                 680                 685

Val Leu Cys Gln Ala His Gly Leu Thr Pro Glu Gln Val Val Ala Ile
            690                 695                 700

Ala Ser His Asp Gly Gly Lys Gln Ala Leu Glu Thr Val Gln Arg Leu
705                 710                 715                 720

Leu Pro Val Leu Cys Gln Ala His Gly Leu Thr Pro Glu Gln Val Val
            725                 730                 735

Ala Ile Ala Ser His Asp Gly Gly Lys Gln Ala Leu Glu Thr Val Gln
            740                 745                 750

Arg Leu Leu Pro Val Leu Cys Gln Ala His Gly Leu Thr Pro Glu Gln
            755                 760                 765

Val Val Ala Ile Ala Ser His Asp Gly Gly Lys Gln Ala Leu Glu Thr
            770                 775                 780

Val Gln Arg Leu Leu Pro Val Leu Cys Gln Ala His Gly Leu Thr Pro
785                 790                 795                 800

Gln Gln Val Val Ala Ile Ala Ser Asn Gly Gly Gly Lys Gln Ala Leu
            805                 810                 815
```

-continued

Glu Thr Val Gln Arg Leu Leu Pro Val Leu Cys Gln Ala His Gly Leu
            820                 825                 830

Thr Pro Glu Gln Val Val Ala Ile Ala Ser His Asp Gly Gly Lys Gln
        835                 840                 845

Ala Leu Glu Thr Val Gln Arg Leu Leu Pro Val Leu Cys Gln Ala His
    850                 855                 860

Gly Leu Thr Pro Gln Gln Val Val Ala Ile Ala Ser Asn Gly Gly Gly
865                 870                 875                 880

Arg Pro Ala Leu Glu Ser Ile Val Ala Gln Leu Ser Arg Pro Asp Pro
                885                 890                 895

Ala Leu Ala Ala Leu Thr Asn Asp His Leu Val Ala Leu Ala Cys Leu
            900                 905                 910

Gly Gly Arg Pro Ala Leu Asp Ala Val Lys Lys Gly Leu Pro His Ala
        915                 920                 925

Pro Ala Leu Ile Lys Arg Thr Asn Arg Arg Ile Pro Glu Arg Thr Ser
    930                 935                 940

His Arg Val Ala Asp His Ala Gln Val Val Arg Val Leu Gly Phe Phe
945                 950                 955                 960

Gln Cys His Ser His Pro Ala Gln Ala Phe Asp Asp Ala Met Thr Gln
                965                 970                 975

Phe Gly Met Ser Arg His Gly Leu Leu Gln Leu Phe Arg Arg Val Gly
            980                 985                 990

Val Thr Glu Leu Glu Ala Arg Ser Gly Thr Leu Pro Pro Ala Ser Gln
        995                 1000                1005

Arg Trp Asp Arg Ile Leu Gln Ala Ser Gly Met Lys Arg Ala Lys
    1010                1015                1020

Pro Ser Pro Thr Ser Thr Gln Thr Pro Asp Gln Ala Ser Leu His
    1025                1030                1035

Ala Phe Ala Asp Ser Leu Glu Arg Asp Leu Asp Ala Pro Ser Pro
    1040                1045                1050

Met His Glu Gly Asp Gln Thr Arg Ala Ser Ser Arg Lys Arg Ser
    1055                1060                1065

Arg Ser Asp Arg Ala Val Thr Gly Pro Ser Ala Gln Gln Ser Phe
    1070                1075                1080

Glu Val Arg Val Pro Glu Gln Arg Asp Ala Leu His Leu Pro Leu
    1085                1090                1095

Ser Trp Arg Val Lys Arg Pro Arg Thr Ser Ile Gly Gly Gly Leu
    1100                1105                1110

Pro Asp Pro
    1115

<210> SEQ ID NO 261
<211> LENGTH: 745
<212> TYPE: PRT
<213> ORGANISM: artificial sequence
<220> FEATURE:
<223> OTHER INFORMATION: TALE scaffold:bT2-Avr

<400> SEQUENCE: 261

Val Asp Leu Arg Thr Leu Gly Tyr Ser Gln Gln Gln Gln Glu Lys Ile
1               5                   10                  15

Lys Pro Lys Val Arg Ser Thr Val Ala Gln His His Glu Ala Leu Val
            20                  25                  30

Gly His Gly Phe Thr His Ala His Ile Val Ala Leu Ser Gln His Pro
        35                  40                  45

Ala Ala Leu Gly Thr Val Ala Val Lys Tyr Gln Asp Met Ile Ala Ala
 50                  55                  60

Leu Pro Glu Ala Thr His Glu Ala Ile Val Gly Val Gly Lys Gln Trp
 65                  70                  75                  80

Ser Gly Ala Arg Ala Leu Glu Ala Leu Leu Thr Val Ala Gly Glu Leu
                 85                  90                  95

Arg Gly Pro Pro Leu Gln Leu Asp Thr Gly Gln Leu Leu Lys Ile Ala
             100                 105                 110

Lys Arg Gly Gly Val Thr Ala Val Glu Ala Val His Ala Trp Arg Asn
         115                 120                 125

Ala Leu Thr Gly Ala Pro Leu Asn Leu Thr Pro Glu Gln Val Val Ala
 130                 135                 140

Ile Ala Ser Asn Ile Gly Gly Lys Gln Ala Leu Glu Thr Val Gln Ala
145                 150                 155                 160

Leu Leu Pro Val Leu Cys Gln Ala His Gly Leu Thr Pro Gln Gln Val
                 165                 170                 175

Val Ala Ile Ala Ser Asn Gly Gly Gly Lys Gln Ala Leu Glu Thr Val
             180                 185                 190

Gln Arg Leu Leu Pro Val Leu Cys Gln Ala His Gly Leu Thr Pro Glu
         195                 200                 205

Gln Val Val Ala Ile Ala Ser Asn Ile Gly Gly Lys Gln Ala Leu Glu
 210                 215                 220

Thr Val Gln Ala Leu Leu Pro Val Leu Cys Gln Ala His Gly Leu Thr
225                 230                 235                 240

Pro Gln Gln Val Val Ala Ile Ala Ser Asn Gly Gly Gly Lys Gln Ala
                 245                 250                 255

Leu Glu Thr Val Gln Arg Leu Leu Pro Val Leu Cys Gln Ala His Gly
             260                 265                 270

Leu Thr Pro Glu Gln Val Val Ala Ile Ala Ser Asn Ile Gly Gly Lys
         275                 280                 285

Gln Ala Leu Glu Thr Val Gln Ala Leu Leu Pro Val Leu Cys Gln Ala
 290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Ala Leu Leu Pro Val Leu Cys
                 325                 330                 335

Gln Ala His Gly Leu Thr Pro Glu Gln Val Val Ala Ile Ala Ser Asn
             340                 345                 350

Ile Gly Gly Lys Gln Ala Leu Glu Thr Val Gln Ala Leu Leu Pro Val
         355                 360                 365

Leu Cys Gln Ala His Gly Leu Thr Pro Glu Gln Val Val Ala Ile Ala
 370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                 405                 410                 415

Ile Ala Ser His Asp Gly Gly Lys Gln Ala Leu Glu Thr Val Gln Arg
             420                 425                 430

Leu Leu Pro Val Leu Cys Gln Ala His Gly Leu Thr Pro Gln Gln Val
         435                 440                 445

Val Ala Ile Ala Ser Asn Gly Gly Gly Lys Gln Ala Leu Glu Thr Val
 450                 455                 460

Gln Arg Leu Leu Pro Val Leu Cys Gln Ala His Gly Leu Thr Pro Glu

```
                465                 470                 475                 480
        Gln Val Val Ala Ile Ala Ser Asn Ile Gly Gly Lys Gln Ala Leu Glu
                        485                 490                 495
        Thr Val Gln Ala Leu Leu Pro Val Leu Cys Gln Ala His Gly Leu Thr
                        500                 505                 510
        Pro Glu Gln Val Val Ala Ile Ala Ser Asn Ile Gly Gly Lys Gln Ala
                        515                 520                 525
        Leu Glu Thr Val Gln Ala Leu Leu Pro Val Leu Cys Gln Ala His Gly
                        530                 535                 540
        Leu Thr Pro Glu Gln Val Val Ala Ile Ala Ser His Asp Gly Gly Lys
        545                 550                 555                 560
        Gln Ala Leu Glu Thr Val Gln Arg Leu Leu Pro Val Leu Cys Gln Ala
                        565                 570                 575
        His Gly Leu Thr Pro Glu Gln Val Val Ala Ile Ala Ser His Asp Gly
                        580                 585                 590
        Gly Lys Gln Ala Leu Glu Thr Val Gln Arg Leu Leu Pro Val Leu Cys
                        595                 600                 605
        Gln Ala His Gly Leu Thr Pro Glu Gln Val Val Ala Ile Ala Ser His
                        610                 615                 620
        Asp Gly Gly Lys Gln Ala Leu Glu Thr Val Gln Arg Leu Leu Pro Val
        625                 630                 635                 640
        Leu Cys Gln Ala His Gly Leu Thr Pro Gln Gln Val Val Ala Ile Ala
                        645                 650                 655
        Ser Asn Gly Gly Gly Lys Gln Ala Leu Glu Thr Val Gln Arg Leu Leu
                        660                 665                 670
        Pro Val Leu Cys Gln Ala His Gly Leu Thr Pro Glu Gln Val Val Ala
                        675                 680                 685
        Ile Ala Ser His Asp Gly Gly Lys Gln Ala Leu Glu Thr Val Gln Arg
                        690                 695                 700
        Leu Leu Pro Val Leu Cys Gln Ala His Gly Leu Thr Pro Gln Gln Val
        705                 710                 715                 720
        Val Ala Ile Ala Ser Asn Gly Gly Gly Arg Pro Ala Leu Glu Ser Ile
                        725                 730                 735
        Val Ala Gln Leu Ser Arg Pro Asp Pro
                        740                 745

<210> SEQ ID NO 262
<211> LENGTH: 1320
<212> TYPE: PRT
<213> ORGANISM: artificial sequence
<220> FEATURE:
<223> OTHER INFORMATION: TALE scaffold:bT1-Pth

<400> SEQUENCE: 262

Asp Pro Ile Arg Ser Arg Thr Pro Ser Pro Ala Arg Glu Leu Leu Pro
1               5                   10                  15

Gly Pro Gln Pro Asp Gly Val Gln Pro Thr Ala Asp Arg Gly Val Ser
                20                  25                  30

Pro Pro Ala Gly Gly Pro Leu Asp Gly Leu Pro Ala Arg Arg Thr Met
            35                  40                  45

Ser Arg Thr Arg Leu Pro Ser Pro Pro Ala Pro Ser Pro Ala Phe Ser
        50                  55                  60

Ala Gly Ser Phe Ser Asp Leu Leu Arg Gln Phe Asp Pro Ser Leu Phe
65                  70                  75                  80

Asn Thr Ser Leu Phe Asp Ser Leu Pro Pro Phe Gly Ala His His Thr
```

```
                        85               90                  95
Glu Ala Ala Thr Gly Glu Trp Asp Glu Val Gln Ser Gly Leu Arg Ala
                100             105                 110

Ala Asp Ala Pro Pro Thr Met Arg Val Ala Val Thr Ala Ala Arg
        115              120                 125

Pro Pro Arg Ala Lys Pro Ala Pro Arg Arg Ala Ala Gln Pro Ser
        130                 135             140

Asp Ala Ser Pro Ala Ala Gln Val Asp Leu Arg Thr Leu Gly Tyr Ser
145                 150                 155                 160

Gln Gln Gln Gln Glu Lys Ile Lys Pro Lys Val Arg Ser Thr Val Ala
                165                 170                 175

Gln His His Glu Ala Leu Val Gly His Gly Phe Thr His Ala His Ile
                180                 185                 190

Val Ala Leu Ser Gln His Pro Ala Ala Leu Gly Thr Val Ala Val Lys
                195                 200                 205

Tyr Gln Asp Met Ile Ala Ala Leu Pro Glu Ala Thr His Glu Ala Ile
        210                 215                 220

Val Gly Val Gly Lys Gln Trp Ser Gly Ala Arg Ala Leu Glu Ala Leu
225                 230                 235                 240

Leu Thr Val Ala Gly Glu Leu Arg Gly Pro Pro Leu Gln Leu Asp Thr
                245                 250                 255

Gly Gln Leu Leu Lys Ile Ala Lys Arg Gly Gly Val Thr Ala Val Glu
                260                 265                 270

Ala Val His Ala Trp Arg Asn Ala Leu Thr Gly Ala Pro Leu Asn Leu
                275                 280                 285

Thr Pro Glu Gln Val Val Ala Ile Ala Ser Asn Lys Gly Gly Lys Gln
        290                 295                 300

Ala Leu Glu Thr Val Gln Arg Leu Leu Pro Val Leu Cys Gln Ala His
305                 310                 315                 320

Gly Leu Thr Pro Glu Gln Val Val Ala Ile Ala Ser His Asp Gly Gly
                325                 330                 335

Lys Gln Ala Leu Glu Thr Val Gln Arg Leu Leu Pro Val Leu Cys Gln
                340                 345                 350

Ala His Gly Leu Thr Pro Glu Gln Val Val Ala Ile Ala Ser Asn Ile
                355                 360                 365

Gly Gly Lys Gln Ala Leu Glu Thr Val Gln Ala Leu Leu Pro Val Leu
                370                 375                 380

Cys Gln Ala His Gly Leu Thr Pro Gln Gln Val Val Ala Ile Ala Ser
385                 390                 395                 400

Asn Gly Gly Gly Lys Gln Ala Leu Glu Thr Val Gln Arg Leu Leu Pro
                        405                 410                 415

Val Leu Cys Gln Ala His Gly Leu Thr Pro Glu Gln Val Val Ala Ile
                420                 425                 430

Ala Ser His Asp Gly Gly Lys Gln Ala Leu Glu Thr Val Gln Arg Leu
                435                 440                 445

Leu Pro Val Leu Cys Gln Ala His Gly Leu Thr Pro Gln Gln Val Val
        450                 455                 460

Ala Ile Ala Ser Asn Gly Gly Gly Lys Gln Ala Leu Glu Thr Val Gln
465                 470                 475                 480

Arg Leu Leu Pro Val Leu Cys Gln Ala His Gly Leu Thr Pro Glu Gln
                        485                 490                 495

Val Val Ala Ile Ala Ser His Asp Gly Gly Lys Gln Ala Leu Glu Thr
                500                 505                 510
```

```
Val Gln Arg Leu Leu Pro Val Leu Cys Gln Ala His Gly Leu Thr Pro
        515                 520                 525
Glu Gln Val Val Ala Ile Ala Ser His Asp Gly Gly Lys Gln Ala Leu
        530                 535                 540
Glu Thr Val Gln Arg Leu Leu Pro Val Leu Cys Gln Ala His Gly Leu
545                 550                 555                 560
Thr Pro Glu Gln Val Val Ala Ile Ala Ser His Asp Gly Gly Lys Gln
                565                 570                 575
Ala Leu Glu Thr Val Gln Arg Leu Leu Pro Val Leu Cys Gln Ala His
            580                 585                 590
Gly Leu Thr Pro Glu Gln Val Val Ala Ile Ala Ser His Asp Gly Gly
        595                 600                 605
Lys Gln Ala Leu Glu Thr Val Gln Arg Leu Leu Pro Val Leu Cys Gln
        610                 615                 620
Ala His Gly Leu Thr Pro Glu Gln Val Val Ala Ile Ala Ser His Asp
625                 630                 635                 640
Gly Gly Lys Gln Ala Leu Glu Thr Val Gln Arg Leu Leu Pro Val Leu
                645                 650                 655
Cys Gln Ala His Gly Leu Thr Pro Gln Gln Val Val Ala Ile Ala Ser
            660                 665                 670
Asn Gly Gly Lys Gln Ala Leu Glu Thr Val Gln Arg Leu Leu Pro
        675                 680                 685
Val Leu Cys Gln Ala His Gly Leu Thr Pro Glu Gln Val Val Ala Ile
        690                 695                 700
Ala Ser Asn Ile Gly Lys Gln Ala Leu Glu Thr Val Gln Ala Leu
705                 710                 715                 720
Leu Pro Val Leu Cys Gln Ala His Gly Leu Thr Pro Glu Gln Val Val
                725                 730                 735
Ala Ile Ala Ser His Asp Gly Gly Lys Gln Ala Leu Glu Thr Val Gln
            740                 745                 750
Arg Leu Leu Pro Val Leu Cys Gln Ala His Gly Leu Thr Pro Gln Gln
        755                 760                 765
Val Val Ala Ile Ala Ser Asn Gly Gly Lys Gln Ala Leu Glu Thr
        770                 775                 780
Val Gln Arg Leu Leu Pro Val Leu Cys Gln Ala His Gly Leu Thr Pro
785                 790                 795                 800
Glu Gln Val Val Ala Ile Ala Ser Asn Lys Gly Gly Lys Gln Ala Leu
                805                 810                 815
Glu Thr Val Gln Arg Leu Leu Pro Val Leu Cys Gln Ala His Gly Leu
            820                 825                 830
Thr Pro Gln Gln Val Val Ala Ile Ala Ser Asn Gly Gly Lys Gln
        835                 840                 845
Ala Leu Glu Thr Val Gln Arg Leu Leu Pro Val Leu Cys Gln Ala His
        850                 855                 860
Gly Leu Thr Pro Glu Gln Val Val Ala Ile Ala Ser Asn Ile Gly Gly
865                 870                 875                 880
Lys Gln Ala Leu Glu Thr Val Gln Ala Leu Leu Pro Val Leu Cys Gln
                885                 890                 895
Ala His Gly Leu Thr Pro Glu Gln Val Val Ala Ile Ala Ser His Asp
            900                 905                 910
Gly Gly Lys Gln Ala Leu Glu Thr Val Gln Arg Leu Leu Pro Val Leu
        915                 920                 925
```

```
Cys Gln Ala His Gly Leu Thr Pro Glu Gln Val Val Ala Ile Ala Ser
930                 935                 940

Asn Ile Gly Gly Lys Gln Ala Leu Glu Thr Val Gln Ala Leu Leu Pro
945                 950                 955                 960

Val Leu Cys Gln Ala His Gly Leu Thr Pro Glu Gln Val Val Ala Ile
                965                 970                 975

Ala Ser His Asp Gly Gly Lys Gln Ala Leu Glu Thr Val Gln Arg Leu
                980                 985                 990

Leu Pro Val Leu Cys Gln Ala His Gly Leu Thr Pro Glu Gln Val Val
        995                 1000                1005

Ala Ile Ala Ser His Asp Gly Gly Lys Gln Ala Leu Glu Thr Val
    1010                1015                1020

Gln Arg Leu Leu Pro Val Leu Cys Gln Ala His Gly Leu Thr Pro
    1025                1030                1035

Glu Gln Val Val Ala Ile Ala Ser Asn Ile Gly Gly Lys Gln Ala
    1040                1045                1050

Leu Glu Thr Val Gln Ala Leu Leu Pro Val Leu Cys Gln Ala His
    1055                1060                1065

Gly Leu Thr Pro Gln Gln Val Val Ala Ile Ala Ser His Asp Gly
    1070                1075                1080

Gly Arg Pro Ala Leu Glu Ser Ile Val Ala Gln Leu Ser Arg Pro
    1085                1090                1095

Asp Pro Ala Leu Ala Ala Leu Thr Asn Asp His Leu Val Ala Leu
    1100                1105                1110

Ala Cys Leu Gly Gly Arg Pro Ala Leu Asp Ala Val Lys Lys Gly
    1115                1120                1125

Leu Pro His Ala Pro Ala Leu Ile Lys Arg Thr Asn Arg Arg Ile
    1130                1135                1140

Pro Glu Arg Thr Ser His Arg Val Ala Asp His Ala Gln Val Val
    1145                1150                1155

Arg Val Leu Gly Phe Phe Gln Cys His Ser His Pro Ala Gln Ala
    1160                1165                1170

Phe Asp Asp Ala Met Thr Gln Phe Gly Met Ser Arg His Gly Leu
    1175                1180                1185

Leu Gln Leu Phe Arg Arg Val Gly Val Thr Glu Leu Glu Ala Arg
    1190                1195                1200

Ser Gly Thr Leu Pro Pro Ala Ser Gln Arg Trp Asp Arg Ile Leu
    1205                1210                1215

Gln Ala Ser Gly Met Lys Arg Ala Lys Pro Ser Pro Thr Ser Thr
    1220                1225                1230

Gln Thr Pro Asp Gln Ala Ser Leu His Ala Phe Ala Asp Ser Leu
    1235                1240                1245

Glu Arg Asp Leu Asp Ala Pro Ser Pro Met His Glu Gly Asp Gln
    1250                1255                1260

Thr Arg Ala Ser Ser Arg Lys Arg Ser Arg Ser Asp Arg Ala Val
    1265                1270                1275

Thr Gly Pro Ser Ala Gln Gln Ser Phe Glu Val Arg Val Pro Glu
    1280                1285                1290

Gln Arg Asp Ala Leu His Leu Pro Leu Ser Trp Arg Val Lys Arg
    1295                1300                1305

Pro Arg Thr Ser Ile Gly Gly Gly Leu Pro Asp Pro
    1310                1315                1320
```

<210> SEQ ID NO 263
<211> LENGTH: 949
<212> TYPE: PRT
<213> ORGANISM: artificial sequence
<220> FEATURE:
<223> OTHER INFORMATION: TALE scaffold:bT2-Pth

<400> SEQUENCE: 263

```
Val Asp Leu Arg Thr Leu Gly Tyr Ser Gln Gln Gln Gln Glu Lys Ile
1               5                   10                  15

Lys Pro Lys Val Arg Ser Thr Val Ala Gln His His Glu Ala Leu Val
            20                  25                  30

Gly His Gly Phe Thr His Ala His Ile Val Ala Leu Ser Gln His Pro
        35                  40                  45

Ala Ala Leu Gly Thr Val Ala Val Lys Tyr Gln Asp Met Ile Ala Ala
    50                  55                  60

Leu Pro Glu Ala Thr His Glu Ala Ile Val Gly Val Gly Lys Gln Trp
65                  70                  75                  80

Ser Gly Ala Arg Ala Leu Glu Ala Leu Leu Thr Val Ala Gly Glu Leu
                85                  90                  95

Arg Gly Pro Pro Leu Gln Leu Asp Thr Gly Gln Leu Leu Lys Ile Ala
            100                 105                 110

Lys Arg Gly Gly Val Thr Ala Val Glu Ala Val His Ala Trp Arg Asn
        115                 120                 125

Ala Leu Thr Gly Ala Pro Leu Asn Leu Thr Pro Glu Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Gln Gln Val Val Ala Ile Ala Ser Asn Gly Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
```

```
              370                 375                 380
Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
                420                 425                 430

Leu Leu Pro Val Leu Cys Gln Ala His Gly Leu Thr Pro Glu Gln Val
            435                 440                 445

Val Ala Ile Ala Ser His Asp Gly Gly Lys Gln Ala Leu Glu Thr Val
        450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
                500                 505                 510

Pro Gln Gln Val Val Ala Ile Ala Ser Asn Gly Gly Lys Gln Ala
            515                 520                 525

Leu Glu Thr Val Gln Arg Leu Leu Pro Val Leu Cys Gln Ala His Gly
            530                 535                 540

Leu Thr Pro Glu Gln Val Val Ala Ile Ala Ser Asn Ile Gly Gly Lys
545                 550                 555                 560

Gln Ala Leu Glu Thr Val Gln Ala Leu Leu Pro Val Leu Cys Gln Ala
                565                 570                 575

His Gly Leu Thr Pro Glu Gln Val Val Ala Ile Ala Ser His Asp Gly
            580                 585                 590

Gly Lys Gln Ala Leu Glu Thr Val Gln Arg Leu Leu Pro Val Leu Cys
        595                 600                 605

Gln Ala His Gly Leu Thr Pro Gln Gln Val Val Ala Ile Ala Ser Asn
        610                 615                 620

Gly Gly Lys Gln Ala Leu Glu Thr Val Gln Arg Leu Leu Pro Val
625                 630                 635                 640

Leu Cys Gln Ala His Gly Leu Thr Pro Glu Gln Val Val Ala Ile Ala
                645                 650                 655

Ser Asn Asn Gly Gly Lys Gln Ala Leu Glu Thr Val Gln Arg Leu Leu
            660                 665                 670

Pro Val Leu Cys Gln Ala His Gly Leu Thr Pro Gln Gln Val Val Ala
            675                 680                 685

Ile Ala Ser Asn Gly Gly Lys Gln Ala Leu Glu Thr Val Gln Arg
        690                 695                 700

Leu Leu Pro Val Leu Cys Gln Ala His Gly Leu Thr Pro Glu Gln Val
705                 710                 715                 720

Val Ala Ile Ala Ser Asn Ile Gly Gly Lys Gln Ala Leu Glu Thr Val
                725                 730                 735

Gln Ala Leu Leu Pro Val Leu Cys Gln Ala His Gly Leu Thr Pro Glu
                740                 745                 750

Gln Val Val Ala Ile Ala Ser His Asp Gly Gly Lys Gln Ala Leu Glu
            755                 760                 765

Thr Val Gln Arg Leu Leu Pro Val Leu Cys Gln Ala His Gly Leu Thr
        770                 775                 780

Pro Glu Gln Val Val Ala Ile Ala Ser Asn Ile Gly Gly Lys Gln Ala
785                 790                 795                 800
```

```
Leu Glu Thr Val Gln Ala Leu Leu Pro Val Leu Cys Gln Ala His Gly
                805                 810                 815

Leu Thr Pro Glu Gln Val Val Ala Ile Ala Ser His Asp Gly Gly Lys
            820                 825                 830

Gln Ala Leu Glu Thr Val Gln Arg Leu Leu Pro Val Leu Cys Gln Ala
        835                 840                 845

His Gly Leu Thr Pro Glu Gln Val Val Ala Ile Ala Ser His Asp Gly
    850                 855                 860

Gly Lys Gln Ala Leu Glu Thr Val Gln Arg Leu Leu Pro Val Leu Cys
865                 870                 875                 880

Gln Ala His Gly Leu Thr Pro Glu Gln Val Val Ala Ile Ala Ser Asn
                885                 890                 895

Ile Gly Gly Lys Gln Ala Leu Glu Thr Val Gln Ala Leu Leu Pro Val
            900                 905                 910

Leu Cys Gln Ala His Gly Leu Thr Pro Gln Gln Val Val Ala Ile Ala
        915                 920                 925

Ser His Asp Gly Gly Arg Pro Ala Leu Glu Ser Ile Val Ala Gln Leu
    930                 935                 940

Ser Arg Pro Asp Pro
945

<210> SEQ ID NO 264
<211> LENGTH: 771
<212> TYPE: PRT
<213> ORGANISM: Burkholderia rhizoxinica
<220> FEATURE:
<221> NAME/KEY: MISC_FEATURE
<223> OTHER INFORMATION: MBBBD scaffold: E5AV36_BURRH

<400> SEQUENCE: 264

Met Ser Thr Ala Phe Val Asp Gln Asp Lys Gln Met Ala Asn Arg Leu
1               5                   10                  15

Asn Leu Ser Pro Leu Glu Arg Ser Lys Ile Glu Lys Gln Tyr Gly Gly
            20                  25                  30

Ala Thr Thr Leu Ala Phe Ile Ser Asn Lys Gln Asn Glu Leu Ala Gln
        35                  40                  45

Ile Leu Ser Arg Ala Asp Ile Leu Lys Ile Ala Ser Tyr Asp Cys Ala
    50                  55                  60

Ala His Ala Leu Gln Ala Val Leu Asp Cys Gly Pro Met Leu Gly Lys
65                  70                  75                  80

Arg Gly Phe Ser Gln Ser Asp Ile Val Lys Ile Ala Gly Asn Ile Gly
                85                  90                  95

Gly Ala Gln Ala Leu Gln Ala Val Leu Asp Leu Glu Ser Met Leu Gly
            100                 105                 110

Lys Arg Gly Phe Ser Arg Asp Asp Ile Ala Lys Met Ala Gly Asn Ile
        115                 120                 125

Gly Gly Ala Gln Thr Leu Gln Ala Val Leu Asp Leu Glu Ser Ala Phe
    130                 135                 140

Arg Glu Arg Gly Phe Ser Gln Ala Asp Ile Val Lys Ile Ala Gly Asn
145                 150                 155                 160

Asn Gly Gly Ala Gln Ala Leu Tyr Ser Val Leu Asp Val Glu Pro Thr
                165                 170                 175

Leu Gly Lys Arg Gly Phe Ser Arg Ala Asp Ile Val Lys Ile Ala Gly
            180                 185                 190

Asn Thr Gly Gly Ala Gln Ala Leu His Thr Val Leu Asp Leu Glu Pro
```

-continued

```
            195                 200                 205
Ala Leu Gly Lys Arg Gly Phe Ser Arg Ile Asp Ile Val Lys Ile Ala
        210                 215                 220
Ala Asn Asn Gly Gly Ala Gln Ala Leu His Ala Val Leu Asp Leu Gly
225                 230                 235                 240
Pro Thr Leu Arg Glu Cys Gly Phe Ser Gln Ala Thr Ile Ala Lys Ile
                245                 250                 255
Ala Gly Asn Ile Gly Gly Ala Gln Ala Leu Gln Met Val Leu Asp Leu
            260                 265                 270
Gly Pro Ala Leu Gly Lys Arg Gly Phe Ser Gln Ala Thr Ile Ala Lys
        275                 280                 285
Ile Ala Gly Asn Ile Gly Gly Ala Gln Ala Leu Gln Thr Val Leu Asp
        290                 295                 300
Leu Glu Pro Ala Leu Cys Glu Arg Gly Phe Ser Gln Ala Thr Ile Ala
305                 310                 315                 320
Lys Met Ala Gly Asn Asn Gly Gly Ala Gln Ala Leu Gln Thr Val Leu
                325                 330                 335
Asp Leu Glu Pro Ala Leu Arg Lys Arg Asp Phe Arg Gln Ala Asp Ile
            340                 345                 350
Ile Lys Ile Ala Gly Asn Asp Gly Gly Ala Gln Ala Leu Gln Ala Val
        355                 360                 365
Ile Glu His Gly Pro Thr Leu Arg Gln His Gly Phe Asn Leu Ala Asp
        370                 375                 380
Ile Val Lys Met Ala Gly Asn Ile Gly Gly Ala Gln Ala Leu Gln Ala
385                 390                 395                 400
Val Leu Asp Leu Lys Pro Val Leu Asp Glu His Gly Phe Ser Gln Pro
                405                 410                 415
Asp Ile Val Lys Met Ala Gly Asn Ile Gly Gly Ala Gln Ala Leu Gln
            420                 425                 430
Ala Val Leu Ser Leu Gly Pro Ala Leu Arg Glu Arg Gly Phe Ser Gln
        435                 440                 445
Pro Asp Ile Val Lys Ile Ala Gly Asn Thr Gly Gly Ala Gln Ala Leu
        450                 455                 460
Gln Ala Val Leu Asp Leu Glu Leu Thr Leu Val Glu His Gly Phe Ser
465                 470                 475                 480
Gln Pro Asp Ile Val Arg Ile Thr Gly Asn Arg Gly Gly Ala Gln Ala
                485                 490                 495
Leu Gln Ala Val Leu Ala Leu Glu Leu Thr Leu Arg Glu Arg Gly Phe
            500                 505                 510
Ser Gln Pro Asp Ile Val Lys Ile Ala Gly Asn Ser Gly Gly Ala Gln
        515                 520                 525
Ala Leu Gln Ala Val Leu Asp Leu Glu Leu Thr Phe Arg Glu Arg Gly
        530                 535                 540
Phe Ser Gln Ala Asp Ile Val Lys Ile Ala Gly Asn Asp Gly Gly Thr
545                 550                 555                 560
Gln Ala Leu His Ala Val Leu Asp Leu Glu Arg Met Leu Gly Glu Arg
                565                 570                 575
Gly Phe Ser Arg Ala Asp Ile Val Asn Val Ala Gly Asn Asn Gly Gly
            580                 585                 590
Ala Gln Ala Leu Lys Ala Val Leu Glu His Glu Ala Thr Leu Asn Glu
        595                 600                 605
Arg Gly Phe Ser Arg Ala Asp Ile Val Lys Ile Ala Gly Asn Gly Gly
        610                 615                 620
```

Gly Ala Gln Ala Leu Lys Ala Val Leu Glu His Gly Ala Thr Leu Asp
625                 630                 635                 640

Glu Arg Gly Phe Ser Arg Ala Asp Ile Val Arg Ile Ala Gly Asn Gly
            645                 650                 655

Gly Gly Ala Gln Ala Leu Lys Ala Val Leu Glu His Gly Pro Thr Leu
            660                 665                 670

Asn Glu Arg Gly Phe Asn Leu Thr Asp Ile Val Glu Met Ala Ala Asn
            675                 680                 685

Ser Gly Gly Ala Gln Ala Leu Lys Ala Val Leu Glu His Gly Pro Thr
690                 695                 700

Leu Arg Gln Arg Gly Leu Ser Leu Ile Asp Ile Val Glu Ile Ala Ser
705                 710                 715                 720

Asn Gly Gly Ala Gln Ala Leu Lys Ala Val Leu Lys Tyr Gly Pro Val
            725                 730                 735

Leu Met Gln Ala Gly Arg Ser Asn Glu Glu Ile Val His Val Ala Ala
            740                 745                 750

Arg Arg Gly Gly Ala Gly Arg Ile Arg Lys Met Val Ala Pro Leu Leu
            755                 760                 765

Glu Arg Gln
    770

<210> SEQ ID NO 265
<211> LENGTH: 310
<212> TYPE: PRT
<213> ORGANISM: Burkholderia rhizoxinica
<220> FEATURE:
<221> NAME/KEY: MISC_FEATURE
<223> OTHER INFORMATION: MBBBD scaffold: E5AW43_BURRH

<400> SEQUENCE: 265

Met Pro Val Thr Ser Val Tyr Gln Lys Asp Lys Pro Phe Gly Ala Arg
1               5                   10                  15

Leu Asn Leu Ser Pro Phe Glu Cys Leu Lys Ile Glu Lys His Ser Gly
            20                  25                  30

Gly Ala Asp Ala Leu Glu Phe Ile Ser Asn Lys Tyr Asp Ala Leu Thr
        35                  40                  45

Gln Val Leu Ser Arg Ala Asp Ile Leu Lys Ile Ala Cys His Asp Cys
50                  55                  60

Ala Ala His Ala Leu Gln Ala Val Leu Asp Tyr Glu Gln Val Phe Arg
65                  70                  75                  80

Gln Arg Gly Phe Ala Arg Ala Asp Ile Ile Lys Ile Thr Gly Asn Gly
            85                  90                  95

Gly Gly Ala Gln Ala Leu Lys Ala Val Val His Gly Pro Thr Leu
            100                 105                 110

Asn Glu Cys Gly Phe Ser Gln Ala Asp Ile Val Arg Ile Ala Asp Asn
            115                 120                 125

Ile Gly Ala Gln Ala Leu Lys Ala Val Leu Glu His Gly Pro Thr Leu
130                 135                 140

Asn Glu Arg Asp Tyr Ser Gly Ala Asp Ile Val Lys Ile Ala Gly Asn
145                 150                 155                 160

Gly Gly Gly Ala Arg Ala Leu Lys Ala Val Val Met His Gly Pro Thr
            165                 170                 175

Leu Cys Glu Ser Gly Tyr Ser Gly Ala Asp Ile Val Lys Ile Ala Ser
            180                 185                 190

Asn Gly Gly Gly Ala Gln Ala Leu Glu Ala Val Ala Met His Gly Ser

```
                    195                 200                 205
Thr Leu Cys Glu Arg Gly Tyr Cys Arg Thr Asp Ile Ala Lys Ile Ala
210                 215                 220

Gly Asn Gly Gly Gly Ala Gln Ala Leu Lys Ala Ile Val Met His Gly
225                 230                 235                 240

Pro Thr Leu Cys Glu Arg Gly Tyr Ser Arg Thr Asp Ile Val Lys Ile
                245                 250                 255

Ala Asp Asn Asn Gly Gly Ala Gln Ala Leu Lys Ala Val Phe Glu His
                260                 265                 270

Gly Pro Ala Leu Thr Gln Ala Gly Arg Ser Asn Glu Asp Ile Val Asn
                275                 280                 285

Met Ala Ala Arg Thr Gly Ala Ala Gly Gln Ile Arg Lys Met Ala Ala
                290                 295                 300

Gln Leu Ser Gly Arg Gln
305                 310

<210> SEQ ID NO 266
<211> LENGTH: 997
<212> TYPE: PRT
<213> ORGANISM: Burkholderia rhizoxinica
<220> FEATURE:
<221> NAME/KEY: MISC_FEATURE
<223> OTHER INFORMATION: MBBBD scaffold: E5AW45_BURRH

<400> SEQUENCE: 266

Met Pro Ala Thr Ser Met His Gln Glu Asp Lys Gln Ser Ala Asn Gly
1               5                   10                  15

Leu Asn Leu Ser Pro Leu Glu Arg Ile Lys Ile Glu Lys His Tyr Gly
                20                  25                  30

Gly Gly Ala Thr Leu Ala Phe Ile Ser Asn Gln His Asp Glu Leu Ala
            35                  40                  45

Gln Val Leu Ser Arg Ala Asp Ile Leu Lys Ile Ala Ser Tyr Asp Cys
        50                  55                  60

Ala Ala Gln Ala Leu Gln Ala Val Leu Asp Cys Gly Pro Met Leu Gly
65                  70                  75                  80

Lys Arg Gly Phe Ser Arg Ala Asp Ile Val Arg Ile Ala Gly Asn Gly
                85                  90                  95

Gly Gly Ala Gln Ala Leu Tyr Ser Val Leu Asp Val Glu Pro Thr Leu
            100                 105                 110

Gly Lys Arg Gly Phe Ser Gln Val Asp Val Lys Ile Ala Gly Gly
        115                 120                 125

Gly Ala Gln Ala Leu His Thr Val Leu Glu Ile Gly Pro Thr Leu Gly
    130                 135                 140

Glu Arg Gly Phe Ser Arg Gly Asp Ile Val Thr Ile Ala Gly Asn Asn
145                 150                 155                 160

Gly Gly Ala Gln Ala Leu Gln Ala Val Leu Glu Leu Glu Pro Thr Leu
                165                 170                 175

Arg Glu Arg Gly Phe Asn Gln Ala Asp Ile Val Lys Ile Ala Gly Asn
            180                 185                 190

Gly Gly Gly Ala Gln Ala Leu Gln Ala Val Leu Asp Val Glu Pro Ala
        195                 200                 205

Leu Gly Lys Arg Gly Phe Ser Arg Val Asp Ile Ala Lys Ile Ala Gly
    210                 215                 220

Gly Gly Ala Gln Ala Leu Gln Ala Val Leu Gly Leu Glu Pro Thr Leu
225                 230                 235                 240
```

```
Arg Lys Arg Gly Phe His Pro Thr Asp Ile Lys Ile Ala Gly Asn
            245                 250                 255
Asn Gly Gly Ala Gln Ala Leu Gln Ala Val Leu Asp Leu Glu Leu Met
        260                 265                 270
Leu Arg Glu Arg Gly Phe Ser Gln Ala Asp Ile Val Lys Met Ala Ser
    275                 280                 285
Asn Ile Gly Gly Ala Gln Ala Leu Gln Ala Val Leu Asn Leu Glu Pro
290                 295                 300
Ala Leu Cys Glu Arg Gly Phe Ser Gln Pro Asp Ile Val Lys Met Ala
305                 310                 315                 320
Gly Asn Ser Gly Gly Ala Gln Ala Leu Gln Ala Val Leu Asp Leu Glu
            325                 330                 335
Leu Ala Phe Arg Glu Arg Gly Phe Ser Gln Ala Asp Ile Val Lys Met
        340                 345                 350
Ala Ser Asn Ile Gly Gly Ala Gln Ala Leu Gln Ala Val Leu Glu Leu
    355                 360                 365
Glu Pro Ala Leu His Glu Arg Gly Phe Ser Gln Ala Asn Ile Val Lys
370                 375                 380
Met Ala Gly Asn Ser Gly Gly Ala Gln Ala Leu Gln Ala Val Leu Asp
385                 390                 395                 400
Leu Glu Leu Val Phe Arg Glu Arg Gly Phe Ser Gln Pro Glu Ile Val
            405                 410                 415
Glu Met Ala Gly Asn Ile Gly Gly Ala Gln Ala Leu His Thr Val Leu
        420                 425                 430
Asp Leu Glu Leu Ala Phe Arg Glu Arg Gly Val Arg Gln Ala Asp Ile
    435                 440                 445
Val Lys Ile Val Gly Asn Asn Gly Gly Ala Gln Ala Leu Gln Ala Val
450                 455                 460
Phe Glu Leu Glu Pro Thr Leu Arg Glu Arg Gly Phe Asn Gln Ala Thr
465                 470                 475                 480
Ile Val Lys Ile Ala Ala Asn Gly Gly Ala Gln Ala Leu Tyr Ser
            485                 490                 495
Val Leu Asp Val Glu Pro Thr Leu Asp Lys Arg Gly Phe Ser Arg Val
        500                 505                 510
Asp Ile Val Lys Ile Ala Gly Gly Ala Gln Ala Leu His Thr Ala
    515                 520                 525
Phe Glu Leu Glu Pro Thr Leu Arg Lys Arg Gly Phe Asn Pro Thr Asp
530                 535                 540
Ile Val Lys Ile Ala Gly Asn Lys Gly Gly Ala Gln Ala Leu Gln Ala
545                 550                 555                 560
Val Leu Glu Leu Glu Pro Ala Leu Arg Glu Arg Gly Phe Asn Gln Ala
            565                 570                 575
Thr Ile Val Lys Met Ala Gly Asn Ala Gly Gly Ala Gln Ala Leu Tyr
        580                 585                 590
Ser Val Leu Asp Val Glu Pro Ala Leu Arg Glu Arg Gly Phe Ser Gln
    595                 600                 605
Pro Glu Ile Val Lys Ile Ala Gly Asn Ile Gly Gly Ala Gln Ala Leu
610                 615                 620
His Thr Val Leu Glu Leu Pro Thr Leu His Lys Arg Gly Phe Asn
625                 630                 635                 640
Pro Thr Asp Ile Val Lys Ile Ala Gly Asn Ser Gly Gly Ala Gln Ala
            645                 650                 655
Leu Gln Ala Val Leu Glu Leu Glu Pro Ala Phe Arg Glu Arg Gly Phe
```

```
                    660                 665                 670
Gly Gln Pro Asp Ile Val Lys Met Ala Ser Asn Ile Gly Gly Ala Gln
            675                 680                 685
Ala Leu Gln Ala Val Leu Glu Leu Glu Pro Ala Leu Arg Glu Arg Gly
            690                 695                 700
Phe Ser Gln Pro Asp Ile Val Glu Met Ala Gly Asn Ile Gly Gly Ala
705                 710                 715                 720
Gln Ala Leu Gln Ala Val Leu Glu Leu Glu Pro Ala Phe Arg Glu Arg
                725                 730                 735
Gly Phe Ser Gln Ser Asp Ile Val Lys Ile Ala Gly Asn Ile Gly Gly
            740                 745                 750
Ala Gln Ala Leu Gln Ala Val Leu Glu Leu Glu Pro Thr Leu Arg Glu
            755                 760                 765
Ser Asp Phe Arg Gln Ala Asp Ile Val Asn Ile Ala Gly Asn Asp Gly
            770                 775                 780
Ser Thr Gln Ala Leu Lys Ala Val Ile Glu His Gly Pro Arg Leu Arg
785                 790                 795                 800
Gln Arg Gly Phe Asn Arg Ala Ser Ile Val Lys Ile Ala Gly Asn Ser
                805                 810                 815
Gly Gly Ala Gln Ala Leu Gln Ala Val Leu Lys His Gly Pro Thr Leu
            820                 825                 830
Asp Glu Arg Gly Phe Asn Leu Thr Asn Ile Val Lys Ile Ala Gly Asn
            835                 840                 845
Gly Gly Gly Ala Gln Ala Leu Lys Ala Val Ile Glu His Gly Pro Thr
            850                 855                 860
Leu Gln Gln Arg Gly Phe Asn Leu Thr Asp Ile Val Glu Met Ala Gly
865                 870                 875                 880
Lys Gly Gly Gly Ala Gln Ala Leu Lys Ala Val Leu Glu His Gly Pro
                885                 890                 895
Thr Leu Arg Gln Arg Gly Phe Asn Leu Ile Asp Ile Val Glu Met Ala
            900                 905                 910
Ser Asn Thr Gly Gly Ala Gln Ala Leu Lys Thr Val Leu Glu His Gly
            915                 920                 925
Pro Thr Leu Arg Gln Arg Asp Leu Ser Leu Ile Asp Ile Val Glu Ile
            930                 935                 940
Ala Ser Asn Gly Gly Ala Gln Ala Leu Lys Ala Val Leu Lys Tyr Gly
945                 950                 955                 960
Pro Val Leu Met Gln Ala Gly Arg Ser Asn Glu Glu Ile Val His Val
                965                 970                 975
Ala Ala Arg Arg Gly Gly Ala Gly Arg Ile Arg Lys Met Val Ala Leu
            980                 985                 990
Leu Leu Glu Arg Gln
        995

<210> SEQ ID NO 267
<211> LENGTH: 63
<212> TYPE: PRT
<213> ORGANISM: Burkholderia rhizoxinica
<220> FEATURE:
<221> NAME/KEY: MISC_FEATURE
<223> OTHER INFORMATION: MBBBD scaffold: E5AW46_BURRH

<400> SEQUENCE: 267

Met Gln Ala Val Leu Asp Cys Gly Pro Met Leu Ser Lys Arg Gly Phe
1               5                   10                  15
```

Ser Gln Ala Asp Ile Val Lys Ile Ala Cys Asn Gly Gly Ala Gln Ala
         20                  25                  30

Leu Tyr Ser Val Leu Asp Val Glu Pro Thr Leu Arg Glu Arg Gly Phe
             35                  40                  45

Ser Arg Val Asp Ile Val Lys Ile Ala Gly Asn Asn Gly Gly Ala
 50                  55                  60

<210> SEQ ID NO 268
<211> LENGTH: 184
<212> TYPE: PRT
<213> ORGANISM: artificial sequence
<220> FEATURE:
<223> OTHER INFORMATION: TevD02

<400> SEQUENCE: 268

Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
         35                  40                  45

Ser Phe Asn Lys His Gly Asn Val Phe Glu Cys Ser Ile Leu Glu Glu
     50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ser Lys Asn Gly Arg Trp
    130                 135                 140

Asn Pro Glu Thr His Lys Phe Cys Lys Cys Gly Val Arg Ile Gln Thr
145                 150                 155                 160

Ser Ala Tyr Thr Cys Ser Lys Cys Arg Asn Arg Ser Gly Glu Asn Asn
                165                 170                 175

Ser Phe Phe Asn His Lys His Ser
            180

<210> SEQ ID NO 269
<211> LENGTH: 354
<212> TYPE: PRT
<213> ORGANISM: artificial sequence
<220> FEATURE:
<223> OTHER INFORMATION: TevCreD02

<400> SEQUENCE: 269

Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
         35                  40                  45

Ser Phe Asn Lys His Gly Asn Val Phe Glu Cys Ser Ile Leu Glu Glu
     50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
            85                  90                  95

Phe Gly Asp Thr Cys Ser Thr His Pro Leu Lys Glu Ile Ile Lys
    100                 105                 110

Lys Arg Ser Glu Thr Val Lys Ala Lys Met Leu Lys Leu Gly Pro Asp
            115                 120                 125

Gly Arg Lys Ala Leu Tyr Ser Lys Pro Gly Ser Lys Asn Gly Arg Trp
130                 135                 140

Asn Pro Glu Thr His Lys Phe Cys Lys Cys Gly Val Arg Ile Gln Thr
145                 150                 155                 160

Ser Ala Tyr Thr Cys Ser Lys Cys Arg Asn Arg Ser Gly Glu Asn Asn
                165                 170                 175

Ser Phe Phe Asn His Lys His Ser Gln Gly Pro Ser Gly Asn Thr Lys
                180                 185                 190

Tyr Asn Lys Glu Phe Leu Leu Tyr Leu Ala Gly Phe Val Asp Gly Asn
                195                 200                 205

Gly Ser Ile Ile Ala Gln Ile Lys Pro Asn Gln Ser Tyr Lys Phe Lys
    210                 215                 220

His Gln Leu Ser Leu Thr Phe Gln Val Thr Gln Lys Thr Gln Arg Arg
225                 230                 235                 240

Trp Phe Leu Asp Lys Leu Val Asp Glu Ile Gly Val Gly Tyr Val Arg
                245                 250                 255

Asp Arg Gly Ser Val Ser Asp Tyr Ile Leu Ser Glu Ile Lys Pro Leu
                260                 265                 270

His Asn Phe Leu Thr Gln Leu Gln Pro Phe Leu Lys Leu Lys Gln Lys
                275                 280                 285

Gln Ala Asn Leu Val Leu Lys Ile Ile Glu Gln Leu Pro Ser Ala Lys
    290                 295                 300

Glu Ser Pro Asp Lys Phe Leu Glu Val Cys Thr Trp Val Asp Gln Ile
305                 310                 315                 320

Ala Ala Leu Asn Asp Ser Lys Thr Arg Lys Thr Thr Ser Glu Thr Val
                325                 330                 335

Arg Ala Val Leu Asp Ser Leu Ser Glu Lys Lys Ser Ser Pro Ala
                340                 345                 350

Ala Asp

<210> SEQ ID NO 270
<211> LENGTH: 9363
<212> TYPE: DNA
<213> ORGANISM: artificial sequence
<220> FEATURE:
<223> OTHER INFORMATION: pCLS6615

<400> SEQUENCE: 270
ttccataggc tccgcccccc tgacgagcat cacaaaaatc gacgctcaag tcagaggtgg     60
cgaaacccga caggactata aagataccag gcgtttcccc ctggaagctc cctcgtgcgc    120
tctcctgttc cgaccctgcc gcttaccgga tacctgtccg cctttctccc ttcgggaagc    180
gtggcgcttt ctcatagctc acgctgtagg tatctcagtt cggtgtaggt cgttcgctcc    240
aagctgggct gtgtgcacga accccccgtt cagcccgacc gctgcgcctt atccggtaac    300
tatcgtcttg agtccaaccc ggtaagacac gacttatcgc cactggcagc agccactggt    360
aacaggatta gcagagcgag gtatgtaggc ggtgctacag agttcttgaa gtggtggcct    420
aactacggct acactagaag gacagtattt ggtatctgcg ctctgctgaa gccagttacc    480

```
ttcggaaaaa gagttggtag ctcttgatcc ggcaaacaaa ccaccgctgg tagcggtggt    540 tttttttgttt gcaagcagca gattacgcgc agaaaaaaag gatctcaaga agatcctttg    600
atcttttcta cggggtctga cgctcagtgg aacgaaaact cacgttaagg gattttggtc    660
atgagattat caaaaaggat cttcacctag atccttttaa attaaaaatg aagttttaaa    720
tcaatctaaa gtatatatga gtaaacttgg tctgacagtt accaatgctt aatcagtgag    780
gcacctatct cagcgatctg tctatttcgt tcatccatag ttgcctgact ccccgtcgtg    840
tagataacta cgatacggga gggcttacca tctggcccca gtgctgcaat gataccgcga    900
gacccacgct caccggctcc agatttatca gcaataaacc agccagccgg aagggccgag    960
cgcagaagtg gtcctgcaac tttatccgcc tccatccagt ctattaattg ttgccgggaa   1020
gctagagtaa gtagttcgcc agttaatagt ttgcgcaacg ttgttgccat tgctacaggc   1080
atcgtggtgt cacgctcgtc gtttggtatg gcttcattca gctccggttc ccaacgatca   1140
aggcgagtta catgatcccc catgttgtgc aaaaaagcgg ttagctcctt cggtcctccg   1200
atcgttgtca gaagtaagtt ggccgcagtg ttatcactca tggttatggc agcactgcat   1260
aattctctta ctgtcatgcc atccgtaaga tgcttttctg tgactggtga gtactcaacc   1320
aagtcattct gagaatagtg tatgcggcga ccgagttgct cttgcccggc gtcaatacgg   1380
gataataccg cgccacatag cagaacttta aaagtgctca tcattggaaa acgttcttcg   1440
gggcgaaaac tctcaaggat cttaccgctg ttgagatcca gttcgatgta acccactcgt   1500
gcacccaact gatcttcagc atcttttact ttcaccagcg tttctgggtg agcaaaaaca   1560
ggaaggcaaa atgccgcaaa aaagggaata agggcgacac ggaaatgttg aatactcata   1620
ctcttccttt ttcaatatta ttgaagcatt tatcagggtt attgtctcat gagcggatac   1680
atatttgaat gtatttagaa aaataaacaa ataggggttc cgcgcacatt tccccgaaaa   1740
gtgccacctg acgtccgatc aaaaatcatc gcttcgctga ttaattaccc cagaaataag   1800
gctaaaaaac taatcgcatt atcatcctat ggttgttaat ttgattcgtt catttgaagg   1860 tttgtgggggc caggttactg ccaattttttc ctcttcataa ccataaaagc tagtattgta   1920
gaatctttat tgttcggagc agtgcggcgc gaggcacatc tgcgtttcag gaacgcgacc   1980
ggtgaagacg aggacgcacg gaggagagtc ttccttcgga gggctgtcac ccgctcggcg   2040
gcttctaatc cgtacttcaa tatagcaatg agcagttaag cgtattactg aaagttccaa   2100
agagaaggtt ttttttaggct aatcgacctc gagcagatcc gccaggcgtg tatatagcgt   2160
ggatggccag gcaactttag tgctgacaca tacaggcata tatatatgtg tgcgacgaca   2220
catgatcata tggcatgcat gtgctctgta tgtatataaa actcttgttt tcttctttttc   2280 tctaaatatt ctttccttat acattaggtc ctttgtagca taaattacta tacttctata   2340
gacacgcaaa cacaaataca cagcggcctt gccaccatgg ccaagtctgg catctaccag   2400
attaagaaca ccctgaataa caaagtgtat gttggatctg ccaaggactt tgagaaagga   2460
tggaagaggc acttcaagga tctggaaaag ggttgccaca gctccatcaa gctccaaagg   2520
tctttcaaca acatggcaa tgtctttgag tgctccattt tggaagagat cccttatgaa   2580
aaggacctca ttatagagag ggaaaacttc tggatcaag agctgaactc aaaaatcaat   2640
ggatacaaca ttgcagatgc cacatttggt gacacctgtt ctactcaccc ccttaaggaa   2700
gagatcatta aaaagaggtc tgagactgtg aaggctaaga tgttgaaact ggggcctgat   2760
ggcagaaagg cactctactc taagccaggt agcaaaaatg gaaggtggaa ccctgagacc   2820
```

```
cacaagttct gcaaatgtgg ggtgagaata cagacatcag cctacacttg cagcaagtgt   2880
aggaacagat caggagagaa taactccttt ttcaaccaca agcattctca aggtccatct   2940
ggcaatacca aatataacaa agagttcctg ctgtacctgg ccggctttgt ggacggtaac   3000
ggtagcatca tcgctcagat taaaccaaac cagtcttata agtttaaaca tcagctaagc   3060
ttgacctttc aggtgactca aaagacccag cgccgttggt ttctggacaa actagtggat   3120
gaaattggcg ttggttacgt acgtgatcgc ggatccgttt ccgattacat tttaagcgaa   3180
atcaagccgc tgcacaactt cctgactcaa ctgcagccgt ttctgaaact gaaacagaaa   3240
caggcaaacc tggttctgaa aattatcgaa cagctgccgt ctgcaaaaga tccccggac   3300 aaattcctgg aagtttgtac ctgggtggat cagattgcag ctctgaacga ttctaagacg   3360
cgtaaaacca cttctgaaac cgttcgtgct gtgctggaca gcctgagcga agaagaaaa   3420 tcctccccgg cggccgactg ataactcgag cgatcctcta gacgagctcc tcgagcctgc   3480
agcagctgaa gctttggact tcttcgccag aggtttggtc aagtctccaa tcaaggttgt   3540
cggcttgtct accttgccag aaatttacga aagatggaa aagggtcaaa tcgttggtag   3600
atacgttgtt gacacttcta ataagcgaa tttcttatga tttatgattt ttattattaa   3660
ataagttata aaaaaataa gtgtatacaa atttaaagt gactcttagg ttttaaaacg   3720
aaaattctta ttcttgagta actctttcct gtaggtcagg ttgctttctc aggtatagca   3780
tgaggtcgct cttattgacc acctctac cggcatgcaa gcttggcgta atcatggtca   3840
tagctgtttc ctgtgtgaaa ttgttatccg ctcacaattc cacacaacat acgagccgga   3900
agcataaagt gtaaagcctg gggtgcctaa tgagtgagct aactcacatt aattgcgttg   3960
cgctcactgc ccgctttcca gtcgggaaac ctgtcgtgcc agcagatcta ttacattatg   4020
ggtggtatgt tggaataaaa atcaactatc atctactaac tagtatttac gttactagta   4080
tattatcata tacggtgtta aagatgacg caaatgatga gaaatagtca tctaaattag   4140
tggaagctga aacgcaagga ttgataatgt aataggatca atgaatatta acatataaaa   4200
tgatgataat aatatttata gaattgtgta gaattgcaga ttcccttta tggattccta   4260 aatcctcgag gagaacttct agtatatcta catacctaat attattgcct tattaaaaat   4320
ggaatcccaa caattacatc aaaatccaca ttctcttcaa aatcaattgt cctgtacttc   4380
cttgttcatg tgtgttcaaa aacgttatat ttataggata attatactct atttctcaac   4440
aagtaattgg ttgtttggcc gagcggtcta aggcgcctga ttcaagaaat atcttgaccg   4500
cagttaactg tgggaatact caggtatcgt aagatgcaag agttcgaatc tcttagcaac   4560
cattattttt ttcctcaaca taacgagaac acacaggggc gctatcgcac agaatcaaat   4620
tcgatgactg gaaattttt gttaatttca gaggtcgcct gacgcatata cctttttcaa   4680
ctgaaaaatt gggagaaaaa ggaaaggtga gagccgcgga accggctttt catatagaat   4740
agagaagcgt tcatgactaa atgcttgcat cacaatactt gaagttgaca atattattta   4800
aggacctatt gttttttcca ataggtggtt agcaatcgtc ttactttcta actttcttta   4860
ccttttacat ttcagcaata tatatatata tatttcaagg ataccatt ctaatgtctg   4920 cccctaagaa gatcgtcgtt ttgccaggtg accacgttgg tcaagaaatc acagccgaag   4980
ccattaaggt tcttaaagct atttctgatg ttcgttccaa tgtcaagttc gatttcgaaa   5040
atcatttaat tggtggtgct gctatcgatg ctacaggtgt cccacttcca gatgaggcgc   5100
tggaagcctc caagaaggtt gatgccgttt tgttaggtgc tgtgggtggt cctaaatggg   5160
gtaccggtag tgttagacct gaacaaggtt tactaaaaat ccgtaaagaa cttcaattgt   5220
```

```
acgccaactt aagaccatgt aactttgcat ccgactctct tttagactta tctccaatca    5280
agccacaatt tgctaaaggt actgacttcg ttgttgtcag agaattagtg ggaggtattt    5340
actttggtaa gagaaaggaa gacgatggtg atggtgtcgc ttgggatagt gaacaataca    5400
ccgttccaga agtgcaaaga atcacaagaa tggccgcttt catggcccta caacatgagc    5460
caccattgcc tatttggtcc ttggataaag ctaatgtttt ggcctcttca agattatgga    5520
gaaaaactgt ggaggaaacc atcaagaacg aattccctac attgaaggtt caacatcaat    5580
tgattgattc tgccgccatg atcctagtta agaacccaac ccacctaaat ggtattataa    5640
tcaccagcaa catgtttggt gatatcatct ccgatgaagc ctccgttatc ccaggttcct    5700
tgggtttgtt gccatctgcg tccttggcct ctttgccaga caagaacacc gcatttggtt    5760
tgtacgaacc atgccacggt tctgctccag atttgccaaa gaataaggtc aaccctatcg    5820
ccactatctt gtctgctgca atgatgttga aattgtcatt gaacttgcct gaagaaggta    5880
aggccattga agatgcagtt aaaaaggttt tggatgcagg tatcagaact ggtgatttag    5940
gtggttccaa cagtaccacg gaagtcggtg atgctgtcgc cgaagaagtt aagaaaatcc    6000
ttgcttaaaa agattctctt tttttatgat atttgtacat aaactttata aatgaaattc    6060
ataatagaaa cgacacgaaa ttacaaaatg gaatatgttc atagggtaga cgaaactata    6120
tacgcaatct acatacattt atcaagaagg agaaaaagga ggatgtaaag gaatacaggt    6180
aagcaaattg atactaatgg ctcaacgtga taaggaaaaa gaattgcact ttaacattaa    6240
tattgacaag gaggagggca ccacacaaaa agttaggtgt aacagaaaat catgaaacta    6300
tgattcctaa tttatatatt ggaggatttt ctctaaaaaa aaaaaaatac aacaaataaa    6360
aaacactcaa tgacctgacc atttgatgga gtttaagtca ataccttctt gaaccatttc    6420
ccataatggt gaaagttccc tcaagaattt tactctgtca gaaacggcct taacgacgta    6480
gtcgacctcc tcttcagtac taaatctacc aataccaaat ctgatggaag aatgggctaa    6540
tgcatcatcc ttacccagcg catgtaaaac ataagaaggt tctagggaag cagatgtaca    6600
ggctgaaccc gaggataatg cgatatccct tagtgccatc aataaagatt ctccttccac    6660
gtaggcgaaa gaaacgttaa cacaccctgg ataacgatga tctggagatc cgttcaacgt    6720
ggtatgttca gcggataata gacctttgac taatttatcg gatagtcttt tgatgtgagc    6780
ttggtcgttg tcaaattctt tcttcatcaa tctcgcagct tcaccaaatc ccgctaccaa    6840
tgggggggcc aaagtaccag atctgctgca ttaatgaatc ggccaacgcg cggggagagg    6900
cggtttgcgt attgggcgct cttccgcttc ctcgctcact gactcgctgc gctcggtcgt    6960
tcggctgcgg cgagcggtat cagcatcgat gaattccacg gactatagac tatactagta    7020
tactccgtct actgtacgat acacttccgc tcaggtcctt gtcctttaac gaggccttac    7080
cactcttttg ttactctatt gatccagctc agcaaaggca gtgtgatcta agattctatc    7140
ttcgcgatgt agtaaaacta gctagaccga gaaagagact agaaatgcaa aaggcacttc    7200
tacaatggct gccatcatta ttatccgatg tgacgctgca gcttctcaat gatattcgaa    7260
tacgctttga ggagatacag cctaatatcc gacaaactgt tttacagatt tacgatcgta    7320
cttgttaccc atcattgaat tttgaacatc cgaacctggg agttttccct gaaacagata    7380
gtatatttga acctgtataa taatatatag tctagcgctt tacggaagac aatgtatgta    7440
tttcggttcc tggagaaact attgcatcta ttgcataggt aatcttgcac gtcgcatccc    7500
cggttcattt tctgcgtttc catcttgcac ttcaatagca tatctttgtt aacgaagcat    7560
```

```
ctgtgcttca ttttgtagaa caaaaatgca acgcgagagc gctaatttt caaacaaaga    7620 atctgagctg cattttaca gaacagaaat gcaacgcgaa agcgctattt taccaacgaa     7680
gaatctgtgc ttcatttttg taaaacaaaa atgcaacgcg agagcgctaa tttttcaaac    7740
aaagaatctg agctgcattt ttacagaaca gaaatgcaac gcgagagcgc tatttacca    7800 acaaagaatc tatacttctt ttttgttcta caaaaatgca tcccgagagc gctattttc    7860 taacaaagca tcttagatta ctttttttct cctttgtgcg ctctataatg cagtctcttg    7920
ataacttttt gcactgtagg tccgttaagg ttagaagaag gctactttgg tgtctatttt    7980
ctcttccata aaaaagcct gactccactt cccgcgttta ctgattacta gcgaagctgc     8040
gggtgcattt tttcaagata aaggcatccc cgattatatt ctataccgat gtggattgcg    8100
catactttgt gaacagaaag tgatagcgtt gatgattctt cattggtcag aaaattatga    8160
acggtttctt ctattttgtc tctatatact acgtatagga aatgtttaca ttttcgtatt    8220
gttttcgatt cactctatga atagttctta ctacaatttt tttgtctaaa gagtaatact    8280
agagataaac ataaaaatg tagaggtcga gtttagatgc aagttcaagg agcgaaaggt     8340
ggatgggtag ttatataggg gatatagcac agagatatat agcaaagaga tacttttgag   8400
caatgtttgt ggaagcggta ttcgcaatat tttagtagct cgttacagtc cggtgcgttt   8460 ttggttttt gaaagtgcgt cttcagagcg cttttggttt tcaaaagcgc tctgaagttc    8520
ctatactttc tagagaatag gaacttcgga ataggaactt caaagcgttt ccgaaaacga    8580
gcgcttccga aaatgcaacg cgagctgcgc acatacagct cactgttcac gtcgcaccta   8640
tatctgcgtg ttgcctgtat atatatac atgagaagaa cggcatagtg cgtgttatg      8700 cttaaatgcg tactatatg cgtctattta tgtaggatga aaggtagtct agtacctcct    8760
gtgatattat cccattccat gcggggtatc gtatgcttcc ttcagcacta ccctttagct   8820
gttctatatg ctgccactcc tcaattggat tagtctcatc cttcaatgct atcatttcct   8880
ttgatattgg atcatatgca tagtaccgag aaactagtgc gaagtagtga tcaggtattg   8940
ctgttatctg atgagtatac gttgtcctgg ccacggcaga agcacgctta tcgctccaat   9000
ttcccacaac attagtcaac tccgttaggc ccttcattga aagaaatgag gtcatcaaat   9060
gtcttccaat gtgagatttt gggccatttt ttatagcaaa gattgaataa ggcgcatttt   9120
tcttcaaagc tttattgtac gatctgacta agttatcttt taataattgg tattcctgtt  9180
tattgcttga agaattgccg gtcctatta ctcgttttag gactggttca gaattcatcg    9240
atgctcactc aaaggtcggt aatacggtta tccacagaat cagggataa cgcaggaaag    9300 aacatgtgag caaaaggcca gcaaaaggcc aggaaccgta aaaaggccgc gttgctggcg   9360
ttt                                                                 9363
```

<210> SEQ ID NO 271
<211> LENGTH: 39
<212> TYPE: DNA
<213> ORGANISM: artificial sequence
<220> FEATURE:
<223> OTHER INFORMATION: Primer CMP_G001

<400> SEQUENCE: 271
acacgcaaac acaaatacac agcggccttg ccaccatgg                          39

<210> SEQ ID NO 272
<211> LENGTH: 37
<212> TYPE: DNA
<213> ORGANISM: artificial sequence
<220> FEATURE:
<223> OTHER INFORMATION: Primer CMP_G068

<400> SEQUENCE: 272
ggtatttccg gatggacctt gagaatgctt gtggttg                              37

<210> SEQ ID NO 273
<211> LENGTH: 3509
<212> TYPE: DNA
<213> ORGANISM: artificial sequence
<220> FEATURE:
<223> OTHER INFORMATION: pCLS9008

<400> SEQUENCE: 273

```
ggtctttcct gcgttatccc ctgattctgt ggataaccgt attaccgcct ttgagtgagc      60
tgataccgct cgccgcagcc gaacgaccga gcgcagcgag tcagtgagcg aggaagcgga     120
gagcgcccaa tacgcaaacc gcctctcccc gcgcgttggc cgattcatta atgcagctgg    180
cacgacaggt ttcccgactg gaaagcgggc agtgagcgca acgcaattaa tgtgagttag    240
ctcactcatt aggcacccca ggctttacac tttatgcttc cggctcgtat gttgtgtgga    300
attgtgagcg gataacaatt tcacacagga aacagctatg accatgatta cgccaagcgc    360
gtcaattaac cctcactaaa gggaacaaaa gctgttaatt aagcgcgcca cacgcaaaca    420
caaatacaca gcggccttgc caccatggca aacaccggtg gatcctccgg agtggatcta    480
cgcacgctcg gctacagcca gcagcaacag gagaagatca aaccgaaggt tcgttcgaca    540
gtggcgcagc accacgaggc actggtcggc cacgggttta cacgcgcgca catcgttgcg    600
ttaagccaac acccggcagc gttagggacc gtcgctgtca agtatcagga catgatcgca    660
gcgttgccag aggcgacaca cgaagcgatc gttggcgtcg gcaaacagtg gtccggcgca    720
cgcgctctgg aggccttgct cacggtggcg ggagagttga gaggtccacc gttacagttg    780
gacacaggcc aacttctcaa gattgcaaaa cgtggcggcg tgaccgcagt ggaggcagtg    840
catgcatggc gcaatgcact gacgggtgcc ccgctcaact tgaccggaga cgcccggggg    900
atcaggtcac gtgcgtctcg gagcattgtt gcccagttat ctcgccctga tccgtcggcc    960
gactgataag tcgaccacca ccaccaccac cactgataag agctcctcga gcctgcagca   1020
gctgaagctt tggacttctg gcgcgcccaa ttcgccctat agtgagtcgt attacgtcgc   1080
gctcactggc cgtcgtttta caacgtcgtg actgggaaaa ccctggcgtt acccaactta   1140
atcgccttgc agcacatccc cctttcgcca gctggcgtaa tagcgaagag gcccgcaccg   1200
aaacgccctt cccaacagtt gcgcagcctg aatggcgaat gggagcgccc tgtagcggcg   1260
cattaagcgc ggcgggtgtg gtggttacgc gcagcgtgac cgctacactt gccagcgccc   1320
tagcgcccgc tcctttcgct ttcttccctt cctttctcgc cacgttcgcc ggctttcccc   1380
gtcaagctct aaatcggggg ctcccttag ggttccgatt tagtgcttta cggcacctcg    1440
accccaaaaa acttgattag ggtgatggtt ggcctgtagt gggccatagc cctgatagac   1500 ggttttcgc cctttgacgt tggagtccac gttctttaat agtggactct gttccaaac     1560 tggaacaaca ctcaacccta tctcggtcta ttcttttgat ttataaggga ttttgccgat   1620
ttcggcctat tggttaaaaa atgagctgat ttaacaaaaa tttaacgcga attttaacaa   1680
aatattaacg cttacaattt aggtggcact tttcggggaa atgtgcgcgg aacccctatt   1740
tgtttatttt tctaaataca ttcaaatatg tatccgctca tgagacaata accctgataa   1800
atgcttcaat aatattgaaa aaggaagagt atgagtattc aacatttccg tgtcgccctt   1860
```

-continued

| | |
|---|---|
| attccctttt ttgcggcatt ttgccttcct gtttttgctc acccagaaac gctggtgaaa | 1920 |
| gtaaaagatg ctgaagatca gttgggtgca cgagtgggtt acatcgaact ggatctcaac | 1980 |
| agcggtaaga tccttgagag ttttcgcccc gaagaacgtt ttccaatgat gagcactttt | 2040 |
| aaagttctgc tatgtggcgc ggtattatcc cgtattgacg ccgggcaaga gcaactcggt | 2100 |
| cgccgcatac actattctca gaatgacttg gttgagtact caccagtcac agaaaagcat | 2160 |
| cttacggatg gcatgacagt aagagaatta tgcagtgctg ccataaccat gagtgataac | 2220 |
| actgcggcca acttacttct gacaacgatc ggaggaccga aggagctaac cgcttttttg | 2280 |
| cacaacatgg gggatcatgt aactcgcctt gatcgttggg aaccggagct gaatgaagcc | 2340 |
| ataccaaacg acgagcgtga caccacgatg cctgtagcaa tggcaacaac gttgcgcaaa | 2400 |
| ctattaactg gcgaactact tactctagct tcccggcaac aattaataga ctggatggag | 2460 |
| gcggataaag ttgcaggacc acttctgcgc tcggcccttc cggctggctg gtttattgct | 2520 |
| gataaatctg gagccggtga gcgtggttct cgcggtatca ttgcagcact ggggccagat | 2580 |
| ggtaagccct cccgtatcgt agttatctac acgacgggga gtcaggcaac tatggatgaa | 2640 |
| cgaaatagac agatcgctga gataggtgcc tcactgatta agcattggta actgtcagac | 2700 |
| caagtttact catatatact ttagattgat ttaaaacttc atttttaatt taaaaggatc | 2760 |
| taggtgaaga tcctttttga atctctcatg accaaaatcc cttaacgtga gttttcgttc | 2820 |
| cactgagcgt cagaccccgt agaaaagatc aaaggatctt cttgagatcc ttttttttctg | 2880 |
| cgcgtaatct gctgcttgca acaaaaaaa ccaccgctac cagcggtggt ttgtttgccg | 2940 |
| gatcaagagc taccaactct ttttccgaag gtaactggct tcagcagagc gcagatacca | 3000 |
| aatactgttc ttctagtgta gccgtagtta ggccaccact tcaagaactc tgtagcaccg | 3060 |
| cctacatacc tcgctctgct aatcctgtta ccagtggctg ctgccagtgg cgataagtcg | 3120 |
| tgtcttaccg ggttggactc aagacgatag ttaccggata aggcgcagcg gtcgggctga | 3180 |
| acggggggtt cgtgcacaca gcccagcttg gagcgaacga cctacaccga actgagatac | 3240 |
| ctacagcgtg agctatgaga aagcgccacg cttcccgaag ggagaaaggc ggacaggtat | 3300 |
| ccggtaagcg gcagggtcgg aacaggagag cgcacgaggg agcttccagg gggaaacgcc | 3360 |
| tggtatcttt atagtcctgt cgggtttcgc cacctctgac ttgagcgtcg attttttgtga | 3420 |
| tgctcgtcag gggggcggag cctatggaaa aacgccagca acgcggcctt tttacggttc | 3480 |
| ctggccttttt gctggccttt tgctcacat | 3509 |

<210> SEQ ID NO 274
<211> LENGTH: 4049
<212> TYPE: DNA
<213> ORGANISM: artificial sequence
<220> FEATURE:
<223> OTHER INFORMATION: pCLS12730

<400> SEQUENCE: 274

| | |
|---|---|
| ggtctttcct gcgttatccc ctgattctgt ggataaccgt attaccgcct ttgagtgagc | 60 |
| tgataccgct cgccgcagcc gaacgaccga gcgcagcgag tcagtgagcg aggaagcgga | 120 |
| gagcgcccaa tacgcaaacc gcctctcccc gcgcgttggc cgattcatta atgcagctgg | 180 |
| cacgacaggt ttcccgactg gaaagcgggc agtgagcgca acgcaattaa tgtgagttag | 240 |
| ctcactcatt aggcacccca ggctttacac tttatgcttc cggctcgtat gttgtgtgga | 300 |
| attgtgagcg ataacaatt tcacacagga aacagctatg accatgatta cgccaagcgc | 360 |
| gtcaattaac cctcactaaa gggaacaaaa gctgttaatt aagcgcgcca cacgcaaaca | 420 |

```
caaatacaca gcggccttgc caccatggcc aagtctggca tctaccagat taagaacacc      480
ctgaataaca aagtgtatgt tggatctgcc aaggactttg agaaaagatg aagaggcac      540 ttcaaggatc tggaaaaggg ttgccacagc tccatcaagc tccaaaggtc tttcaacaaa      600
catggcaatg tctttgagtg ctccattttg gaagagatcc cttatgaaaa ggacctcatt      660
atagagaggg aaaacttctg gatcaaggag ctgaactcaa aaatcaatgg atacaacatt      720
gcagatgcca catttggtga cacctgttct actcaccccc ttaaggaaga gatcattaaa      780
aagaggtctg agactgtgaa ggctaagatg ttgaaactgg ggcctgatgg cagaaaggca      840
ctctactcta agccaggtag caaaaatgga aggtggaacc ctgagaccca caagttctgc      900
aaatgtgggg tgagaataca gacatcagcc tacacttgca gcaagtgtag aacagatca      960 ggagagaata actcctttt caaccacaag cattctcaag gtccatccgg agtggatcta     1020
cgcacgctcg gctacagcca gcagcaacag gagaagatca aaccgaaggt tcgttcgaca     1080
gtggcgcagc accacgaggc actggtcggc cacgggttta cacacgcgca catcgttgcg     1140
ttaagccaac acccggcagc gttagggacc gtcgctgtca agtatcagga catgatcgca     1200
gcgttgccag aggcgacaca cgaagcgatc gttggcgtcg gcaaacagtg gtccggcgca     1260
cgcgctctgg aggccttgct cacggtggcg ggagagttga gaggtccacc gttacagttg     1320
gacacaggcc aacttctcaa gattgcaaaa cgtggcggcg tgaccgcagt ggaggcagtg     1380
catgcatggc gcaatgcact gacgggtgcc ccgctcaact tgaccggaga cgcccggggg     1440
atcaggtcac gtgcgtctcg gagcattgtt gcccagttat ctcgccctga tccgtcggcc     1500
gactgataag tcgaccacca ccaccaccac cactgataag agctcctcga gcctgcagca     1560
gctgaagctt tggacttctg gcgcgcccaa ttcgccctat agtgagtcgt attacgtcgc     1620
gctcactggc cgtcgtttta caacgtcgtg actgggaaaa ccctggcgtt acccaactta     1680
atcgccttgc agcacatccc cctttcgcca gctggcgtaa tagcgaagag gcccgcaccg     1740
aaacgccctt cccaacagtt gcgcagcctg aatggcgaat gggagcgccc tgtagcggcg     1800
cattaagcgc ggcgggtgtg gtggttacgc gcagcgtgac cgctacactt gccagcgccc     1860
tagcgcccgc tcctttcgct ttcttccctt cctttctcgc cacgttcgcc ggctttcccc     1920
gtcaagctct aaatcggggg ctccctttag ggttccgatt tagtgcttta cggcacctcg     1980
accccaaaaa acttgattag ggtgatggtt ggcctgtagt gggccatagc cctgatagac     2040 ggttttttcgc cctttgacgt tggagtccac gttctttaat agtggactct tgttccaaac     2100
tggaacaaca ctcaacccta tctcggtcta ttcttttgat ttataaggga ttttgccgat     2160
ttcggcctat tggttaaaaa atgagctgat ttaacaaaaa tttaacgcga attttaacaa     2220
aatattaacg cttacaattt aggtggcact tttcggggaa atgtgcgcgg aaccctatt     2280 tgtttatttt tctaaataca ttcaaatatg tatccgctca tgagacaata accctgataa     2340
atgcttcaat aatattgaaa aaggaagagt atgagtattc aacatttccg tgtcgccctt     2400
attccctttt ttgcggcatt ttgccttcct gttttttgctc acccagaaac gctggtgaaa     2460
gtaaaagatg ctgaagatca gttgggtgca cgagtgggtt acatcgaact ggatctcaac     2520
agcggtaaga tccttgagag ttttcgcccc gaagaacgtt ttccaatgat gagcactttt     2580
aaagttctgc tatgtggcgc ggtattatcc cgtattgacg ccgggcaaga gcaactcggt     2640
cgccgcatac actattctca gaatgacttg gttgagtact caccagtcac agaaaagcat     2700
cttacggatg gcatgacagt aagagaatta tgcagtgctg ccataaccat gagtgataac     2760
```

```
actgcggcca acttacttct gacaacgatc ggaggaccga aggagctaac cgcttttttg    2820
cacaacatgg gggatcatgt aactcgcctt gatcgttggg aaccggagct gaatgaagcc    2880
ataccaaacg acgagcgtga caccacgatg cctgtagcaa tggcaacaac gttgcgcaaa    2940
ctattaactg gcgaactact tactctagct tcccggcaac aattaataga ctggatggag    3000
gcggataaag ttgcaggacc acttctgcgc tcggcccttc cggctggctg gtttattgct    3060
gataaatctg gagccggtga gcgtggttct cgcggtatca ttgcagcact ggggccagat    3120
ggtaagccct cccgtatcgt agttatctac acgacgggga gtcaggcaac tatggatgaa    3180
cgaaatagac agatcgctga gataggtgcc tcactgatta gcattggta actgtcagac    3240
caagtttact catatatact ttagattgat ttaaaacttc atttttaatt taaaaggatc    3300
taggtgaaga tccttttga taatctcatg accaaaatcc cttaacgtga gttttcgttc    3360
cactgagcgt cagaccccgt agaaaagatc aaaggatctt cttgagatcc ttttttttctg    3420
cgcgtaatct gctgcttgca acaaaaaaa ccaccgctac cagcggtggt ttgtttgccg    3480
gatcaagagc taccaactct ttttccgaag gtaactggct tcagcagagc gcagatacca    3540
aatactgttc ttctagtgta gccgtagtta ggccaccact tcaagaactc tgtagcaccg    3600
cctacatacc tcgctctgct aatcctgtta ccagtgctg ctgccagtgg cgataagtcg    3660
tgtcttaccg ggttggactc aagacgatag ttaccggata aggcgcagcg gtcgggctga    3720
acggggggtt cgtgcacaca gcccagcttg gagcgaacga cctacaccga actgagatac    3780
ctacagcgtg agctatgaga aagcgccacg cttcccgaag ggagaaaggc ggacaggtat    3840
ccggtaagcg gcagggtcgg aacaggagag cgcacgaggg agcttccagg gggaaacgcc    3900
tggtatcttt atagtcctgt cgggtttcgc cacctctgac ttgagcgtcg atttttgtga    3960
tgctcgtcag gggggcggag cctatggaaa aacgccagca acgcggcctt tttacggttc    4020
ctggcctttt gctggccttt tgctcacat                                     4049
```

<210> SEQ ID NO 275
<211> LENGTH: 1795
<212> TYPE: DNA
<213> ORGANISM: artificial sequence
<220> FEATURE:
<223> OTHER INFORMATION: DNA binding array of TALE recognizing AvrBs3
      site

<400> SEQUENCE: 275

```
ttgaccccgg agcaggtggt ggccatcgcc agccacgatg gcggcaagca ggcgctggag      60
acggtccagc ggctgttgcc ggtgctgtgc caggcccacg gcttgacccc ccagcaggtg     120
gtggccatcg ccagcaatgg cggtggcaag caggcgctgg agacggtcca gcggctgttg     180
ccggtgctgt gccaggccca cggcttgacc ccggagcagg tggtggccat cgccagcaat     240
attggtggca gcaggcgct ggagacggtg caggcgctgt tgccggtgct gtgccaggcc     300
cacggcttga ccccccagca ggtggtggcc atcgccagca atggcggtgg caagcaggcg     360
ctggagacgg tccagcggct gttgccggtg ctgtgccagg cccacggctt gaccccggag     420
caggtggtgg ccatcgccag caatattggt ggcaagcagg cgctggagac ggtgcaggcg     480
ctgttgccgg tgctgtgcca ggcccacggc ttgaccccgg agcaggtggt ggccatcgcc     540
agcaatattg gtggcaagca ggcgctggag acggtgcagg cgctgttgcc ggtgctgtgc     600
caggcccacg gcttgacccc ggagcaggtg gtggccatcg ccagcaatat tggtggcaag     660
caggcgctgg agacggtgca ggcgctgttg ccggtgctgt gccaggccca cggcttgacc     720
```

| | |
|---|---|
| ccggagcagg tggtggccat cgccagccac gatggcggca agcaggcgct ggagacggtc | 780 |
| cagcggctgt tgccggtgct gtgccaggcc cacggcttga ccccggagca ggtggtggcc | 840 |
| atcgccagcc acgatggcgg caagcaggcg ctggagacgg tccagcggct gttgccggtg | 900 |
| ctgtgccagg cccacggctt gaccccccag caggtggtgg ccatcgccag caatggcggt | 960 |
| ggcaagcagg cgctggagac ggtccagcgg ctgttgccgg tgctgtgcca ggcccacggc | 1020 |
| ttgaccccgg agcaggtggt ggccatcgcc agcaatattg gtggcaagca ggcgctggag | 1080 |
| acggtgcagg cgctgttgcc ggtgctgtgc caggcccacg gcttgacccc ggagcaggtg | 1140 |
| gtggccatcg ccagcaatat tggtggcaag caggcgctgg agacggtgca ggcgctgttg | 1200 |
| ccggtgctgt gccaggccca cggcttgacc ccggagcagg tggtggccat cgccagccac | 1260 |
| gatggcggca agcaggcgct ggagacggtc agcggctgt tgccggtgct gtgccaggcc | 1320 |
| cacggcttga ccccggagca ggtggtggcc atcgccagcc acgatggcgg caagcaggcg | 1380 |
| ctggagacgg tccagcggct gttgccggtg ctgtgccagg cccacggctt gaccccggag | 1440 |
| caggtggtgg ccatcgccag ccacgatggc ggcaagcagg cgctggagac ggtccagcgg | 1500 |
| ctgttgccgg tgctgtgcca ggcccacggc ttgaccccccc agcaggtggt ggccatcgcc | 1560 |
| agcaatggcg gtggcaagca ggcgctggag acggtccagc ggctgttgcc ggtgctgtgc | 1620 |
| caggcccacg gcttgacccc ggagcaggtg gtggccatcg ccagccacga tggcggcaag | 1680 |
| caggcgctgg agacggtcca gcggctgttg ccggtgctgt gccaggccca cggcttgacc | 1740 |
| cctcagcagg tggtggccat cgccagcaat ggcggcggca ggccggcgct ggaga | 1795 |

<210> SEQ ID NO 276
<211> LENGTH: 5801
<212> TYPE: DNA
<213> ORGANISM: artificial sequence
<220> FEATURE:
<223> OTHER INFORMATION: pCLS12731

<400> SEQUENCE: 276

| | |
|---|---|
| ggtctttcct gcgttatccc ctgattctgt ggataaccgt attaccgcct ttgagtgagc | 60 |
| tgataccgct cgccgcagcc gaacgaccga gcgcagcgag tcagtgagcg aggaagcgga | 120 |
| gagcgcccaa tacgcaaacc gcctctcccc gcgcgttggc cgattcatta atgcagctgg | 180 |
| cacgacaggt ttcccgactg gaaagcgggc agtgagcgca acgcaattaa tgtgagttag | 240 |
| ctcactcatt aggcacccca ggctttacac tttatgcttc cggctcgtat gttgtgtgga | 300 |
| attgtgagcg gataacaatt tcacacagga aacagctatg accatgatta cgccaagcgc | 360 |
| gtcaattaac cctcactaaa gggaacaaaa gctgttaatt aagcgcgcca cacgcaaaca | 420 |
| caaatacaca gcggccttgc caccatggcc aagtctggca tctaccagat taagaacacc | 480 |
| ctgaataaca agtgtatgt tggatctgcc aaggactttg agaaagatg gaagaggcac | 540 |
| ttcaaggatc tggaaaaggg ttgccacagc tccatcaagc tccaaggtc tttcaacaaa | 600 |
| catggcaatg tctttgagtg ctccattttg gaagagatcc ttatgaaaaa ggacctcatt | 660 |
| atagagaggg aaaacttctg gatcaaggag ctgaactcaa aaatcaatgg atacaacatt | 720 |
| gcagatgcca catttggtga cacctgttct actcaccccc ttaaggaaga gatcattaaa | 780 |
| aagaggtctg agactgtgaa ggctaagatg ttgaaactgg ggcctgatgg cagaaaggca | 840 |
| ctctactcta agccaggtag caaaaatgga aggtggaacc ctgagaccca caagttctgc | 900 |
| aaatgtgggg tgagaataca gacatcagcc tacacttgca gcaagtgtag gaacagatca | 960 |
| ggagagaata actccttttt caaccacaag cattctcaag gtccatccgg agtggatcta | 1020 |

```
cgcacgctcg gctacagcca gcagcaacag gagaagatca aaccgaaggt tcgttcgaca    1080
gtggcgcagc accacgaggc actggtcggc cacgggttta cacacgcgca catcgttgcg    1140
ttaagccaac acccggcagc gttagggacc gtcgctgtca agtatcagga catgatcgca    1200
gcgttgccag aggcgacaca cgaagcgatc gttggcgtcg gcaaacagtg gtccggcgca    1260
cgcgctctgg aggccttgct cacggtggcg ggagagttga gaggtccacc gttacagttg    1320
gacacaggcc aacttctcaa gattgcaaaa cgtggcggcg tgaccgcagt ggaggcagtg    1380
catgcatggc gcaatgcact gacgggtgcc ccgctcaact tgaccccgga gcaggtggtg    1440
gccatcgcca ccacgatgg cggcaagcag gcgctggaga cggtccagcg gctgttgccg    1500
gtgctgtgcc aggcccacgg cttgacccccc cagcaggtgg tggccatcgc cagcaatggc    1560
ggtggcaagc aggcgctgga gacggtccag cggctgttgc cggtgctgtg ccaggcccac    1620
ggcttgaccc cggagcaggt ggtggccatc gccagcaata ttggtggcaa gcaggcgctg    1680
gagacggtgc aggcgctgtt gccggtgctg tgccaggccc acggcttgac ccccagcag    1740 gtggtggcca tcgccagcaa tggcggtggc aagcaggcgc tggagacggt ccagcggctg    1800
ttgccggtgc tgtgccaggc ccacggcttg accccggagc aggtggtggc catcgccagc    1860
aatattggtg gcaagcaggc gctggagacg gtgcaggcgc tgttgccggt gctgtgccag    1920
gcccacggct tgaccccgga gcaggtggtg gccatcgcca gcaatattgg tggcaagcag    1980
gcgctggaga cggtgcaggc gctgttgccg gtgctgtgcc aggcccacgg cttgaccccg    2040
gagcaggtgg tggccatcgc cagcaatatt ggtggcaagc aggcgctgga gacggtgcag    2100
gcgctgttgc cggtgctgtg ccaggcccac ggcttgaccc cggagcaggt ggtggccatc    2160
gccagccacg atggcggcaa gcaggcgctg gagacggtcc agcggctgtt gccggtgctg    2220
tgccaggccc acggcttgac cccggagcag gtggtggcca tcgccagcca cgatggcggc    2280
aagcaggcgc tggagacggt ccagcggctg ttgccggtgc tgtgccaggc ccacggcttg    2340
accccccagc aggtggtggc catcgccagc aatggcggtg gcaagcaggc gctggagacg    2400
gtccagcggc tgttgccggt gctgtgccag gcccacggct tgaccccgga gcaggtggtg    2460
gccatcgcca gcaatattgg tggcaagcag gcgctggaga cggtgcaggc gctgttgccg    2520
gtgctgtgcc aggcccacgg cttgaccccg gagcaggtgg tggccatcgc cagcaatatt    2580
ggtggcaagc aggcgctgga gacggtgcag gcgctgttgc cggtgctgtg ccaggcccac    2640
ggcttgaccc cggagcaggt ggtggccatc gccagccacg atggcggcaa gcaggcgctg    2700
gagacggtcc agcggctgtt gccggtgctg tgccaggccc acggcttgac cccggagcag    2760
gtggtggcca tcgccagcca cgatggcggc aagcaggcgc tggagacggt ccagcggctg    2820
ttgccggtgc tgtgccaggc ccacggcttg accccggagc aggtggtggc catcgccagc    2880
cacgatggcg gcaagcaggc gctggagacg gtccagcggc tgttgccggt gctgtgccag    2940
gcccacggct gaccccccca gcaggtggtg gccatcgcca gcaatggcgg tgcaagcag    3000 gcgctggaga cggtccagcg gctgttgccg gtgctgtgcc aggcccacgg cttgaccccg    3060
gagcaggtgg tggccatcgc cagccacgat ggcggcaagc aggcgctgga gacggtccag    3120
cggctgttgc cggtgctgtg ccaggcccac ggcttgaccc ctcagcaggt ggtggccatc    3180
gccagcaatg gcggcggcag gccggcgctg gagagcattg ttgcccagtt atctcgccct    3240
gatccgtcgg ccgactgata agtcgaccac caccaccacc accactgata agagctcctc    3300
gagcctgcag cagctgaagc tttggacttc tggcgcgccc aattcgccct atagtgagtc    3360
```

```
gtattacgtc gcgctcactg gccgtcgttt tacaacgtcg tgactgggaa aaccctggcg    3420
ttacccaact taatcgcctt gcagcacatc cccctttcgc cagctggcgt aatagcgaag    3480
aggcccgcac cgaaacgccc ttcccaacag ttgcgcagcc tgaatggcga atgggagcgc    3540
cctgtagcgg cgcattaagc gcggcgggtg tggtggttac gcgcagcgtg accgctacac    3600
ttgccagcgc cctagcgccc gctcctttcg ctttcttccc ttcctttctc gccacgttcg    3660
ccggctttcc ccgtcaagct ctaaatcggg gctcccttt agggttccga tttagtgctt    3720
tacggcacct cgaccccaaa aaacttgatt agggtgatgg ttggcctgta gtgggccata    3780
gccctgatag acggttttc gccctttgac gttggagtcc acgttcttta atagtggact    3840
cttgttccaa actggaacaa cactcaaccc tatctcggtc tattcttttg atttataagg    3900
gattttgccg atttcggcct attggttaaa aaatgagctg atttaacaaa aatttaacgc    3960
gaattttaac aaaatattaa cgcttacaat ttaggtggca cttttcgggg aaatgtgcgc    4020 ggaacccta tttgtttatt tttctaaata cattcaaata tgtatccgct catgagacaa    4080
taaccctgat aaatgcttca ataatattga aaaggaaga gtatgagtat tcaacatttc    4140
cgtgtcgccc ttattccctt ttttgcggca ttttgccttc ctgtttttgc tcacccagaa    4200
acgctggtga agtaaaaga tgctgaagat cagttgggtg cacgagtggg ttacatcgaa    4260
ctggatctca acagcggtaa gatccttgag agttttcgcc ccgaagaacg ttttccaatg    4320
atgagcactt ttaaagttct gctatgtggc gcggtattat cccgtattga cgccgggcaa    4380
gagcaactcg gtcgccgcat acactattct cagaatgact tggttgagta ctcaccagtc    4440
acagaaaagc atcttacgga tggcatgaca gtaagagaat tatgcagtgc tgccataacc    4500
atgagtgata acactgcggc caacttactt ctgacaacga tcggaggacc gaaggagcta    4560
accgcttttt tgcacaacat gggggatcat gtaactcgcc ttgatcgttg ggaaccggag    4620
ctgaatgaag ccataccaaa cgacgagcgt gacaccacga tgcctgtagc aatggcaaca    4680
acgttgcgca aactattaac tggcgaacta cttactctag cttcccggca acaattaata    4740
gactggatgg aggcggataa agttgcagga ccacttctgc gctcggccct tccggctggc    4800
tggtttattg ctgataaatc tggagccggt gagcgtggtt ctcgcggtat cattgcagca    4860
ctggggccag atggtaagcc ctcccgtatc gtagttatct acacgacggg gagtcaggca    4920 actatgatg aacgaaatag acagatcgct gagataggtg cctcactgat taagcattgg    4980
taactgtcag accaagttta ctcatatata ctttagattg atttaaaact tcattttaa    5040 tttaaaagga tctaggtgaa gatcctttt gataatctca tgaccaaaat cccttaacgt    5100
gagttttcgt tccactgagc gtcagacccc gtagaaaaga tcaaaggatc ttcttgagat    5160
cctttttttc tgcgcgtaat ctgctgcttg caaacaaaaa aaccaccgct accagcggtg    5220
gtttgtttgc cggatcaaga gctaccaact cttttttccga aggtaactgg cttcagcaga    5280
gcgcagatac caaatactgt tcttctagtg tagccgtagt taggccacca cttcaagaac    5340
tctgtagcac cgcctacata cctcgctctg ctaatcctgt taccagtggc tgctgccagt    5400
ggcgataagt cgtgtcttac cgggttggac tcaagacgat agttaccgga taaggcgcag    5460
cggtcgggct gaacgggggg ttcgtgcaca cagcccagct tggagcgaac gacctacacc    5520
gaactgagat acctacagcg tgagctatga gaaagcgcca cgcttcccga agggagaaag    5580
gcggacaggt atccggtaag cggcagggtc ggaacaggag agcgcacgag ggagcttcca    5640
gggggaaacg cctggtatct ttatagtcct gtcgggtttc gccacctctg acttgagcgt    5700
cgatttttgt gatgctcgtc aggggggcgg agcctatgga aaaacgccag caacgcggcc    5760
```

```
tttttacggt tcctggcctt ttgctggcct tttgctcaca t                    5801
```

<210> SEQ ID NO 277
<211> LENGTH: 11112
<212> TYPE: DNA
<213> ORGANISM: artificial sequence
<220> FEATURE:
<223> OTHER INFORMATION: pCLS8522

<400> SEQUENCE: 277

```
atgtgagcaa aaggccagca aaaggccagg aaccgtaaaa aggccgcgtt gctggcgttt      60
ttccataggc tccgcccccc tgacgagcat cacaaaaatc gacgctcaag tcagaggtgg     120
cgaaacccga caggactata agataccagg cgtttccccc tggaagctcc ctcgtgcgc     180
tctcctgttc cgaccctgcc gcttaccgga tacctgtccg cctttctccc ttcgggaagc     240
gtggcgcttt ctcatagctc acgctgtagg tatctcagtt cggtgtaggt cgttcgctcc     300
aagctgggct gtgtgcacga accccccgtt cagcccgacc gctgcgcctt atccggtaac     360
tatcgtcttg agtccaaccc ggtaagacac gacttatcgc cactggcagc agccactggt     420
aacaggatta gcagagcgag gtatgtaggc ggtgctacag agttcttgaa gtggtggcct     480
aactacggct acactagaag gacagtattt ggtatctgcg ctctgctgaa gccagttacc     540
ttcggaaaaa gagttggtag ctcttgatcc ggcaaacaaa ccaccgctgg tagcggtggt     600
ttttttgttt gcaagcagca gattacgcgc agaaaaaaag gatctcaaga gatcctttg     660
atcttttcta cggggtctga cgctcagtgg aacgaaaact cacgttaagg gattttggtc     720
atgagattat caaaaaggat cttcacctag atccttttaa attaaaaatg aagttttaaa     780
tcaatctaaa gtatatatga gtaaacttgg tctgacagtt accaatgctt aatcagtgag     840
gcacctatct cagcgatctg tctatttcgt tcatccatag ttgcctgact ccccgtcgtg     900
tagataacta cgatacggga gggcttacca tctggcccca gtgctgcaat gataccgcga     960
gacccacgct caccggctcc agatttatca gcaataaacc agccagccgg aagggccgag    1020
cgcagaagtg gtcctgcaac tttatccgcc tccatccagt ctattaattg ttgccgggaa    1080
gctagagtaa gtagttcgcc agttaatagt ttgcgcaacg ttgttgccat tgctacaggc    1140
atcgtggtgt cacgctcgtc gtttggtatg gcttcattca gctccggttc ccaacgatca    1200
aggcgagtta catgatcccc catgttgtgc aaaaaagcgg ttagctcctt cggtcctccg    1260
atcgttgtca agtaagtt ggccgcagtg ttatcactca tggttatggc agcactgcat    1320
aattctctta ctgtcatgcc atccgtaaga tgcttttctg tgactggtga gtactcaacc    1380
aagtcattct gagaatagtg tatgcggcga ccgagttgct cttgcccggc gtcaatacgg    1440
gataataccg cgccacatag cagaacttta aaagtgctca tcattggaaa acgttcttcg    1500
gggcgaaaac tctcaaggat cttaccgctg ttgagatcca gttcgatgta acccactcgt    1560
gcacccaact gatcttcagc atcttttact ttcaccagcg tttctgggtg agcaaaaaca    1620
ggaaggcaaa atgccgcaaa aaagggaata agggcgacac ggaaatgttg aatactcata    1680
ctcttccttt ttcaatatta ttgaagcatt tatcagggtt attgtctcat gagcggatac    1740
atatttgaat gtatttagaa aaataaacaa ataggggttc cgcgcacatt tccccgaaaa    1800
gtgccacctg acgtccgatc aaaaatcatc gcttcgctga ttaattaccc cagaaataag    1860
gctaaaaaac taatcgcatt atcatccat ggttgttaat ttgattcgtt catttgaagg    1920
tttgtggggc caggttactg ccaattttc ctcttcataa ccataaaagc tagtattgta    1980
```

```
gaatctttat tgttcggagc agtgcggcgc gaggcacatc tgcgtttcag gaacgcgacc      2040
ggtgaagacg aggacgcacg gaggagagtc ttccttcgga gggctgtcac ccgctcggcg      2100
gcttctaatc cgtacttcaa tatagcaatg agcagttaag cgtattactg aaagttccaa      2160
agagaaggtt tttttaggct aatcgacctc gagcagatcc gccaggcgtg tatatagcgt      2220
ggatggccag gcaactttag tgctgacaca tacaggcata tatatatgtg tgcgacgaca      2280
catgatcata tggcatgcat gtgctctgta tgtatataaa actcttgttt tcttcttttc      2340
tctaaatatt cttccttat acattaggtc ctttgtagca taaattacta tacttctata      2400
gacacgcaaa cacaaataca cagcggcctt gccaccatgg ccaagtctgg catctaccag      2460
attaagaaca ccctgaataa caaagtgtat gttggatctg ccaaggactt tgagaaaaga      2520
tggaagaggc acttcaagga tctggaaaag ggttgccaca gctccatcaa gctccaaagg      2580
tctttcaaca aacatggcaa tgtctttgag tgctccattt tggaagagat cccttatgaa      2640
aaggacctca ttatagagag ggaaaacttc tggatcaagg agctgaactc aaaaatcaat      2700
ggatacaaca ttgcagatgc cacatttggt gacacctgtt ctactcaccc ccttaaggaa      2760
gagatcatta aaagaggtc tgagactgtg aaggctaaga tgttgaaact ggggcctgat      2820
ggcagaaagg cactctactc taagccaggt agcaaaaatg gaaggtggaa ccctgagacc      2880
cacaagttct gcaaatgtgg ggtgagaata cagacatcag cctacacttg cagcaagtgt      2940
aggaacagat caggagagaa taactccttt ttcaaccaca gcattctca aggtccatcc      3000 ggagtggatc tacgcacgct cggctacagc cagcagcaac aggagaagat caaaccgaag      3060
gttcgttcga cagtggcgca gcaccacgag gcactggtcg ccacgggtt tacacacgcg      3120 cacatcgttg cgttaagcca acacccggca gcgttaggga ccgtcgctgt caagtatcag      3180
gacatgatcg cagcgttgcc agaggcgaca cacgaagcga tcgttggcgt cggcaaacag      3240
tggtccggcg cacgcgctct ggaggccttg ctcacggtgg cgggagagtt gagaggtcca      3300
ccgttacagt tggacacagg ccaacttctc aagattgcaa aacgtggcgg cgtgaccgca      3360
gtggaggcag tgcatgcatg gcgcaatgca ctgacgggtg ccccgctcaa cttgaccccg      3420
gagcaggtgg tggccatcgc cagccacgat ggcggcaagc aggcgctgga cgcgtccag      3480 cggctgttgc cggtgctgtg ccaggcccac ggcttgaccc ccagcaggt ggtggccatc      3540 gccagcaatg gcgtggcaa gcaggcgctg gagacggtcc agcggctgtt gccggtgctg      3600
tgccaggccc acggcttgac cccggagcag gtggtggcca tcgccagcaa tattggtggc      3660
aagcaggcgc tggagacggt gcaggcgctg ttgccggtgc tgtgccaggc ccacggcttg      3720
accccccagc aggtggtggc catcgccagc aatggcggtg gcaagcaggc gctggagacg      3780
gtccagcggc tgttgccggt gctgtgccag gcccacggct tgaccccgga gcaggtggtg      3840
gccatcgcca gcaatattgg tggcaagcag gcgctggaga cggtgcaggc gctgttgccg      3900
gtgctgtgcc aggcccacgg cttgaccccg gagcaggtgg tggccatcgc cagcaatatt      3960
ggtggcaagc aggcgctgga cgcgtgcag gcgctgttgc cggtgctgtg ccaggcccac      4020
ggcttgaccc cggagcaggt ggtggccatc gccagcaata ttggtggcaa gcaggcgctg      4080
gagacggtgc aggcgctgtt gccggtgctg tgccaggccc acggcttgac cccggagcag      4140
gtggtggcca tcgccagcca cgatggcggc aagcaggcgc tggagacggt ccagcggctg      4200
ttgccggtgc tgtgccaggc ccacggcttg accccggagc aggtggtggc catcgccagc      4260
cacgatggcg gcaagcaggc gctggagacg gtccagcggc tgttgccggt gctgtgccag      4320
gcccacggct tgaccccca gcaggtggtg gccatcgcca gcaatggcgg tggcaagcag      4380
```

```
gcgctggaga cggtccagcg gctgttgccg gtgctgtgcc aggcccacgg cttgaccccg    4440
gagcaggtgg tggccatcgc cagcaatatt ggtggcaagc aggcgctgga cgggtgcag     4500
gcgctgttgc cggtgctgtg ccaggcccac ggcttgaccc cggagcaggt ggtggccatc    4560
gccagcaata ttggtggcaa gcaggcgctg agacggtgc aggcgctgtt gccggtgctg     4620
tgccaggccc acggcttgac cccggagcag gtggtggcca tcgccagcca cgatggcggc    4680
aagcaggcgc tggagacggt ccagcggctg ttgccggtgc tgtgccaggc ccacggcttg    4740
accccggagc aggtggtggc catcgccagc acgatggcg gcaagcaggc gctggagacg     4800
gtccagcggc tgttgccggt gctgtgccag gcccacggct tgaccccgga gcaggtggtg    4860
gccatcgcca gccacgatgg cggcaagcag gcgctggaga cggtccagcg gctgttgccg    4920
gtgctgtgcc aggcccacgg cttgaccccc agcaggtgg tggccatcgc cagcaatggc     4980
ggtggcaagc aggcgctgga cggtccag cggctgttgc cggtgctgtg ccaggcccac      5040
ggcttgaccc cggagcaggt ggtggccatc gccagccacg atggcggcaa gcaggcgctg    5100
gagacggtcc agcggctgtt gccggtgctg tgccaggccc acggcttgac ccctcagcag    5160
gtggtggcca tcgccagcaa tggcggcggc aggccggcgc tggagagcat tgttgcccag    5220
ttatctcgcc ctgatccgtc ggccgactga taactcgagc gatcctctag acgagctcct    5280
cgagcctgca gcagctgaag ctttggactt cttcgccaga ggttggtca agtctccaat     5340
caaggttgtc ggcttgtcta ccttgccaga aatttacgaa aagatggaaa agggtcaaat    5400
cgttggtaga tacgttgttg acacttctaa ataagcgaat ttcttatgat ttatgatttt    5460
tattattaaa taagttataa aaaaaataag tgtatacaaa ttttaaagtg actcttaggt    5520
tttaaaacga aaattcttat tcttgagtaa ctctttcctg taggtcaggt tgctttctca    5580
ggtatagcat gaggtcgctc ttattgacca cacctctacc ggcatgcaag cttggcgtaa    5640
tcatggtcat agctgtttcc tgtgtgaaat tgttatccgc tcacaattcc acacaacata    5700
cgagccggaa gcataaagtg taaagcctgg ggtgcctaat gagtgagcta actcacatta    5760
attgcgttgc gctcactgcc cgctttccag tcgggaaacc tgtcgtgcca gcagatctat    5820
tacattatgg gtggtatgtt ggaataaaaa tcaactatca tctactaact agtatttacg    5880
ttactagtat attatcatat acggtgttag aagatgacgc aaatgatgag aaatagtcat    5940
ctaaattagt ggaagctgaa acgcaaggat tgataatgta ataggatcaa tgaatattaa    6000
catataaaat gatgataata atatttatag aattgtgtag aattgcagat tccctttat     6060
ggattcctaa atcctcgagg agaacttcta gtatatctac atacctaata ttattgcctt    6120
attaaaaatg gaatcccaac aattacatca aaatccacat tctcttcaaa atcaattgtc    6180
ctgtacttcc ttgttcatgt gtgttcaaaa acgttatatt tataggataa ttatactcta    6240
tttctcaaca gtaattggt tgtttggccg agcggtctaa ggcgcctgat tcaagaaata    6300
tcttgaccgc agttaactgt gggaatactc aggtatcgta agatgcaaga gttcgaatct    6360
cttagcaacc attattttt tcctcaacat aacgagaaca cacaggggcg ctatcgcaca    6420
gaatcaaatt cgatgactgg aaatttttg ttaatttcag aggtcgcctg acgcatatac     6480
cttttcaac tgaaaaattg ggagaaaaag gaaaggtgag agccgcggaa ccggcttttc     6540
atatagaata gagaagcgtt catgactaaa tgcttgcatc acaatacttg aagttgacaa    6600
tattatttaa ggacctattg ttttttccaa taggtggtta gcaatcgtct tactttctaa    6660
ctttttcttac cttttacatt tcagcaatat atatatatat atttcaagga tataccattc   6720
```

```
taatgtctgc ccctaagaag atcgtcgttt tgccaggtga ccacgttggt caagaaatca    6780
cagccgaagc cattaaggtt cttaaagcta tttctgatgt tcgttccaat gtcaagttcg    6840
atttcgaaaa tcatttaatt ggtggtgctg ctatcgatgc tacaggtgtc ccacttccag    6900
atgaggcgct ggaagcctcc aagaaggttg atgccgtttt gttaggtgct gtgggtggtc    6960
ctaaatgggg taccggtagt gttagacctg aacaaggttt actaaaaatc cgtaaagaac    7020
ttcaattgta cgccaactta agaccatgta actttgcatc cgactctctt ttagacttat    7080
ctccaatcaa gccacaattt gctaaggta ctgacttcgt tgttgtcaga gaattagtgg     7140
gaggtattta ctttggtaag agaaaggaag acgatggtga tggtgtcgct gggatagtg     7200
aacaatacac cgttccagaa gtgcaaagaa tcacaagaat ggccgctttc atggccctac    7260
aacatgagcc accattgcct atttggtcct tggataaagc taatgttttg gcctcttcaa    7320
gattatggag aaaaactgtg gaggaaacca tcaagaacga attccctaca ttgaaggttc    7380
aacatcaatt gattgattct gccgccatga tcctagttaa gaacccaacc cacctaaatg    7440
gtattataat caccagcaac atgtttggtg atatcatctc cgatgaagcc tccgttatcc    7500
caggttcctt gggtttgttg ccatctgcgt ccttggcctc tttgccagac aagaacaccg    7560
catttggttt gtacgaacca tgccacggtt ctgctccaga tttgccaaag aataaggtca    7620
accctatcgc cactatcctt tctgctgcaa tgatgttgaa attgtcattg aacttgcctg    7680
aagaaggtaa ggccattgaa gatgcagtta aaaaggtttt ggatgcaggt atcagaactg    7740
gtgatttagg tggttccaac agtaccacgg aagtcggtga tgctgtcgcc gaagaagtta    7800
agaaaatcct tgcttaaaaa gattctcttt ttttatgata tttgtacata aactttataa    7860
atgaaattca taatagaaac gacacgaaat tacaaaatgg aatatgttca tagggtagac    7920
gaaactatat acgcaatcta catacattta tcaagaagga gaaaaggag gatgtaaagg    7980
aatacaggta agcaaattga tactaatggc tcaacgtgat aaggaaaaag aattgcactt    8040
taacattaat attgacaagg aggagggcac cacacaaaaa gttaggtgta acagaaaatc    8100
atgaaactat gattcctaat ttatatattg gaggattttc tctaaaaaaa aaaaaataca    8160
acaaataaaa aacactcaat gacctgacca tttgatggag tttaagtcaa taccttcttg    8220
aaccatttcc cataatggtg aaagttccct caagaatttt actctgtcag aaacggcctt    8280
aacgacgtag tcgacctcct cttcagtact aaatctacca ataccaaatc tgatggaaga    8340
atgggctaat gcatcatcct tacccagcgc atgtaaaaca taagaaggtt ctagggaagc    8400
agatgtacag gctgaacccg aggataatgc gatatccctt agtgccatca ataaagattc    8460
tccttccacg taggcgaaag aaacgttaac acaccctgga taacgatgat ctggagatcc    8520
gttcaacgtg gtatgttcag cggataatag acctttgact aatttatcgg atagtctttt    8580
gatgtgagct tggtcgttgt caaattcttt cttcatcaat ctcgcagctt caccaaatcc    8640
cgctaccaat gggggggcca agtaccaga tctgctgcat taatgaatcg gccaacgcgc    8700
ggggagaggc ggtttgcgta ttgggcgctc ttccgcttcc tcgctcactg actcgctgcg    8760
ctcggtcgtt cggctgcggc gagcggtatc agctcgatg aattccacgg actatagact    8820
atactagtat actccgtcta ctgtacgata cacttccgct caggtccttg tccttaacg    8880
aggccttacc actctttgt tactctattg atccagctca gcaaaggcag tgtgatctaa    8940
gattctatct tcgcgatgta gtaaaactag ctagaccgag aaagagacta gaaatgcaaa    9000
aggcacttct acaatggctg ccatcattat tatccgatgt gacgctgcag cttctcaatg    9060
atattcgaat acgctttgag gagatacagc ctaatatccg acaaactgtt ttacagattt    9120
```

```
acgatcgtac ttgttaccca tcattgaatt ttgaacatcc gaacctggga gttttccctg    9180
aaacagatag tatatttgaa cctgtataat aatatatagt ctagcgcttt acggaagaca    9240
atgtatgtat ttcggttcct ggagaaacta ttgcatctat tgcataggta atcttgcacg    9300
tcgcatcccc ggttcatttt ctgcgttccc atcttgcact tcaatagcat atctttgtta    9360
acgaagcatc tgtgcttcat tttgtagaac aaaaatgcaa cgcgagagcg ctaattttc     9420 aaacaaagaa tctgagctgc attttacag  aacagaaatg caacgcgaaa gcgctatttt    9480
accaacgaag aatctgtgct tcattttgt  aaaacaaaaa tgcaacgcga gagcgctaat    9540
tttcaaaaca aagaatctga gctgcatttt tacagaacag aaatgcaacg cgagagcgct    9600
attttaccaa caaagaatct atacttcttt tttgttctac aaaaatgcat cccgagagcg    9660
ctatttttct aacaaagcat cttagattac tttttttctc ctttgtgcgc tctataatgc    9720
agtctcttga taacttttg  cactgtaggt ccgttaaggt tagaagaagg ctactttggt    9780
gtctattttc tcttccataa aaaaagcctg actccacttc ccgcgtttac tgattactag    9840
cgaagctgcg ggtgcatttt ttcaagataa aggcatcccc gattatattc tataccgatg    9900
tggattgcgc atactttgtg aacagaaagt gatagcgttg atgattcttc attggtcaga    9960
aaattatgaa cggtttcttc tattttgtct ctatatacta cgtataggaa atgtttacat   10020
tttcgtattg ttttcgattc actctatgaa tagttcttac tacaattttt ttgtctaaag   10080
agtaatacta gagataaaca taaaaaatgt agaggtcgag tttagatgca agttcaagga   10140
gcgaaaggtg gatgggtagg ttatataggg atatagcaca gagatatata gcaaagagat   10200
acttttgagc aatgtttgtg gaagcggtat tcgcaatatt ttagtagctc gttacagtcc   10260
ggtgcgtttt tggttttttg aaagtgcgtc ttcagagcgc ttttggtttt caaaagcgct   10320
ctgaagttcc tatactttct agagaatagg aacttcggaa taggaacttc aaagcgtttc   10380
cgaaaacgag cgcttccgaa aatgcaacgc gagctgcgca catacagctc actgttcacg   10440
tcgcacctat atctgcgtgt tgcctgtata tatatataca tgaagaac  ggcatagtgc    10500 gtgtttatgc ttaaatgcgt acttatatgc gtctatttat gtaggatgaa aggtagtcta   10560
gtacctcctg tgatattatc ccattccatg cggggtatcg tatgcttcct tcagcactac   10620
cctttagctg ttctatatgc tgccactcct caattggatt agtctcatcc ttcaatgcta   10680
tcatttcctt tgatattgga tcatatgcat agtaccgaga aactagtgcg aagtagtgat   10740
caggtattgc tgttatctga tgagtatacg ttgtcctggc cacggcagaa gcacgcttat   10800
cgctccaatt tcccacaaca ttagtcaact ccgttaggcc cttcattgaa agaaatgagg   10860
tcatcaaatg tcttccaatg tgagattttg gccattttt  tatagcaaag attgaataag   10920
gcgcattttt cttcaaagct ttattgtacg atctgactaa gttatctttt aataattggt   10980
attcctgttt attgcttgaa gaattgccgg tcctatttac tcgttttagg actggttcag   11040
aattcatcga tgctcactca aaggtcggta atacggttat ccacagaatc agggggataac   11100 gcaggaaaga ac                                                       11112
```

<210> SEQ ID NO 278
<211> LENGTH: 8334
<212> TYPE: DNA
<213> ORGANISM: artificial sequence
<220> FEATURE:
<223> OTHER INFORMATION: pCLS0542

<400> SEQUENCE: 278

-continued

| | |
|---|---|
| tgtgtgcggc cgactgataa ctcgagcgat cctctagacg agctcctcga gcctgcagca | 60 |
| gctgaagctt tggacttctt cgccagaggt ttggtcaagt ctccaatcaa ggttgtcggc | 120 |
| ttgtctacct tgccagaaat ttacgaaaag atggaaaagg gtcaaatcgt tggtagatac | 180 |
| gttgttgaca cttctaaata agcgaatttc ttatgattta tgattttat tattaaataa | 240 |
| gttataaaaa aataagtgt atacaaattt taaagtgact cttaggtttt aaaacgaaaa | 300 |
| ttcttattct tgagtaactc tttcctgtag gtcaggttgc tttctcaggt atagcatgag | 360 |
| gtcgctctta ttgaccacac ctctaccggc atgcaagctt ggcgtaatca tggtcatagc | 420 |
| tgtttcctgt gtgaaattgt tatccgctca caattccaca caacatacga gccgaagca | 480 |
| taaagtgtaa agcctggggt gcctaatgag tgagctaact cacattaatt gcgttgcgct | 540 |
| cactgcccgc tttccagtcg ggaaacctgt cgtgccagca gatctattac attatgggtg | 600 |
| gtatgttgga ataaaaatca actatcatct actaactagt atttacgtta ctagtatatt | 660 |
| atcatatacg gtgttagaag atgacgcaaa tgatgagaaa tagtcatcta aattagtgga | 720 |
| agctgaaacg caaggattga taatgtaata ggatcaatga atattaacat ataaaatgat | 780 |
| gataataata tttatagaat tgtgtagaat tgcagattcc ctttttatgga ttcctaaatc | 840 |
| ctcgaggaga acttctagta tatctacata cctaatatta ttgccttatt aaaaatggaa | 900 |
| tcccaacaat tacatcaaaa tccacattct cttcaaaatc aattgtcctg tacttccttg | 960 |
| ttcatgtgtg ttcaaaaacg ttatatttat aggataatta tactctatttt ctcaacaagt | 1020 |
| aattggttgt ttggccgagc ggtctaaggc gcctgattca agaaatatct tgaccgcagt | 1080 |
| taactgtggg aatactcagg tatcgtaaga tgcaagagtt cgaatctctt agcaaccatt | 1140 |
| atttttttcc tcaacataac gagaacacac agggcgcta tcgcacagaa tcaaattcga | 1200 |
| tgactggaaa ttttttgtta atttcagagg tcgcctgacg catataccgt tttcaactga | 1260 |
| aaaattggga gaaaaggaa aggtgagagc cgcggaaccg gcttttcata tagaatagag | 1320 |
| aagcgttcat gactaaatgc ttgcatcaca atacttgaag ttgacaatat tatttaagga | 1380 |
| cctattgttt tttccaatag gtggttagca atcgtcttac tttctaactt ttcttacctt | 1440 |
| ttacatttca gcaatatata tatatatatt tcaaggatat accattctaa tgtctgcccc | 1500 |
| taagaagatc gtcgttttgc caggtgacca cgttggtcaa gaaatcacag ccgaagccat | 1560 |
| taaggttctt aaagctattt ctgatgttcg ttccaatgtc aagttcgatt cgaaaatca | 1620 |
| tttaattggt ggtgctgcta tcgatgctac aggtgtccca cttccagatg aggcgctgga | 1680 |
| agcctccaag aaggttgatg ccgttttgtt aggtgctgtg ggtggtccta atgggtac | 1740 |
| cggtagtgtt agacctgaac aaggtttact aaaaatccgt aaagaacttc aattgtacgc | 1800 |
| caacttaaga ccatgtaact ttgcatccga ctctcttta gacttatctc caatcaagcc | 1860 |
| acaatttgct aaaggtactg acttcgttgt tgtcagagaa ttagtgggag gtatttactt | 1920 |
| tggtaagaga aaggaagacg atggtgatgg tgtcgcttgg gatagtgaac aatacaccgt | 1980 |
| tccagaagtg caaagaatca aagaatggc cgctttcatg gccctacaac atgagccacc | 2040 |
| attgcctatt tggtccttgg ataaagctaa tgttttggcc tcttcaagat tatggagaaa | 2100 |
| aactgtggag gaaaccatca agaacgaatt ccctacattg aaggttcaac atcaattgat | 2160 |
| tgattctgcc gccatgatcc tagttaagaa cccaacccac ctaaatggta ttataatcac | 2220 |
| cagcaacatg tttggtgata tcatctccga tgaagcctcc gttatcccag gttccttggg | 2280 |
| tttgttgcca tctgcgtcct tggcctcttt gccagacaag aacaccgcat ttggtttgta | 2340 |
| cgaaccatgc cacggttctg ctccagattt gccaaagaat aaggtcaacc ctatcgccac | 2400 |

-continued

```
tatcttgtct gctgcaatga tgttgaaatt gtcattgaac ttgcctgaag aaggtaaggc    2460
cattgaagat gcagttaaaa aggttttgga tgcaggtatc agaactggtg atttaggtgg    2520
ttccaacagt accacggaag tcggtgatgc tgtcgccgaa gaagttaaga aaatccttgc    2580
ttaaaaagat tctcttttt tatgatattt gtacataaac tttataaatg aaattcataa    2640
tagaaacgac acgaaattac aaaatggaat atgttcatag ggtagacgaa actatatacg    2700
caatctacat acatttatca agaaggagaa aaaggaggat gtaaaggaat acaggtaagc    2760
aaattgatac taatggctca acgtgataag gaaaagaat tgcactttaa cattaatatt    2820
gacaaggagg agggcaccac acaaaaagtt aggtgtaaca gaaaatcatg aaactatgat    2880
tcctaattta tatattggag gattttctct aaaaaaaaaa aaatacaaca ataaaaaaac    2940
actcaatgac ctgaccattt gatggagttt aagtcaatac cttcttgaac catttcccat    3000
aatggtgaaa gttccctcaa gaattttact ctgtcagaaa cggccttaac gacgtagtcg    3060
acctcctctt cagtactaaa tctaccaata ccaaatctga tggaagaatg ggctaatgca    3120
tcatccttac ccagcgcatg taaaacataa gaaggttcta gggaagcaga tgtacaggct    3180
gaacccgagg ataatgcgat atcccttagt gccatcaata aagattctcc ttccacgtag    3240
gcgaaagaaa cgttaacaca ccctggataa cgatgatctg gagatccgtt caacgtggta    3300
tgttcagcgg ataatagacc tttgactaat ttatcggata gtcttttgat gtgagcttgg    3360
tcgttgtcaa attctttctt catcaatctc gcagcttcac caaatcccgc taccaatggg    3420
ggggccaaag taccagatct gctgcattaa tgaatcggcc aacgcgcggg gagaggcggt    3480
ttgcgtattg ggcgctcttc cgcttcctcg ctcactgact cgctgcgctc ggtcgttcgg    3540
ctgcggcgag cggtatcagc atcgatgaat tccacggact atagactata ctagtatact    3600
ccgtctactg tacgatacac ttccgctcag gtccttgtcc tttaacgagg ccttaccact    3660
cttttgttac tctattgatc cagctcagca aaggcagtgt gatctaagat tctatcttcg    3720
cgatgtagta aaactagcta gaccgagaaa gagactagaa atgcaaaagg cacttctaca    3780
atggctgcca tcattattat ccgatgtgac gctgcagctt ctcaatgata ttcgaatacg    3840 cttttgaggag atacagccta atatccgaca aactgtttta cagatttacg atcgtacttg    3900
ttacccatca ttgaattttg aacatccgaa cctgggagtt ttccctgaaa cagatagtat    3960
atttgaacct gtataataat atatagtcta gcgctttacg gaagacaatg tatgtatttc    4020
ggttcctgga gaaactattg catctattgc ataggtaatc ttgcacgtcg catcccggt     4080 tcattttctg cgtttccatc ttgcacttca atagcatatc tttgttaacg aagcatctgt    4140
gcttcatttt gtagaacaaa aatgcaacgc gagagcgcta attttcaaa caaagaatct    4200 gagctgcatt tttacagaac agaaatgcaa cgcgaaagcg ctatttacc aacgaagaat    4260 ctgtgcttca ttttttgtaaa acaaaaatgc aacgcgagag cgctaatttt tcaaacaaag    4320
aatctgagct gcatttttac agaacagaaa tgcaacgcga gagcgctatt ttaccaacaa    4380
agaatctata cttcttttt gttctacaaa aatgcatccc gagagcgcta tttttctaac    4440
aaagcatctt agattacttt ttttctcctt tgtgcgctct ataatgcagt ctcttgataa    4500
cttttgtcac tgtaggtccg ttaaggttag aagaaggcta ctttggtgtc tatttctct    4560 tccataaaaa aagcctgact ccacttcccg cgtttactga ttactagcga agctgcgggt    4620
gcattttttc aagataaagg catccccgat tatattctat accgatgtgg attgcgcata    4680
ctttgtgaac agaaagtgat agcgttgatg attcttcatt ggtcagaaaa ttatgaacgg    4740
```

```
tttcttctat tttgtctcta tatactacgt ataggaaatg tttacatttt cgtattgttt    4800
tcgattcact ctatgaatag ttcttactac aattttttg tctaaagagt aatactagag    4860
ataaacataa aaaatgtaga ggtcgagttt agatgcaagt tcaaggagcg aaaggtggat    4920
gggtaggtta tatagggata tagcacagag atatatagca aagagatact tttgagcaat    4980
gtttgtggaa gcggtattcg caatatttta gtagctcgtt acagtccggt gcgttttgg    5040
tttttgaaa gtgcgtcttc agagcgcttt tggttttcaa aagcgctctg aagttcctat    5100
actttctaga gaataggaac ttcggaatag gaacttcaaa gcgtttccga aaacgagcgc    5160
ttccgaaaat gcaacgcgag ctgcgcacat acagctcact gttcacgtcg cacctatatc    5220
tgcgtgttgc ctgtatatat atatacatga gaagaacggc atagtgcgtg tttatgctta    5280
aatgcgtact tatatgcgtc tatttatgta ggatgaaagg tagtctagta cctcctgtga    5340
tattatccca ttccatgcgg ggtatcgtat gcttccttca gcactaccct ttagctgttc    5400
tatatgctgc cactcctcaa ttggattagt ctcatccttc aatgctatca tttcctttga    5460
tattggatca tatgcatagt accgagaaac tagtgcgaag tagtgatcag gtattgctgt    5520
tatctgatga gtatacgttg tcctggccac ggcagaagca cgcttatcgc tccaatttcc    5580
cacaacatta gtcaactccg ttaggccctt cattgaaaga aatgaggtca tcaaatgtct    5640
tccaatgtga gattttgggc catttttat agcaaagatt gaataaggcg cattttctt    5700
caaagcttta ttgtacgatc tgactaagtt atcttttaat aattggtatt cctgtttatt    5760
gcttgaagaa ttgccggtcc tatttactcg ttttaggact ggttcagaat tcatcgatgc    5820
tcactcaaag gtcggtaata cggttatcca cagaatcagg ggataacgca ggaaagaaca    5880
tgtgagcaaa aggccagcaa aaggccagga accgtaaaaa ggccgcgttg ctggcgtttt    5940
tccataggct ccgccccct gacgagcatc acaaaaatcg acgctcaagt cagaggtggc    6000
gaaacccgac aggactataa agataccagg cgtttccccc tggaagctcc ctcgtgcgct    6060
ctcctgttcc gaccctgccg cttaccggat acctgtccgc ctttctccct tcgggaagcg    6120
tggcgctttc tcatagctca cgctgtaggt atctcagttc ggtgtaggtc gttcgctcca    6180
agctgggctg tgtgcacgaa ccccccgttc agcccgaccg ctgcgcctta tccggtaact    6240
atcgtcttga gtccaacccg gtaagacacg acttatcgcc actggcagca gccactggta    6300
acaggattag cagagcgagg tatgtaggcg gtgctacaga gttcttgaag tggtggccta    6360
actacggcta cactagaagg acagtatttg gtatctgcgc tctgctgaag ccagttacct    6420
tcggaaaaag agttggtagc tcttgatccg gcaaacaaac caccgctggt agcggtggtt    6480
tttttgtttg caagcagcag attacgcgca gaaaaaaagg atctcaagaa gatcctttga    6540
tcttttctac ggggtctgac gctcagtgga acgaaaactc acgttaaggg attttggtca    6600
tgagattatc aaaaaggatc ttcacctaga tccttttaaa ttaaaaatga agttttaaat    6660
caatctaaag tatatatgag taaacttggt ctgacagtta ccaatgctta atcagtgagg    6720
cacctatctc agcgatctgt ctatttcgtt catccatagt tgcctgactc cccgtcgtgt    6780
agataactac gatacgggag ggcttaccat ctggccccag tgctgcaatg ataccgcgag    6840
acccacgctc accggctcca gatttatcag caataaacca gccagccgga agggccgagc    6900
gcagaagtgg tcctgcaact ttatccgcct ccatccagtc tattaattgt tgccgggaag    6960
ctagagtaag tagttcgcca gttaatagtt tgcgcaacgt tgttgccatt gctacaggca    7020
tcgtggtgtc acgctcgtcg tttggtatgg cttcattcag ctccggttcc caacgatcaa    7080
ggcgagttac atgatccccc atgttgtgca aaaaagcggt tagctccttc ggtcctccga    7140
```

```
tcgttgtcag aagtaagttg gccgcagtgt tatcactcat ggttatggca gcactgcata    7200
attctcttac tgtcatgcca tccgtaagat gcttttctgt gactggtgag tactcaacca    7260
agtcattctg agaatagtgt atgcggcgac cgagttgctc ttgcccggcg tcaatacggg    7320
ataataccgc gccacatagc agaactttaa aagtgctcat cattggaaaa cgttcttcgg    7380
ggcgaaaact ctcaaggatc ttaccgctgt tgagatccag ttcgatgtaa cccactcgtg    7440
cacccaactg atcttcagca tcttttactt tcaccagcgt ttctgggtga caaaaacag     7500 gaaggcaaaa tgccgcaaaa aagggaataa gggcgacacg gaaatgttga atactcatac    7560
tcttcctttt tcaatattat tgaagcattt atcagggtta ttgtctcatg agcggataca    7620
tatttgaatg tatttagaaa aataaacaaa taggggttcc gcgcacattt ccccgaaaag    7680
tgccacctga cgtccgatca aaaatcatcg cttcgctgat taattacccc agaaataagg    7740
ctaaaaaact aatcgcatta tcatcctatg gttgttaatt tgattcgttc atttgaaggt    7800
ttgtggggcc aggttactgc caattttttcc tcttcataac cataaaagct agtattgtag    7860
aatctttatt gttcggagca gtgcggcgcg aggcacatct gcgtttcagg aacgcgaccg    7920
gtgaagacga ggacgcacgg aggagagtct tccttcggag ggctgtcacc cgctcggcgg    7980
cttctaatcc gtacttcaat atagcaatga gcagttaagc gtattactga aagttccaaa    8040
gagaaggttt ttttaggcta atcgacctcg agcagatccg ccaggcgtgt atatagcgtg    8100
gatggccagg caactttagt gctgacacat acaggcatat atatatgtgt gcgacgacac    8160
atgatcatat ggcatgcatg tgctctgtat gtatataaaa ctcttgtttt cttcttttct    8220
ctaaatattc tttccttata cattaggtcc tttgtagcat aaattactat acttctatag    8280
acacgcaaac acaaatacac agcggccttg ccaccatggc cggcgcgccc acta          8334
```

<210> SEQ ID NO 279
<211> LENGTH: 937
<212> TYPE: PRT
<213> ORGANISM: artificial sequence
<220> FEATURE:
<223> OTHER INFORMATION: TevD02-TALE chimeric endonuclease

<400> SEQUENCE: 279

Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
                20                  25                  30

Phe Lys Asp Leu Glu Lys Gly Cys His Ser Ser Ile Lys Leu Gln Arg
            35                  40                  45

Ser Phe Asn Lys His Gly Asn Val Phe Glu Cys Ser Ile Leu Glu Glu
        50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ser Lys Asn Gly Arg Trp
    130                 135                 140

Asn Pro Glu Thr His Lys Phe Cys Lys Cys Gly Val Arg Ile Gln Thr

-continued

```
             145                 150                 155                 160
        Ser Ala Tyr Thr Cys Ser Lys Cys Arg Asn Arg Ser Gly Glu Asn Asn
                         165                 170                 175

Ser Phe Phe Asn His Lys His Ser Gln Gly Pro Ser Gly Val Asp Leu
                         180                 185                 190

Arg Thr Leu Gly Tyr Ser Gln Gln Gln Glu Lys Ile Lys Pro Lys
                         195                 200                 205

Val Arg Ser Thr Val Ala Gln His His Glu Ala Leu Val Gly His Gly
                 210                 215                 220

Phe Thr His Ala His Ile Val Ala Leu Ser Gln His Pro Ala Ala Leu
        225                 230                 235                 240

Gly Thr Val Ala Val Lys Tyr Gln Asp Met Ile Ala Ala Leu Pro Glu
                         245                 250                 255

Ala Thr His Glu Ala Ile Val Gly Val Gly Lys Gln Trp Ser Gly Ala
                         260                 265                 270

Arg Ala Leu Glu Ala Leu Leu Thr Val Ala Gly Glu Leu Arg Gly Pro
                         275                 280                 285

Pro Leu Gln Leu Asp Thr Gly Gln Leu Leu Lys Ile Ala Lys Arg Gly
                         290                 295                 300

Gly Val Thr Ala Val Glu Ala Val His Ala Trp Arg Asn Ala Leu Thr
        305                 310                 315                 320

Gly Ala Pro Leu Asn Leu Thr Pro Glu Gln Val Val Ala Ile Ala Ser
                         325                 330                 335

His Asp Gly Gly Lys Gln Ala Leu Glu Thr Val Gln Arg Leu Leu Pro
                         340                 345                 350

Val Leu Cys Gln Ala His Gly Leu Thr Pro Gln Gln Val Val Ala Ile
                         355                 360                 365

Ala Ser Asn Gly Gly Lys Gln Ala Leu Glu Thr Val Gln Arg Leu
                         370                 375                 380

Leu Pro Val Leu Cys Gln Ala His Gly Leu Thr Pro Glu Gln Val Val
        385                 390                 395                 400

Ala Ile Ala Ser Asn Ile Gly Gly Lys Gln Ala Leu Glu Thr Val Gln
                         405                 410                 415

Ala Leu Leu Pro Val Leu Cys Gln Ala His Gly Leu Thr Pro Gln Gln
                         420                 425                 430

Val Val Ala Ile Ala Ser Asn Gly Gly Lys Gln Ala Leu Glu Thr
                         435                 440                 445

Val Gln Arg Leu Leu Pro Val Leu Cys Gln Ala His Gly Leu Thr Pro
        450                 455                 460

Glu Gln Val Val Ala Ile Ala Ser Asn Ile Gly Gly Lys Gln Ala Leu
        465                 470                 475                 480

Glu Thr Val Gln Ala Leu Leu Pro Val Leu Cys Gln Ala His Gly Leu
                         485                 490                 495

Thr Pro Glu Gln Val Val Ala Ile Ala Ser Asn Ile Gly Gly Lys Gln
                         500                 505                 510

Ala Leu Glu Thr Val Gln Ala Leu Leu Pro Val Leu Cys Gln Ala His
                         515                 520                 525

Gly Leu Thr Pro Glu Gln Val Val Ala Ile Ala Ser Asn Ile Gly Gly
                         530                 535                 540

Lys Gln Ala Leu Glu Thr Val Gln Ala Leu Leu Pro Val Leu Cys Gln
        545                 550                 555                 560

Ala His Gly Leu Thr Pro Glu Gln Val Val Ala Ile Ala Ser His Asp
                         565                 570                 575
```

Gly Gly Lys Gln Ala Leu Glu Thr Val Gln Arg Leu Leu Pro Val Leu
            580                 585                 590

Cys Gln Ala His Gly Leu Thr Pro Glu Gln Val Val Ala Ile Ala Ser
            595                 600                 605

His Asp Gly Gly Lys Gln Ala Leu Glu Thr Val Gln Arg Leu Leu Pro
610                 615                 620

Val Leu Cys Gln Ala His Gly Leu Thr Pro Gln Gln Val Val Ala Ile
625                 630                 635                 640

Ala Ser Asn Gly Gly Lys Gln Ala Leu Glu Thr Val Gln Arg Leu
            645                 650                 655

Leu Pro Val Leu Cys Gln Ala His Gly Leu Thr Pro Glu Gln Val Val
            660                 665                 670

Ala Ile Ala Ser Asn Ile Gly Gly Lys Gln Ala Leu Glu Thr Val Gln
            675                 680                 685

Ala Leu Leu Pro Val Leu Cys Gln Ala His Gly Leu Thr Pro Glu Gln
            690                 695                 700

Val Val Ala Ile Ala Ser Asn Ile Gly Gly Lys Gln Ala Leu Glu Thr
705                 710                 715                 720

Val Gln Ala Leu Leu Pro Val Leu Cys Gln Ala His Gly Leu Thr Pro
            725                 730                 735

Glu Gln Val Val Ala Ile Ala Ser His Asp Gly Gly Lys Gln Ala Leu
            740                 745                 750

Glu Thr Val Gln Arg Leu Leu Pro Val Leu Cys Gln Ala His Gly Leu
            755                 760                 765

Thr Pro Glu Gln Val Val Ala Ile Ala Ser His Asp Gly Gly Lys Gln
            770                 775                 780

Ala Leu Glu Thr Val Gln Arg Leu Leu Pro Val Leu Cys Gln Ala His
785                 790                 795                 800

Gly Leu Thr Pro Glu Gln Val Val Ala Ile Ala Ser His Asp Gly Gly
            805                 810                 815

Lys Gln Ala Leu Glu Thr Val Gln Arg Leu Leu Pro Val Leu Cys Gln
            820                 825                 830

Ala His Gly Leu Thr Pro Gln Gln Val Val Ala Ile Ala Ser Asn Gly
            835                 840                 845

Gly Gly Lys Gln Ala Leu Glu Thr Val Gln Arg Leu Leu Pro Val Leu
            850                 855                 860

Cys Gln Ala His Gly Leu Thr Pro Glu Gln Val Val Ala Ile Ala Ser
865                 870                 875                 880

His Asp Gly Gly Lys Gln Ala Leu Glu Thr Val Gln Arg Leu Leu Pro
            885                 890                 895

Val Leu Cys Gln Ala His Gly Leu Thr Pro Gln Gln Val Val Ala Ile
            900                 905                 910

Ala Ser Asn Gly Gly Gly Arg Pro Ala Leu Glu Ser Ile Val Ala Gln
            915                 920                 925

Leu Ser Arg Pro Asp Pro Ser Ala Asp
            930                 935

<210> SEQ ID NO 280
<211> LENGTH: 498
<212> TYPE: DNA
<213> ORGANISM: artificial sequence
<220> FEATURE:
<223> OTHER INFORMATION: BurrH_36 core scaffold

<400> SEQUENCE: 280

| | |
|---|---|
| ggcgcgccta cacagcggcc ttgccaccat gggcgatcct aaaaagaaac gtaaggtcat | 60 |
| cgattaccca tacgatgttc cagattacgc tatcgatatc gcctcaaccg ccttcgtgga | 120 |
| ccaggataag caaatggcca accgcttgaa cctgagtccc ctggagaggt ctaagattga | 180 |
| gaagcagtac ggcggggcca caactctggc ctttatctcc aacaagcaga acgagctggc | 240 |
| ccagatcctt agccgggcag acatcttgaa gattgcctcc tatgattgtg ctgcacacgc | 300 |
| cctccaggct gtcctcgatt gcgggccaat gctggggaag agaggattct ccggagacgc | 360 |
| ccggggatc aggtcacgtg cgtctcggag aagcaatgag gaaatcgtcc atgtggccgc | 420 |
| tagaaggggc ggagccggca ggattcggaa aatggtggcc cctctcctgg agcggcaggg | 480 |
| cagatctggc tcggatcc | 498 |

<210> SEQ ID NO 281
<211> LENGTH: 3032
<212> TYPE: DNA
<213> ORGANISM: artificial sequence
<220> FEATURE:
<223> OTHER INFORMATION: pCLS7865

<400> SEQUENCE: 281

| | |
|---|---|
| gggcggagcc tatggaaaaa cgccagcaac gcggccttt tacggttcct ggccttttgc | 60 |
| tggccttttg ctcacatggt ctttcctgcg ttatccctg attctgtgga taaccgtatt | 120 |
| accgcctttg agtgagctga taccgctcgc cgcagccgaa cgaccgagcg cagcgagtca | 180 |
| gtgagcgagg aagcggagag cgcccaatac gcaaaccgcc tctccccgcg cgttggccga | 240 |
| ttcattaatg cagctggcac gacaggtttc ccgactggaa agcgggcagt gagcgcaacg | 300 |
| caattaatgt gagttagctc actcattagg caccccaggc tttacacttt atgcttccgg | 360 |
| ctcgtatgtt gtgtggaatt gtgagcggat aacaatttca cacaggaaac agctatgacc | 420 |
| atgattacgc caagcgcgtc aattaaccct cactaaaggg aacaaaagct gttaattaag | 480 |
| cgcgccacac gcaaacacaa atacacagcg gccttgccac catggcaaac accggtggat | 540 |
| cctccggaag atcttcggcc gactgataag tcgaccacca ccaccaccac cactgataag | 600 |
| agctcctcga gcctgcagca gctgaagctt tggacttctg gcgcgcccaa ttcgccctat | 660 |
| agtgagtcgt attacgtcgc gctcactggc cgtcgtttta caacgtcgtg actgggaaaa | 720 |
| ccctggcgtt acccaactta atcgccttgc agcacatccc cctttcgcca gctggcgtaa | 780 |
| tagcgaagag gcccgcaccg aaacgcccct cccaacagtt gcgcagcctg aatggcgaat | 840 |
| gggagcgccc tgtagcggcg cattaagcgc ggcgggtgtg tggttacgc gcagcgtgac | 900 |
| cgctacactt gccagcgccc tagcgcccgc tcctttcgct ttcttccctt cctttctcgc | 960 |
| cacgttcgcc ggctttcccc gtcaagctct aaatcggggg ctcccttag ggttccgatt | 1020 |
| tagtgcttta cggcacctcg accccaaaaa acttgattag ggtgatggtt ggcctgtagt | 1080 |
| gggccatagc cctgatagac ggttttcgc cctttgacgt tggagtccac gttctttaat | 1140 |
| agtggactct tgttccaaac tggaacaaca ctcaaccta tctcggtcta ttcttttgat | 1200 |
| ttataaggga ttttgccgat ttcggcctat tggttaaaaa atgagctgat ttaacaaaaa | 1260 |
| tttaacgcga attttaacaa atattaacg cttacaattt aggtggcact tttcggggaa | 1320 |
| atgtgcgcgg aacccctatt tgtttatttt tctaaataca ttcaaatatg tatccgctca | 1380 |
| tgagacaata accctgataa atgcttcaat aatattgaaa aaggaagagt atgagtattc | 1440 |
| aacatttccg tgtcgccctt attccctttt ttgcggcatt ttgccttcct gtttttgctc | 1500 |

```
acccagaaac gctggtgaaa gtaaaagatg ctgaagatca gttgggtgca cgagtgggtt    1560
acatcgaact ggatctcaac agcggtaaga tccttgagag ttttcgcccc gaagaacgtt    1620
ttccaatgat gagcactttt aaagttctgc tatgtggcgc ggtattatcc cgtattgacg    1680
ccgggcaaga gcaactcggt cgccgcatac actattctca gaatgacttg gttgagtact    1740
caccagtcac agaaaagcat cttacggatg gcatgacagt aagagaatta tgcagtgctg    1800
ccataaccat gagtgataac actgcggcca acttacttct gacaacgatc ggaggaccga    1860
aggagctaac cgcttttttg cacaacatgg gggatcatgt aactcgcctt gatcgttggg    1920
aaccggagct gaatgaagcc ataccaaacg acgagcgtga caccacgatg cctgtagcaa    1980
tggcaacaac gttgcgcaaa ctattaactg gcgaactact tactctagct tcccggcaac    2040
aattaataga ctggatggag gcggataaag ttgcaggacc acttctgcgc tcggcccttc    2100
cggctggctg gtttattgct gataaatctg gagccggtga gcgtggttct cgcggtatca    2160
ttgcagcact ggggccagat ggtaagccct cccgtatcgt agttatctac acgacgggga    2220
gtcaggcaac tatggatgaa cgaaatagac agatcgctga gataggtgcc tcactgatta    2280
agcattggta actgtcagac caagtttact catatatact ttagattgat ttaaaacttc    2340
atttttaatt taaaaggatc taggtgaaga tcctttttga taatctcatg accaaaatcc    2400
cttaacgtga gttttcgttc cactgagcgt cagaccccgt agaaaagatc aaaggatctt    2460
cttgagatcc ttttttttctg cgcgtaatct gctgcttgca acaaaaaaa ccaccgctac    2520 cagcggtggt ttgtttgccg gatcaagagc taccaactct ttttccgaag gtaactggct    2580
tcagcagagc gcagatacca atactgttc ttctagtgta gccgtagtta ggccaccact    2640
tcaagaactc tgtagcaccg cctacatacc tcgctctgct aatcctgtta ccagtggctg    2700
ctgccagtgg cgataagtcg tgtcttaccg ggttggactc aagacgatag ttaccggata    2760
aggcgcagcg gtcgggctga acggggggtt cgtgcacaca gcccagcttg gagcgaacga    2820
cctacaccga actgagatac ctacagcgtg agctatgaga aagcgccacg cttcccgaag    2880
ggagaaaggc ggacaggtat ccggtaagcg gcagggtcgg aacaggagag cgcacgaggg    2940
agcttccagg gggaaacgcc tggtatcttt atagtcctgt cgggtttcgc cacctctgac    3000
ttgagcgtcg atttttgtga tgctcgtcag gg                                  3032
```

<210> SEQ ID NO 282  
<211> LENGTH: 1782  
<212> TYPE: DNA  
<213> ORGANISM: artificial sequence  
<220> FEATURE:  
<223> OTHER INFORMATION: DNA binding array of Burrh_36 recognizing AvrBs3 site

<400> SEQUENCE: 282

```
ttctcccagt cagatatagt caagatagca ggacatgatg gtggcgctca ggcgttgcaa      60
gcggttctcg acctggagag catgctgggc aagaggggct tttcacgcga cgacattgct     120
aagatggctg ggaacggcgg cggggcccag acacttcagg cagtactgga cctggagtca     180
gcttttcgag agcgcggctt ctcccaggca gacatagtga aaatcgcagg caacatcgga     240
ggcgcacaag ccctgtacag tgtgctggac gtggagccaa ctctgggaa gcggggggttt     300 tctagagcag atattgtcaa gattgcaggg aacggtggcg gtgcgcaagc cctgcacact     360
gtgctggatc ttgaacctgc gcttggtaag agaggattct ctcgcatcga catcgtaaag     420
attgcggcca acattggcgg ggctcaggct ctccacgccg tactggactt gggccccacg     480
```

```
ctccgagagt gtgggttcag ccaggccacc atcgctaaga tcgccggaaa catcggcggg      540
gcacaggcac tccagatggt gcttgatctg ggcccggccc tgggcaaacg cgggttctcc      600
caagctacga ttgccaagat cgcaggaaat atcggcggag cgcaggctct tcagaccgtg      660
ctggaccttg agcctgcctt gtgcgagcgc gggtttagtc aggccacaat tgccaaaatg      720
gctggccacg atggaggtgc ccaagctctc cagactgtgc ttgacctgga acccgccctc      780
cgaaaaaggg attttcggca ggccgacatc atcaaaattg ccggcacga cggtggagcg       840 caagccttgc aagcagttat cgaacacggg ccaaccctgc ggcagcatgg ctttaacctc      900
gccgacatcg tgaagatggc cggaaatgga ggtggcgcac aggccctcca ggccgtcttg      960
gatctgaagc cagttcttga tgagcacgga tttagccagc tgacattgt gaaaatggcc      1020 gggaatatcg gtggagcaca agcactccag gctgtcctga gtctgggtcc agctctgcgg      1080
gaacggggct tctctcaacc tgacatagtc aaaatcgctg gtaatattgg cggtgctcag      1140
gcattgcagg ccgttctcga tctggagctg accctcgtgg aacacgggtt ttcccaggcc      1200
gatattgtga agatagccgg acacgatggg gggacacagg cgctgcatgc cgtcctggat      1260
ctggagagga tgctgggcga gagagggttc tccagagctg acatcgtcaa cgtcgccggg      1320
catgatgggg gagcacaggc tttgaaggct gtactggaac atgaggctac cctgaatgag      1380 agggggattca gccgggctga tattgttaag atcgctggac atgacggagg cgctcaagct      1440
ctcaaagccg tgctcgaaca cgaggcaact ctggatgagc ggggcttcag cagggcagac      1500
atcgttaatg ttgccggaaa cggtgggggt gcccaggccc tcaaagcagt cctggaacac      1560
gaagccacac tcaacgagcg aggattcaat ttgaccgaca ttgtggaaat ggcagcccac      1620
gatggcggcg cccaggcgtt gaaagccgtg ttggaacatg cccccacact caggcagaga      1680
gggctgtctc ttatcgacat agtggaaatt gcaggcaatg gcggggagc ccaggctctg       1740 aaagcggtgc tgaagtatgg acccgtgctt atgcaggccg gg                        1782
```

<210> SEQ ID NO 283
<211> LENGTH: 897
<212> TYPE: PRT
<213> ORGANISM: artificial sequence
<220> FEATURE:
<223> OTHER INFORMATION: TevD02-BurrH chimeric endonuclease

<400> SEQUENCE: 283

```
Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
        35                  40                  45

Ser Phe Asn Lys His Gly Asn Val Phe Glu Cys Ser Ile Leu Glu Glu
    50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ser Lys Asn Gly Arg Trp
```

```
           130                 135                 140
Asn Pro Glu Thr His Lys Phe Cys Lys Cys Gly Val Arg Ile Gln Thr
145                 150                 155                 160

Ser Ala Tyr Thr Cys Ser Lys Cys Arg Asn Arg Ser Gly Glu Asn Asn
                    165                 170                 175

Ser Phe Phe Asn His Lys His Ser Gln Gly Pro Ser Gly Ser Thr Ala
                    180                 185                 190

Phe Val Asp Gln Asp Lys Gln Met Ala Asn Arg Leu Asn Leu Ser Pro
            195                 200                 205

Leu Glu Arg Ser Lys Ile Glu Lys Gln Tyr Gly Gly Ala Thr Thr Leu
    210                 215                 220

Ala Phe Ile Ser Asn Lys Gln Asn Glu Leu Ala Gln Ile Leu Ser Arg
225                 230                 235                 240

Ala Asp Ile Leu Lys Ile Ala Ser Tyr Asp Cys Ala Ala His Ala Leu
                245                 250                 255

Gln Ala Val Leu Asp Cys Gly Pro Met Leu Gly Lys Arg Gly Phe Ser
                260                 265                 270

Gln Ser Asp Ile Val Lys Ile Ala Gly His Asp Gly Gly Ala Gln Ala
            275                 280                 285

Leu Gln Ala Val Leu Asp Leu Glu Ser Met Leu Gly Lys Arg Gly Phe
    290                 295                 300

Ser Arg Asp Asp Ile Ala Lys Met Ala Gly Asn Gly Gly Gly Ala Gln
305                 310                 315                 320

Thr Leu Gln Ala Val Leu Asp Leu Glu Ser Ala Phe Arg Glu Arg Gly
                325                 330                 335

Phe Ser Gln Ala Asp Ile Val Lys Ile Ala Gly Asn Ile Gly Gly Ala
                340                 345                 350

Gln Ala Leu Tyr Ser Val Leu Asp Val Glu Pro Thr Leu Gly Lys Arg
            355                 360                 365

Gly Phe Ser Arg Ala Asp Ile Val Lys Ile Ala Gly Asn Gly Gly Gly
    370                 375                 380

Ala Gln Ala Leu His Thr Val Leu Asp Leu Glu Pro Ala Leu Gly Lys
385                 390                 395                 400

Arg Gly Phe Ser Arg Ile Asp Ile Val Lys Ile Ala Ala Asn Ile Gly
                405                 410                 415

Gly Ala Gln Ala Leu His Ala Val Leu Asp Leu Gly Pro Thr Leu Arg
                420                 425                 430

Glu Cys Gly Phe Ser Gln Ala Thr Ile Ala Lys Ile Ala Gly Asn Ile
            435                 440                 445

Gly Gly Ala Gln Ala Leu Gln Met Val Leu Asp Leu Gly Pro Ala Leu
    450                 455                 460

Gly Lys Arg Gly Phe Ser Gln Ala Thr Ile Ala Lys Ile Ala Gly Asn
465                 470                 475                 480

Ile Gly Gly Ala Gln Ala Leu Gln Thr Val Leu Asp Leu Glu Pro Ala
                485                 490                 495

Leu Cys Glu Arg Gly Phe Ser Gln Ala Thr Ile Ala Lys Met Ala Gly
                500                 505                 510

His Asp Gly Gly Ala Gln Ala Leu Gln Thr Val Leu Asp Leu Glu Pro
            515                 520                 525

Ala Leu Arg Lys Arg Asp Phe Arg Gln Ala Asp Ile Ile Lys Ile Ala
    530                 535                 540

Gly His Asp Gly Gly Ala Gln Ala Leu Gln Ala Val Ile Glu His Gly
545                 550                 555                 560
```

Pro Thr Leu Arg Gln His Gly Phe Asn Leu Ala Asp Ile Val Lys Met
            565                 570                 575

Ala Gly Asn Gly Gly Ala Gln Ala Leu Gln Ala Val Leu Asp Leu
        580                 585                 590

Lys Pro Val Leu Asp Glu His Gly Phe Ser Gln Pro Asp Ile Val Lys
        595                 600                 605

Met Ala Gly Asn Ile Gly Gly Ala Gln Ala Leu Gln Ala Val Leu Ser
610                 615                 620

Leu Gly Pro Ala Leu Arg Glu Arg Gly Phe Ser Gln Pro Asp Ile Val
625                 630                 635                 640

Lys Ile Ala Gly Asn Ile Gly Gly Ala Gln Ala Leu Gln Ala Val Leu
                645                 650                 655

Asp Leu Glu Leu Thr Leu Val Glu His Gly Phe Ser Gln Ala Asp Ile
                660                 665                 670

Val Lys Ile Ala Gly His Asp Gly Gly Thr Gln Ala Leu His Ala Val
                675                 680                 685

Leu Asp Leu Glu Arg Met Leu Gly Glu Arg Gly Phe Ser Arg Ala Asp
            690                 695                 700

Ile Val Asn Val Ala Gly His Asp Gly Gly Ala Gln Ala Leu Lys Ala
705                 710                 715                 720

Val Leu Glu His Glu Ala Thr Leu Asn Glu Arg Gly Phe Ser Arg Ala
                725                 730                 735

Asp Ile Val Lys Ile Ala Gly His Asp Gly Gly Ala Gln Ala Leu Lys
                740                 745                 750

Ala Val Leu Glu His Glu Ala Thr Leu Asp Glu Arg Gly Phe Ser Arg
            755                 760                 765

Ala Asp Ile Val Asn Val Ala Gly Asn Gly Gly Ala Gln Ala Leu
            770                 775                 780

Lys Ala Val Leu Glu His Glu Ala Thr Leu Asn Glu Arg Gly Phe Asn
785                 790                 795                 800

Leu Thr Asp Ile Val Glu Met Ala His Asp Gly Gly Ala Gln Ala
                805                 810                 815

Leu Lys Ala Val Leu Glu His Gly Pro Thr Leu Arg Gln Arg Gly Leu
            820                 825                 830

Ser Leu Ile Asp Ile Val Glu Ile Ala Gly Asn Gly Gly Ala Gln
                835                 840                 845

Ala Leu Lys Ala Val Leu Lys Tyr Gly Pro Val Leu Met Gln Ala Gly
        850                 855                 860

Arg Ser Asn Glu Glu Ile Val His Val Ala Ala Arg Arg Gly Gly Ala
865                 870                 875                 880

Gly Arg Ile Arg Lys Met Val Ala Pro Leu Leu Glu Arg Gln Ser Ala
                885                 890                 895

Asp

<210> SEQ ID NO 284
<211> LENGTH: 138
<212> TYPE: PRT
<213> ORGANISM: artificial sequence
<220> FEATURE:
<223> OTHER INFORMATION: TevM01

<400> SEQUENCE: 284

Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
            35                  40                  45

Ser Phe Asn Lys His Gly Asn Val Phe Glu Cys Ser Ile Leu Glu Glu
            50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
            85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
            115                 120                 125

Gly Arg Lys Ala Leu Tyr Ser Lys Pro Gly
            130                 135

<210> SEQ ID NO 285
<211> LENGTH: 888
<212> TYPE: PRT
<213> ORGANISM: artificial sequence
<220> FEATURE:
<223> OTHER INFORMATION: TevM01-TALE chimeric endonuclease

<400> SEQUENCE: 285

Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
            35                  40                  45

Ser Phe Asn Lys His Gly Asn Val Phe Glu Cys Ser Ile Leu Glu Glu
            50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
            85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
            115                 120                 125

Gly Arg Lys Ala Leu Tyr Ser Lys Pro Gly Ser Gly Val Asp Leu Arg
            130                 135                 140

Thr Leu Gly Tyr Ser Gln Gln Gln Glu Lys Ile Lys Pro Lys Val
145                 150                 155                 160

Arg Ser Thr Val Ala Gln His His Glu Ala Leu Val Gly His Gly Phe
            165                 170                 175

Thr His Ala His Ile Val Ala Leu Ser Gln His Pro Ala Ala Leu Gly
            180                 185                 190

Thr Val Ala Val Lys Tyr Gln Asp Met Ile Ala Ala Leu Pro Glu Ala
            195                 200                 205

Thr His Glu Ala Ile Val Gly Val Gly Lys Gln Trp Ser Gly Ala Arg
            210                 215                 220

Ala Leu Glu Ala Leu Leu Thr Val Ala Gly Glu Leu Arg Gly Pro Pro
225                 230                 235                 240

```
Leu Gln Leu Asp Thr Gly Gln Leu Leu Lys Ile Ala Lys Arg Gly
            245                 250                 255
Val Thr Ala Val Glu Ala Val His Ala Trp Arg Asn Ala Leu Thr Gly
            260                 265                 270
Ala Pro Leu Asn Leu Thr Pro Glu Gln Val Val Ala Ile Ala Ser His
            275                 280                 285
Asp Gly Gly Lys Gln Ala Leu Glu Thr Val Gln Arg Leu Leu Pro Val
            290                 295                 300
Leu Cys Gln Ala His Gly Leu Thr Pro Gln Gln Val Val Ala Ile Ala
305                 310                 315                 320
Ser Asn Gly Gly Gly Lys Gln Ala Leu Glu Thr Val Gln Arg Leu Leu
                325                 330                 335
Pro Val Leu Cys Gln Ala His Gly Leu Thr Pro Glu Gln Val Val Ala
            340                 345                 350
Ile Ala Ser Asn Ile Gly Gly Lys Gln Ala Leu Glu Thr Val Gln Ala
            355                 360                 365
Leu Leu Pro Val Leu Cys Gln Ala His Gly Leu Thr Pro Gln Gln Val
            370                 375                 380
Val Ala Ile Ala Ser Asn Gly Gly Gly Lys Gln Ala Leu Glu Thr Val
385                 390                 395                 400
Gln Arg Leu Leu Pro Val Leu Cys Gln Ala His Gly Leu Thr Pro Glu
                405                 410                 415
Gln Val Val Ala Ile Ala Ser Asn Ile Gly Gly Lys Gln Ala Leu Glu
            420                 425                 430
Thr Val Gln Ala Leu Leu Pro Val Leu Cys Gln Ala His Gly Leu Thr
            435                 440                 445
Pro Glu Gln Val Val Ala Ile Ala Ser Asn Ile Gly Gly Lys Gln Ala
            450                 455                 460
Leu Glu Thr Val Gln Ala Leu Leu Pro Val Leu Cys Gln Ala His Gly
465                 470                 475                 480
Leu Thr Pro Glu Gln Val Val Ala Ile Ala Ser Asn Ile Gly Gly Lys
                485                 490                 495
Gln Ala Leu Glu Thr Val Gln Ala Leu Leu Pro Val Leu Cys Gln Ala
            500                 505                 510
His Gly Leu Thr Pro Glu Gln Val Val Ala Ile Ala Ser His Asp Gly
            515                 520                 525
Gly Lys Gln Ala Leu Glu Thr Val Gln Arg Leu Leu Pro Val Leu Cys
            530                 535                 540
Gln Ala His Gly Leu Thr Pro Glu Gln Val Val Ala Ile Ala Ser His
545                 550                 555                 560
Asp Gly Gly Lys Gln Ala Leu Glu Thr Val Gln Arg Leu Leu Pro Val
                565                 570                 575
Leu Cys Gln Ala His Gly Leu Thr Pro Gln Gln Val Val Ala Ile Ala
            580                 585                 590
Ser Asn Gly Gly Gly Lys Gln Ala Leu Glu Thr Val Gln Arg Leu Leu
            595                 600                 605
Pro Val Leu Cys Gln Ala His Gly Leu Thr Pro Glu Gln Val Val Ala
            610                 615                 620
Ile Ala Ser Asn Ile Gly Gly Lys Gln Ala Leu Glu Thr Val Gln Ala
625                 630                 635                 640
Leu Leu Pro Val Leu Cys Gln Ala His Gly Leu Thr Pro Glu Gln Val
                645                 650                 655
Val Ala Ile Ala Ser Asn Ile Gly Gly Lys Gln Ala Leu Glu Thr Val
```

```
                    660                 665                 670
Gln Ala Leu Leu Pro Val Leu Cys Gln Ala His Gly Leu Thr Pro Glu
            675                 680                 685

Gln Val Val Ala Ile Ala Ser His Asp Gly Gly Lys Gln Ala Leu Glu
        690                 695                 700

Thr Val Gln Arg Leu Leu Pro Val Leu Cys Gln Ala His Gly Leu Thr
705                 710                 715                 720

Pro Glu Gln Val Val Ala Ile Ala Ser His Asp Gly Gly Lys Gln Ala
                725                 730                 735

Leu Glu Thr Val Gln Arg Leu Leu Pro Val Leu Cys Gln Ala His Gly
            740                 745                 750

Leu Thr Pro Glu Gln Val Val Ala Ile Ala Ser His Asp Gly Gly Lys
        755                 760                 765

Gln Ala Leu Glu Thr Val Gln Arg Leu Leu Pro Val Leu Cys Gln Ala
    770                 775                 780

His Gly Leu Thr Pro Gln Val Val Ala Ile Ala Ser Asn Gly Gly
785                 790                 795                 800

Gly Lys Gln Ala Leu Glu Thr Val Gln Arg Leu Leu Pro Val Leu Cys
                805                 810                 815

Gln Ala His Gly Leu Thr Pro Glu Gln Val Val Ala Ile Ala Ser His
            820                 825                 830

Asp Gly Gly Lys Gln Ala Leu Glu Thr Val Gln Arg Leu Leu Pro Val
        835                 840                 845

Leu Cys Gln Ala His Gly Leu Thr Pro Gln Gln Val Val Ala Ile Ala
    850                 855                 860

Ser Asn Gly Gly Gly Arg Pro Ala Leu Glu Ser Ile Val Ala Gln Leu
865                 870                 875                 880

Ser Arg Pro Asp Pro Ser Ala Asp
                885

<210> SEQ ID NO 286
<211> LENGTH: 851
<212> TYPE: PRT
<213> ORGANISM: artificial sequence
<220> FEATURE:
<223> OTHER INFORMATION: TevM01-BurrH chimeric endonuclease

<400> SEQUENCE: 286

Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
        35                  40                  45

Ser Phe Asn Lys His Gly Asn Val Phe Glu Cys Ser Ile Leu Glu Glu
    50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ile Ala Ser Thr Ala Phe
```

```
                130                 135                 140
Val Asp Gln Asp Lys Gln Met Ala Asn Arg Leu Asn Leu Ser Pro Leu
145                 150                 155                 160

Glu Arg Ser Lys Ile Glu Lys Gln Tyr Gly Gly Ala Thr Thr Leu Ala
                165                 170                 175

Phe Ile Ser Asn Lys Gln Asn Glu Leu Ala Gln Ile Leu Ser Arg Ala
                180                 185                 190

Asp Ile Leu Lys Ile Ala Ser Tyr Asp Cys Ala Ala His Ala Leu Gln
                195                 200                 205

Ala Val Leu Asp Cys Gly Pro Met Leu Gly Lys Arg Gly Phe Ser Gln
        210                 215                 220

Ser Asp Ile Val Lys Ile Ala Gly His Asp Gly Ala Gln Ala Leu
225                 230                 235                 240

Gln Ala Val Leu Asp Leu Glu Ser Met Leu Gly Lys Arg Gly Phe Ser
                245                 250                 255

Arg Asp Asp Ile Ala Lys Met Ala Gly Asn Gly Gly Ala Gln Thr
                260                 265                 270

Leu Gln Ala Val Leu Asp Leu Glu Ser Ala Phe Arg Glu Arg Gly Phe
        275                 280                 285

Ser Gln Ala Asp Ile Val Lys Ile Ala Gly Asn Ile Gly Gly Ala Gln
        290                 295                 300

Ala Leu Tyr Ser Val Leu Asp Val Glu Pro Thr Leu Gly Lys Arg Gly
305                 310                 315                 320

Phe Ser Arg Ala Asp Ile Val Lys Ile Ala Gly Asn Gly Gly Ala
                325                 330                 335

Gln Ala Leu His Thr Val Leu Asp Leu Glu Pro Ala Leu Gly Lys Arg
                340                 345                 350

Gly Phe Ser Arg Ile Asp Ile Val Lys Ile Ala Ala Asn Ile Gly Gly
                355                 360                 365

Ala Gln Ala Leu His Ala Val Leu Asp Leu Gly Pro Thr Leu Arg Glu
        370                 375                 380

Cys Gly Phe Ser Gln Ala Thr Ile Ala Lys Ile Ala Gly Asn Ile Gly
385                 390                 395                 400

Gly Ala Gln Ala Leu Gln Met Val Leu Asp Leu Gly Pro Ala Leu Gly
                405                 410                 415

Lys Arg Gly Phe Ser Gln Ala Thr Ile Ala Lys Ile Ala Gly Asn Ile
                420                 425                 430

Gly Gly Ala Gln Ala Leu Gln Thr Val Leu Asp Leu Glu Pro Ala Leu
        435                 440                 445

Cys Glu Arg Gly Phe Ser Gln Ala Thr Ile Ala Lys Met Ala Gly His
        450                 455                 460

Asp Gly Gly Ala Gln Ala Leu Gln Thr Val Leu Asp Leu Glu Pro Ala
465                 470                 475                 480

Leu Arg Lys Arg Asp Phe Arg Gln Ala Asp Ile Ile Lys Ile Ala Gly
                485                 490                 495

His Asp Gly Gly Ala Gln Ala Leu Gln Ala Val Ile Glu His Gly Pro
                500                 505                 510

Thr Leu Arg Gln His Gly Phe Asn Leu Ala Asp Ile Val Lys Met Ala
        515                 520                 525

Gly Asn Gly Gly Gly Ala Gln Ala Leu Gln Ala Val Leu Asp Leu Lys
        530                 535                 540

Pro Val Leu Asp Glu His Gly Phe Ser Gln Pro Asp Ile Val Lys Met
545                 550                 555                 560
```

```
Ala Gly Asn Ile Gly Gly Ala Gln Ala Leu Gln Ala Val Leu Ser Leu
            565                 570                 575

Gly Pro Ala Leu Arg Glu Arg Gly Phe Ser Gln Pro Asp Ile Val Lys
        580                 585                 590

Ile Ala Gly Asn Ile Gly Gly Ala Gln Ala Leu Gln Ala Val Leu Asp
            595                 600                 605

Leu Glu Leu Thr Leu Val Glu His Gly Phe Ser Gln Ala Asp Ile Val
        610                 615                 620

Lys Ile Ala Gly His Asp Gly Thr Gln Ala Leu His Ala Val Leu
625                 630                 635                 640

Asp Leu Glu Arg Met Leu Gly Glu Arg Gly Phe Ser Arg Ala Asp Ile
            645                 650                 655

Val Asn Val Ala Gly His Asp Gly Gly Ala Gln Ala Leu Lys Ala Val
            660                 665                 670

Leu Glu His Glu Ala Thr Leu Asn Glu Arg Gly Phe Ser Arg Ala Asp
        675                 680                 685

Ile Val Lys Ile Ala Gly His Asp Gly Gly Ala Gln Ala Leu Lys Ala
        690                 695                 700

Val Leu Glu His Glu Ala Thr Leu Asp Glu Arg Gly Phe Ser Arg Ala
705                 710                 715                 720

Asp Ile Val Asn Val Ala Gly Asn Gly Gly Ala Gln Ala Leu Lys
            725                 730                 735

Ala Val Leu Glu His Glu Ala Thr Leu Asn Glu Arg Gly Phe Asn Leu
            740                 745                 750

Thr Asp Ile Val Glu Met Ala Ala His Asp Gly Gly Ala Gln Ala Leu
        755                 760                 765

Lys Ala Val Leu Glu His Gly Pro Thr Leu Arg Gln Arg Gly Leu Ser
770                 775                 780

Leu Ile Asp Ile Val Glu Ile Ala Gly Asn Gly Gly Ala Gln Ala
785                 790                 795                 800

Leu Lys Ala Val Leu Lys Tyr Gly Pro Val Leu Met Gln Ala Gly Arg
            805                 810                 815

Ser Asn Glu Glu Ile Val His Val Ala Ala Arg Arg Gly Gly Ala Gly
            820                 825                 830

Arg Ile Arg Lys Met Val Ala Pro Leu Leu Glu Arg Gln Gly Arg Ser
            835                 840                 845

Ser Ala Asp
    850

<210> SEQ ID NO 287
<211> LENGTH: 18
<212> TYPE: DNA
<213> ORGANISM: artificial sequence
<220> FEATURE:
<223> OTHER INFORMATION: AvrBs3 recognition site

<400> SEQUENCE: 287
atataaacct aaccctct                                                     18

<210> SEQ ID NO 288
<211> LENGTH: 75
<212> TYPE: DNA
<213> ORGANISM: artificial sequence
<220> FEATURE:
<223> OTHER INFORMATION: spacer 01

<400> SEQUENCE: 288
```

```
actagatcaa tcagtcatct aatacaagct actgtactta cgatactaat caacgctata    60
taaacctaac cctct                                                     75

<210> SEQ ID NO 289
<211> LENGTH: 75
<212> TYPE: DNA
<213> ORGANISM: artificial sequence
<220> FEATURE:
<223> OTHER INFORMATION: spacer 02

<400> SEQUENCE: 289
actagatcaa tcagtcatct aatacaagct actgtactta cgatactaac aacgcttata    60
taaacctaac cctct                                                     75

<210> SEQ ID NO 290
<211> LENGTH: 75
<212> TYPE: DNA
<213> ORGANISM: artificial sequence
<220> FEATURE:
<223> OTHER INFORMATION: spacer 03

<400> SEQUENCE: 290
actagatcaa tcagtcatct aatacaagct actgtactta cgatactaca acgcattata    60
taaacctaac cctct                                                     75

<210> SEQ ID NO 291
<211> LENGTH: 75
<212> TYPE: DNA
<213> ORGANISM: artificial sequence
<220> FEATURE:
<223> OTHER INFORMATION: spacer 04

<400> SEQUENCE: 291
actagatcaa tcagtcatct aatacaagct actgtactta cgatactcaa cgcaattata    60
taaacctaac cctct                                                     75

<210> SEQ ID NO 292
<211> LENGTH: 75
<212> TYPE: DNA
<213> ORGANISM: artificial sequence
<220> FEATURE:
<223> OTHER INFORMATION: spacer 05

<400> SEQUENCE: 292
actagatcaa tcagtcatct aatacaagct actgtactta cgataccaac gcatattata    60
taaacctaac cctct                                                     75

<210> SEQ ID NO 293
<211> LENGTH: 75
<212> TYPE: DNA
<213> ORGANISM: artificial sequence
<220> FEATURE:
<223> OTHER INFORMATION: spacer 06

<400> SEQUENCE: 293
actagatcaa tcagtcatct aatacaagct actgtactta cgatacaacg catgattata    60
taaacctaac cctct                                                     75

<210> SEQ ID NO 294
<211> LENGTH: 75
<212> TYPE: DNA
```

```
<213> ORGANISM: artificial sequence
<220> FEATURE:
<223> OTHER INFORMATION: spacer 07

<400> SEQUENCE: 294
actagatcaa tcagtcatct aatacaagct actgtactta cgatcaacgc atgcattata    60
taaacctaac cctct                                                    75

<210> SEQ ID NO 295
<211> LENGTH: 75
<212> TYPE: DNA
<213> ORGANISM: artificial sequence
<220> FEATURE:
<223> OTHER INFORMATION: spacer 08

<400> SEQUENCE: 295
actagatcaa tcagtcatct aatacaagct actgtactta cgacaacgca tgctattata    60
taaacctaac cctct                                                    75

<210> SEQ ID NO 296
<211> LENGTH: 75
<212> TYPE: DNA
<213> ORGANISM: artificial sequence
<220> FEATURE:
<223> OTHER INFORMATION: spacer 09

<400> SEQUENCE: 296
actagatcaa tcagtcatct aatacaagct actgtactta cgcaacgcat gcgtattata    60
taaacctaac cctct                                                    75

<210> SEQ ID NO 297
<211> LENGTH: 75
<212> TYPE: DNA
<213> ORGANISM: artificial sequence
<220> FEATURE:
<223> OTHER INFORMATION: spacer 10

<400> SEQUENCE: 297
actagatcaa tcagtcatct aatacaagct actgtactta ccaacgcatg ccgtattata    60
taaacctaac cctct                                                    75

<210> SEQ ID NO 298
<211> LENGTH: 75
<212> TYPE: DNA
<213> ORGANISM: artificial sequence
<220> FEATURE:
<223> OTHER INFORMATION: spacer 11

<400> SEQUENCE: 298
actagatcaa tcagtcatct aatacaagct actgtactta caacgcatgc tcgtattata    60
taaacctaac cctct                                                    75

<210> SEQ ID NO 299
<211> LENGTH: 75
<212> TYPE: DNA
<213> ORGANISM: artificial sequence
<220> FEATURE:
<223> OTHER INFORMATION: spacer 12

<400> SEQUENCE: 299
actagatcaa tcagtcatct aatacaagct actgtacttc aacgcatgct tcgtattata    60
taaacctaac cctct                                                    75
```

<210> SEQ ID NO 300
<211> LENGTH: 75
<212> TYPE: DNA
<213> ORGANISM: artificial sequence
<220> FEATURE:
<223> OTHER INFORMATION: spacer 12a

<400> SEQUENCE: 300
actagatcaa tcagtcatct aatacaagct actgtacttc aacgcatgct tcatattata    60
taaacctaac cctct                                                    75

<210> SEQ ID NO 301
<211> LENGTH: 75
<212> TYPE: DNA
<213> ORGANISM: artificial sequence
<220> FEATURE:
<223> OTHER INFORMATION: spacer 13

<400> SEQUENCE: 301
actagatcaa tcagtcatct aatacaagct actgtactca acgcatgcat tcgtattata    60
taaacctaac cctct                                                    75

<210> SEQ ID NO 302
<211> LENGTH: 75
<212> TYPE: DNA
<213> ORGANISM: artificial sequence
<220> FEATURE:
<223> OTHER INFORMATION: spacer 14

<400> SEQUENCE: 302
actagatcaa tcagtcatct aatacaagct actgtaccaa cgcatgcaat tcgtattata    60
taaacctaac cctct                                                    75

<210> SEQ ID NO 303
<211> LENGTH: 75
<212> TYPE: DNA
<213> ORGANISM: artificial sequence
<220> FEATURE:
<223> OTHER INFORMATION: spacer 15

<400> SEQUENCE: 303
actagatcaa tcagtcatct aatacaagct actgtacaac gcatgctaat tcgtattata    60
taaacctaac cctct                                                    75

<210> SEQ ID NO 304
<211> LENGTH: 75
<212> TYPE: DNA
<213> ORGANISM: artificial sequence
<220> FEATURE:
<223> OTHER INFORMATION: spacer 16

<400> SEQUENCE: 304
actagatcaa tcagtcatct aatacaagct actgtcaacg catgcctaat tcgtattata    60
taaacctaac cctct                                                    75

<210> SEQ ID NO 305
<211> LENGTH: 75
<212> TYPE: DNA
<213> ORGANISM: artificial sequence
<220> FEATURE:
<223> OTHER INFORMATION: spacer 17

```
<400> SEQUENCE: 305
actagatcaa tcagtcatct aatacaagct actgcaacgc atgcactaat tcgtattata    60
taaacctaac cctct                                                     75

<210> SEQ ID NO 306
<211> LENGTH: 75
<212> TYPE: DNA
<213> ORGANISM: artificial sequence
<220> FEATURE:
<223> OTHER INFORMATION: spacer 18

<400> SEQUENCE: 306
actagatcaa tcagtcatct aatacaagct actcaacgca tgctactaat tcgtattata    60
taaacctaac cctct                                                     75

<210> SEQ ID NO 307
<211> LENGTH: 75
<212> TYPE: DNA
<213> ORGANISM: artificial sequence
<220> FEATURE:
<223> OTHER INFORMATION: spacer 19

<400> SEQUENCE: 307
actagatcaa tcagtcatct aatacaagct accaacgcat gcatactaat tcgtattata    60
taaacctaac cctct                                                     75

<210> SEQ ID NO 308
<211> LENGTH: 75
<212> TYPE: DNA
<213> ORGANISM: artificial sequence
<220> FEATURE:
<223> OTHER INFORMATION: spacer 20

<400> SEQUENCE: 308
actagatcaa tcagtcatct aatacaagct caacgcatgc cgatactaat tcgtattata    60
taaacctaac cctct                                                     75

<210> SEQ ID NO 309
<211> LENGTH: 75
<212> TYPE: DNA
<213> ORGANISM: artificial sequence
<220> FEATURE:
<223> OTHER INFORMATION: spacer 21

<400> SEQUENCE: 309
actagatcaa tcagtcatct aatacaagcc aacgcatgca cgatactaat tcgtattata    60
taaacctaac cctct                                                     75

<210> SEQ ID NO 310
<211> LENGTH: 75
<212> TYPE: DNA
<213> ORGANISM: artificial sequence
<220> FEATURE:
<223> OTHER INFORMATION: spacer 21a

<400> SEQUENCE: 310
actagatcaa tcagtcatct aatacaagca acgcatgcta cgatactaat tcgtattata    60
taaacctaac cctct                                                     75

<210> SEQ ID NO 311
<211> LENGTH: 75
```

```
<212> TYPE: DNA
<213> ORGANISM: artificial sequence
<220> FEATURE:
<223> OTHER INFORMATION: spacer 22

<400> SEQUENCE: 311
actagatcaa tcagtcatct aatacaagca acgcatgcta caatactaat tcgtattata    60
taaacctaac cctct                                                     75

<210> SEQ ID NO 312
<211> LENGTH: 75
<212> TYPE: DNA
<213> ORGANISM: artificial sequence
<220> FEATURE:
<223> OTHER INFORMATION: spacer 23

<400> SEQUENCE: 312
actagatcaa tcagtcatct aatacaacaa cgcatgctta cgatactaat tcgtattata    60
taaacctaac cctct                                                     75

<210> SEQ ID NO 313
<211> LENGTH: 75
<212> TYPE: DNA
<213> ORGANISM: artificial sequence
<220> FEATURE:
<223> OTHER INFORMATION: spacer 24

<400> SEQUENCE: 313
actagatcaa tcagtcatct aatacacaac gcatgcctta cgatactaat tcgtattata    60
taaacctaac cctct                                                     75

<210> SEQ ID NO 314
<211> LENGTH: 75
<212> TYPE: DNA
<213> ORGANISM: artificial sequence
<220> FEATURE:
<223> OTHER INFORMATION: spacer 25

<400> SEQUENCE: 314
actagatcaa tcagtcatct aataccaacg catgcactta cgatactaat tcgtattata    60
taaacctaac cctct                                                     75

<210> SEQ ID NO 315
<211> LENGTH: 75
<212> TYPE: DNA
<213> ORGANISM: artificial sequence
<220> FEATURE:
<223> OTHER INFORMATION: spacer 26

<400> SEQUENCE: 315
actagatcaa tcagtcatct aatacaacgc atgctactta cgatactaat tcgtattata    60
taaacctaac cctct                                                     75

<210> SEQ ID NO 316
<211> LENGTH: 75
<212> TYPE: DNA
<213> ORGANISM: artificial sequence
<220> FEATURE:
<223> OTHER INFORMATION: spacer 27

<400> SEQUENCE: 316
actagatcaa tcagtcatct aatcaacgca tgcgtactta cgatactaat tcgtattata    60
```
taaacctaac cctct    75

<210> SEQ ID NO 317
<211> LENGTH: 75
<212> TYPE: DNA
<213> ORGANISM: artificial sequence
<220> FEATURE:
<223> OTHER INFORMATION: spacer 28

<400> SEQUENCE: 317
actagatcaa tcagtcatct aacaacgcat gctgtactta cgatactaat tcgtattata    60
taaacctaac cctct    75

<210> SEQ ID NO 318
<211> LENGTH: 75
<212> TYPE: DNA
<213> ORGANISM: artificial sequence
<220> FEATURE:
<223> OTHER INFORMATION: spacer 29

<400> SEQUENCE: 318
actagatcaa tcagtcatct acaacgcatg cctgtactta cgatactaat tcgtattata    60
taaacctaac cctct    75

<210> SEQ ID NO 319
<211> LENGTH: 75
<212> TYPE: DNA
<213> ORGANISM: artificial sequence
<220> FEATURE:
<223> OTHER INFORMATION: spacer 29a

<400> SEQUENCE: 319
actagatcaa tcagtcatct caacgcatgc actgtactta cgatactaat tcgtattata    60
taaacctaac cctct    75

<210> SEQ ID NO 320
<211> LENGTH: 75
<212> TYPE: DNA
<213> ORGANISM: artificial sequence
<220> FEATURE:
<223> OTHER INFORMATION: spacer 30

<400> SEQUENCE: 320
actagatcaa tcagtcatct caacgcatgc actatactta cgatactaat tcgtattata    60
taaacctaac cctct    75

<210> SEQ ID NO 321
<211> LENGTH: 75
<212> TYPE: DNA
<213> ORGANISM: artificial sequence
<220> FEATURE:
<223> OTHER INFORMATION: spacer 31

<400> SEQUENCE: 321
actagatcaa tcagtcatcc aacgcatgct actgtactta cgatactaat tcgtattata    60
taaacctaac cctct    75

<210> SEQ ID NO 322
<211> LENGTH: 75
<212> TYPE: DNA
<213> ORGANISM: artificial sequence
<220> FEATURE:
<223> OTHER INFORMATION: spacer 32

<400> SEQUENCE: 322
actagatcaa tcagtcatca acgcatgcgt actgtactta cgatactaat tcgtattata    60
taaacctaac cctct                                                     75

<210> SEQ ID NO 323
<211> LENGTH: 75
<212> TYPE: DNA
<213> ORGANISM: artificial sequence
<220> FEATURE:
<223> OTHER INFORMATION: spacer 33

<400> SEQUENCE: 323
actagatcaa tcagtcacaa cgcatgcgct actgtactta cgatactaat tcgtattata    60
taaacctaac cctct                                                     75

<210> SEQ ID NO 324
<211> LENGTH: 75
<212> TYPE: DNA
<213> ORGANISM: artificial sequence
<220> FEATURE:
<223> OTHER INFORMATION: spacer 34

<400> SEQUENCE: 324
actagatcaa tcagtccaac gcatgcagct actgtactta cgatactaat tcgtattata    60
taaacctaac cctct                                                     75

<210> SEQ ID NO 325
<211> LENGTH: 75
<212> TYPE: DNA
<213> ORGANISM: artificial sequence
<220> FEATURE:
<223> OTHER INFORMATION: spacer 35

<400> SEQUENCE: 325
actagatcaa tcagtcaacg catgcaagct actgtactta cgatactaat tcgtattata    60
taaacctaac cctct                                                     75

<210> SEQ ID NO 326
<211> LENGTH: 75
<212> TYPE: DNA
<213> ORGANISM: artificial sequence
<220> FEATURE:
<223> OTHER INFORMATION: spacer 36

<400> SEQUENCE: 326
actagatcaa tcagcaacgc atgccaagct actgtactta cgatactaat tcgtattata    60
taaacctaac cctct                                                     75

<210> SEQ ID NO 327
<211> LENGTH: 75
<212> TYPE: DNA
<213> ORGANISM: artificial sequence
<220> FEATURE:
<223> OTHER INFORMATION: spacer 37

<400> SEQUENCE: 327
actagatcaa tcagcaacgc atgccaaact actgtactta cgatactaat tcgtattata    60
taaacctaac cctct                                                     75

<210> SEQ ID NO 328

```
<211> LENGTH: 75
<212> TYPE: DNA
<213> ORGANISM: artificial sequence
<220> FEATURE:
<223> OTHER INFORMATION: spacer 38

<400> SEQUENCE: 328
actagatcaa tcacaacgca tgcacaagct actgtactta cgatactaat tcgtattata    60
taaacctaac cctct                                                    75

<210> SEQ ID NO 329
<211> LENGTH: 75
<212> TYPE: DNA
<213> ORGANISM: artificial sequence
<220> FEATURE:
<223> OTHER INFORMATION: spacer 39

<400> SEQUENCE: 329
actagatcaa tccaacgcat gctacaagct actgtactta cgatactaat tcgtattata    60
taaacctaac cctct                                                    75

<210> SEQ ID NO 330
<211> LENGTH: 75
<212> TYPE: DNA
<213> ORGANISM: artificial sequence
<220> FEATURE:
<223> OTHER INFORMATION: spacer 40

<400> SEQUENCE: 330
actagatcaa tcaacgcatg catacaagct actgtactta cgatactaat tcgtattata    60
taaacctaac cctct                                                    75

<210> SEQ ID NO 331
<211> LENGTH: 75
<212> TYPE: DNA
<213> ORGANISM: artificial sequence
<220> FEATURE:
<223> OTHER INFORMATION: spacer 41

<400> SEQUENCE: 331
actagatcaa caacgcatgc aatacaagct actgtactta cgatactaat tcgtattata    60
taaacctaac cctct                                                    75

<210> SEQ ID NO 332
<211> LENGTH: 75
<212> TYPE: DNA
<213> ORGANISM: artificial sequence
<220> FEATURE:
<223> OTHER INFORMATION: spacer 42

<400> SEQUENCE: 332
actagatcac aacgcatgct aatacaagct actgtactta cgatactaat tcgtattata    60
taaacctaac cctct                                                    75

<210> SEQ ID NO 333
<211> LENGTH: 75
<212> TYPE: DNA
<213> ORGANISM: artificial sequence
<220> FEATURE:
<223> OTHER INFORMATION: spacer 43

<400> SEQUENCE: 333
actagatcca acgcatgcct aatacaagct actgtactta cgatactaat tcgtattata    60
```
taaacctaac cctct                                                          75

<210> SEQ ID NO 334
<211> LENGTH: 75
<212> TYPE: DNA
<213> ORGANISM: artificial sequence
<220> FEATURE:
<223> OTHER INFORMATION: spacer 44

<400> SEQUENCE: 334
actagatcaa cgcatgctct aatacaagct actgtactta cgatactaat tcgtattata        60
taaacctaac cctct                                                          75

<210> SEQ ID NO 335
<211> LENGTH: 75
<212> TYPE: DNA
<213> ORGANISM: artificial sequence
<220> FEATURE:
<223> OTHER INFORMATION: spacer 45

<400> SEQUENCE: 335
actagacaac gcatgcatct aatacaagct actgtactta cgatactaat tcgtattata        60
taaacctaac cctct                                                          75

<210> SEQ ID NO 336
<211> LENGTH: 75
<212> TYPE: DNA
<213> ORGANISM: artificial sequence
<220> FEATURE:
<223> OTHER INFORMATION: spacer 46

<400> SEQUENCE: 336
actagcaacg catgccatct aatacaagct actgtactta cgatactaat tcgtattata        60
taaacctaac cctct                                                          75

<210> SEQ ID NO 337
<211> LENGTH: 75
<212> TYPE: DNA
<213> ORGANISM: artificial sequence
<220> FEATURE:
<223> OTHER INFORMATION: spacer 47

<400> SEQUENCE: 337
actacaacgc atgctcatct aatacaagct actgtactta cgatactaat tcgtattata        60
taaacctaac cctct                                                          75

<210> SEQ ID NO 338
<211> LENGTH: 75
<212> TYPE: DNA
<213> ORGANISM: artificial sequence
<220> FEATURE:
<223> OTHER INFORMATION: spacer 48

<400> SEQUENCE: 338
actcaacgca tgcgtcatct aatacaagct actgtactta cgatactaat tcgtattata        60
taaacctaac cctct                                                          75

<210> SEQ ID NO 339
<211> LENGTH: 75
<212> TYPE: DNA
<213> ORGANISM: artificial sequence
<220> FEATURE:

```
<223> OTHER INFORMATION: spacer 49

<400> SEQUENCE: 339
accaacgcat gcagtcatct aatacaagct actgtactta cgatactaat tcgtattata    60
taaacctaac cctct                                                    75

<210> SEQ ID NO 340
<211> LENGTH: 75
<212> TYPE: DNA
<213> ORGANISM: artificial sequence
<220> FEATURE:
<223> OTHER INFORMATION: spacer 50

<400> SEQUENCE: 340
acaacgcatg ccagtcatct aatacaagct actgtactta cgatactaat tcgtattata    60
taaacctaac cctct                                                    75

<210> SEQ ID NO 341
<211> LENGTH: 75
<212> TYPE: DNA
<213> ORGANISM: artificial sequence
<220> FEATURE:
<223> OTHER INFORMATION: spacer 51

<400> SEQUENCE: 341
caacgcatgc tcagtcatct aatacaagct actgtactta cgatactaat tcgtattata    60
taaacctaac cctct                                                    75

<210> SEQ ID NO 342
<211> LENGTH: 75
<212> TYPE: DNA
<213> ORGANISM: artificial sequence
<220> FEATURE:
<223> OTHER INFORMATION: spacer 51a

<400> SEQUENCE: 342
caacgcatgc tcaatcatct aatacaagct actgtactta cgatactaat tcgtattata    60
taaacctaac cctct                                                    75

<210> SEQ ID NO 343
<211> LENGTH: 61
<212> TYPE: DNA
<213> ORGANISM: artificial sequence
<220> FEATURE:
<223> OTHER INFORMATION: TG10RGAr_CNNGN
<220> FEATURE:
<221> NAME/KEY: misc_feature
<222> LOCATION: (29)..(31)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

<400> SEQUENCE: 343
ataagtaacc ataaacaata cacttatcnn ngnataccgt attatataaa cctaaccctc    60
t                                                                   61

<210> SEQ ID NO 344
<211> LENGTH: 17
<212> TYPE: DNA
<213> ORGANISM: artificial sequence
<220> FEATURE:
<223> OTHER INFORMATION: TALE recognition site
```

-continued

```
<400> SEQUENCE: 344
ttgtatgcca atcgaat                                                  17

<210> SEQ ID NO 345
<211> LENGTH: 32
<212> TYPE: DNA
<213> ORGANISM: artificial sequence
<220> FEATURE:
<223> OTHER INFORMATION: Target TG10_CGACGG_NNN
<220> FEATURE:
<221> NAME/KEY: misc_feature
<222> LOCATION: (7)..(9)
<223> OTHER INFORMATION: n is a, c, g, or t

<400> SEQUENCE: 345
cgacggnnng aaactttgta tgccaatcga at                                 32

<210> SEQ ID NO 346
<211> LENGTH: 32
<212> TYPE: DNA
<213> ORGANISM: artificial sequence
<220> FEATURE:
<223> OTHER INFORMATION: Target TG10_CGACGG_1

<400> SEQUENCE: 346
cgacgggctg aaactttgta tgccaatcga at                                 32

<210> SEQ ID NO 347
<211> LENGTH: 32
<212> TYPE: DNA
<213> ORGANISM: artificial sequence
<220> FEATURE:
<223> OTHER INFORMATION: Target TG10_CGACGG_2

<400> SEQUENCE: 347
cgacgggatg aaactttgta tgccaatcga at                                 32

<210> SEQ ID NO 348
<211> LENGTH: 32
<212> TYPE: DNA
<213> ORGANISM: artificial sequence
<220> FEATURE:
<223> OTHER INFORMATION: Target TG10_CGACGG_3

<400> SEQUENCE: 348
cgacggcggg aaactttgta tgccaatcga at                                 32

<210> SEQ ID NO 349
<211> LENGTH: 32
<212> TYPE: DNA
<213> ORGANISM: artificial sequence
<220> FEATURE:
<223> OTHER INFORMATION: Target TG10_CGACGG_4

<400> SEQUENCE: 349
cgacggcatg aaactttgta tgccaatcga at                                 32

<210> SEQ ID NO 350
<211> LENGTH: 32
<212> TYPE: DNA
<213> ORGANISM: artificial sequence
<220> FEATURE:
<223> OTHER INFORMATION: Target TG10_CGACGG_5

<400> SEQUENCE: 350
```

-continued cgacggcccg aaactttgta tgccaatcga at          32

<210> SEQ ID NO 351
<211> LENGTH: 32
<212> TYPE: DNA
<213> ORGANISM: artificial sequence
<220> FEATURE:
<223> OTHER INFORMATION: Target TG10_CGACGG_6

<400> SEQUENCE: 351
cgacggcctg aaactttgta tgccaatcga at          32

<210> SEQ ID NO 352
<211> LENGTH: 32
<212> TYPE: DNA
<213> ORGANISM: artificial sequence
<220> FEATURE:
<223> OTHER INFORMATION: Target TG10_CGACGG_7

<400> SEQUENCE: 352
cgacggcgtg aaactttgta tgccaatcga at          32

<210> SEQ ID NO 353
<211> LENGTH: 32
<212> TYPE: DNA
<213> ORGANISM: artificial sequence
<220> FEATURE:
<223> OTHER INFORMATION: Target TG10_CGACGG_8

<400> SEQUENCE: 353
cgacggggtg aaactttgta tgccaatcga at          32

<210> SEQ ID NO 354
<211> LENGTH: 32
<212> TYPE: DNA
<213> ORGANISM: artificial sequence
<220> FEATURE:
<223> OTHER INFORMATION: Target TG10_CGACGG_9

<400> SEQUENCE: 354
cgacgggcgg aaactttgta tgccaatcga at          32

<210> SEQ ID NO 355
<211> LENGTH: 32
<212> TYPE: DNA
<213> ORGANISM: artificial sequence
<220> FEATURE:
<223> OTHER INFORMATION: Target TG10_CGACGG_10

<400> SEQUENCE: 355 cgacggggg aaactttgta tgccaatcga at          32

<210> SEQ ID NO 356
<211> LENGTH: 32
<212> TYPE: DNA
<213> ORGANISM: artificial sequence
<220> FEATURE:
<223> OTHER INFORMATION: Target TG10_CGACGG_11

<400> SEQUENCE: 356
cgacggctcg aaactttgta tgccaatcga at          32

<210> SEQ ID NO 357
<211> LENGTH: 32
<212> TYPE: DNA
<213> ORGANISM: artificial sequence

```
<220> FEATURE:
<223> OTHER INFORMATION: Target TG10_CGACGG_12

<400> SEQUENCE: 357 cgacggggttg aaactttgta tgccaatcga at                                    32

<210> SEQ ID NO 358
<211> LENGTH: 32
<212> TYPE: DNA
<213> ORGANISM: artificial sequence
<220> FEATURE:
<223> OTHER INFORMATION: Target TG10_CGACGG_13

<400> SEQUENCE: 358
cgacggcagg aaactttgta tgccaatcga at                                     32

<210> SEQ ID NO 359
<211> LENGTH: 32
<212> TYPE: DNA
<213> ORGANISM: artificial sequence
<220> FEATURE:
<223> OTHER INFORMATION: Target TG10_CGACGG_14

<400> SEQUENCE: 359
cgacgggagg aaactttgta tgccaatcga at                                     32

<210> SEQ ID NO 360
<211> LENGTH: 32
<212> TYPE: DNA
<213> ORGANISM: artificial sequence
<220> FEATURE:
<223> OTHER INFORMATION: Target TG10_CGACGG_15

<400> SEQUENCE: 360
cgacggcacg aaactttgta tgccaatcga at                                     32

<210> SEQ ID NO 361
<211> LENGTH: 32
<212> TYPE: DNA
<213> ORGANISM: artificial sequence
<220> FEATURE:
<223> OTHER INFORMATION: Target TG10_CGACGG_16

<400> SEQUENCE: 361
cgacggctag aaactttgta tgccaatcga at                                     32

<210> SEQ ID NO 362
<211> LENGTH: 32
<212> TYPE: DNA
<213> ORGANISM: artificial sequence
<220> FEATURE:
<223> OTHER INFORMATION: Target TG10_CGACGG_17

<400> SEQUENCE: 362
cgacgggacg aaactttgta tgccaatcga at                                     32

<210> SEQ ID NO 363
<211> LENGTH: 32
<212> TYPE: DNA
<213> ORGANISM: artificial sequence
<220> FEATURE:
<223> OTHER INFORMATION: Target TG10_CGACGG_18

<400> SEQUENCE: 363
cgacggctgg aaactttgta tgccaatcga at                                     32
```

<210> SEQ ID NO 364
<211> LENGTH: 32
<212> TYPE: DNA
<213> ORGANISM: artificial sequence
<220> FEATURE:
<223> OTHER INFORMATION: Target TG10_CGACGG_19

<400> SEQUENCE: 364
cgacggcgcg aaactttgta tgccaatcga at                                    32

<210> SEQ ID NO 365
<211> LENGTH: 32
<212> TYPE: DNA
<213> ORGANISM: artificial sequence
<220> FEATURE:
<223> OTHER INFORMATION: Target TG10_CGACGG_20

<400> SEQUENCE: 365
cgacggccag aaactttgta tgccaatcga at                                    32

<210> SEQ ID NO 366
<211> LENGTH: 32
<212> TYPE: DNA
<213> ORGANISM: artificial sequence
<220> FEATURE:
<223> OTHER INFORMATION: Target TG10_CGACGG_21

<400> SEQUENCE: 366
cgacggccgg aaactttgta tgccaatcga at                                    32

<210> SEQ ID NO 367
<211> LENGTH: 32
<212> TYPE: DNA
<213> ORGANISM: artificial sequence
<220> FEATURE:
<223> OTHER INFORMATION: Target TG10_CGACGG_22

<400> SEQUENCE: 367
cgacgggcag aaactttgta tgccaatcga at                                    32

<210> SEQ ID NO 368
<211> LENGTH: 32
<212> TYPE: DNA
<213> ORGANISM: artificial sequence
<220> FEATURE:
<223> OTHER INFORMATION: Target TG10_CGACGG_23

<400> SEQUENCE: 368
cgacggcgag aaactttgta tgccaatcga at                                    32

<210> SEQ ID NO 369
<211> LENGTH: 32
<212> TYPE: DNA
<213> ORGANISM: artificial sequence
<220> FEATURE:
<223> OTHER INFORMATION: Target TG10_CGACGG_24

<400> SEQUENCE: 369 cgacgggag aaactttgta tgccaatcga at                                     32

<210> SEQ ID NO 370
<211> LENGTH: 32
<212> TYPE: DNA
<213> ORGANISM: artificial sequence
<220> FEATURE:
<223> OTHER INFORMATION: Target TG10_CGACGG_25

<400> SEQUENCE: 370
cgacggattg aaactttgta tgccaatcga at                                32

<210> SEQ ID NO 371
<211> LENGTH: 32
<212> TYPE: DNA
<213> ORGANISM: artificial sequence
<220> FEATURE:
<223> OTHER INFORMATION: Target TG10_CGACGG_26

<400> SEQUENCE: 371
cgacgggtcg aaactttgta tgccaatcga at                                32

<210> SEQ ID NO 372
<211> LENGTH: 32
<212> TYPE: DNA
<213> ORGANISM: artificial sequence
<220> FEATURE:
<223> OTHER INFORMATION: Target TG10_CGACGG_27

<400> SEQUENCE: 372
cgacgggtgg aaactttgta tgccaatcga at                                32

<210> SEQ ID NO 373
<211> LENGTH: 32
<212> TYPE: DNA
<213> ORGANISM: artificial sequence
<220> FEATURE:
<223> OTHER INFORMATION: Target TG10_CGACGG_28

<400> SEQUENCE: 373
cgacgggtag aaactttgta tgccaatcga at                                32

<210> SEQ ID NO 374
<211> LENGTH: 32
<212> TYPE: DNA
<213> ORGANISM: artificial sequence
<220> FEATURE:
<223> OTHER INFORMATION: Target TG10_CGACGG_29

<400> SEQUENCE: 374
cgacggtatg aaactttgta tgccaatcga at                                32

<210> SEQ ID NO 375
<211> LENGTH: 32
<212> TYPE: DNA
<213> ORGANISM: artificial sequence
<220> FEATURE:
<223> OTHER INFORMATION: Target TG10_CGACGG_30

<400> SEQUENCE: 375
cgacggtttg aaactttgta tgccaatcga at                                32

<210> SEQ ID NO 376
<211> LENGTH: 32
<212> TYPE: DNA
<213> ORGANISM: artificial sequence
<220> FEATURE:
<223> OTHER INFORMATION: Target TG10_CGACGG_31

<400> SEQUENCE: 376
cgacgggaag aaactttgta tgccaatcga at                                32

<210> SEQ ID NO 377

```
<210> SEQ ID NO 377
<211> LENGTH: 32
<212> TYPE: DNA
<213> ORGANISM: artificial sequence
<220> FEATURE:
<223> OTHER INFORMATION: Target TG10_CGACGG_32

<400> SEQUENCE: 377
cgacggcaag aaactttgta tgccaatcga at                                    32

<210> SEQ ID NO 378
<211> LENGTH: 32
<212> TYPE: DNA
<213> ORGANISM: artificial sequence
<220> FEATURE:
<223> OTHER INFORMATION: Target TG10_CGACGG_33

<400> SEQUENCE: 378
cgacggatcg aaactttgta tgccaatcga at                                    32

<210> SEQ ID NO 379
<211> LENGTH: 32
<212> TYPE: DNA
<213> ORGANISM: artificial sequence
<220> FEATURE:
<223> OTHER INFORMATION: Target TG10_CGACGG_34

<400> SEQUENCE: 379
cgacggaatg aaactttgta tgccaatcga at                                    32

<210> SEQ ID NO 380
<211> LENGTH: 32
<212> TYPE: DNA
<213> ORGANISM: artificial sequence
<220> FEATURE:
<223> OTHER INFORMATION: Target TG10_CGACGG_35

<400> SEQUENCE: 380
cgacggatag aaactttgta tgccaatcga at                                    32

<210> SEQ ID NO 381
<211> LENGTH: 32
<212> TYPE: DNA
<213> ORGANISM: artificial sequence
<220> FEATURE:
<223> OTHER INFORMATION: Target TG10_CGACGG_36

<400> SEQUENCE: 381
cgacggactg aaactttgta tgccaatcga at                                    32

<210> SEQ ID NO 382
<211> LENGTH: 32
<212> TYPE: DNA
<213> ORGANISM: artificial sequence
<220> FEATURE:
<223> OTHER INFORMATION: Target TG10_CGACGG_37

<400> SEQUENCE: 382
cgacggttag aaactttgta tgccaatcga at                                    32

<210> SEQ ID NO 383
<211> LENGTH: 32
<212> TYPE: DNA
<213> ORGANISM: artificial sequence
<220> FEATURE:
<223> OTHER INFORMATION: Target TG10_CGACGG_38

<400> SEQUENCE: 383
```
cgacggtacg aaactttgta tgccaatcga at                              32

<210> SEQ ID NO 384
<211> LENGTH: 32
<212> TYPE: DNA
<213> ORGANISM: artificial sequence
<220> FEATURE:
<223> OTHER INFORMATION: Target TG10_CGACGG_39

<400> SEQUENCE: 384
cgacggatgg aaactttgta tgccaatcga at                              32

<210> SEQ ID NO 385
<211> LENGTH: 32
<212> TYPE: DNA
<213> ORGANISM: artificial sequence
<220> FEATURE:
<223> OTHER INFORMATION: Target TG10_CGACGG_40

<400> SEQUENCE: 385
cgacggttgg aaactttgta tgccaatcga at                              32

<210> SEQ ID NO 386
<211> LENGTH: 32
<212> TYPE: DNA
<213> ORGANISM: artificial sequence
<220> FEATURE:
<223> OTHER INFORMATION: Target TG10_CGACGG_41

<400> SEQUENCE: 386
cgacggaccg aaactttgta tgccaatcga at                              32

<210> SEQ ID NO 387
<211> LENGTH: 32
<212> TYPE: DNA
<213> ORGANISM: artificial sequence
<220> FEATURE:
<223> OTHER INFORMATION: Target TG10_CGACGG_42

<400> SEQUENCE: 387
cgacggacgg aaactttgta tgccaatcga at                              32

<210> SEQ ID NO 388
<211> LENGTH: 32
<212> TYPE: DNA
<213> ORGANISM: artificial sequence
<220> FEATURE:
<223> OTHER INFORMATION: Target TG10_CGACGG_43

<400> SEQUENCE: 388
cgacggttcg aaactttgta tgccaatcga at                              32

<210> SEQ ID NO 389
<211> LENGTH: 32
<212> TYPE: DNA
<213> ORGANISM: artificial sequence
<220> FEATURE:
<223> OTHER INFORMATION: Target TG10_CGACGG_44

<400> SEQUENCE: 389
cgacggtagg aaactttgta tgccaatcga at                              32

<210> SEQ ID NO 390
<211> LENGTH: 32
<212> TYPE: DNA

```
<213> ORGANISM: artificial sequence
<220> FEATURE:
<223> OTHER INFORMATION: Target TG10_CGACGG_45

<400> SEQUENCE: 390
cgacggtgtg aaactttgta tgccaatcga at                          32

<210> SEQ ID NO 391
<211> LENGTH: 32
<212> TYPE: DNA
<213> ORGANISM: artificial sequence
<220> FEATURE:
<223> OTHER INFORMATION: Target TG10_CGACGG_46

<400> SEQUENCE: 391
cgacggagtg aaactttgta tgccaatcga at                          32

<210> SEQ ID NO 392
<211> LENGTH: 32
<212> TYPE: DNA
<213> ORGANISM: artificial sequence
<220> FEATURE:
<223> OTHER INFORMATION: Target TG10_CGACGG_47

<400> SEQUENCE: 392
cgacggtggg aaactttgta tgccaatcga at                          32

<210> SEQ ID NO 393
<211> LENGTH: 32
<212> TYPE: DNA
<213> ORGANISM: artificial sequence
<220> FEATURE:
<223> OTHER INFORMATION: Target TG10_CGACGG_48

<400> SEQUENCE: 393
cgacggaagg aaactttgta tgccaatcga at                          32

<210> SEQ ID NO 394
<211> LENGTH: 32
<212> TYPE: DNA
<213> ORGANISM: artificial sequence
<220> FEATURE:
<223> OTHER INFORMATION: Target TG10_CGACGG_49

<400> SEQUENCE: 394
cgacggtcag aaactttgta tgccaatcga at                          32

<210> SEQ ID NO 395
<211> LENGTH: 32
<212> TYPE: DNA
<213> ORGANISM: artificial sequence
<220> FEATURE:
<223> OTHER INFORMATION: Target TG10_CGACGG_50

<400> SEQUENCE: 395
cgacggaaag aaactttgta tgccaatcga at                          32

<210> SEQ ID NO 396
<211> LENGTH: 32
<212> TYPE: DNA
<213> ORGANISM: artificial sequence
<220> FEATURE:
<223> OTHER INFORMATION: Target TG10_CGACGG_51

<400> SEQUENCE: 396
cgacggaacg aaactttgta tgccaatcga at                          32
```

<210> SEQ ID NO 397
<211> LENGTH: 32
<212> TYPE: DNA
<213> ORGANISM: artificial sequence
<220> FEATURE:
<223> OTHER INFORMATION: Target TG10_CGACGG_52

<400> SEQUENCE: 397
cgacggtgtg aaactttgta tgccaatcga at            32

<210> SEQ ID NO 398
<211> LENGTH: 32
<212> TYPE: DNA
<213> ORGANISM: artificial sequence
<220> FEATURE:
<223> OTHER INFORMATION: Target TG10_CGACGG_53

<400> SEQUENCE: 398
cgacggtcgg aaactttgta tgccaatcga at            32

<210> SEQ ID NO 399
<211> LENGTH: 32
<212> TYPE: DNA
<213> ORGANISM: artificial sequence
<220> FEATURE:
<223> OTHER INFORMATION: Target TG10_CGACGG_54

<400> SEQUENCE: 399
cgacggtccg aaactttgta tgccaatcga at            32

<210> SEQ ID NO 400
<211> LENGTH: 32
<212> TYPE: DNA
<213> ORGANISM: artificial sequence
<220> FEATURE:
<223> OTHER INFORMATION: Target TG10_CGACGG_55

<400> SEQUENCE: 400
cgacggtaag aaactttgta tgccaatcga at            32

<210> SEQ ID NO 401
<211> LENGTH: 32
<212> TYPE: DNA
<213> ORGANISM: artificial sequence
<220> FEATURE:
<223> OTHER INFORMATION: Target TG10_CGACGG_56

<400> SEQUENCE: 401
cgacggtgag aaactttgta tgccaatcga at            32

<210> SEQ ID NO 402
<211> LENGTH: 32
<212> TYPE: DNA
<213> ORGANISM: artificial sequence
<220> FEATURE:
<223> OTHER INFORMATION: Target TG10_CGACGG_57

<400> SEQUENCE: 402
cgacggagag aaactttgta tgccaatcga at            32

<210> SEQ ID NO 403
<211> LENGTH: 32
<212> TYPE: DNA
<213> ORGANISM: artificial sequence
<220> FEATURE:

<223> OTHER INFORMATION: Target TG10_CGACGG_58

<400> SEQUENCE: 403
cgacggagcg aaactttgta tgccaatcga at        32

<210> SEQ ID NO 404
<211> LENGTH: 32
<212> TYPE: DNA
<213> ORGANISM: artificial sequence
<220> FEATURE:
<223> OTHER INFORMATION: Target TG10_CGACGG_59

<400> SEQUENCE: 404
cgacggtgcg aaactttgta tgccaatcga at        32

<210> SEQ ID NO 405
<211> LENGTH: 1590
<212> TYPE: DNA
<213> ORGANISM: artificial sequence
<220> FEATURE:
<223> OTHER INFORMATION: RVD_NNNT01g10

<400> SEQUENCE: 405 ttgaccccc  agcaggtggt ggccatcgcc agcaatggcg gtggcaagca ggcgctggag      60
acggtccagc ggctgttgcc ggtgctgtgc caggcccacg gcttgacccc ccagcaggtg     120
gtggccatcg ccagcaataa tggtggcaag caggcgctgg agacggtcca gcggctgttg     180
ccggtgctgt gccaggccca cggcttgacc cccagcagg tggtggccat cgccagcaat     240
ggcggtggca agcaggcgct ggagacggtc agcggctgt tgccggtgct gtgccaggcc     300
cacggcttga ccccggagca ggtggtggcc atcgccagca atattggtgg caagcaggcg     360
ctggagacgg tgcaggcgct gttgccggtg ctgtgccagg cccacggctt gaccccccag     420
caggtggtgg ccatcgccag caatggcggt ggcaagcagg cgctggagac ggtccagcgg     480
ctgttgccgg tgctgtgcca ggcccacggc ttgaccccc  agcaggtggt ggccatcgcc     540
agcaataatg gtggcaagca ggcgctggag acggtccagc ggctgttgcc ggtgctgtgc     600
caggcccacg gcttgacccc ggagcaggtg gtggccatcg ccagccacga tgcggcaag     660
caggcgctgg agacggtcca gcggctgttg ccggtgctgt gccaggccca cggcttgacc     720
ccggagcagg tggtggccat cgccagccac gatggcggca agcaggcgct ggagacggtc     780
agcggctgt tgccggtgct gtgccaggcc cacggcttga ccccggagca ggtggtggcc     840
atcgccagca atattggtgg caagcaggcg ctggagacgg tgcaggcgct gttgccggtg     900
ctgtgccagg cccacggctt gaccccggag caggtggtgg ccatcgccag caatattggt     960
ggcaagcagg cgctggagac ggtgcaggcg ctgttgccgg tgctgtgcca ggcccacggc    1020
ttgaccccc  agcaggtggt ggccatcgcc agcaatggcg gtggcaagca ggcgctggag    1080
acggtccagc ggctgttgcc ggtgctgtgc caggcccacg gcttgacccc ggagcaggtg    1140
gtggccatcg ccagccacga tggcggcaag caggcgctgg agacggtcca gcggctgttg    1200
ccggtgctgt gccaggccca cggcttgacc cccagcagg tggtggccat cgccagcaat    1260
aatggtggca agcaggcgct ggagacggtc agcggctgt tgccggtgct gtgccaggcc    1320
cacggcttga ccccggagca ggtggtggcc atcgccagca atattggtgg caagcaggcg    1380
ctggagacgg tgcaggcgct gttgccggtg ctgtgccagg cccacggctt gaccccggag    1440
caggtggtgg ccatcgccag caatattggt ggcaagcagg cgctggagac ggtgcaggcg    1500
ctgttgccgg tgctgtgcca ggcccacggc ttgaccccctc agcaggtggt ggccatcgcc    1560

```
                                                                    -continued agcaatggcg gcggcaggcc ggcgctggag                                       1590

<210> SEQ ID NO 406
<211> LENGTH: 9213
<212> TYPE: DNA
<213> ORGANISM: artificial sequence
<220> FEATURE:
<223> OTHER INFORMATION: pCLS20649

<400> SEQUENCE: 406
atgtgagcaa aaggccagca aaaggccagg aaccgtaaaa aggccgcgtt gctggcgttt      60
ttccataggc tccgcccccc tgacgagcat cacaaaaatc gacgctcaag tcagaggtgg     120
cgaaacccga caggactata aagataccag gcgtttcccc ctggaagctc cctcgtgcgc     180
tctcctgttc cgaccctgcc gcttaccgga tacctgtccg cctttctccc ttcgggaagc     240
gtggcgcttt ctcatagctc acgctgtagg tatctcagtt cggtgtaggt cgttcgctcc     300
aagctgggct gtgtgcacga accccccgtt cagcccgacc gctgcgcctt atccggtaac     360
tatcgtcttg agtccaaccc ggtaagacac gacttatcgc cactggcagc agccactggt     420
aacaggatta gcagagcgag gtatgtaggc ggtgctacag agttcttgaa gtggtggcct     480
aactacggct acactagaag gacagtattt ggtatctgcg ctctgctgaa gccagttacc     540
ttcggaaaaa gagttggtag ctcttgatcc ggcaaacaaa ccaccgctgg tagcggtggt     600 tttttttgttt gcaagcagca gattacgcgc agaaaaaaag gatctcaaga agatcctttg     660
atcttttcta cggggtctga cgctcagtgg aacgaaaact cacgttaagg gattttggtc     720
atgagattat caaaaaggat cttcacctag atccttttaa attaaaaatg aagttttaaa     780
tcaatctaaa gtatatatga gtaaacttgg tctgacagtt accaatgctt aatcagtgag     840
gcacctatct cagcgatctg tctatttcgt tcatccatag ttgcctgact ccccgtcgtg     900
tagataacta cgatacggga gggcttacca tctggcccca gtgctgcaat gataccgcga     960
gacccacgct caccggctcc agatttatca gcaataaacc agccagccgg aagggccgag    1020
cgcagaagtg gtcctgcaac tttatccgcc tccatccagt ctattaattg ttgccgggaa    1080
gctagagtaa gtagttcgcc agttaatagt ttgcgcaacg ttgttgccat tgctacaggc    1140
atcgtggtgt cacgctcgtc gtttggtatg gcttcattca gctccggttc caacgatca    1200 aggcgagtta catgatcccc catgttgtgc aaaaaagcgg ttagctcctt cggtcctccg    1260
atcgttgtca agtaagtt ggccgcagtg ttatcactca tggttatggc agcactgcat    1320
aattctctta ctgtcatgcc atccgtaaga tgcttttctg tgactggtga gtactcaacc    1380
aagtcattct gagaatagtg tatgcggcga ccgagttgct cttgcccggc gtcaatacgg    1440
gataataccg cgccacatag cagaacttta aaagtgctca tcattggaaa acgttcttcg    1500
gggcgaaaac tctcaaggat cttaccgctg ttgagatcca gttcgatgta acccactcgt    1560
gcacccaact gatcttcagc atcttttact ttcaccagcg tttctgggtg agcaaaaaca    1620
ggaaggcaaa atgccgcaaa aaagggaata agggcgacac ggaaatgttg aatactcata    1680
ctcttccttt ttcaatatta ttgaagcatt tatcagggtt attgtctcat gagcggatac    1740
atatttgaat gtatttagaa aaataaacaa ataggggttc cgcgcacatt tccccgaaaa    1800
gtgccacctg acgtccgatc aaaaatcatc gcttcgctga ttaattaccc cagaaataag    1860
gctaaaaaac taatcgcatt atcatcctat ggttgttaat ttgattcgtt catttgaagg    1920
tttgtggggc caggttactg ccaattttc ctcttcataa ccataaaagc tagtattgta    1980
```

```
gaatctttat tgttcggagc agtgcggcgc gaggcacatc tgcgtttcag gaacgcgacc    2040
ggtgaagacg aggacgcacg gaggagagtc ttccttcgga gggctgtcac ccgctcggcg    2100
gcttctaatc cgtacttcaa tatagcaatg agcagttaag cgtattactg aaagttccaa    2160
agagaaggtt ttttaggct aatcgacctc gagcagatcc gccaggcgtg tatatagcgt     2220
ggatggccag gcaactttag tgctgacaca tacaggcata tatatatgtg tgcgacgaca    2280
catgatcata tggcatgcat gtgctctgta tgtatataaa actcttgttt tcttcttttc    2340
tctaaatatt ctttccttat acattaggtc ctttgtagca taaattacta tacttctata    2400
gacacgcaaa cacaaataca cagcggcctt gccaccatgg ccaagtctgg catctaccag    2460
attaagaaca ccctgaataa caaagtgtat gttggatctg ccaaggactt tgagaaaaga    2520
tggaagaggc acttcaagga tctggaaaag ggttgccaca gctccatcaa gctccaaagg    2580
tctttcaaca aacatggcaa tgtctttgag tgctccattt tggaagagat cccttatgaa    2640
aaggacctca ttatagagag ggaaaacttc tggatcaagg agctgaactc aaaaatcaat    2700
ggatacaaca ttgcagatgc cacatttggt gacacctgtt ctactcaccc ccttaaggaa    2760
gagatcatta aaaagaggtc tgagactgtg aaggctaaga tgttgaaact ggggcctgat    2820
ggcagaaagg cactctactc taagccaggt tccggagtgg atctacgcac gctcggctac    2880
agccagcagc aacaggagaa gatcaaaccg aaggttcgtt cgacagtggc gcagcaccac    2940
gaggcactgg tcggcacgg gtttacacac gcgcacatcg ttgcgttaag ccaacacccg    3000
gcagcgttag ggaccgtcgc tgtcaagtat caggacatga tcgcagcgtt gccagaggcg    3060
acacacgaag cgatcgttgg cgtcggcaaa cagtggtccg cgcacgcgc tctggaggcc     3120
ttgctcacgg tggcgggaga gttgagaggt ccaccgttac agttggacac aggccaactt    3180
ctcaagattg caaacgtgg cggcgtgacc gcagtggagg cagtgcatgc atggcgcaat    3240
gcactgacgg gtgccccgct caacttgacc ggagacgccc gggggatcag gtcacgtgcg    3300
tctcggagca ttgttgccca gttatctcgc cctgatccgt cggccgactg ataactcgag    3360
cgatcctcta gacgagctcc tcgagcctgc agcagctgaa gctttggact tcttcgccag    3420
aggtttggtc aagtctccaa tcaaggttgt cggcttgtct accttgccag aaatttacga    3480
aaagatggaa aagggtcaaa tcgttggtag atacgttgtt gacacttcta ataagcgaa     3540
tttcttatga tttatgattt ttattattaa ataagttata aaaaaaataa gtgtatacaa    3600
attttaaagt gactcttagg ttttaaaacg aaaattctta ttcttgagta actcttttcct   3660
gtaggtcagg ttgctttctc aggtatagca tgaggtcgct cttattgacc acacctctac    3720
cggcatgcaa gcttggcgta atcatggtca tagctgtttc ctgtgtgaaa ttgttatccg    3780
ctcacaattc cacacaacat acgagccgga agcataaagt gtaaagcctg gggtgcctaa    3840
tgagtgagct aactcacatt aattgcgttg cgctcactgc ccgctttcca gtcgggaaac    3900
ctgtcgtgcc agcagatcta ttacattatg ggtggtatgt tggaataaaa atcaactatc    3960
atctactaac tagtatttac gttactagta tattatcata tacggtgtta aagatgacg     4020
caaatgatga gaaatagtca tctaaattag tggaagctga aacgcaagga ttgataatgt    4080
aataggatca atgaatatta acatataaaa tgatgataat aatatttata gaattgtgta    4140
gaattgcaga ttcccttta tggattccta atcctcgag gagaacttct agtatatcta     4200
catacctaat attattgcct tattaaaaat ggaatcccaa caattacatc aaaatccaca    4260
ttctcttcaa aatcaattgt cctgtacttc cttgttcatg tgtgttcaaa aacgttatat    4320
ttataggata attatactct atttctcaac aagtaattgg ttgtttggcc gagcggtcta    4380
```

```
aggcgcctga ttcaagaaat atcttgaccg cagttaactg tgggaatact caggtatcgt    4440
aagatgcaag agttcgaatc tcttagcaac cattattttt ttcctcaaca taacgagaac    4500 acacagggc gctatcgcac agaatcaaat tcgatgactg gaaattttt gttaatttca      4560 gaggtcgcct gacgcatata cctttttcaa ctgaaaaatt gggagaaaaa ggaaggtga     4620 gagccgcgga accggctttt catatagaat agagaagcgt tcatgactaa atgcttgcat    4680
cacaatactt gaagttgaca atattattta aggacctatt gttttttcca ataggtggtt    4740
agcaatcgtc ttactttcta acttttctta ccttttacat ttcagcaata tatatatata    4800
tatttcaagg ataccatt ctaatgtctg cccctaagaa gatcgtcgtt ttgccaggtg      4860
accacgttgg tcaagaaatc acagccgaag ccattaaggt tcttaaagct atttctgatg    4920
ttcgttccaa tgtcaagttc gatttcgaaa atcatttaat tggtggtgct gctatcgatg    4980
ctacaggtgt cccacttcca gatgaggcgc tggaagcctc caagaaggtt gatgccgttt    5040
tgttaggtgc tgtgggtggt cctaaatggg gtaccggtag tgttagacct gaacaaggtt    5100
tactaaaaat ccgtaaagaa cttcaattgt acgccaactt aagaccatgt aactttgcat    5160
ccgactctct tttagactta tctccaatca agccacaatt tgctaaaggt actgacttcg    5220
ttgttgtcag agaattagtg ggaggtattt actttggtaa gagaaaggaa gacgatggtg    5280
atggtgtcgc ttgggatagt gaacaataca ccgttccaga agtgcaaaga atcacaagaa    5340
tggccgcttt catggcccta caacatgagc caccattgcc tatttggtcc ttggataaag    5400
ctaatgtttt ggcctcttca agattatgga gaaaaactgt ggaggaaacc atcaagaacg    5460
aattccctac attgaaggtt caacatcaat tgattgattc tgccgccatg atcctagtta    5520
agaacccaac ccacctaaat ggtattataa tcaccagcaa catgtttggt gatatcatct    5580
ccgatgaagc ctccgttatc ccaggttcct tgggtttgtt gccatctgcg tccttggcct    5640
ctttgccaga caagaacacc gcatttggtt tgtacgaacc atgccacggt tctgctccag    5700
atttgccaaa gaataaggtc aaccctatcg ccactatctt gtctgctgca atgatgttga    5760
aattgtcatt gaacttgcct gaagaaggta aggccattga agatgcagtt aaaaaggttt    5820
tggatgcagg tatcagaact ggtgatttag gtggttccaa cagtaccacg gaagtcggtg    5880
atgctgtcgc cgaagaagtt aagaaaatcc ttgcttaaaa agattctctt ttttatgat     5940 atttgtacat aaactttata aatgaaattc ataatagaaa cgacacgaaa ttacaaaatg    6000
gaatatgttc ataggtagac gaaactata tacgcaatct acatacattt atcaagaagg     6060 agaaaagga ggatgtaaag gaatacaggt aagcaaattg atactaatgg ctcaacgtga     6120
taaggaaaaa gaattgcact ttaacattaa tattgacaag gaggagggca ccacacaaaa    6180
agttaggtgt aacagaaaat catgaaacta tgattcctaa tttatatatt ggaggatttt    6240
ctctaaaaaa aaaaaatac aacaaataaa aaacactcaa tgacctgacc atttgatgga    6300
gtttaagtca ataccttctt gaaccatttc ccataatggt gaaagttccc tcaagaattt    6360
tactctgtca gaaacggcct taacgacgta gtcgacctcc tcttcagtac taaatctacc    6420 ataccaaat ctgatggaag aatgggctaa tgcatcatcc ttacccagcg catgtaaaac    6480
ataagaaggt tctagggaag cagatgtaca ggctgaaccc gaggataatg cgatatccct    6540
tagtgccatc aataaagatt ctccttccac gtaggcgaaa gaaacgttaa cacaccctgg    6600
ataacgatga tctggagatc cgttcaacgt ggtatgttca gcggataata gacctttgac    6660
taatttatcg gatagtcttt tgatgtgagc ttggtcgttg tcaaattctt tcttcatcaa    6720
```

```
tctcgcagct tcaccaaatc ccgctaccaa tgggggggcc aaagtaccag atctgctgca    6780
ttaatgaatc ggccaacgcg cggggagagg cggtttgcgt attgggcgct cttccgcttc    6840
ctcgctcact gactcgctgc gctcggtcgt tcggctgcgg cgagcggtat cagcatcgat    6900
gaattccacg gactatagac tatactagta tactccgtct actgtacgat acacttccgc    6960
tcaggtcctt gtcctttaac gaggccttac cactcttttg ttactctatt gatccagctc    7020
agcaaaggca gtgtgatcta agattctatc ttcgcgatgt agtaaaacta gctagaccga    7080
gaaagagact agaaatgcaa aaggcacttc tacaatggct gccatcatta ttatccgatg    7140
tgacgctgca gcttctcaat gatattcgaa tacgctttga ggagatacag cctaatatcc    7200
gacaaactgt tttacagatt tacgatcgta cttgttaccc atcattgaat tttgaacatc    7260
cgaacctggg agttttccct gaaacagata gtatatttga acctgtataa taatatatag    7320
tctagcgctt tacggaagac aatgtatgta tttcggttcc tggagaaact attgcatcta    7380
ttgcataggt aatcttgcac gtcgcatccc cggttcattt tctgcgtttc catcttgcac    7440
ttcaatagca tatctttgtt aacgaagcat ctgtgcttca ttttgtagaa caaaaatgca    7500
acgcgagagc gctaattttt caaacaaaga atctgagctg cattttttaca gaacagaaat    7560
gcaacgcgaa agcgctattt taccaacgaa gaatctgtgc ttcattttttg taaaacaaaa    7620
atgcaacgcg agagcgctaa tttttcaaac aaagaatctg agctgcattt ttacagaaca    7680
gaaatgcaac gcgagagcgc tattttacca acaaagaatc tatacttctt ttttgttcta    7740
caaaaatgca tcccgagagc gctattttttc taacaaagca tcttagatta cttttttttct    7800
cctttgtgcg ctctataatg cagtctcttg ataactttttt gcactgtagg tccgttaagg    7860
ttagaagaag gctactttgg tgtctatttt ctcttccata aaaaagcct gactccactt     7920
cccgcgttta ctgattacta gcgaagctgc gggtgcattt tttcaagata aaggcatccc    7980
cgattatatt ctataccgat gtggattgcg catactttgt gaacagaaag tgatagcgtt    8040
gatgattctt cattggtcag aaaattatga acgtttctt ctattttgtc tctatatact     8100
acgtatagga atgtttaca ttttcgtatt gttttcgatt cactctatga atagttctta    8160
ctacaattttt tttgtctaaa gagtaatact agagataaac ataaaaaatg tagaggtcga    8220
gtttagatgc aagttcaagg agcgaaaggt ggatgggtag gttatatagg gatatagcac    8280
agagatatat agcaaagaga tacttttgag caatgtttgt ggaagcggta ttcgcaatat    8340
tttagtagct cgttacagtc cggtgcgttt ttggtttttt gaaagtgcgt cttcagagcg    8400
cttttggttt tcaaaagcgc tctgaagttc ctatactttc tagagaatag gaacttcgga    8460
ataggaactt caaagcgttt ccgaaaacga gcgcttccga aaatgcaacg cgagctgcgc    8520
acatacagct cactgttcac gtcgcaccta tatctgcgtg ttgcctgtat atatatatac    8580
atgagaagaa cggcatagtg cgtgtttatg cttaaatgcg tacttatatg cgtctattta    8640
tgtaggatga aaggtagtct agtacctcct gtgatattat cccattccat gcggggtatc    8700
gtatgcttcc ttcagcacta cccttttagct gttctatatg ctgccactcc tcaattggat    8760
tagtctcatc cttcaatgct atcatttcct ttgatattgg atcatatgca tagtaccgag    8820
aaactagtgc gaagtagtga tcaggtattg ctgttatctg atgagtatac gttgtcctgg    8880
ccacggcaga agcacgctta tcgctccaat ttcccacaac attagtcaac tccgttaggc    8940
ccttcattga aagaaatgag gtcatcaaat gtcttccaat gtgagatttt gggccatttt    9000
ttatagcaaa gattgaataa ggcgcatttt tcttcaaagc tttattgtac gatctgacta    9060
agttatcttt taataattgg tattcctgtt tattgcttga agaattgccg gtcctatttta   9120
```

```
ctcgttttag gactggttca gaattcatcg atgctcactc aaaggtcggt aatacggtta    9180
tccacagaat cagggggataa cgcaggaaag aac                                9213
```

<210> SEQ ID NO 407
<211> LENGTH: 820
<212> TYPE: PRT
<213> ORGANISM: artificial sequence
<220> FEATURE:
<223> OTHER INFORMATION: TevM01::cT11NNNT01g10 (pCLS 23422)

<400> SEQUENCE: 407

```
Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
        35                  40                  45

Ser Phe Asn Lys His Gly Asn Val Phe Glu Cys Ser Ile Leu Glu Glu
    50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ser Gly Val Asp Leu Arg
    130                 135                 140

Thr Leu Gly Tyr Ser Gln Gln Gln Glu Lys Ile Lys Pro Lys Val
145                 150                 155                 160

Arg Ser Thr Val Ala Gln His His Glu Ala Leu Val Gly His Gly Phe
                165                 170                 175

Thr His Ala His Ile Val Ala Leu Ser Gln His Pro Ala Ala Leu Gly
            180                 185                 190

Thr Val Ala Val Lys Tyr Gln Asp Met Ile Ala Ala Leu Pro Glu Ala
        195                 200                 205

Thr His Glu Ala Ile Val Gly Val Gly Lys Gln Trp Ser Gly Ala Arg
    210                 215                 220

Ala Leu Glu Ala Leu Leu Thr Val Ala Gly Glu Leu Arg Gly Pro Pro
225                 230                 235                 240

Leu Gln Leu Asp Thr Gly Gln Leu Leu Lys Ile Ala Lys Arg Gly Gly
                245                 250                 255

Val Thr Ala Val Glu Ala Val His Ala Trp Arg Asn Ala Leu Thr Gly
            260                 265                 270

Ala Pro Leu Asn Leu Thr Pro Gln Gln Val Val Ala Ile Ala Ser Asn
        275                 280                 285

Gly Gly Gly Lys Gln Ala Leu Glu Thr Val Gln Arg Leu Leu Pro Val
    290                 295                 300

Leu Cys Gln Ala His Gly Leu Thr Pro Gln Gln Val Val Ala Ile Ala
305                 310                 315                 320

Ser Asn Asn Gly Gly Lys Gln Ala Leu Glu Thr Val Gln Arg Leu Leu
                325                 330                 335

Pro Val Leu Cys Gln Ala His Gly Leu Thr Pro Gln Gln Val Val Ala
```

```
                    340             345             350
Ile Ala Ser Asn Gly Gly Gly Lys Gln Ala Leu Glu Thr Val Gln Arg
            355             360             365
Leu Leu Pro Val Leu Cys Gln Ala His Gly Leu Thr Pro Glu Gln Val
            370             375             380
Val Ala Ile Ala Ser Asn Ile Gly Gly Lys Gln Ala Leu Glu Thr Val
385             390             395             400
Gln Ala Leu Leu Pro Val Leu Cys Gln Ala His Gly Leu Thr Pro Gln
                405             410             415
Gln Val Val Ala Ile Ala Ser Asn Gly Gly Gly Lys Gln Ala Leu Glu
            420             425             430
Thr Val Gln Arg Leu Leu Pro Val Leu Cys Gln Ala His Gly Leu Thr
            435             440             445
Pro Gln Gln Val Val Ala Ile Ala Ser Asn Asn Gly Gly Lys Gln Ala
            450             455             460
Leu Glu Thr Val Gln Arg Leu Leu Pro Val Leu Cys Gln Ala His Gly
465             470             475             480
Leu Thr Pro Glu Gln Val Val Ala Ile Ala Ser His Asp Gly Gly Lys
                485             490             495
Gln Ala Leu Glu Thr Val Gln Arg Leu Leu Pro Val Leu Cys Gln Ala
            500             505             510
His Gly Leu Thr Pro Glu Gln Val Val Ala Ile Ala Ser His Asp Gly
            515             520             525
Gly Lys Gln Ala Leu Glu Thr Val Gln Arg Leu Leu Pro Val Leu Cys
            530             535             540
Gln Ala His Gly Leu Thr Pro Glu Gln Val Val Ala Ile Ala Ser Asn
545             550             555             560
Ile Gly Gly Lys Gln Ala Leu Glu Thr Val Gln Ala Leu Leu Pro Val
                565             570             575
Leu Cys Gln Ala His Gly Leu Thr Pro Glu Gln Val Val Ala Ile Ala
            580             585             590
Ser Asn Ile Gly Gly Lys Gln Ala Leu Glu Thr Val Gln Ala Leu Leu
            595             600             605
Pro Val Leu Cys Gln Ala His Gly Leu Thr Pro Gln Gln Val Val Ala
            610             615             620
Ile Ala Ser Asn Gly Gly Gly Lys Gln Ala Leu Glu Thr Val Gln Arg
625             630             635             640
Leu Leu Pro Val Leu Cys Gln Ala His Gly Leu Thr Pro Glu Gln Val
                645             650             655
Val Ala Ile Ala Ser His Asp Gly Gly Lys Gln Ala Leu Glu Thr Val
            660             665             670
Gln Arg Leu Leu Pro Val Leu Cys Gln Ala His Gly Leu Thr Pro Gln
            675             680             685
Gln Val Val Ala Ile Ala Ser Asn Asn Gly Gly Lys Gln Ala Leu Glu
            690             695             700
Thr Val Gln Arg Leu Leu Pro Val Leu Cys Gln Ala His Gly Leu Thr
705             710             715             720
Pro Glu Gln Val Val Ala Ile Ala Ser Asn Ile Gly Gly Lys Gln Ala
                725             730             735
Leu Glu Thr Val Gln Ala Leu Leu Pro Val Leu Cys Gln Ala His Gly
            740             745             750
Leu Thr Pro Glu Gln Val Val Ala Ile Ala Ser Asn Ile Gly Gly Lys
            755             760             765
```

Gln Ala Leu Glu Thr Val Gln Ala Leu Leu Pro Val Leu Cys Gln Ala
         770                 775                 780

His Gly Leu Thr Pro Gln Gln Val Val Ala Ile Ala Ser Asn Gly Gly
785                 790                 795                 800

Gly Arg Pro Ala Leu Glu Ser Ile Val Ala Gln Leu Ser Arg Pro Asp
                805                 810                 815

Pro Ser Ala Asp
            820

<210> SEQ ID NO 408
<211> LENGTH: 610
<212> TYPE: DNA
<213> ORGANISM: artificial sequence
<220> FEATURE:
<223> OTHER INFORMATION: RVD_ctEGFP_T03g12-L1

<400> SEQUENCE: 408
ggtccagcgg ctgttgccgg tgctgtgcca ggcccacggc ttgaccccc agcaggtggt      60 ggccatcgcc agcaatggcg gtggcaagca ggcgctggag acggtccagc ggctgttgcc     120
ggtgctgtgc caggcccacg gcttgacccc ccagcaggtg gtggccatcg ccagcaataa     180
tggtggcaag caggcgctgg agacggtcca gcggctgttg ccggtgctgt gccaggccca     240
cggcttgacc ccggagcagg tggtggccat cgccagccac gatggcggca agcaggcgct     300
ggagacggtc cagcggctgt tgccggtgct gtgccaggcc cacggcttga ccccggagca     360
ggtggtggcc atcgccagca atattggtgg caagcaggcg ctggagacgg tgcaggcgct     420
gttgccggtg ctgtgccagg cccacggctt gaccccggag caggtggtgg ccatcgccag     480
ccacgatggc ggcaagcagg cgctggagac ggtccagcgg ctgttgccgg tgctgtgcca     540
ggcccacggc ttgaccccctc agcaggtggt ggccatcgcc agcaatggcg gcggcaggcc     600
ggcgctggag                                                            610

<210> SEQ ID NO 409
<211> LENGTH: 40
<212> TYPE: DNA
<213> ORGANISM: artificial sequence
<220> FEATURE:
<223> OTHER INFORMATION: RVD_ctEGFP_T03g12-L1 target

<400> SEQUENCE: 409
tgccacctac ggcaagctga ccctgaagtt catctgcacc                            40

<210> SEQ ID NO 410
<211> LENGTH: 5673
<212> TYPE: DNA
<213> ORGANISM: artificial sequence
<220> FEATURE:
<223> OTHER INFORMATION: pCLS1853

<400> SEQUENCE: 410
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag cttgaccga caattgcatg aagaatctgc      180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360

```
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa atgaattcga ctcactgttg ggagacccaa gctggctagt    900
taagctatca acaagtttgt acaaaaaagc aggctggcgc gcctacacag cggccttgcc    960
accatggcca ataccaaata taacaaagag ttcctgctgt acctggccgg ctttgtggac   1020
ggtgacggta gcatcatcgc tcagattaaa ccaaaccagt cttataagtt taaacatcag   1080
ctaagcttga cctttcaggt gactcaaaag acccagcgcc gttggtttct ggacaaacta   1140
gtggatgaaa ttggcgttgg ttacgtacgt gatcgcggat ccgtttccaa ctacatctta   1200
agcgaaatca agccgctgca caacttcctg actcaactgc agccgtttct gaaactgaaa   1260
cagaaacagg caaacctggt tctgaaaatt atcgaacagc tgccgtctgc aaaagaatcc   1320
ccggacaaat cctggaagt ttgtacctgg gtggatcaga ttgcagctct gaacgattct   1380
aagacgcgta aaaccacttc tgaaaccgtt cgtgctgtgc tggacagcct gagcgagaag   1440
aagaaatcct ccccggcggc cgactgataa ctcgagcgct agcacccagc tttcttgtac   1500
aaagtggtga tctagagggc ccgcggttcg aaggtaagcc tatccctaac cctctcctcg   1560
gtctcgattc tacgcgtacc ggttagtaat gagtttaaac gggggaggct aactgaaaca   1620
cggaaggaga caataccgga aggaacccgc gctatgacgg caataaaaag acagaataaa   1680
acgcacgggt gttgggtcgt tgttcataa acgcggggtt cggtcccagg ctggcactc    1740
tgtcgatacc ccaccgagac cccattgggg ccaatacgcc cgcgtttctt ccttttcccc   1800
accccacccc ccaagttcgg gtgaaggccc agggctcgca gccaacgtcg gggcggcagg   1860
ccctgccata gcagatctgc gcagctgggg ctctaggggg tatccccacg cgccctgtag   1920
cggcgcatta agcgcggcgg gtgtggtggt tacgcgcagc gtgaccgcta cacttgccag   1980
cgccctagcg cccgctcctt tcgctttctt cccttccttt ctcgccacgt tcgccggctt   2040
tccccgtcaa gctctaaatc ggggcatccc tttagggttc cgatttagtg ctttacggca   2100
cctcgacccc aaaaaacttg attagggtga tggttcacgt agtgggccat cgccctgata   2160
gacggttttt cgccctttga cgttggagtc cacgttcttt aatagtggac tcttgttcca   2220
aactggaaca cactcaacc ctatctcggt ctattctttt gatttataag ggattttggg   2280
gatttcggcc tattggttaa aaaatgagct gatttaacaa aaatttaacg cgaattaatt   2340
ctgtggaatg tgtgtcagtt agggtgtgga aagtccccag gctccccagc aggcagaagt   2400
atgcaaagca tgcatctcaa ttagtcagca accaggtgtg gaaagtcccc aggctcccca   2460
gcaggcagaa gtatgcaaag catgcatctc aattagtcag caaccatagt cccgccccta   2520
actccgccca tcccgcccct aactccgccc agttccgccc attctccgcc ccatggctga   2580
ctaattttt tatttatgc agaggccgag gccgcctctg cctctgagct attccagaag   2640
tagtgaggag gcttttttgg aggcctaggc ttttgcaaaa agctcccggg agcttgtata   2700
tccatttcg gatctgatca gcacgtgttg acaattaatc atcggcatag tatatcggca   2760
```

```
tagtataata cgacaaggtg aggaactaaa ccatggccaa gcctttgtct caagaagaat   2820
ccaccctcat tgaaagagca acggctacaa tcaacagcat ccccatctct gaagactaca   2880
gcgtcgccag cgcagctctc tctagcgacg gccgcatctt cactggtgtc aatgtatatc   2940
attttactgg gggaccttgt gcagaactcg tggtgctggg cactgctgct gctgcggcag   3000
ctggcaacct gacttgtatc gtcgcgatcg gaaatgagaa caggggcatc ttgagcccct   3060
gcggacggtg ccgacaggtg cttctcgatc tgcatcctgg gatcaaagcc atagtgaagg   3120
acagtgatgg acagccgacg gcagttggga ttcgtgaatt gctgccctct ggttatgtgt   3180
gggagggcta agcacttcgt ggccgaggag caggactgac acgtgctacg agatttcgat   3240
tccaccgccg ccttctatga aaggttgggc ttcggaatcg ttttccggga cgccggctgg   3300
atgatcctcc agcgcgggga tctcatgctg gagttcttcg cccacccaa cttgtttatt   3360 gcagcttata atggttacaa ataaagcaat agcatcacaa atttcacaaa taaagcattt   3420
ttttcactgc attctagttg tggtttgtcc aaactcatca atgtatctta tcatgtctgt   3480
ataccgtcga cctctagcta gagcttggcg taatcatggt catagctgtt tcctgtgtga   3540
aattgttatc cgctcacaat tccacacaac atacgagccg aagcataaa gtgtaaagcc   3600 tggggtgcct aatgagtgag ctaactcaca ttaattgcgt tgcgctcact gcccgctttc   3660
cagtcgggaa acctgtcgtg ccagctgcat taatgaatcg gccaacgcgc ggggagaggc   3720
ggtttgcgta ttgggcgctc ttccgcttcc tcgctcactg actcgctgcg ctcggtcgtt   3780
cggctgcggc gagcggtatc agctcactca aaggcggtaa tacggttatc cacagaatca   3840
ggggataacg caggaaagaa catgtgagca aaaggccagc aaaaggccag gaaccgtaaa   3900
aaggccgcgt tgctggcgtt tttccatagg ctccgccccc ctgacgagca tcacaaaaat   3960
cgacgctcaa gtcagaggtg gcgaaacccg acaggactat aaagatacca ggcgtttccc   4020
cctggaagct ccctcgtgcg ctctcctgtt ccgaccctgc cgcttaccgg atacctgtcc   4080
gcctttctcc cttcgggaag cgtggcgctt tctcatagct cacgctgtag gtatctcagt   4140
tcggtgtagg tcgttcgctc caagctgggc tgtgtgcacg aacccccgt tcagcccgac   4200 cgctgcgcct tatccggtaa ctatcgtctt gagtccaacc cggtaagaca cgacttatcg   4260
ccactggcag cagccactgg taacaggatt agcagagcga gtatgtagg cggtgctaca   4320 gagttcttga agtggtggcc taactacggc tacactagaa gaacagtatt tggtatctgc   4380
gctctgctga agccagttac cttcggaaaa agagttggta gctcttgatc cggcaaacaa   4440
accaccgctg gtagcggttt ttttgtttgc aagcagcaga ttacgcgcag aaaaaagga   4500 tctcaagaag atcctttgat cttttctacg gggtctgacg ctcagtggaa cgaaaactca   4560
cgttaaggga ttttggtcat gagattatca aaaggatct tcacctagat ccttttaaat   4620
taaaaatgaa gttttaaatc aatctaaagt atatatgagt aaacttggtc tgacagttac   4680
caatgcttaa tcagtgaggc acctatctca gcgatctgtc tatttcgttc atccatagtt   4740
gcctgactcc ccgtcgtgta gataactacg atacgggagg gcttaccatc tggccccagt   4800
gctgcaatga taccgcgaga cccacgctca ccggctccag atttatcagc aataaaccag   4860
ccagccggaa gggccgagcg cagaagtggt cctgcaactt tatccgcctc catccagtct   4920
attaattgtt gccgggaagc tagagtaagt agttcgccag ttaatagttt gcgcaacgtt   4980
gttgccattg ctacaggcat cgtggtgtca cgctcgtcgt ttggtatggc ttcattcagc   5040
tccggttccc aacgatcaag gcgagttaca tgatccccca tgttgtgcaa aaaagcggtt   5100
```

```
agctccttcg gtcctccgat cgttgtcaga agtaagttgg ccgcagtgtt atcactcatg    5160
gttatggcag cactgcataa ttctcttact gtcatgccat ccgtaagatg cttttctgtg    5220
actggtgagt actcaaccaa gtcattctga gaatagtgta tgcggcgacc gagttgctct    5280
tgcccggcgt caatacggga taataccgcg ccacatagca aactttaaaa gtgctcatc    5340 attggaaaac gttcttcggg gcgaaaactc tcaaggatct taccgctgtt gagatccagt    5400
tcgatgtaac ccactcgtgc acccaactga tcttcagcat cttttacttt caccagcgtt    5460
tctgggtgag caaaaacagg aaggcaaaat gccgcaaaaa agggaataag ggcgacacgg    5520
aaatgttgaa tactcatact cttcctttt caatattatt gaagcattta tcagggttat    5580
tgtctcatga gcggatacat atttgaatgt atttagaaaa ataaacaaat aggggttccg    5640
cgcacatttc cccgaaaagt gccacctgac gtc                                 5673
```

<210> SEQ ID NO 411
<211> LENGTH: 6134
<212> TYPE: DNA
<213> ORGANISM: artificial sequence
<220> FEATURE:
<223> OTHER INFORMATION: pCLS20650

<400> SEQUENCE: 411

```
atgtgagcaa aaggccagca aaaggccagg aaccgtaaaa aggccgcgtt gctggcgttt      60
ttccataggc tccgcccccc tgacgagcat cacaaaaatc gacgctcaag tcagaggtgg    120
cgaaacccga caggactata agataccag gcgtttcccc ctggaagctc cctcgtgcgc    180
tctcctgttc cgaccctgcc gcttaccgga tacctgtccg cctttctccc ttcgggaagc    240
gtggcgcttt ctcatagctc acgctgtagg tatctcagtt cggtgtaggt cgttcgctcc    300
aagctgggct gtgtgcacga accccccgtt cagcccgacc gctgcgcctt atccggtaac    360
tatcgtcttg agtccaaccc ggtaagacac gacttatcgc cactggcagc agccactggt    420
aacaggatta gcagagcgag gtatgtaggc ggtgctacag agttcttgaa gtggtggcct    480
aactacggct acactagaag aacagtattt ggtatctgcg ctctgctgaa gccagttacc    540
ttcggaaaaa gagttggtag ctcttgatcc ggcaaacaaa ccaccgctgg tagcggtttt    600
tttgtttgca agcagcagat tacgcgcaga aaaaaggat ctcaagaaga tcctttgatc    660
ttttctacgg ggtctgacgc tcagtggaac gaaaactcac gttaagggat tttggtcatg    720
agattatcaa aaaggatctt cacctagatc cttttaaatt aaaaatgaag ttttaaatca    780
atctaaagta tatatgagta aacttggtct gacagttacc aatgcttaat cagtgaggca    840
cctatctcag cgatctgtct atttcgttca tccatagttg cctgactccc cgtcgtgtag    900
ataactacga tacgggaggg cttaccatct ggccccagtg ctgcaatgat accgcgagac    960
ccacgctcac cggctccaga tttatcagca ataaaccagc cagccggaag ggccgagcgc   1020
agaagtggtc ctgcaacttt atccgcctcc atccagtcta ttaattgttg ccgggaagct   1080
agagtaagta gttcgccagt taatagtttg cgcaacgttg ttgccattgc tacaggcatc   1140
gtggtgtcac gctcgtcgtt tggtatggct tcattcagct ccggttccca acgatcaagg   1200
cgagttacat gatcccccat gttgtgcaaa aaagcggtta gctccttcgg tcctccgatc   1260
gttgtcagaa gtaagttggc cgcagtgtta tcactcatgg ttatggcagc actgcataat   1320
tctcttactg tcatgccatc cgtaagatgc ttttctgtga ctggtgagta ctcaaccaag   1380
tcattctgag aatagtgtat gcggcgaccg agttgctctt gcccggcgtc aatacggat   1440 aataccgcgc cacatagcag aactttaaaa gtgctcatca ttggaaaacg ttcttcgggg   1500
```

-continued

```
cgaaaactct caaggatctt accgctgttg agatccagtt cgatgtaacc cactcgtgca   1560
cccaactgat cttcagcatc ttttactttc accagcgttt ctgggtgagc aaaaacagga   1620
aggcaaaatg ccgcaaaaaa gggaataagg gcgacacgga aatgttgaat actcatactc   1680
ttcctttttc aatattattg aagcatttat cagggttatt gtctcatgag cggatacata   1740
tttgaatgta tttagaaaaa taaacaaata ggggttccgc gcacatttcc ccgaaaagtg   1800
ccacctgacg tcgacggatc gggagatctc ccgatcccct atggtgcact ctcagtacaa   1860
tctgctctga tgccgcatag ttaagccagt atctgctccc tgcttgtgtg ttggaggtcg   1920
ctgagtagtg cgcgagcaaa atttaagcta caacaaggca aggcttgacc gacaattgca   1980
tgaagaatct gcttagggtt aggcgttttg cgctgcttcg cgatgtacgg gccagatata   2040
cgcgttgaca ttgattattg actagttatt aatagtaatc aattacgggg tcattagttc   2100
atagcccata tatggagttc cgcgttacat aacttacggt aaatggcccg cctggctgac   2160
cgcccaacga ccccgccca ttgacgtcaa taatgacgta tgttcccata gtaacgccaa   2220
tagggacttt ccattgacgt caatgggtgg agtatttacg gtaaactgcc cacttggcag   2280
tacatcaagt gtatcatatg ccaagtacgc cccctattga cgtcaatgac ggtaaatggc   2340
ccgcctggca ttatgcccag tacatgacct tatgggactt tcctacttgg cagtacatct   2400
acgtattagt catcgctatt accatggtga tgcggttttg gcagtacatc aatgggcgtg   2460
gatagcggtt tgactcacgg ggatttccaa gtctccaccc cattgacgtc aatgggagtt   2520
tgttttggca ccaaaatcaa cgggactttc caaaatgtcg taacaactcc gccccattga   2580
cgcaaatggg cggtaggcgt gtacggtggg aggtctatat aagcagagct ctctggctaa   2640
ctagagaacc cactgcttac tggcttatcg aaatgaattc gactcactgt tgggagaccc   2700
aagctggcta gttaagctat cacaagtttg tacaaaaaag caggctggcg cgccacacgc   2760
aaacacaaat acacagcggc cttgccacca tggccaagtc tggcatctac cagattaaga   2820
acaccctgaa taacaaagtg tatgttggat ctgccaagga ctttgagaaa agatggaaga   2880
ggcacttcaa ggatctggaa aagggttgcc acagctccat caagctccaa aggtctttca   2940
acaaacatgg caatgtcttt gagtgctcca ttttggaaga gatcccttat gaaaaggacc   3000
tcattataga gagggaaaac ttctggatca aggagctgaa ctcaaaaatc aatggataca   3060
acattgcaga tgccacattt ggtgacacct gttctactca ccccttaag gaagagatca   3120
ttaaaagag gtctgagact gtgaaggcta agatgttgaa actggggcct gatggcagaa   3180
aggcactcta ctctaagcca ggttccggag tggatctacg cacgctcggc tacagccagc   3240
agcaacagga gaagatcaaa ccgaaggttc gttcgacagt ggcgcagcac cacgaggcac   3300
tggtcggcca cgggtttaca cacgcgcaca tcgttgcgtt aagccaacac ccggcagcgt   3360
tagggaccgt cgctgtcaag tatcaggaca tgatcgcagc gttgccagag cgacacacg   3420
aagcgatcgt tggcgtcggc aaacagtggt ccggcgcacg cgctctggag ccttgctca   3480
cggtggcggg agagttgaga ggtccaccgt tacagttgga cacaggccaa cttctcaaga   3540
ttgcaaaacg tggcggcgtg accgcagtgg aggcagtgca tgcatggcgc aatgcactga   3600
cgggtgcccc gctcaacttg accggagacg cccgggggat caggtcacgt gcgtctcgga   3660
gcattgttgc ccagttatct cgccctgatc cgtcggccga ctgataagtc gaccaccacc   3720
accaccacca ctgataagag ctcctcgagc gctagcaccc agctttcttg tacaaagtgg   3780
tgatctagag ggcccgcggt tcgaaggtaa gcctatccct aaccctctcc tcggtctcga   3840
```

```
ttctacgcgt accggttagt aatgagttta acggggggag gctaactgaa acacggaagg    3900
agacaatacc ggaaggaacc cgcgctatga cggcaataaa aagacagaat aaaacgcacg    3960
ggtgttgggt cgtttgttca taaacgcggg gttcggtccc agggctggca ctctgtcgat    4020
accccaccga gacccattg gggccaatac gcccgcgttt cttccttttc cccacccccac    4080
cccccaagtt cgggtgaagg cccagggctc gcagccaacg tcgggcggc aggccctgcc    4140
atagcagatc tgcgcagctg gggctctagg gggtatcccc acgcgccctg tagcggcgca    4200
ttaagcgcgg cgggtgtggt ggttacgcgc agcgtgaccg ctacacttgc cagcgcccta    4260
gcgcccgctc ctttcgcttt cttcccttcc tttctcgcca cgttcgccgg ctttccccgt    4320
caagctctaa atcggggcat ccctttaggg ttccgattta gtgctttacg gcacctcgac    4380
cccaaaaaac ttgattaggg tgatggttca cgtagtgggc catcgccctg atagacggtt    4440
tttcgccctt tgacgttgga gtccacgttc tttaatagtg gactcttgtt ccaaactgga    4500
acaacactca accctatctc ggtctattct tttgatttat aagggatttt ggggatttcg    4560
gcctattggt taaaaaatga gctgatttaa caaaaattta acgcgaatta attctgtgga    4620
atgtgtgtca gttagggtgt ggaaagtccc caggctcccc agcaggcaga agtatgcaaa    4680
gcatgcatct caattagtca gcaaccaggt gtggaaagtc cccaggctcc ccagcaggca    4740
gaagtatgca aagcatgcat ctcaattagt cagcaaccat agtcccgccc ctaactccgc    4800
ccatcccgcc cctaactccg cccagttccg cccattctcc gccccatggc tgactaattt    4860
ttttttattta tgcagaggcc gaggccgcct ctgcctctga gctattccag aagtagtgag    4920
gaggcttttt tggaggccta ggcttttgca aaaagctccc gggagcttgt atatccattt    4980
tcggatctga tcagcacgtg ttgacaatta atcatcggca tagtatatcg gcatagtata    5040
atacgacaag gtgaggaact aaaccatggc caagcctttg tctcaagaag aatccaccct    5100
cattgaaaga gcaacggcta caatcaacag catccccatc tctgaagact acagcgtcgc    5160
cagcgcagct ctctctagcg acggccgcat cttcactggt gtcaatgtat atcattttac    5220
tggggggacct tgtgcagaac tcgtggtgct gggcactgct gctgctgcgg cagctggcaa    5280
cctgacttgt atcgtcgcga tcggaaatga gaacaggggc atcttgagcc cctgcggacg    5340
gtgccgacag gtgcttctcg atctgcatcc tgggatcaaa gccatagtga aggacagtga    5400
tggacagccg acggcagttg ggattcgtga attgctgccc tctggttatg tgtgggaggg    5460
ctaagcactt cgtggccgag gagcaggact gacacgtgct acgagatttc gattccaccg    5520
ccgccttcta tgaaaggttg gcttcggaa tcgttttccg ggacgccggc tggatgatcc    5580
tccagcgcgg ggatctcatg ctggagttct tcgcccaccc caacttgttt attgcagctt    5640
ataatggtta caaataaagc aatagcatca caaatttcac aaataaagca ttttttttcac    5700
tgcattctag ttgtggtttg tccaaactca tcaatgtatc ttatcatgtc tgtataccgt    5760
cgacctctag ctagagcttg gcgtaatcat ggtcatagct gtttcctgtg tgaaattgtt    5820
atccgctcac aattccacac aacatacgag ccggaagcat aaagtgtaaa gcctggggtg    5880
cctaatgagt gagctaactc acattaattg cgttgcgctc actgcccgct ttccagtcgg    5940
gaaacctgtc gtgccagctg cattaatgaa tcggccaacg cgcggggaga ggcggtttgc    6000
gtattgggcg ctcttccgct tcctcgctca ctgactcgct gcgctcggtc gttcggctgc    6060
ggcgagcggt atcagctcac tcaaaggcgg taatacggtt atccacagaa tcaggggata    6120
acgcaggaaa gaac                                                     6134
```

```
<210> SEQ ID NO 412
<211> LENGTH: 820
<212> TYPE: PRT
<213> ORGANISM: artificial sequence
<220> FEATURE:
<223> OTHER INFORMATION: TevI::cT11EGfpT3g12

<400> SEQUENCE: 412

Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
        35                  40                  45

Ser Phe Asn Lys His Gly Asn Val Phe Glu Cys Ser Ile Leu Glu Glu
    50                  55                  60

Ile Pro Tyr Glu Lys Asp Leu Ile Ile Glu Arg Glu Asn Phe Trp Ile
65              70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ser Gly Val Asp Leu Arg
    130                 135                 140

Thr Leu Gly Tyr Ser Gln Gln Gln Glu Lys Ile Lys Pro Lys Val
145                 150                 155                 160

Arg Ser Thr Val Ala Gln His His Glu Ala Leu Val Gly His Gly Phe
                165                 170                 175

Thr His Ala His Ile Val Ala Leu Ser Gln His Pro Ala Ala Leu Gly
            180                 185                 190

Thr Val Ala Val Lys Tyr Gln Asp Met Ile Ala Ala Leu Pro Glu Ala
        195                 200                 205

Thr His Glu Ala Ile Val Gly Val Gly Lys Gln Trp Ser Gly Ala Arg
    210                 215                 220

Ala Leu Glu Ala Leu Leu Thr Val Ala Gly Glu Leu Arg Gly Pro Pro
225                 230                 235                 240

Leu Gln Leu Asp Thr Gly Gln Leu Leu Lys Ile Ala Lys Arg Gly Gly
                245                 250                 255

Val Thr Ala Val Glu Ala Val His Ala Trp Arg Asn Ala Leu Thr Gly
            260                 265                 270

Ala Pro Leu Asn Leu Thr Pro Gln Gln Val Val Ala Ile Ala Ser Asn
        275                 280                 285

Asn Gly Gly Lys Gln Ala Leu Glu Thr Val Gln Arg Leu Leu Pro Val
    290                 295                 300

Leu Cys Gln Ala His Gly Leu Thr Pro Glu Gln Val Val Ala Ile Ala
305                 310                 315                 320

Ser Asn Ile Gly Gly Lys Gln Ala Leu Glu Thr Val Gln Ala Leu Leu
                325                 330                 335

Pro Val Leu Cys Gln Ala His Gly Leu Thr Pro Glu Gln Val Val Ala
            340                 345                 350

Ile Ala Ser Asn Ile Gly Gly Lys Gln Ala Leu Glu Thr Val Gln Ala
        355                 360                 365

Leu Leu Pro Val Leu Cys Gln Ala His Gly Leu Thr Pro Gln Gln Val
```

```
                    370                 375                 380
Val Ala Ile Ala Ser Asn Asn Gly Gly Lys Gln Ala Leu Glu Thr Val
385                 390                 395                 400

Gln Arg Leu Leu Pro Val Leu Cys Gln Ala His Gly Leu Thr Pro Gln
                    405                 410                 415

Gln Val Val Ala Ile Ala Ser Asn Gly Gly Lys Gln Ala Leu Glu
                    420                 425                 430

Thr Val Gln Arg Leu Leu Pro Val Leu Cys Gln Ala His Gly Leu Thr
                435                 440                 445

Pro Gln Gln Val Val Ala Ile Ala Ser Asn Gly Gly Lys Gln Ala
450                 455                 460

Leu Glu Thr Val Gln Arg Leu Leu Pro Val Leu Cys Gln Ala His Gly
465                 470                 475                 480

Leu Thr Pro Glu Gln Val Val Ala Ile Ala Ser His Asp Gly Gly Lys
                485                 490                 495

Gln Ala Leu Glu Thr Val Gln Arg Leu Leu Pro Val Leu Cys Gln Ala
                500                 505                 510

His Gly Leu Thr Pro Glu Gln Val Val Ala Ile Ala Ser Asn Ile Gly
                515                 520                 525

Gly Lys Gln Ala Leu Glu Thr Val Gln Ala Leu Leu Pro Val Leu Cys
530                 535                 540

Gln Ala His Gly Leu Thr Pro Gln Gln Val Val Ala Ile Ala Ser Asn
545                 550                 555                 560

Gly Gly Gly Lys Gln Ala Leu Glu Thr Val Gln Arg Leu Leu Pro Val
                565                 570                 575

Leu Cys Gln Ala His Gly Leu Thr Pro Glu Gln Val Val Ala Ile Ala
                580                 585                 590

Ser His Asp Gly Gly Lys Gln Ala Leu Glu Thr Val Gln Arg Leu Leu
                595                 600                 605

Pro Val Leu Cys Gln Ala His Gly Leu Thr Pro Gln Gln Val Val Ala
                610                 615                 620

Ile Ala Ser Asn Gly Gly Gly Lys Gln Ala Leu Glu Thr Val Gln Arg
625                 630                 635                 640

Leu Leu Pro Val Leu Cys Gln Ala His Gly Leu Thr Pro Gln Gln Val
                    645                 650                 655

Val Ala Ile Ala Ser Asn Asn Gly Gly Lys Gln Ala Leu Glu Thr Val
                    660                 665                 670

Gln Arg Leu Leu Pro Val Leu Cys Gln Ala His Gly Leu Thr Pro Glu
                675                 680                 685

Gln Val Val Ala Ile Ala Ser His Asp Gly Gly Lys Gln Ala Leu Glu
                690                 695                 700

Thr Val Gln Arg Leu Leu Pro Val Leu Cys Gln Ala His Gly Leu Thr
705                 710                 715                 720

Pro Glu Gln Val Val Ala Ile Ala Ser Asn Ile Gly Gly Lys Gln Ala
                    725                 730                 735

Leu Glu Thr Val Gln Ala Leu Leu Pro Val Leu Cys Gln Ala His Gly
                740                 745                 750

Leu Thr Pro Glu Gln Val Val Ala Ile Ala Ser His Asp Gly Gly Lys
                755                 760                 765

Gln Ala Leu Glu Thr Val Gln Arg Leu Leu Pro Val Leu Cys Gln Ala
                770                 775                 780

His Gly Leu Thr Pro Gln Gln Val Val Ala Ile Ala Ser Asn Gly Gly
785                 790                 795                 800
```

Gly Arg Pro Ala Leu Glu Ser Ile Val Ala Gln Leu Ser Arg Pro Asp
            805                 810                 815

Pro Ser Ala Asp
            820

<210> SEQ ID NO 413
<211> LENGTH: 5428
<212> TYPE: DNA
<213> ORGANISM: artificial sequence
<220> FEATURE:
<223> OTHER INFORMATION: pCLS0003

<400> SEQUENCE: 413

| | | | | | |
|---|---|---|---|---|---|
| gacggatcgg | gagatctccc | gatcccctat | ggtgcactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggag | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctagc | 900 |
| gtttaaactt | aagcttggta | ccgagctcgg | atccactagt | ccagtgtggt | ggaattctgc | 960 |
| agatatccag | cacagtggcg | gccgctcgag | tctagagggc | ccgtttaaac | ccgctgatca | 1020 |
| gcctcgactg | tgccttctag | ttgccagcca | tctgttgttt | gcccctcccc | cgtgccttcc | 1080 |
| ttgaccctgg | aaggtgccac | tcccactgtc | ctttcctaat | aaaatgagga | aattgcatcg | 1140 |
| cattgtctga | gtaggtgtca | ttctattctg | gggggtgggg | tggggcagga | cagcaagggg | 1200 |
| gaggattggg | aagacaatag | caggcatgct | ggggatgcgg | tgggctctat | ggcttctgag | 1260 |
| gcggaaagaa | ccagctgggg | ctctaggggg | tatccccacg | cgccctgtag | cggcgcatta | 1320 |
| agcgcggcgg | gtgtggtggt | tacgcgcagc | gtgaccgcta | cacttgccag | cgccctagcg | 1380 |
| cccgctcctt | tcgctttctt | cccttccttt | ctcgccacgt | tcgccggctt | tccccgtcaa | 1440 |
| gctctaaatc | gggggctccc | tttagggttc | cgatttagtg | ctttacggca | cctcgacccc | 1500 |
| aaaaaacttg | attagggtga | tggttcacgt | agtgggccat | cgccctgata | gacggttttt | 1560 |
| cgccctttga | cgttggagtc | acgttcttta | atagtggac | tcttgttcca | aactggaaca | 1620 |
| acactcaacc | ctatctcggt | ctattctttt | gatttataag | ggattttgcc | gatttcggcc | 1680 |
| tattggttaa | aaaatgagct | gatttaacaa | aaatttaacg | cgaattaatt | ctgtggaatg | 1740 |
| tgtgtcagtt | agggtgtgga | aagtccccag | gctccccagc | aggcagaagt | atgcaaagca | 1800 |
| tgcatctcaa | ttagtcagca | accaggtgtg | gaaagtcccc | aggctcccca | gcaggcagaa | 1860 |

-continued

```
gtatgcaaag catgcatctc aattagtcag caaccatagt cccgcccta actccgccca      1920 tcccgcccct aactccgccc agttccgccc attctccgcc ccatggctga ctaattttt      1980 ttatttatgc agaggccgag gccgcctctg cctctgagct attccagaag tagtgaggag     2040
gcttttttgg aggcctaggc ttttgcaaaa agctcccggg agcttgtata tccattttcg     2100
gatctgatca agagacagga tgaggatcgt ttcgcatgat tgaacaagat ggattgcacg     2160
caggttctcc ggccgcttgg gtggagaggc tattcggcta tgactgggca acagacaa      2220 tcggctgctc tgatgccgcc gtgttccggc tgtcagcgca ggggcgcccg ttcttttg      2280 tcaagaccga cctgtccggt gccctgaatg aactgcagga cgaggcagcg cggctatcgt     2340
ggctggccac gacgggcgtt ccttgcgcag ctgtgctcga cgttgtcact gaagcgggaa     2400
gggactggct gctattgggc gaagtgccgg ggcaggatct cctgtcatct caccttgctc     2460
ctgccgagaa agtatccatc atggctgatg caatgcggcg gctgcatacg cttgatccgg     2520
ctacctgccc attcgaccac caagcgaaac atcgcatcga gcgagcacgt actcggatgg     2580
aagccggtct tgtcgatcag gatgatctgg acgaagagca tcaggggctc gcgccagccg     2640
aactgttcgc caggctcaag gcgcgcatgc ccgacggcga ggatctcgtc gtgacccatg     2700
gcgatgcctg cttgccgaat atcatggtgg aaaatggccg cttttctgga ttcatcgact     2760
gtggccggct gggtgtggcg gaccgctatc aggacatagc gttggctacc cgtgatattg     2820
ctgaagagct tggcggcgaa tgggctgacc gcttcctcgt gctttacggt atcgccgctc     2880
ccgattcgca gcgcatcgcc ttctatcgcc ttcttgacga gttcttctga gcgggactct     2940
ggggttcgaa atgaccgacc aagcgacgcc caacctgcca tcacgagatt tcgattccac     3000
cgccgccttc tatgaaaggt tgggcttcgg aatcgttttc cgggacgccg gctggatgat     3060
cctccagcgc gggatctca tgctggagtt cttcgcccac cccaacttgt ttattgcagc      3120
ttataatggt tacaaataaa gcaatagcat cacaaatttc acaaataaag catttttttc     3180
actgcattct agttgtggtt tgtccaaact catcaatgta tcttatcatg tctgtatacc     3240
gtcgacctct agctagagct tggcgtaatc atggtcatag ctgtttcctg tgtgaaattg     3300
ttatccgctc acaattccac acaacatacg agccggaagc ataaagtgta aagcctgggg     3360
tgcctaatga gtgagctaac tcacattaat tgcgttgcgc tcactgcccg ctttccagtc     3420
gggaaacctg tcgtgccagc tgcattaatg aatcggccaa cgcgcgggga gaggcggttt     3480
gcgtattggg cgctcttccg cttcctcgct cactgactcg ctgcgctcgg tcgttcggct     3540
gcggcgagcg gtatcagctc actcaaaggc ggtaatacgg ttatccacag aatcaggga     3600 taacgcagga aagaacatgt gagcaaaagg ccagcaaaag gccaggaacc gtaaaaaggc     3660
cgcgttgctg gcgtttttcc ataggctccg ccccctgac gagcatcaca aaaatcgacg     3720
ctcaagtcag aggtggcgaa acccgacagg actataaaga taccaggcgt tccccctgg     3780 aagctccctc gtgcgctctc ctgttccgac cctgccgctt accggatacc tgtccgcctt     3840
tctcccttcg ggaagcgtgg cgctttctca gctcacgc tgtaggtatc tcagttcggt      3900
gtaggtcgtt cgctccaagc tgggctgtgt gcacgaaccc cccgttcagc ccgaccgctg     3960
cgccttatcc ggtaactatc gtcttgagtc caacccggta agacacgact tatcgccact     4020
ggcagcagcc actggtaaca ggattagcag agcgaggtat gtaggcggtg ctacagagtt     4080
cttgaagtgg tggcctaact acggctacac tagaagaaca gtatttggta tctgcgctct     4140
gctgaagcca gttaccttcg gaaaaagagt tggtagctct tgatccggca aacaaaccac     4200
cgctggtagc ggttttttg tttgcaagca gcagattacg cgcagaaaaa aaggatctca     4260
```

```
agaagatcct ttgatctttt ctacggggtc tgacgctcag tggaacgaaa actcacgtta    4320
agggattttg gtcatgagat tatcaaaaag gatcttcacc tagatccttt taaattaaaa    4380
atgaagtttt aaatcaatct aaagtatata tgagtaaact tggtctgaca gttaccaatg    4440
cttaatcagt gaggcaccta tctcagcgat ctgtctattt cgttcatcca tagttgcctg    4500
actccccgtc gtgtagataa ctacgatacg ggagggctta ccatctggcc ccagtgctgc    4560
aatgataccg cgagacccac gctcaccggc tccagattta tcagcaataa accagccagc    4620
cggaagggcc gagcgcagaa gtggtcctgc aactttatcc gcctccatcc agtctattaa    4680
ttgttgccgg gaagctagag taagtagttc gccagttaat agtttgcgca acgttgttgc    4740
cattgctaca ggcatcgtgg tgtcacgctc gtcgtttggt atggcttcat tcagctccgg    4800
ttcccaacga tcaaggcgag ttacatgatc ccccatgttg tgcaaaaaag cggttagctc    4860
cttcggtcct ccgatcgttg tcagaagtaa gttggccgca gtgttatcac tcatggttat    4920
ggcagcactg cataattctc ttactgtcat gccatccgta agatgctttt ctgtgactgg    4980
tgagtactca accaagtcat tctgagaata gtgtatgcgg cgaccgagtt gctcttgccc    5040
ggcgtcaata cgggataata ccgcgccaca tagcagaact ttaaaagtgc tcatcattgg    5100
aaaacgttct cgggggcgaa aactctcaag gatcttaccg ctgttgagat ccagttcgat    5160
gtaacccact cgtgcaccca actgatcttc agcatctttt actttcacca gcgtttctgg    5220
gtgagcaaaa acaggaaggc aaaatgccgc aaaaaaggga ataagggcga cacggaaatg    5280
ttgaatactc atactcttcc ttttttcaata ttattgaagc atttatcagg gttattgtct    5340
catgagcgga tacatatttg aatgtattta gaaaaataaa caaatagggg ttccgcgcac    5400
atttccccga aaagtgccac ctgacgtc                                       5428
```

<210> SEQ ID NO 414
<211> LENGTH: 6627
<212> TYPE: DNA
<213> ORGANISM: artificial sequence
<220> FEATURE:
<223> OTHER INFORMATION: pCLS8982

<400> SEQUENCE: 414

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
```

```
ctgcttactg gcttatcgaa atgaattcga ctcactgttg ggagacccaa gctggctagt    900
taagctatca acaagtttgt acaaaaaagc aggctggcgc gcctacacag cggccttgcc    960
accatgggtt ccgaggcacc ccgggccgag acctttgtct tcctggacct ggaagccact   1020
gggctcccca gtgtggagcc cgagattgcc gagctgtccc tctttgctgt ccaccgctcc   1080
tccctggaga acccggagca cgacgagtct ggtgccctag tattgccccg ggtcctggac   1140
aagctcacgc tgtgcatgtg cccggagcgc cccttcactg ccaaggccag cgagatcacc   1200
ggcctgagca gtgagggcct ggcgcgatgc cggaaggctg gctttgatgg cgccgtggtg   1260
cggacgctgc aggccttcct gagccgccag gcagggccca tctgccttgt ggcccacaat   1320
ggctttgatt atgatttccc cctgctgtgt gccgagctgc ggcgcctggg tgcccgcctg   1380
ccccgggaca ctgtctgcct ggacacgctg ccggccctgc ggggcctgga ccgcgcccac   1440
agccacggca cccgggcccg gggccgccag ggttacagcc tcggcagcct cttccaccgc   1500
tacttccggg cagagccaag cgcagcccac tcagccgagg cgacgtgca  cacccctgctc   1560
ctgatcttcc tgcaccgcgc cgcagagctg ctcgcctggg ccgatgagca ggcccgtggg   1620
tgggcccaca tcgagcccat gtacttgccg cctgatgacc ccagcctgga ggcgactcct   1680
ccacagaccg gtctggatgt tccttactcc gaggcacccc gggccgagac ctttgtcttc   1740
ctggacctgg aagccactgg gctccccagt gtggagcccg agattgccga gctgtccctc   1800
tttgctgtcc accgctcctc cctggagaac ccggagcacg acgagtctgg tgccctagta   1860
ttgccccggg tcctggacaa gctcacgctg tgcatgtgcc cggagcgccc cttcactgcc   1920
aaggccagca gatcaccgg cctgagcagt gagggcctgg cgcgatgccg gaaggctggc   1980
tttgatggcg ccgtggtgcg gacgctgcag gccttcctga gccgccaggc agggcccatc   2040
tgccttgtgg cccacaatgg ctttgattat gatttccccc tgctgtgtgc cgagctgcgg   2100
cgcctgggtg cccgcctgcc ccgggacact gtctgcctgg acacgctgcc ggccctgcgg   2160
ggcctggacc gcgcccacag ccacggcacc cgggcccggg gccgccaggg ttacagcctc   2220
ggcagcctct tccaccgcta cttccgggca gagccaagcg cagcccactc agccgagggc   2280
gacgtgcaca cccctgctcc tgatcttcct gcaccgcgcc gcagagctgc tcgcctgggcc   2340
gatgagcagg cccgtgggtg ggcccacatc gagcccatgt acttgccgcc tgatgacccc   2400
agcctggagg cggccgactg ataactcgag cgctagcacc cagctttctt gtacaaagtg   2460
gtgatctaga gggcccgcgg ttcgaaggta agcctatccc taaccctctc ctcggtctcg   2520
attctacgcg taccggttag taatgagttt aaacgggggga ggctaactga acacgcgaag   2580
gagacaatac cggaaggaac ccgcgctatg acggcaataa aaagacagaa taaaacgcac   2640
gggtgttggg tcgtttgttc ataaacgcgg ggttcggtcc cagggctggc actctgtcga   2700
taccccaccg agacccccatt ggggccaata cgcccgcgtt tcttcctttt ccccaccccca   2760
ccccccaagt tcgggtgaag gcccagggct cgcagccaac gtcggggcgg caggccctgc   2820
catagcagat ctgcgcagct ggggctctag ggggtatccc cacgcgccct gtagcggcgc   2880
attaagcgcg gcgggtgtgg tggttacgcg cagcgtgacc gctacacttg ccagcgccct   2940
agcgcccgct cctttcgctt tcttcccttc ctttctcgcc acgttcgccg gctttccccg   3000
tcaagctcta aatcggggca tccctttagg gttccgattt agtgctttac ggcacctcga   3060
ccccaaaaaa cttgattagg gtgatggttc acgtagtggg ccatcgccct gatagacggt   3120
ttttcgccct ttgacgttgg agtccacgtt ctttaatagt ggactcttgt tccaaactgg   3180
aacaacactc aaccctatct cggtctattc ttttgattta agggatttt gggg gatttc   3240
```

```
ggcctattgg ttaaaaaatg agctgattta acaaaaattt aacgcgaatt aattctgtgg   3300
aatgtgtgtc agttagggtg tggaaagtcc ccaggctccc cagcaggcag aagtatgcaa   3360
agcatgcatc tcaattagtc agcaaccagg tgtggaaagt ccccaggctc cccagcaggc   3420
agaagtatgc aaagcatgca tctcaattag tcagcaacca tagtcccgcc cctaactccg   3480
cccatcccgc ccctaactcc gcccagttcc gcccattctc cgcccatggg ctgactaatt   3540
tttttatttt atgcagaggc cgaggccgcc tctgcctctg agctattcca gaagtagtga   3600
ggaggctttt ttggaggcct aggcttttgc aaaaagctcc cgggagcttg tatatccatt   3660
ttcggatctg atcagcacgt gttgacaatt aatcatcggc atagtatatc ggcatagtat   3720
aatacgacaa ggtgaggaac taaaccatgg ccaagccttt gtctcaagaa gaatccaccc   3780
tcattgaaag agcaacggct acaatcaaca gcatccccat ctctgaagac tacagcgtcg   3840
ccagcgcagc tctctctagc gacggccgca tcttcactgg tgtcaatgta tatcatttta   3900
ctgggggacc ttgtgcagaa ctcgtggtgc tgggcactgc tgctgctgcg gcagctggca   3960
acctgacttg tatcgtcgcg atcggaaatg agaacagggg catcttgagc ccctgcggac   4020
ggtgccgaca ggtgcttctc gatctgcatc ctgggatcaa agccatagtg aaggacagtg   4080
atggacagcc gacggcagtt gggattcgtg aattgctgcc ctctggttat gtgtgggagg   4140
gctaagcact tcgtggccga ggagcaggac tgacacgtgc tacgagattt cgattccacc   4200
gccgccttct atgaaaggtt gggcttcgga atcgttttcc gggacgccgg ctggatgatc   4260
ctccagcgcg gggatctcat gctggagttc ttcgcccacc ccaacttgtt tattgcagct   4320
tataatggtt acaaataaag caatagcatc acaaatttca caaataaagc atttttttca   4380
ctgcattcta gttgtggttt gtccaaactc atcaatgtat cttatcatgt ctgtataccg   4440
tcgacctcta gctagagctt ggcgtaatca tggtcatagc tgtttcctgt gtgaaattgt   4500
tatccgctca caattccaca acatacga gccggaagca taaagtgtaa agcctggggt   4560
gcctaatgag tgagctaact cacattaatt gcgttgcgct cactgcccgc tttccagtcg   4620
ggaaacctgt cgtgccagct gcattaatga atcggccaac gcgcggggag aggcggtttg   4680
cgtattgggc gctcttccgc ttcctcgctc actgactcgc tgcgctcggt cgttcggctg   4740
cggcgagcgg tatcagctca ctcaaaggcg gtaatacggt tatccacaga atcaggggat   4800
aacgcaggaa agaacatgtg agcaaaaggc cagcaaaagg ccaggaaccg taaaaaggcc   4860
gcgttgctgg cgttttccca taggctccgc cccctgacg agcatcacaa aaatcgacgc   4920
tcaagtcaga ggtggcgaaa cccgacagga ctataaagat accaggcgtt ccccctggaa   4980
agctccctcg tgcgctctcc tgttccgacc ctgccgctta ccggatacct gtccgccttt   5040
ctcccttcgg gaagcgtggc gctttctcat agctcacgct gtaggtatct cagttcggtg   5100
taggtcgttc gctccaagct gggctgtgtg cacgaacccc ccgttcagcc cgaccgctgc   5160
gccttatccg gtaactatcg tcttgagtcc aacccggtaa gacacgactt atcgccactg   5220
gcagcagcca ctggtaacag gattagcaga gcgaggtatg taggcggtgc tacagagttc   5280
ttgaagtggt ggcctaacta cggctacact agaagaacag tatttggtat ctgcgctctg   5340
ctgaagccag ttaccttcgg aaaaagagtt ggtagctctt gatccggcaa acaaaccacc   5400
gctggtagcg gtttttttgt ttgcaagcag cagattacgc gcagaaaaaa aggatctcaa   5460
gaagatcctt tgatcttttc tacggggtct gacgctcagt ggaacgaaaa ctcacgttaa   5520
gggattttgg tcatgagatt atcaaaaagg atcttcacct agatcctttt aaattaaaaa   5580
```

| tgaagttta aatcaatcta aagtatatat gagtaaactt ggtctgacag ttaccaatgc | 5640 |
| ttaatcagtg aggcacctat ctcagcgatc tgtctatttc gttcatccat agttgcctga | 5700 |
| ctccccgtcg tgtagataac tacgatacgg gagggcttac catctggccc cagtgctgca | 5760 |
| atgataccgc gagacccacg ctcaccggct ccagatttat cagcaataaa ccagccagcc | 5820 |
| ggaagggccg agcgcagaag tggtcctgca actttatccg cctccatcca gtctattaat | 5880 |
| tgttgccggg aagctagagt aagtagttcg ccagttaata gtttgcgcaa cgttgttgcc | 5940 |
| attgctacag gcatcgtggt gtcacgctcg tcgtttggta tggcttcatt cagctccggt | 6000 |
| tcccaacgat caaggcgagt tacatgatcc cccatgttgt gcaaaaaagc ggttagctcc | 6060 |
| ttcggtcctc cgatcgttgt cagaagtaag ttggccgcag tgttatcact catggttatg | 6120 |
| gcagcactgc ataattctct tactgtcatg ccatccgtaa gatgcttttc tgtgactggt | 6180 |
| gagtactcaa ccaagtcatt ctgagaatag tgtatgcggc gaccgagttg ctcttgcccg | 6240 |
| gcgtcaatac gggataatac cgcgccacat agcagaactt taaaagtgct catcattgga | 6300 |
| aaacgttctt cggggcgaaa actctcaagg atcttaccgc tgttgagatc cagttcgatg | 6360 |
| taacccactc gtgcacccaa ctgatcttca gcatctttta ctttcaccag cgtttctggg | 6420 |
| tgagcaaaaa caggaaggca aaatgccgca aaaaagggaa taagggcgac acggaaatgt | 6480 |
| tgaatactca tactcttcct ttttcaatat tattgaagca tttatcaggg ttattgtctc | 6540 |
| atgagcggat acatatttga atgtatttag aaaaataaac aatagggggt ccgcgcaca | 6600 |
| tttccccgaa aagtgccacc tgacgtc | 6627 |

<210> SEQ ID NO 415
<211> LENGTH: 3165
<212> TYPE: DNA
<213> ORGANISM: artificial sequence
<220> FEATURE:
<223> OTHER INFORMATION: pCLS2198

<400> SEQUENCE: 415

| gcggccgcaa taaatatct ttattttcat tacatctgtg tgttggtttt tgtgtgaat | 60 |
| cgtaactaac atacgctctc catcaaaaca aaacgaaaca aaacaaacta gcaaaatagg | 120 |
| ctgtccccag tgcaagtgca ggtgccagaa catttctcta tcgaaggatc tgcgatcgct | 180 |
| ccggtgcccg tcagtgggca gagcgcacat cgcccacagt ccccgagaag ttgggggag | 240 |
| gggtcggcaa ttgaacgggt gcctagagaa ggtggcgcgg ggtaaactgg gaaagtgatg | 300 |
| tcgtgtactg gctccgcctt ttccccgagg gtgggggaga accgtatata agtgcagtag | 360 |
| tcgccgtgaa cgttcttttt cgcaacgggt ttgccgccag aacacagctg aagcttcgag | 420 |
| gggctcgcat ctctccttca cgcgcccgcc gccctacctg aggccgccat ccacgccggt | 480 |
| tgagtcgcgt tctccgcct cccgcctgtg gtgcctcctg aactgcgtcc gccgtctagg | 540 |
| taagtttaaa gctcaggtcg agaccgggcc tttgtccggc gctcccttgg agcctaccta | 600 |
| gactcagccg gctctccacg ctttgcctga ccctgcttgc tcaactctac gtctttgttt | 660 |
| cgttttctgt tctgcgccgt tacagatcca agctgtgacc ggcgcctacc tgagatcacc | 720 |
| ggcgtgtcga cggatccagc gctctgcagc catgggctag ctggccagac atgataagat | 780 |
| acattgatga gtttggacaa accacaacta gaatgcagtg aaaaaaatgc tttatttgtg | 840 |
| aaatttgtga tgctattgct ttatttgtaa ccattataag ctgcaataaa caagttaaca | 900 |
| acaacaattg cattcatttt atgtttcagg ttcaggggga ggtgtgggag gtttttaaa | 960 |
| gcaagtaaaa cctctacaaa tgtggtatgg aattctaaaa tacagcatag caaaacttta | 1020 |

```
acctccaaat caagcctcta cttgaatcct tttctgaggg atgaataagg cataggcatc    1080
aggggctgtt gccaatgtgc attagctgtt tgcagcctca ccttctttca tggagtttaa    1140
gatatagtgt attttcccaa ggtttgaact agctcttcat ttctttatgt tttaaatgca    1200
ctgacctccc acattccctt tttagtaaaa tattcagaaa taatttaaat acatcattgc    1260
aatgaaaata aatgtttttt attaggcaga atccagatgc tcaaggccct tcataatatc    1320
ccccagttta gtagttggac ttagggaaca aaggaacctt taatagaaat tggacagcaa    1380
gaaagcgagc ttctagctta tcctcagtcc tgctcctctg ccacaaagtg cacgcagttg    1440
ccggccgggt cgcgcagggc gaactcccgc cccacggct gctcgccgat ctcggtcatg     1500
gccggcccgg aggcgtcccg gaagttcgtg gacacgacct ccgaccactc ggcgtacagc    1560
tcgtccaggc cgcgcaccca cacccaggcc agggtgttgt ccggcaccac ctggtcctgg    1620
accgcgctga tgaacagggt cacgtcgtcc cggaccacac cggcgaagtc gtcctccacg    1680
aagtcccggg agaacccgag ccggtcggtc cagaactcga ccgctccggc gacgtcgcgc    1740
gcggtgagca ccggaacggc actggtcaac ttggccatga tggccctcct atagtgagtc    1800
gtattatact atgccgatat actatgccga tgattaattg tcaaaacagc gtggatggcg    1860
tctccagctt atctgacggt tcactaaacg agctctgctt atatagacct cccaccgtac    1920
acgcctaccg cccatttgcg tcaatggggc ggagttgtta cgacattttg gaaagtcccg    1980
ttgatttact agtcaaaaca aactcccatt gacgtcaatg gggtggagac ttggaaatcc    2040
ccgtgagtca aaccgctatc cacgcccatt gatgtactgc caaaaccgca tcatcatggt    2100
aatagcgatg actaatacgt agatgtactg ccaagtagga aagtcccata aggtcatgta    2160
ctgggcataa tgccaggcgg gccatttacc gtcattgacg tcaataggg gcgtacttgg     2220 catatgatac acttgatgta ctgccaagtg gcagtttac cgtaaatact ccacccattg     2280
acgtcaatgg aaagtcccta ttggcgttac tatgggaaca tacgtcatta ttgacgtcaa    2340 tgggcgggg tcgttgggcg gtcagccagg cgggccattt accgtaagtt atgtaacgcc     2400
tgcaggttaa ttaagaacat gtgagcaaaa ggccagcaaa aggccaggaa ccgtaaaaag    2460
gccgcgttgc tggcgttttt ccataggctc cgcccccctg acgagcatca aaaaatcga    2520 cgctcaagtc agaggtggcg aaacccgaca ggactataaa gataccaggc gtttccccct    2580
ggaagctccc tcgtgcgctc tcctgttccg accctgccgc ttaccggata cctgtccgcc    2640
tttctccctt cgggaagcgt ggcgctttct catagctcac gctgtaggta tctcagttcg    2700
gtgtaggtcg ttcgctccaa gctgggctgt gtgcacgaac ccccgttca gcccgaccgc     2760 tgcgccttat ccggtaacta tcgtcttgag tccaacccgg taagacacga cttatcgcca    2820
ctggcagcag ccactggtaa caggattagc agagcgaggt atgtaggcgg tgctacagag    2880
ttcttgaagt ggtggcctaa ctacggctac actagaagaa cagtatttgg tatctgcgct    2940
ctgctgaagc cagttacctt cggaaaaaga gttggtagct cttgatccgg caaacaaacc    3000
accgctggta gcggtggttt ttttgtttgc aagcagcaga ttacgcgcag aaaaaaagga    3060
tctcaagaag atcctttgat cttttctacg gggtctgacg ctcagtggaa cgaaaactca    3120
cgttaaggga ttttggtcat ggctagttaa ttaacattta aatca                   3165

<210> SEQ ID NO 416
<211> LENGTH: 1605
<212> TYPE: DNA
<213> ORGANISM: artificial sequence
<220> FEATURE:
```

<223> OTHER INFORMATION: RVD_bhEGFP_T03g06

<400> SEQUENCE: 416

```
accgcgtctc tctcccagag cgacatcgtc aagattgccg ggaataacgg gggagcacaa      60
gccctgcaag ctgtcctcga cctggagagt atgctcggga agagaggctt ctcacgcgat     120
gacatcgcca agatggccgg gaacatcggc ggcgcacaga cccttcaggc cgtgctcgat     180
ttggagtccg ccttcaggga gcggggattc agccaggctg acattgtcaa gatcgctgga     240
catgacggcg agcacaggc tctctacagt gtgctggatg tggaacccac tctgggcaag     300
cggggcttca gccgggccga tattgtcaaa atcgcaggcc acgacggggg ggcccaagcc     360
cttcacactg tgttggattt ggagcccgcc ctggggaagc gggggttttc cagaatcgac     420
attgtgaaaa ttgccgccca tgacggaggc gctcaggccc ttcacgccgt gctggacctg     480
ggaccaacac tgagggagtg tgggtttct caggctacca tcgccaaaat cgccgggaac     540
gggggcggag cccaggcact ccagatggtg ctggacttgg ggccagccct gggcaagagg     600
gggtttagcc aggccaccat cgctaagatc gccggcaaca atggaggcgc ccaagcactg     660
caaacagtcc tggatcttga gcctgccctc tgcgagagag gttttccca ggccacaatt     720
gccaaaatgg ccggcaacat tggggcgca caggccctcc agacagtgct ggatctggaa     780
cccgccctgc ggaagaggga cttcaggcag gccgacatca ttaaaattgc tgggaatatc     840
ggcggagccc aagccttgca ggcagtcatc gaacacgggc ctacactcag acagcacggc     900
ttcaatctgg cagatattgt caagatggcc ggaaataatg ggggcgccca gcccttcag      960
gccgtgcttg acctcaagcc cgtgttggac gagcatgggt ttagtcagcc cgacattgtg    1020
aaaatggctg gcaacggcgg gggcgctcag gcactgcaag ccgtcctgtc actcggaccc    1080
gccctgcggg agagagggtt ttctcagcct gacatcgtga aaattgccgg gaacggggg      1140
ggcgcacaag ctcttcaggc tgtgctggac ctcgaactga ctctcgtgga gcacgggttc    1200
tcccaggccg acatcgtcaa aatcgccggg cacgatggag ggacacaggc cctgcacgcc    1260
gtcctcgatc tggagaggat gctgggcgag cggggattta gcagggccga tattgtgaac    1320
gtggccggga acattggcgg ggctcaggcc ctgaaggcag tgttggagca cgaagccacc    1380
ctgaacgagc gcggcttcaa cctgacagac atcgtcgaga tggctgccaa tggcggaggg    1440
gcccaagcat gaaggctgt cctggaacat ggcccaaccc tgaggcagcg gggcctctcc    1500
ctcattgata ttgtggagat cgccggccac gacggcggcg cccaggcact gaaggccgtg    1560
ttgaagtatg cccagtgct gatgcaggcc gggagaggag acgcc                     1605
```

<210> SEQ ID NO 417
<211> LENGTH: 785
<212> TYPE: PRT
<213> ORGANISM: artificial sequence
<220> FEATURE:
<223> OTHER INFORMATION: TevM01_b36EGfpT3g6

<400> SEQUENCE: 417

```
Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
                20                  25                  30

Phe Lys Asp Leu Glu Lys Gly Cys His Ser Ser Ile Lys Leu Gln Arg
            35                  40                  45

Ser Phe Asn Lys His Gly Asn Val Phe Glu Cys Ser Ile Leu Glu Glu
        50                  55                  60
```

-continued

```
Ile Pro Tyr Glu Lys Asp Leu Ile Ile Glu Arg Glu Asn Phe Trp Ile
 65                  70                  75                  80

Lys Glu Leu Asn Ser Lys Ile Asn Gly Tyr Asn Ile Ala Asp Ala Thr
                 85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ile Ala Ser Thr Ala Phe
    130                 135                 140

Val Asp Gln Asp Lys Gln Met Ala Asn Arg Leu Asn Leu Ser Pro Leu
145                 150                 155                 160

Glu Arg Ser Lys Ile Glu Lys Gln Tyr Gly Gly Ala Thr Thr Leu Ala
                165                 170                 175

Phe Ile Ser Asn Lys Gln Asn Glu Leu Ala Gln Ile Leu Ser Arg Ala
            180                 185                 190

Asp Ile Leu Lys Ile Ala Ser Tyr Asp Cys Ala Ala His Ala Leu Gln
        195                 200                 205

Ala Val Leu Asp Cys Gly Pro Met Leu Gly Lys Arg Gly Phe Ser Gln
    210                 215                 220

Ser Asp Ile Val Lys Ile Ala Gly Asn Gly Gly Ala Gln Ala Leu
225                 230                 235                 240

Gln Ala Val Leu Asp Leu Glu Ser Met Leu Gly Lys Arg Gly Phe Ser
                245                 250                 255

Arg Asp Asp Ile Ala Lys Met Ala Gly Asn Ile Gly Gly Ala Gln Thr
            260                 265                 270

Leu Gln Ala Val Leu Asp Leu Glu Ser Ala Phe Arg Glu Arg Gly Phe
        275                 280                 285

Ser Gln Ala Asp Ile Val Lys Ile Ala Gly His Asp Gly Gly Ala Gln
    290                 295                 300

Ala Leu Tyr Ser Val Leu Asp Val Glu Pro Thr Leu Gly Lys Arg Gly
305                 310                 315                 320

Phe Ser Arg Ala Asp Ile Val Lys Ile Ala Gly His Asp Gly Gly Ala
                325                 330                 335

Gln Ala Leu His Thr Val Leu Asp Leu Glu Pro Ala Leu Gly Lys Arg
            340                 345                 350

Gly Phe Ser Arg Ile Asp Ile Val Lys Ile Ala Ala His Asp Gly Gly
        355                 360                 365

Ala Gln Ala Leu His Ala Val Leu Asp Leu Gly Pro Thr Leu Arg Glu
    370                 375                 380

Cys Gly Phe Ser Gln Ala Thr Ile Ala Lys Ile Ala Gly Asn Gly Gly
385                 390                 395                 400

Gly Ala Gln Ala Leu Gln Met Val Leu Asp Leu Gly Pro Ala Leu Gly
                405                 410                 415

Lys Arg Gly Phe Ser Gln Ala Thr Ile Ala Lys Ile Ala Gly Asn Asn
            420                 425                 430

Gly Gly Ala Gln Ala Leu Gln Thr Val Leu Asp Leu Glu Pro Ala Leu
        435                 440                 445

Cys Glu Arg Gly Phe Ser Gln Ala Thr Ile Ala Lys Met Ala Gly Asn
    450                 455                 460

Ile Gly Gly Ala Gln Ala Leu Gln Thr Val Leu Asp Leu Glu Pro Ala
465                 470                 475                 480
```

```
Leu Arg Lys Arg Asp Phe Arg Gln Ala Asp Ile Ile Lys Ile Ala Gly
                485                 490                 495

Asn Ile Gly Gly Ala Gln Ala Leu Gln Ala Val Ile Glu His Gly Pro
            500                 505                 510

Thr Leu Arg Gln His Gly Phe Asn Leu Ala Asp Ile Val Lys Met Ala
            515                 520                 525

Gly Asn Asn Gly Gly Ala Gln Ala Leu Gln Ala Val Leu Asp Leu Lys
            530                 535                 540

Pro Val Leu Asp Glu His Gly Phe Ser Gln Pro Asp Ile Val Lys Met
545                 550                 555                 560

Ala Gly Asn Gly Gly Gly Ala Gln Ala Leu Gln Ala Val Leu Ser Leu
                565                 570                 575

Gly Pro Ala Leu Arg Glu Arg Gly Phe Ser Gln Pro Asp Ile Val Lys
                580                 585                 590

Ile Ala Gly Asn Gly Gly Gly Ala Gln Ala Leu Gln Ala Val Leu Asp
                595                 600                 605

Leu Glu Leu Thr Leu Val Glu His Gly Phe Ser Gln Ala Asp Ile Val
            610                 615                 620

Lys Ile Ala Gly His Asp Gly Gly Thr Gln Ala Leu His Ala Val Leu
625                 630                 635                 640

Asp Leu Glu Arg Met Leu Gly Glu Arg Gly Phe Ser Arg Ala Asp Ile
                645                 650                 655

Val Asn Val Ala Gly Asn Ile Gly Gly Ala Gln Ala Leu Lys Ala Val
                660                 665                 670

Leu Glu His Glu Ala Thr Leu Asn Glu Arg Gly Phe Asn Leu Thr Asp
                675                 680                 685

Ile Val Glu Met Ala Ala Asn Gly Gly Ala Gln Ala Leu Lys Ala
            690                 695                 700

Val Leu Glu His Gly Pro Thr Leu Arg Gln Arg Gly Leu Ser Leu Ile
705                 710                 715                 720

Asp Ile Val Glu Ile Ala Gly His Asp Gly Gly Ala Gln Ala Leu Lys
                725                 730                 735

Ala Val Leu Lys Tyr Gly Pro Val Leu Met Gln Ala Gly Arg Ser Asn
                740                 745                 750

Glu Glu Ile Val His Val Ala Ala Arg Arg Gly Gly Ala Gly Arg Ile
            755                 760                 765

Arg Lys Met Val Ala Pro Leu Leu Glu Arg Gln Gly Arg Ser Ser Ala
            770                 775                 780

Asp
785

<210> SEQ ID NO 418
<211> LENGTH: 343
<212> TYPE: PRT
<213> ORGANISM: artificial sequence
<220> FEATURE:
<223> OTHER INFORMATION: TevM01_cT11n3h

<400> SEQUENCE: 418

Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
                20                  25                  30

Phe Lys Asp Leu Glu Lys Gly Cys His Ser Ser Ile Lys Leu Gln Arg
            35                  40                  45
```

```
Ser Phe Asn Lys His Gly Asn Val Phe Glu Cys Ser Ile Leu Glu Glu
 50                  55                  60

Ile Pro Tyr Glu Lys Asp Leu Ile Ile Glu Arg Glu Asn Phe Trp Ile
 65                  70                  75                  80

Lys Glu Leu Asn Ser Lys Ile Asn Gly Tyr Asn Ile Ala Asp Ala Thr
                 85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ser Gly Val Asp Leu Arg
    130                 135                 140

Thr Leu Gly Tyr Ser Gln Gln Gln Glu Lys Ile Lys Pro Lys Val
145                 150                 155                 160

Arg Ser Thr Val Ala Gln His His Glu Ala Leu Val Gly His Gly Phe
                165                 170                 175

Thr His Ala His Ile Val Ala Leu Ser Gln His Pro Ala Ala Leu Gly
            180                 185                 190

Thr Val Ala Val Lys Tyr Gln Asp Met Ile Ala Ala Leu Pro Glu Ala
        195                 200                 205

Thr His Glu Ala Ile Val Gly Val Gly Lys Gln Trp Ser Gly Ala Arg
    210                 215                 220

Ala Leu Glu Ala Leu Leu Thr Val Ala Gly Glu Leu Arg Gly Pro Pro
225                 230                 235                 240

Leu Gln Leu Asp Thr Gly Gln Leu Leu Lys Ile Ala Lys Arg Gly Gly
                245                 250                 255

Val Thr Ala Val Glu Ala Val His Ala Trp Arg Asn Ala Leu Thr Gly
            260                 265                 270

Ala Pro Leu Asn Leu Thr Gly Asp Ala Arg Gly Ile Arg Ser Arg Ala
        275                 280                 285

Ser Arg Ser Ile Val Ala Gln Leu Ser Arg Pro Asp Pro Gly Ala Pro
    290                 295                 300

Lys Lys Lys Arg Lys Val Glu Ser Pro Lys Lys Lys Arg Lys Val Glu
305                 310                 315                 320

Ser Pro Lys Lys Lys Arg Lys Val Glu Gly Asn Ser Tyr Pro Tyr Asp
                325                 330                 335

Val Pro Asp Tyr Ala Ala Asp
            340

<210> SEQ ID NO 419
<211> LENGTH: 372
<212> TYPE: PRT
<213> ORGANISM: artificial sequence
<220> FEATURE:
<223> OTHER INFORMATION: TevM01_cT40n3h

<400> SEQUENCE: 419

Met Ala Lys Ser Gly Ile Tyr Gln Ile Lys Asn Thr Leu Asn Asn Lys
 1               5                  10                  15

Val Tyr Val Gly Ser Ala Lys Asp Phe Glu Lys Arg Trp Lys Arg His
                20                  25                  30

Phe Lys Asp Leu Glu Lys Gly Cys His Ser Ser Ile Lys Leu Gln Arg
            35                  40                  45

Ser Phe Asn Lys His Gly Asn Val Phe Glu Cys Ser Ile Leu Glu Glu
 50                  55                  60
```

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ser Gly Val Asp Leu Arg
    130                 135                 140

Thr Leu Gly Tyr Ser Gln Gln Gln Glu Lys Ile Lys Pro Lys Val
145                 150                 155                 160

Arg Ser Thr Val Ala Gln His His Glu Ala Leu Val Gly His Gly Phe
                165                 170                 175

Thr His Ala His Ile Val Ala Leu Ser Gln His Pro Ala Ala Leu Gly
            180                 185                 190

Thr Val Ala Val Lys Tyr Gln Asp Met Ile Ala Ala Leu Pro Glu Ala
        195                 200                 205

Thr His Glu Ala Ile Val Gly Val Gly Lys Gln Trp Ser Gly Ala Arg
    210                 215                 220

Ala Leu Glu Ala Leu Leu Thr Val Ala Gly Glu Leu Arg Gly Pro Pro
225                 230                 235                 240

Leu Gln Leu Asp Thr Gly Gln Leu Leu Lys Ile Ala Lys Arg Gly Gly
                245                 250                 255

Val Thr Ala Val Glu Ala Val His Ala Trp Arg Asn Ala Leu Thr Gly
            260                 265                 270

Ala Pro Leu Asn Leu Thr Gly Asp Ala Arg Gly Ile Arg Ser Arg Ala
        275                 280                 285

Ser Arg Ser Ile Val Ala Gln Leu Ser Arg Pro Asp Pro Ala Leu Ala
    290                 295                 300

Ala Leu Thr Asn Asp His Leu Val Ala Leu Ala Cys Leu Gly Gly Arg
305                 310                 315                 320

Pro Ala Leu Asp Ala Val Lys Lys Gly Leu Gly Ala Pro Lys Lys Lys
                325                 330                 335

Arg Lys Val Glu Ser Pro Lys Lys Arg Lys Val Glu Ser Pro Lys
            340                 345                 350

Lys Lys Arg Lys Val Glu Gly Asn Ser Tyr Pro Tyr Asp Val Pro Asp
        355                 360                 365

Tyr Ala Ala Asp
    370

<210> SEQ ID NO 420
<211> LENGTH: 2826
<212> TYPE: DNA
<213> ORGANISM: artificial sequence
<220> FEATURE:
<223> OTHER INFORMATION: pCLS14975

<400> SEQUENCE: 420
gctagcctta ggcgcgccac tagcgctctc gaggtcacgc gccaagccgc caacatgttg      60
ctataagctt cgactgtgcc ttctagttgc cagccatctg ttgtttgccc ctcccccgtg     120
ccttccttga ccctggaagg tgccactccc actgtccttt cctaataaaa tgaggaaatt     180
gcatcgcatt gtctgagtag gtgtcattct attctggggg gtggggtggg caggacagc     240 aagggggagg attgggaaga caatagcagg catgctgggg atgcggtggg ctctatggga     300

| | |
|---|---|
| tatcttctta attaagacct agcatgtgag caaaaggcca gcaaaaggcc aggaaccgta | 360 |
| aaaaggccgc gttgctggcg ttttccata ggctccgccc ccctgacgag catcacaaaa | 420 |
| atcgacgctc aagtcagagg tggcgaaacc cgacaggact ataaagatac caggcgtttc | 480 |
| cccctggaag ctccctcgtg cgctctcctg ttccgaccct gccgcttacc ggatacctgt | 540 |
| ccgcctttct cccttcggga agcgtggcgc tttctcatag ctcacgctgt aggtatctca | 600 |
| gttcggtgta ggtcgttcgc tccaagctgg gctgtgtgca cgaacccccc gttcagcccg | 660 |
| accgctgcgc cttatccggt aactatcgtc ttgagtccaa cccggtaaga cacgacttat | 720 |
| cgccactggc agcagccact ggtaacagga ttagcagagc gaggtatgta ggcggtgcta | 780 |
| cagagttctt gaagtggtgg cctaactacg gctacactag aaggacagta tttggtatct | 840 |
| gcgctctgct gaagccagtt accttcggaa aaagagttgg tagctcttga tccggcaaac | 900 |
| aaaccaccgc tggtagcggt ggtttttttg tttgcaagca gcagattacg cgcagaaaaa | 960 |
| aaggatctca agaagatcct ttgatctttt ctacggggtc tgacgctcag tggaacgaaa | 1020 |
| actcacgtta agggattttg gtcatgagat tatcaaaaag gatcttcacc tagatccttt | 1080 |
| taaattaaaa atgaagtttt aaatcaatct aaagtatata tgagtaaact tggtctgaca | 1140 |
| gttaccaatg cttaatcagt gaggcaccta tctcagcgat ctgtctattt cgttcatcca | 1200 |
| tagttgcctg actccccgtc gtgtagataa ctacgatacg ggagggctta ccatctggcc | 1260 |
| ccagtgctgc aatgataccg cgagacccac gctcaccggc tccagattta tcagcaataa | 1320 |
| accagccagc cggaagggcc gagcgcagaa gtggtcctgc aactttatcc gcctccatcc | 1380 |
| agtctattaa ttgttgccgg gaagctagag taagtagttc gccagttaat agtttgcgca | 1440 |
| acgttgttgc cattgctaca ggcatcgtgg tgtcacgctc gtcgtttggt atggcttcat | 1500 |
| tcagctccgg ttcccaacga tcaaggcgag ttacatgatc ccccatgttg tgcaaaaaag | 1560 |
| cggttagctc cttcggtcct ccgatcgttg tcagaagtaa gttggccgca gtgttatcac | 1620 |
| tcatggttat ggcagcactg cataattctc ttactgtcat gccatccgta agatgctttt | 1680 |
| ctgtgactgg tgagtactca accaagtcat tctgagaata gtgtatgcgg cgaccgagtt | 1740 |
| gctcttgccc ggcgtcaata cgggataata ccgcgccaca tagcagaact ttaaaagtgc | 1800 |
| tcatcattgg aaaacgttct cggggcgaaa actctcaag gatcttaccg ctgttgagat | 1860 |
| ccagttcgat gtaaccccact cgtgcaccca actgatcttc agcatctttt actttcacca | 1920 |
| gcgtttctgg gtgagcaaaa acaggaaggc aaaatgccgc aaaaaaggga taagggcga | 1980 |
| cacggaaatg ttgaatactc atactcttcc tttttcaata ttattgaagc atttatcagg | 2040 |
| gttattgtct catgagcgga tacatatttg aatgtattta gaaaaataaa caaatagggg | 2100 |
| ttccgcgcac atttccccga aaagtgccac ctgacaaact tggtaccata actagttcgg | 2160 |
| cgcgttgaca ttgattattg actagttatt aatagtaatc aattacgggg tcattagttc | 2220 |
| atagcccata tatggagttc cgcgttacat aacttacggt aaatggcccg cctggctgac | 2280 |
| cgcccaacga cccccgccca ttgacgtcaa taatgacgta tgttcccata gtaacgccaa | 2340 |
| tagggacttt ccattgacgt caatgggtgg agtatttacg gtaaactgcc cacttggcag | 2400 |
| tacatcaagt gtatcatatg ccaagtacgc cccctattga cgtcaatgac ggtaaatggc | 2460 |
| ccgcctggca ttatgcccag tacatgacct tatgggactt tcctacttgg cagtacatct | 2520 |
| acgtattagt catcgctatt accatggtga tgcggttttg gcagtacatc aatgggcgtg | 2580 |
| gatagcggtt tgactcacgg ggatttccaa gtctccaccc cattgacgtc aatgggagtt | 2640 |

```
tgttttggca ccaaaatcaa cgggactttc caaaatgtcg taacaactcc gccccattga    2700
cgcaaatggg cggtaggcgt gtacggtggg aggtctatat aagcagagct ctctggctaa    2760
ctagagaacc cactgcttac tggcttatcg aaattaatac gactcactat agggagaccc    2820
aagctg                                                              2826
```

```
<210> SEQ ID NO 421
<211> LENGTH: 859
<212> TYPE: PRT
<213> ORGANISM: artificial sequence
<220> FEATURE:
<223> OTHER INFORMATION: TevM01_cT11n3h_ctEGFP_T03g12-L1

<400> SEQUENCE: 421
```

Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
        35                  40                  45

Ser Phe Asn Lys His Gly Asn Val Phe Glu Cys Ser Ile Leu Glu Glu
    50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ser Gly Val Asp Leu Arg
    130                 135                 140

Thr Leu Gly Tyr Ser Gln Gln Gln Glu Lys Ile Lys Pro Lys Val
145                 150                 155                 160

Arg Ser Thr Val Ala Gln His His Glu Ala Leu Val Gly His Gly Phe
                165                 170                 175

Thr His Ala His Ile Val Ala Leu Ser Gln His Pro Ala Ala Leu Gly
            180                 185                 190

Thr Val Ala Val Lys Tyr Gln Asp Met Ile Ala Ala Leu Pro Glu Ala
        195                 200                 205

Thr His Glu Ala Ile Val Gly Val Gly Lys Gln Trp Ser Gly Ala Arg
    210                 215                 220

Ala Leu Glu Ala Leu Leu Thr Val Ala Gly Glu Leu Arg Gly Pro Pro
225                 230                 235                 240

Leu Gln Leu Asp Thr Gly Gln Leu Leu Lys Ile Ala Lys Arg Gly Gly
                245                 250                 255

Val Thr Ala Val Glu Ala Val His Ala Trp Arg Asn Ala Leu Thr Gly
            260                 265                 270

Ala Pro Leu Asn Leu Thr Pro Gln Gln Val Val Ala Ile Ala Ser Asn
        275                 280                 285

Asn Gly Gly Lys Gln Ala Leu Glu Thr Val Gln Arg Leu Leu Pro Val
    290                 295                 300

Leu Cys Gln Ala His Gly Leu Thr Pro Glu Gln Val Val Ala Ile Ala
305                 310                 315                 320

Ser Asn Ile Gly Gly Lys Gln Ala Leu Glu Thr Val Gln Ala Leu Leu

```
                325                 330                 335
Pro Val Leu Cys Gln Ala His Gly Leu Thr Pro Glu Gln Val Val Ala
            340                 345                 350
Ile Ala Ser Asn Ile Gly Gly Lys Gln Ala Leu Glu Thr Val Gln Ala
            355                 360                 365
Leu Leu Pro Val Leu Cys Gln Ala His Gly Leu Thr Pro Gln Gln Val
            370                 375                 380
Val Ala Ile Ala Ser Asn Asn Gly Gly Lys Gln Ala Leu Glu Thr Val
385                 390                 395                 400
Gln Arg Leu Leu Pro Val Leu Cys Gln Ala His Gly Leu Thr Pro Gln
                405                 410                 415
Gln Val Val Ala Ile Ala Ser Asn Gly Gly Gly Lys Gln Ala Leu Glu
            420                 425                 430
Thr Val Gln Arg Leu Leu Pro Val Leu Cys Gln Ala His Gly Leu Thr
            435                 440                 445
Pro Gln Gln Val Val Ala Ile Ala Ser Asn Gly Gly Gly Lys Gln Ala
            450                 455                 460
Leu Glu Thr Val Gln Arg Leu Leu Pro Val Leu Cys Gln Ala His Gly
465                 470                 475                 480
Leu Thr Pro Glu Gln Val Val Ala Ile Ala Ser His Asp Gly Gly Lys
                485                 490                 495
Gln Ala Leu Glu Thr Val Gln Arg Leu Leu Pro Val Leu Cys Gln Ala
            500                 505                 510
His Gly Leu Thr Pro Glu Gln Val Val Ala Ile Ala Ser Asn Ile Gly
            515                 520                 525
Gly Lys Gln Ala Leu Glu Thr Val Gln Ala Leu Leu Pro Val Leu Cys
            530                 535                 540
Gln Ala His Gly Leu Thr Pro Gln Gln Val Val Ala Ile Ala Ser Asn
545                 550                 555                 560
Gly Gly Gly Lys Gln Ala Leu Glu Thr Val Gln Arg Leu Leu Pro Val
                565                 570                 575
Leu Cys Gln Ala His Gly Leu Thr Pro Glu Gln Val Val Ala Ile Ala
            580                 585                 590
Ser His Asp Gly Gly Lys Gln Ala Leu Glu Thr Val Gln Arg Leu Leu
            595                 600                 605
Pro Val Leu Cys Gln Ala His Gly Leu Thr Pro Gln Gln Val Val Ala
            610                 615                 620
Ile Ala Ser Asn Gly Gly Gly Lys Gln Ala Leu Glu Thr Val Gln Arg
625                 630                 635                 640
Leu Leu Pro Val Leu Cys Gln Ala His Gly Leu Thr Pro Gln Gln Val
                645                 650                 655
Val Ala Ile Ala Ser Asn Asn Gly Gly Lys Gln Ala Leu Glu Thr Val
            660                 665                 670
Gln Arg Leu Leu Pro Val Leu Cys Gln Ala His Gly Leu Thr Pro Glu
            675                 680                 685
Gln Val Val Ala Ile Ala Ser His Asp Gly Gly Lys Gln Ala Leu Glu
            690                 695                 700
Thr Val Gln Arg Leu Leu Pro Val Leu Cys Gln Ala His Gly Leu Thr
705                 710                 715                 720
Pro Glu Gln Val Val Ala Ile Ala Ser Asn Ile Gly Gly Lys Gln Ala
                725                 730                 735
Leu Glu Thr Val Gln Ala Leu Leu Pro Val Leu Cys Gln Ala His Gly
            740                 745                 750
```

```
Leu Thr Pro Glu Gln Val Val Ala Ile Ala Ser His Asp Gly Gly Lys
        755                 760                 765

Gln Ala Leu Glu Thr Val Gln Arg Leu Leu Pro Val Leu Cys Gln Ala
        770                 775                 780

His Gly Leu Thr Pro Gln Gln Val Val Ala Ile Ala Ser Asn Gly Gly
785                 790                 795                 800

Gly Arg Pro Ala Leu Glu Ser Ile Val Ala Gln Leu Ser Arg Pro Asp
                805                 810                 815

Pro Gly Ala Pro Lys Lys Arg Lys Val Glu Ser Pro Lys Lys Lys
                820                 825                 830

Arg Lys Val Glu Ser Pro Lys Lys Arg Lys Val Glu Gly Asn Ser
            835                 840                 845

Tyr Pro Tyr Asp Val Pro Asp Tyr Ala Ala Asp
        850                 855
```

<210> SEQ ID NO 422
<211> LENGTH: 888
<212> TYPE: PRT
<213> ORGANISM: artificial sequence
<220> FEATURE:
<223> OTHER INFORMATION: TevM01_cT40n3h_ctEGFP_T03g12-L1

<400> SEQUENCE: 422

```
Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
        35                  40                  45

Ser Phe Asn Lys His Gly Asn Val Phe Glu Cys Ser Ile Leu Glu Glu
    50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ser Gly Val Asp Leu Arg
    130                 135                 140

Thr Leu Gly Tyr Ser Gln Gln Gln Glu Lys Ile Lys Pro Lys Val
145                 150                 155                 160

Arg Ser Thr Val Ala Gln His His Glu Ala Leu Val Gly His Gly Phe
                165                 170                 175

Thr His Ala His Ile Val Ala Leu Ser Gln His Pro Ala Ala Leu Gly
            180                 185                 190

Thr Val Ala Val Lys Tyr Gln Asp Met Ile Ala Ala Leu Pro Glu Ala
        195                 200                 205

Thr His Glu Ala Ile Val Gly Val Gly Lys Gln Trp Ser Gly Ala Arg
    210                 215                 220

Ala Leu Glu Ala Leu Leu Thr Val Ala Gly Glu Leu Arg Gly Pro Pro
225                 230                 235                 240

Leu Gln Leu Asp Thr Gly Gln Leu Leu Lys Ile Ala Lys Arg Gly Gly
                245                 250                 255
```

```
Val Thr Ala Val Glu Ala Val His Ala Trp Arg Asn Ala Leu Thr Gly
            260                 265                 270

Ala Pro Leu Asn Leu Thr Pro Gln Gln Val Val Ala Ile Ala Ser Asn
            275                 280                 285

Asn Gly Gly Lys Gln Ala Leu Glu Thr Val Gln Arg Leu Leu Pro Val
290                 295                 300

Leu Cys Gln Ala His Gly Leu Thr Pro Glu Gln Val Val Ala Ile Ala
305                 310                 315                 320

Ser Asn Ile Gly Gly Lys Gln Ala Leu Glu Thr Val Gln Ala Leu Leu
            325                 330                 335

Pro Val Leu Cys Gln Ala His Gly Leu Thr Pro Glu Gln Val Val Ala
            340                 345                 350

Ile Ala Ser Asn Ile Gly Gly Lys Gln Ala Leu Glu Thr Val Gln Ala
            355                 360                 365

Leu Leu Pro Val Leu Cys Gln Ala His Gly Leu Thr Pro Gln Gln Val
370                 375                 380

Val Ala Ile Ala Ser Asn Gly Gly Lys Gln Ala Leu Glu Thr Val
385                 390                 395                 400

Gln Arg Leu Leu Pro Val Leu Cys Gln Ala His Gly Leu Thr Pro Gln
                405                 410                 415

Gln Val Val Ala Ile Ala Ser Asn Gly Gly Lys Gln Ala Leu Glu
                420                 425                 430

Thr Val Gln Arg Leu Leu Pro Val Leu Cys Gln Ala His Gly Leu Thr
            435                 440                 445

Pro Gln Gln Val Val Ala Ile Ala Ser Asn Gly Gly Lys Gln Ala
450                 455                 460

Leu Glu Thr Val Gln Arg Leu Leu Pro Val Leu Cys Gln Ala His Gly
465                 470                 475                 480

Leu Thr Pro Glu Gln Val Val Ala Ile Ala Ser His Asp Gly Gly Lys
                485                 490                 495

Gln Ala Leu Glu Thr Val Gln Arg Leu Leu Pro Val Leu Cys Gln Ala
            500                 505                 510

His Gly Leu Thr Pro Glu Gln Val Val Ala Ile Ala Ser Asn Ile Gly
            515                 520                 525

Gly Lys Gln Ala Leu Glu Thr Val Gln Ala Leu Leu Pro Val Leu Cys
            530                 535                 540

Gln Ala His Gly Leu Thr Pro Gln Gln Val Val Ala Ile Ala Ser Asn
545                 550                 555                 560

Gly Gly Gly Lys Gln Ala Leu Glu Thr Val Gln Arg Leu Leu Pro Val
                565                 570                 575

Leu Cys Gln Ala His Gly Leu Thr Pro Glu Gln Val Val Ala Ile Ala
            580                 585                 590

Ser His Asp Gly Gly Lys Gln Ala Leu Glu Thr Val Gln Arg Leu Leu
            595                 600                 605

Pro Val Leu Cys Gln Ala His Gly Leu Thr Pro Gln Gln Val Val Ala
            610                 615                 620

Ile Ala Ser Asn Gly Gly Gly Lys Gln Ala Leu Glu Thr Val Gln Arg
625                 630                 635                 640

Leu Leu Pro Val Leu Cys Gln Ala His Gly Leu Thr Pro Gln Gln Val
                645                 650                 655

Val Ala Ile Ala Ser Asn Asn Gly Gly Lys Gln Ala Leu Glu Thr Val
                660                 665                 670
```

```
            Gln Arg Leu Leu Pro Val Leu Cys Gln Ala His Gly Leu Thr Pro Glu
                    675                 680                 685

Gln Val Val Ala Ile Ala Ser His Asp Gly Lys Gln Ala Leu Glu
                690                 695                 700

Thr Val Gln Arg Leu Leu Pro Val Leu Cys Gln Ala His Gly Leu Thr
            705                 710                 715                 720

Pro Glu Gln Val Val Ala Ile Ala Ser Asn Ile Gly Lys Gln Ala
                            725                 730                 735

Leu Glu Thr Val Gln Ala Leu Leu Pro Val Leu Cys Gln Ala His Gly
                        740                 745                 750

Leu Thr Pro Glu Gln Val Val Ala Ile Ala Ser His Asp Gly Gly Lys
                        755                 760                 765

Gln Ala Leu Glu Thr Val Gln Arg Leu Leu Pro Val Leu Cys Gln Ala
                770                 775                 780

His Gly Leu Thr Pro Gln Gln Val Val Ala Ile Ala Ser Asn Gly Gly
            785                 790                 795                 800

Gly Arg Pro Ala Leu Glu Ser Ile Val Ala Gln Leu Ser Arg Pro Asp
                            805                 810                 815

Pro Ala Leu Ala Ala Leu Thr Asn Asp His Leu Val Ala Leu Ala Cys
                        820                 825                 830

Leu Gly Gly Arg Pro Ala Leu Asp Ala Val Lys Lys Gly Leu Gly Ala
                        835                 840                 845

Pro Lys Lys Lys Arg Lys Val Glu Ser Pro Lys Lys Arg Lys Val
                850                 855                 860

Glu Ser Pro Lys Lys Lys Arg Lys Val Glu Gly Asn Ser Tyr Pro Tyr
            865                 870                 875                 880

Asp Val Pro Asp Tyr Ala Ala Asp
                            885

<210> SEQ ID NO 423
<211> LENGTH: 37
<212> TYPE: DNA
<213> ORGANISM: artificial sequence
<220> FEATURE:
<223> OTHER INFORMATION: primer CMP M001

<400> SEQUENCE: 423
ggctcagaat tcgagcggcc ttggcagcat gggttcc                                37

<210> SEQ ID NO 424
<211> LENGTH: 29
<212> TYPE: DNA
<213> ORGANISM: artificial sequence
<220> FEATURE:
<223> OTHER INFORMATION: primer CMP_M002

<400> SEQUENCE: 424
catccagacc ggtctgtgga ggagtcgcc                                         29

<210> SEQ ID NO 425
<211> LENGTH: 34
<212> TYPE: DNA
<213> ORGANISM: artificial sequence
<220> FEATURE:
<223> OTHER INFORMATION: primer CMP_M003

<400> SEQUENCE: 425
ccacagaccg gtctggatgt tccttactcc gagg                                   34
```

```
<210> SEQ ID NO 426
<211> LENGTH: 90
<212> TYPE: DNA
<213> ORGANISM: artificial sequence
<220> FEATURE:
<223> OTHER INFORMATION: primer CMP_M004

<400> SEQUENCE: 426
ggcatagtcg gccgccgcgt aatcaggaac gtcgtatgga taggatcccg cctccaggct    60
ggggtcatca ggcggcaagt acatgggctc                                    90

<210> SEQ ID NO 427
<211> LENGTH: 863
<212> TYPE: PRT
<213> ORGANISM: artificial sequence
<220> FEATURE:
<223> OTHER INFORMATION: TevM01::cT40NLS3::scTrex2

<400> SEQUENCE: 427
```

Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
        35                  40                  45

Ser Phe Asn Lys His Gly Asn Val Phe Glu Cys Ser Ile Leu Glu Glu
    50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ser Gly Val Asp Leu Arg
    130                 135                 140

Thr Leu Gly Tyr Ser Gln Gln Gln Gln Glu Lys Ile Lys Pro Lys Val
145                 150                 155                 160

Arg Ser Thr Val Ala Gln His His Glu Ala Leu Val Gly His Gly Phe
                165                 170                 175

Thr His Ala His Ile Val Ala Leu Ser Gln His Pro Ala Ala Leu Gly
            180                 185                 190

Thr Val Ala Val Lys Tyr Gln Asp Met Ile Ala Ala Leu Pro Glu Ala
        195                 200                 205

Thr His Glu Ala Ile Val Gly Val Gly Lys Gln Trp Ser Gly Ala Arg
    210                 215                 220

Ala Leu Glu Ala Leu Leu Thr Val Ala Gly Glu Leu Arg Gly Pro Pro
225                 230                 235                 240

Leu Gln Leu Asp Thr Gly Gln Leu Leu Lys Ile Ala Lys Arg Gly Gly
                245                 250                 255

Val Thr Ala Val Glu Ala Val His Ala Trp Arg Asn Ala Leu Thr Gly
            260                 265                 270

Ala Pro Leu Asn Leu Thr Gly Asp Ala Arg Gly Ile Arg Ser Arg Ala
        275                 280                 285

Ser Arg Ser Ile Val Ala Gln Leu Ser Arg Pro Asp Pro Ala Leu Ala
    290                 295                 300

```
Ala Leu Thr Asn Asp His Leu Val Ala Leu Ala Cys Leu Gly Gly Arg
305                 310                 315                 320

Pro Ala Leu Asp Ala Val Lys Lys Gly Leu Gly Ala Pro Lys Lys Lys
            325                 330                 335

Arg Lys Val Glu Ser Pro Lys Lys Arg Lys Val Glu Ser Pro Lys
        340                 345                 350

Lys Lys Arg Lys Val Glu Gly Asn Ser Ser Gly Leu Gly Ser Met Gly
            355                 360                 365

Ser Glu Ala Pro Arg Ala Glu Thr Phe Val Phe Leu Asp Leu Glu Ala
370                 375                 380

Thr Gly Leu Pro Ser Val Glu Pro Glu Ile Ala Glu Leu Ser Leu Phe
385                 390                 395                 400

Ala Val His Arg Ser Ser Leu Glu Asn Pro Glu His Asp Glu Ser Gly
            405                 410                 415

Ala Leu Val Leu Pro Arg Val Leu Asp Lys Leu Thr Leu Cys Met Cys
            420                 425                 430

Pro Glu Arg Pro Phe Thr Ala Lys Ala Ser Glu Ile Thr Gly Leu Ser
            435                 440                 445

Ser Glu Gly Leu Ala Arg Cys Arg Lys Ala Gly Phe Asp Gly Ala Val
450                 455                 460

Val Arg Thr Leu Gln Ala Phe Leu Ser Arg Gln Ala Gly Pro Ile Cys
465                 470                 475                 480

Leu Val Ala His Asn Gly Phe Asp Tyr Asp Phe Pro Leu Leu Cys Ala
            485                 490                 495

Glu Leu Arg Arg Leu Gly Ala Arg Leu Pro Arg Asp Thr Val Cys Leu
            500                 505                 510

Asp Thr Leu Pro Ala Leu Arg Gly Leu Asp Arg Ala His Ser His Gly
            515                 520                 525

Thr Arg Ala Arg Gly Arg Gln Gly Tyr Ser Leu Gly Ser Leu Phe His
530                 535                 540

Arg Tyr Phe Arg Ala Glu Pro Ser Ala Ala His Ser Ala Glu Gly Asp
545                 550                 555                 560

Val His Thr Leu Leu Leu Ile Phe Leu His Arg Ala Ala Glu Leu Leu
            565                 570                 575

Ala Trp Ala Asp Glu Gln Ala Arg Gly Trp Ala His Ile Glu Pro Met
            580                 585                 590

Tyr Leu Pro Pro Asp Asp Pro Ser Leu Glu Ala Thr Pro Pro Gln Thr
            595                 600                 605

Gly Leu Asp Val Pro Tyr Ser Glu Ala Pro Arg Ala Glu Thr Phe Val
            610                 615                 620

Phe Leu Asp Leu Glu Ala Thr Gly Leu Pro Ser Val Glu Pro Glu Ile
625                 630                 635                 640

Ala Glu Leu Ser Leu Phe Ala Val His Arg Ser Ser Leu Glu Asn Pro
            645                 650                 655

Glu His Asp Glu Ser Gly Ala Leu Val Leu Pro Arg Val Leu Asp Lys
            660                 665                 670

Leu Thr Leu Cys Met Cys Pro Glu Arg Pro Phe Thr Ala Lys Ala Ser
            675                 680                 685

Glu Ile Thr Gly Leu Ser Ser Glu Gly Leu Ala Arg Cys Arg Lys Ala
            690                 695                 700

Gly Phe Asp Gly Ala Val Val Arg Thr Leu Gln Ala Phe Leu Ser Arg
705                 710                 715                 720
```

```
Gln Ala Gly Pro Ile Cys Leu Val Ala His Asn Gly Phe Asp Tyr Asp
                725                 730                 735

Phe Pro Leu Leu Cys Ala Glu Leu Arg Arg Leu Gly Ala Arg Leu Pro
            740                 745                 750

Arg Asp Thr Val Cys Leu Asp Thr Leu Pro Ala Leu Arg Gly Leu Asp
        755                 760                 765

Arg Ala His Ser His Gly Thr Arg Ala Arg Gly Arg Gln Gly Tyr Ser
    770                 775                 780

Leu Gly Ser Leu Phe His Arg Tyr Phe Arg Ala Glu Pro Ser Ala Ala
785                 790                 795                 800

His Ser Ala Glu Gly Asp Val His Thr Leu Leu Ile Phe Leu His
                805                 810                 815

Arg Ala Ala Glu Leu Leu Ala Trp Ala Asp Glu Gln Ala Arg Gly Trp
                820                 825                 830

Ala His Ile Glu Pro Met Tyr Leu Pro Pro Asp Pro Ser Leu Glu
            835                 840                 845

Ala Gly Ser Tyr Pro Tyr Asp Val Pro Asp Tyr Ala Ala Ala Asp
    850                 855                 860

<210> SEQ ID NO 428
<211> LENGTH: 529
<212> TYPE: PRT
<213> ORGANISM: artificial sequence
<220> FEATURE:
<223> OTHER INFORMATION: RVD_ cTCD52_T02g10

<400> SEQUENCE: 428

Thr Pro Gln Gln Val Val Ala Ile Ala Ser Asn Asn Gly Gly Lys Gln
1               5                   10                  15

Ala Leu Glu Thr Val Gln Arg Leu Leu Pro Val Leu Cys Gln Ala His
            20                  25                  30

Gly Leu Thr Pro Glu Gln Val Val Ala Ile Ala Ser His Asp Gly Gly
        35                  40                  45

Lys Gln Ala Leu Glu Thr Val Gln Arg Leu Leu Pro Val Leu Cys Gln
    50                  55                  60

Ala His Gly Leu Thr Pro Gln Gln Val Val Ala Ile Ala Ser Asn Gly
65                  70                  75                  80

Gly Gly Lys Gln Ala Leu Glu Thr Val Gln Arg Leu Leu Pro Val Leu
                85                  90                  95

Cys Gln Ala His Gly Leu Thr Pro Glu Gln Val Val Ala Ile Ala Ser
            100                 105                 110

His Asp Gly Gly Lys Gln Ala Leu Glu Thr Val Gln Arg Leu Leu Pro
        115                 120                 125

Val Leu Cys Gln Ala His Gly Leu Thr Pro Gln Gln Val Val Ala Ile
    130                 135                 140

Ala Ser Asn Gly Gly Gly Lys Gln Ala Leu Glu Thr Val Gln Arg Leu
145                 150                 155                 160

Leu Pro Val Leu Cys Gln Ala His Gly Leu Thr Pro Gln Gln Val Val
                165                 170                 175

Ala Ile Ala Ser Asn Gly Gly Gly Lys Gln Ala Leu Glu Thr Val Gln
            180                 185                 190

Arg Leu Leu Pro Val Leu Cys Gln Ala His Gly Leu Thr Pro Glu Gln
        195                 200                 205

Val Val Ala Ile Ala Ser Asn Ile Gly Gly Lys Gln Ala Leu Glu Thr
    210                 215                 220
```

Val Gln Ala Leu Leu Pro Val Leu Cys Gln Ala His Gly Leu Thr Pro
225                 230                 235                 240

Glu Gln Val Val Ala Ile Ala Ser His Asp Gly Gly Lys Gln Ala Leu
            245                 250                 255

Glu Thr Val Gln Arg Leu Leu Pro Val Leu Cys Gln Ala His Gly Leu
        260                 265                 270

Thr Pro Glu Gln Val Val Ala Ile Ala Ser His Asp Gly Gly Lys Gln
            275                 280                 285

Ala Leu Glu Thr Val Gln Arg Leu Leu Pro Val Leu Cys Gln Ala His
    290                 295                 300

Gly Leu Thr Pro Gln Gln Val Val Ala Ile Ala Ser Asn Gly Gly
305                 310                 315                 320

Lys Gln Ala Leu Glu Thr Val Gln Arg Leu Leu Pro Val Leu Cys Gln
                325                 330                 335

Ala His Gly Leu Thr Pro Gln Gln Val Val Ala Ile Ala Ser Asn Asn
            340                 345                 350

Gly Gly Lys Gln Ala Leu Glu Thr Val Gln Arg Leu Leu Pro Val Leu
            355                 360                 365

Cys Gln Ala His Gly Leu Thr Pro Gln Gln Val Val Ala Ile Ala Ser
370                 375                 380

Asn Gly Gly Gly Lys Gln Ala Leu Glu Thr Val Gln Arg Leu Leu Pro
385                 390                 395                 400

Val Leu Cys Gln Ala His Gly Leu Thr Pro Glu Gln Val Val Ala Ile
                405                 410                 415

Ala Ser Asn Ile Gly Gly Lys Gln Ala Leu Glu Thr Val Gln Ala Leu
            420                 425                 430

Leu Pro Val Leu Cys Gln Ala His Gly Leu Thr Pro Glu Gln Val Val
                435                 440                 445

Ala Ile Ala Ser His Asp Gly Gly Lys Gln Ala Leu Glu Thr Val Gln
            450                 455                 460

Arg Leu Leu Pro Val Leu Cys Gln Ala His Gly Leu Thr Pro Glu Gln
465                 470                 475                 480

Val Val Ala Ile Ala Ser His Asp Gly Gly Lys Gln Ala Leu Glu Thr
                485                 490                 495

Val Gln Arg Leu Leu Pro Val Leu Cys Gln Ala His Gly Leu Thr Pro
            500                 505                 510

Gln Gln Val Val Ala Ile Ala Ser Asn Gly Gly Gly Arg Pro Ala Leu
            515                 520                 525

Glu

<210> SEQ ID NO 429
<211> LENGTH: 39
<212> TYPE: DNA
<213> ORGANISM: artificial sequence
<220> FEATURE:
<223> OTHER INFORMATION: Target sequence in CAMPATH-1 antigen

<400> SEQUENCE: 429
tcctggcagt ggtgccaggc gttgctctta cctgtacca                                  39

<210> SEQ ID NO 430
<211> LENGTH: 17
<212> TYPE: DNA
<213> ORGANISM: artificial sequence
<220> FEATURE:
<223> OTHER INFORMATION: TALE recognition site

```
<400> SEQUENCE: 430
tgctcttacc tgtacca                                                    17

<210> SEQ ID NO 431
<211> LENGTH: 888
<212> TYPE: PRT
<213> ORGANISM: artificial sequence
<220> FEATURE:
<223> OTHER INFORMATION: TevI::cT40n3HCD52T02g10

<400> SEQUENCE: 431
```

Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
        35                  40                  45

Ser Phe Asn Lys His Gly Asn Val Phe Glu Cys Ser Ile Leu Glu Glu
    50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ser Gly Val Asp Leu Arg
    130                 135                 140

Thr Leu Gly Tyr Ser Gln Gln Gln Leu Lys Ile Lys Pro Lys Val
145                 150                 155                 160

Arg Ser Thr Val Ala Gln His His Glu Ala Leu Val Gly His Gly Phe
                165                 170                 175

Thr His Ala His Ile Val Ala Leu Ser Gln His Pro Ala Ala Leu Gly
            180                 185                 190

Thr Val Ala Val Lys Tyr Gln Asp Met Ile Ala Ala Leu Pro Glu Ala
        195                 200                 205

Thr His Glu Ala Ile Val Gly Val Gly Lys Gln Trp Ser Gly Ala Arg
    210                 215                 220

Ala Leu Glu Ala Leu Leu Thr Val Ala Gly Glu Leu Arg Gly Pro Pro
225                 230                 235                 240

Leu Gln Leu Asp Thr Gly Gln Leu Leu Lys Ile Ala Lys Arg Gly Gly
                245                 250                 255

Val Thr Ala Val Glu Ala Val His Ala Trp Arg Asn Ala Leu Thr Gly
            260                 265                 270

Ala Pro Leu Asn Leu Thr Pro Gln Gln Val Val Ala Ile Ala Ser Asn
        275                 280                 285

Asn Gly Gly Lys Gln Ala Leu Glu Thr Val Gln Arg Leu Leu Pro Val
    290                 295                 300

Leu Cys Gln Ala His Gly Leu Thr Pro Glu Gln Val Val Ala Ile Ala
305                 310                 315                 320

Ser His Asp Gly Gly Lys Gln Ala Leu Glu Thr Val Gln Arg Leu Leu
                325                 330                 335

Pro Val Leu Cys Gln Ala His Gly Leu Thr Pro Gln Gln Val Val Ala
            340                 345                 350

```
Ile Ala Ser Asn Gly Gly Gly Lys Gln Ala Leu Glu Thr Val Gln Arg
            355                 360                 365

Leu Leu Pro Val Leu Cys Gln Ala His Gly Leu Thr Pro Glu Gln Val
    370                 375                 380

Val Ala Ile Ala Ser His Asp Gly Gly Lys Gln Ala Leu Glu Thr Val
385                 390                 395                 400

Gln Arg Leu Leu Pro Val Leu Cys Gln Ala His Gly Leu Thr Pro Gln
                405                 410                 415

Gln Val Val Ala Ile Ala Ser Asn Gly Gly Gly Lys Gln Ala Leu Glu
            420                 425                 430

Thr Val Gln Arg Leu Leu Pro Val Leu Cys Gln Ala His Gly Leu Thr
        435                 440                 445

Pro Gln Gln Val Val Ala Ile Ala Ser Asn Gly Gly Gly Lys Gln Ala
    450                 455                 460

Leu Glu Thr Val Gln Arg Leu Leu Pro Val Leu Cys Gln Ala His Gly
465                 470                 475                 480

Leu Thr Pro Glu Gln Val Val Ala Ile Ala Ser Asn Ile Gly Gly Lys
                485                 490                 495

Gln Ala Leu Glu Thr Val Gln Ala Leu Leu Pro Val Leu Cys Gln Ala
            500                 505                 510

His Gly Leu Thr Pro Glu Gln Val Val Ala Ile Ala Ser His Asp Gly
        515                 520                 525

Gly Lys Gln Ala Leu Glu Thr Val Gln Arg Leu Leu Pro Val Leu Cys
    530                 535                 540

Gln Ala His Gly Leu Thr Pro Glu Gln Val Val Ala Ile Ala Ser His
545                 550                 555                 560

Asp Gly Gly Lys Gln Ala Leu Glu Thr Val Gln Arg Leu Leu Pro Val
                565                 570                 575

Leu Cys Gln Ala His Gly Leu Thr Pro Gln Gln Val Val Ala Ile Ala
            580                 585                 590

Ser Asn Gly Gly Gly Lys Gln Ala Leu Glu Thr Val Gln Arg Leu Leu
        595                 600                 605

Pro Val Leu Cys Gln Ala His Gly Leu Thr Pro Gln Gln Val Val Ala
    610                 615                 620

Ile Ala Ser Asn Asn Gly Gly Lys Gln Ala Leu Glu Thr Val Gln Arg
625                 630                 635                 640

Leu Leu Pro Val Leu Cys Gln Ala His Gly Leu Thr Pro Gln Gln Val
                645                 650                 655

Val Ala Ile Ala Ser Asn Gly Gly Gly Lys Gln Ala Leu Glu Thr Val
            660                 665                 670

Gln Arg Leu Leu Pro Val Leu Cys Gln Ala His Gly Leu Thr Pro Glu
        675                 680                 685

Gln Val Val Ala Ile Ala Ser Asn Ile Gly Gly Lys Gln Ala Leu Glu
    690                 695                 700

Thr Val Gln Ala Leu Leu Pro Val Leu Cys Gln Ala His Gly Leu Thr
705                 710                 715                 720

Pro Glu Gln Val Val Ala Ile Ala Ser His Asp Gly Gly Lys Gln Ala
                725                 730                 735

Leu Glu Thr Val Gln Arg Leu Leu Pro Val Leu Cys Gln Ala His Gly
            740                 745                 750

Leu Thr Pro Glu Gln Val Val Ala Ile Ala Ser His Asp Gly Gly Lys
        755                 760                 765
```

```
Gln Ala Leu Glu Thr Val Gln Arg Leu Leu Pro Val Leu Cys Gln Ala
770                 775                 780

His Gly Leu Thr Pro Gln Gln Val Val Ala Ile Ala Ser Asn Gly Gly
785                 790                 795                 800

Gly Arg Pro Ala Leu Glu Ser Ile Val Ala Gln Leu Ser Arg Pro Asp
                805                 810                 815

Pro Ala Leu Ala Ala Leu Thr Asn Asp His Leu Val Ala Leu Ala Cys
                820                 825                 830

Leu Gly Gly Arg Pro Ala Leu Asp Ala Val Lys Lys Gly Leu Gly Ala
                835                 840                 845

Pro Lys Lys Lys Arg Lys Val Glu Ser Pro Lys Lys Arg Lys Val
850                 855                 860

Glu Ser Pro Lys Lys Arg Lys Val Glu Gly Asn Ser Tyr Pro Tyr
865                 870                 875                 880

Asp Val Pro Asp Tyr Ala Ala Asp
                885

<210> SEQ ID NO 432
<211> LENGTH: 875
<212> TYPE: PRT
<213> ORGANISM: artificial sequence
<220> FEATURE:
<223> OTHER INFORMATION: TevI::cT40n3H::sc-Trex2CD52T02g10

<400> SEQUENCE: 432

Met Ala Lys Ser Gly Ile Tyr Gln Ile Lys Asn Thr Leu Asn Asn Lys
1                   5                   10                  15

Val Tyr Val Gly Ser Ala Lys Asp Phe Glu Lys Arg Trp Lys Arg His
                20                  25                  30

Phe Lys Asp Leu Glu Lys Gly Cys His Ser Ser Ile Lys Leu Gln Arg
            35                  40                  45

Ser Phe Asn Lys His Gly Asn Val Phe Glu Cys Ser Ile Leu Glu Glu
        50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Glu Ile Ile Lys
                100                 105                 110

Lys Arg Ser Glu Thr Val Lys Ala Lys Met Leu Lys Leu Gly Pro Asp
            115                 120                 125

Gly Arg Lys Ala Leu Tyr Ser Lys Pro Gly Ser Gly Val Asp Leu Arg
        130                 135                 140

Thr Leu Gly Tyr Ser Gln Gln Gln Glu Lys Ile Lys Pro Lys Val
145                 150                 155                 160

Arg Ser Thr Val Ala Gln His His Glu Ala Leu Val Gly His Gly Phe
                165                 170                 175

Thr His Ala His Ile Val Ala Leu Ser Gln His Pro Ala Ala Leu Gly
            180                 185                 190

Thr Val Ala Val Lys Tyr Gln Asp Met Ile Ala Ala Leu Pro Glu Ala
        195                 200                 205

Thr His Glu Ala Ile Val Gly Val Gly Lys Gln Trp Ser Gly Ala Arg
    210                 215                 220

Ala Leu Glu Ala Leu Leu Thr Val Ala Gly Glu Leu Arg Gly Pro Pro
225                 230                 235                 240
```

```
Leu Gln Leu Asp Thr Gly Gln Leu Leu Lys Ile Ala Lys Arg Gly
                    245                 250                 255

Val Thr Ala Val Glu Ala Val His Ala Trp Arg Asn Ala Leu Thr Gly
            260                 265                 270

Ala Pro Leu Asn Leu Thr Pro Gln Gln Val Val Ala Ile Ala Ser Asn
        275                 280                 285

Asn Gly Gly Lys Gln Ala Leu Glu Thr Val Gln Arg Leu Leu Pro Val
    290                 295                 300

Leu Cys Gln Ala His Gly Leu Thr Pro Glu Gln Val Val Ala Ile Ala
305                 310                 315                 320

Ser His Asp Gly Gly Lys Gln Ala Leu Glu Thr Val Gln Arg Leu Leu
                325                 330                 335

Pro Val Leu Cys Gln Ala His Gly Leu Thr Pro Gln Gln Val Val Ala
            340                 345                 350

Ile Ala Ser Asn Gly Gly Lys Gln Ala Leu Glu Thr Val Gln Arg
        355                 360                 365

Leu Leu Pro Val Leu Cys Gln Ala His Gly Leu Thr Pro Glu Gln Val
    370                 375                 380

Val Ala Ile Ala Ser His Asp Gly Gly Lys Gln Ala Leu Glu Thr Val
385                 390                 395                 400

Gln Arg Leu Leu Pro Val Leu Cys Gln Ala His Gly Leu Thr Pro Gln
                405                 410                 415

Gln Val Val Ala Ile Ala Ser Asn Gly Gly Lys Gln Ala Leu Glu
            420                 425                 430

Thr Val Gln Arg Leu Leu Pro Val Leu Cys Gln Ala His Gly Leu Thr
        435                 440                 445

Pro Gln Gln Val Val Ala Ile Ala Ser Asn Gly Gly Lys Gln Ala
    450                 455                 460

Leu Glu Thr Val Gln Arg Leu Leu Pro Val Leu Cys Gln Ala His Gly
465                 470                 475                 480

Leu Thr Pro Glu Gln Val Val Ala Ile Ala Ser Asn Ile Gly Gly Lys
                485                 490                 495

Gln Ala Leu Glu Thr Val Gln Ala Leu Leu Pro Val Leu Cys Gln Ala
            500                 505                 510

His Gly Leu Thr Pro Glu Gln Val Val Ala Ile Ala Ser His Asp Gly
        515                 520                 525

Gly Lys Gln Ala Leu Glu Thr Val Gln Arg Leu Leu Pro Val Leu Cys
    530                 535                 540

Gln Ala His Gly Leu Thr Pro Glu Gln Val Val Ala Ile Ala Ser His
545                 550                 555                 560

Asp Gly Gly Lys Gln Ala Leu Glu Thr Val Gln Arg Leu Leu Pro Val
                565                 570                 575

Leu Cys Gln Ala His Gly Leu Thr Pro Gln Gln Val Val Ala Ile Ala
            580                 585                 590

Ser Asn Gly Gly Gly Lys Gln Ala Leu Glu Thr Val Gln Arg Leu Leu
        595                 600                 605

Pro Val Leu Cys Gln Ala His Gly Leu Thr Pro Gln Gln Val Val Ala
    610                 615                 620

Ile Ala Ser Asn Asn Gly Gly Lys Gln Ala Leu Glu Thr Val Gln Arg
625                 630                 635                 640

Leu Leu Pro Val Leu Cys Gln Ala His Gly Leu Thr Pro Gln Gln Val
                645                 650                 655

Val Ala Ile Ala Ser Asn Gly Gly Gly Lys Gln Ala Leu Glu Thr Val
```

```
              660                 665                 670
Gln Arg Leu Leu Pro Val Leu Cys Gln Ala His Gly Leu Thr Pro Glu
            675                 680                 685

Gln Val Val Ala Ile Ala Ser Asn Ile Gly Gly Lys Gln Ala Leu Glu
        690                 695                 700

Thr Val Gln Ala Leu Leu Pro Val Leu Cys Gln Ala His Gly Leu Thr
705                 710                 715                 720

Pro Glu Gln Val Val Ala Ile Ala Ser His Asp Gly Gly Lys Gln Ala
                725                 730                 735

Leu Glu Thr Val Gln Arg Leu Leu Pro Val Leu Cys Gln Ala His Gly
            740                 745                 750

Leu Thr Pro Glu Gln Val Val Ala Ile Ala Ser His Asp Gly Gly Lys
        755                 760                 765

Gln Ala Leu Glu Thr Val Gln Arg Leu Leu Pro Val Leu Cys Gln Ala
    770                 775                 780

His Gly Leu Thr Pro Gln Gln Val Val Ala Ile Ala Ser Asn Gly Gly
785                 790                 795                 800

Gly Arg Pro Ala Leu Glu Ser Ile Val Ala Gln Leu Ser Arg Pro Asp
                805                 810                 815

Pro Ala Leu Ala Ala Leu Thr Asn Asp His Leu Val Ala Leu Ala Cys
            820                 825                 830

Leu Gly Gly Arg Pro Ala Leu Asp Ala Val Lys Lys Gly Leu Gly Ala
        835                 840                 845

Pro Lys Lys Lys Arg Lys Val Glu Ser Pro Lys Lys Lys Arg Lys Val
    850                 855                 860

Glu Ser Pro Lys Lys Lys Arg Lys Val Glu Gly
865                 870                 875

<210> SEQ ID NO 433
<211> LENGTH: 23
<212> TYPE: DNA
<213> ORGANISM: artificial sequence
<220> FEATURE:
<223> OTHER INFORMATION: primer pair CMP M005

<400> SEQUENCE: 433
tacctcaccc cgcctcctct gcc                                             23

<210> SEQ ID NO 434
<211> LENGTH: 23
<212> TYPE: DNA
<213> ORGANISM: artificial sequence
<220> FEATURE:
<223> OTHER INFORMATION: primer pair CMP_M006

<400> SEQUENCE: 434
ttgggtgccc caacgcgcct agc                                             23

<210> SEQ ID NO 435
<211> LENGTH: 130
<212> TYPE: DNA
<213> ORGANISM: artificial sequence
<220> FEATURE:
<223> OTHER INFORMATION: MRoligoCD52_2

<400> SEQUENCE: 435
ccatcagcct cctggttatg gtacaggtaa gagccacgcc tggcaccact ttaaggcgcg    60
ccggaccgcg gccgctaatt gccaggactc cccaaagttg cttggcatgg agggagggca   120
```
tacaggatgt                                                              130

<210> SEQ ID NO 436
<211> LENGTH: 22
<212> TYPE: DNA
<213> ORGANISM: artificial sequence
<220> FEATURE:
<223> OTHER INFORMATION: primer CMP_M007

<400> SEQUENCE: 436
aattgcggcc gcggtccggc gc                                                22

<210> SEQ ID NO 437
<211> LENGTH: 23
<212> TYPE: DNA
<213> ORGANISM: artificial sequence
<220> FEATURE:
<223> OTHER INFORMATION: primer CMP_M008

<400> SEQUENCE: 437
taaaccagga ttcagcctgc agg                                               23

<210> SEQ ID NO 438
<211> LENGTH: 309
<212> TYPE: PRT
<213> ORGANISM: artificial sequence
<220> FEATURE:
<223> OTHER INFORMATION: TevI::b36N3H

<400> SEQUENCE: 438

Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
        35                  40                  45

Ser Phe Asn Lys His Gly Asn Val Phe Glu Cys Ser Ile Leu Glu Glu
    50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ile Ala Ser Thr Ala Phe
    130                 135                 140

Val Asp Gln Asp Lys Gln Met Ala Asn Arg Leu Asn Leu Ser Pro Leu
145                 150                 155                 160

Glu Arg Ser Lys Ile Glu Lys Gln Tyr Gly Gly Ala Thr Thr Leu Ala
                165                 170                 175

Phe Ile Ser Asn Lys Gln Asn Glu Leu Ala Gln Ile Leu Ser Arg Ala
            180                 185                 190

Asp Ile Leu Lys Ile Ala Ser Tyr Asp Cys Ala Ala His Ala Leu Gln
        195                 200                 205

Ala Val Leu Asp Cys Gly Pro Met Leu Gly Lys Arg Gly Phe Ser Gly
    210                 215                 220

Asp Ala Arg Gly Ile Arg Ser Arg Ala Ser Arg Arg Ser Asn Glu Glu

```
                225                 230                 235                 240
Ile Val His Val Ala Ala Arg Arg Gly Gly Ala Gly Arg Ile Arg Lys
                245                 250                 255

Met Val Ala Pro Leu Glu Arg Gln Gly Arg Ser Gly Ala Pro Lys
                260                 265                 270

Lys Lys Arg Lys Val Glu Ser Pro Lys Lys Arg Lys Val Glu Ser
                275                 280                 285

Pro Lys Lys Lys Arg Lys Val Glu Gly Asn Ser Tyr Pro Tyr Asp Val
                290                 295                 300

Pro Asp Tyr Ala Ala
305

<210> SEQ ID NO 439
<211> LENGTH: 528
<212> TYPE: PRT
<213> ORGANISM: artificial sequence
<220> FEATURE:
<223> OTHER INFORMATION: RVD_bhSH6_T03g06_16

<400> SEQUENCE: 439

Phe Ser Gln Ser Asp Ile Val Lys Ile Ala Gly Asn Asn Gly Gly Ala
1               5                   10                  15

Gln Ala Leu Gln Ala Val Leu Asp Leu Glu Ser Met Leu Gly Lys Arg
                20                  25                  30

Gly Phe Ser Arg Asp Asp Ile Ala Lys Met Ala Gly Asn Asn Gly Gly
                35                  40                  45

Ala Gln Thr Leu Gln Ala Val Leu Asp Leu Glu Ser Ala Phe Arg Glu
                50                  55                  60

Arg Gly Phe Ser Gln Ala Asp Ile Val Lys Ile Ala Gly Asn Asn Gly
65                  70                  75                  80

Gly Ala Gln Ala Leu Tyr Ser Val Leu Asp Val Glu Pro Thr Leu Gly
                85                  90                  95

Lys Arg Gly Phe Ser Arg Ala Asp Ile Val Lys Ile Ala Gly Asn Ile
                100                 105                 110

Gly Gly Ala Gln Ala Leu His Thr Val Leu Asp Leu Glu Pro Ala Leu
                115                 120                 125

Gly Lys Arg Gly Phe Ser Arg Ile Asp Ile Val Lys Ile Ala Ala Asn
                130                 135                 140

Gly Gly Gly Ala Gln Ala Leu His Ala Val Leu Asp Leu Gly Pro Thr
145                 150                 155                 160

Leu Arg Glu Cys Gly Phe Ser Gln Ala Thr Ile Ala Lys Ile Ala Gly
                165                 170                 175

Asn Asn Gly Gly Ala Gln Ala Leu Gln Met Val Leu Asp Leu Gly Pro
                180                 185                 190

Ala Leu Gly Lys Arg Gly Phe Ser Gln Ala Thr Ile Ala Lys Ile Ala
                195                 200                 205

Gly His Asp Gly Gly Ala Gln Ala Leu Gln Thr Val Leu Asp Leu Glu
                210                 215                 220

Pro Ala Leu Cys Glu Arg Gly Phe Ser Gln Ala Thr Ile Ala Lys Met
225                 230                 235                 240

Ala Gly Asn Gly Gly Gly Ala Gln Ala Leu Gln Thr Val Leu Asp Leu
                245                 250                 255

Glu Pro Ala Leu Arg Lys Arg Asp Phe Arg Gln Ala Asp Ile Ile Lys
                260                 265                 270

Ile Ala Gly Asn Ile Gly Gly Ala Gln Ala Leu Gln Ala Val Ile Glu
```

```
                    275                 280                 285
His Gly Pro Thr Leu Arg Gln His Gly Phe Asn Leu Ala Asp Ile Val
    290                 295                 300

Lys Met Ala Gly Asn Gly Gly Ala Gln Ala Leu Gln Ala Val Leu
305                 310                 315                 320

Asp Leu Lys Pro Val Leu Asp Glu His Gly Phe Ser Gln Pro Asp Ile
                325                 330                 335

Val Lys Met Ala Gly Asn Ile Gly Gly Ala Gln Ala Leu Gln Ala Val
            340                 345                 350

Leu Ser Leu Gly Pro Ala Leu Arg Glu Arg Gly Phe Ser Gln Pro Asp
        355                 360                 365

Ile Val Lys Ile Ala Gly His Asp Gly Gly Ala Gln Ala Leu Gln Ala
    370                 375                 380

Val Leu Asp Leu Glu Leu Thr Leu Val Glu His Gly Phe Ser Gln Ala
385                 390                 395                 400

Asp Ile Val Lys Ile Ala Gly Asn Gly Gly Thr Gln Ala Leu His
                405                 410                 415

Ala Val Leu Asp Leu Glu Arg Met Leu Gly Glu Arg Gly Phe Ser Arg
            420                 425                 430

Ala Asp Ile Val Asn Val Ala Gly Asn Asn Gly Gly Ala Gln Ala Leu
        435                 440                 445

Lys Ala Val Leu Glu His Glu Ala Thr Leu Asn Glu Arg Gly Phe Asn
    450                 455                 460

Leu Thr Asp Ile Val Glu Met Ala Ala Asn Asn Gly Gly Ala Gln Ala
465                 470                 475                 480

Leu Lys Ala Val Leu Glu His Gly Pro Thr Leu Arg Gln Arg Gly Leu
                485                 490                 495

Ser Leu Ile Asp Ile Val Glu Ile Ala Gly Asn Gly Gly Ala Gln
            500                 505                 510

Ala Leu Lys Ala Val Leu Lys Tyr Gly Pro Val Leu Met Gln Ala Gly
        515                 520                 525

<210> SEQ ID NO 440
<211> LENGTH: 34
<212> TYPE: DNA
<213> ORGANISM: artificial sequence
<220> FEATURE:
<223> OTHER INFORMATION: SH6 target

<400> SEQUENCE: 440
tttcatcata ggtaaactgg gatgctatac tggt                              34

<210> SEQ ID NO 441
<211> LENGTH: 824
<212> TYPE: PRT
<213> ORGANISM: artificial sequence
<220> FEATURE:
<223> OTHER INFORMATION: TevM01::b36N3H_ SH6_T03g06_16

<400> SEQUENCE: 441

Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
                20                  25                  30

Phe Lys Asp Leu Glu Lys Gly Cys His Ser Ser Ile Lys Leu Gln Arg
            35                  40                  45

Ser Phe Asn Lys His Gly Asn Val Phe Glu Cys Ser Ile Leu Glu Glu
```

```
            50                  55                  60
Ile Pro Tyr Glu Lys Asp Leu Ile Ile Glu Arg Glu Asn Phe Trp Ile
 65                  70                  75                  80

Lys Glu Leu Asn Ser Lys Ile Asn Gly Tyr Asn Ile Ala Asp Ala Thr
                 85                  90                  95

Phe Gly Asp Thr Cys Ser Thr His Pro Leu Lys Glu Glu Ile Ile Lys
                100                 105                 110

Lys Arg Ser Glu Thr Val Lys Ala Lys Met Leu Lys Leu Gly Pro Asp
            115                 120                 125

Gly Arg Lys Ala Leu Tyr Ser Lys Pro Gly Ile Ala Ser Thr Ala Phe
    130                 135                 140

Val Asp Gln Asp Lys Gln Met Ala Asn Arg Leu Asn Leu Ser Pro Leu
145                 150                 155                 160

Glu Arg Ser Lys Ile Glu Lys Gln Tyr Gly Gly Ala Thr Thr Leu Ala
                165                 170                 175

Phe Ile Ser Asn Lys Gln Asn Glu Leu Ala Gln Ile Leu Ser Arg Ala
                180                 185                 190

Asp Ile Leu Lys Ile Ala Ser Tyr Asp Cys Ala Ala His Ala Leu Gln
            195                 200                 205

Ala Val Leu Asp Cys Gly Pro Met Leu Gly Lys Arg Gly Phe Ser Gln
    210                 215                 220

Ser Asp Ile Val Lys Ile Ala Gly Asn Gly Gly Ala Gln Ala Leu
225                 230                 235                 240

Gln Ala Val Leu Asp Leu Glu Ser Met Leu Gly Lys Arg Gly Phe Ser
                245                 250                 255

Arg Asp Asp Ile Ala Lys Met Ala Gly Asn Asn Gly Gly Ala Gln Thr
                260                 265                 270

Leu Gln Ala Val Leu Asp Leu Glu Ser Ala Phe Arg Glu Arg Gly Phe
            275                 280                 285

Ser Gln Ala Asp Ile Val Lys Ile Ala Gly Asn Asn Gly Gly Ala Gln
    290                 295                 300

Ala Leu Tyr Ser Val Leu Asp Val Glu Pro Thr Leu Gly Lys Arg Gly
305                 310                 315                 320

Phe Ser Arg Ala Asp Ile Val Lys Ile Ala Gly Asn Ile Gly Gly Ala
                325                 330                 335

Gln Ala Leu His Thr Val Leu Asp Leu Glu Pro Ala Leu Gly Lys Arg
                340                 345                 350

Gly Phe Ser Arg Ile Asp Ile Val Lys Ile Ala Ala Asn Gly Gly Gly
            355                 360                 365

Ala Gln Ala Leu His Ala Val Leu Asp Leu Gly Pro Thr Leu Arg Glu
    370                 375                 380

Cys Gly Phe Ser Gln Ala Thr Ile Ala Lys Ile Ala Gly Asn Asn Gly
385                 390                 395                 400

Gly Ala Gln Ala Leu Gln Met Val Leu Asp Leu Gly Pro Ala Leu Gly
                405                 410                 415

Lys Arg Gly Phe Ser Gln Ala Thr Ile Ala Lys Ile Ala Gly His Asp
                420                 425                 430

Gly Gly Ala Gln Ala Leu Gln Thr Val Leu Asp Leu Glu Pro Ala Leu
            435                 440                 445

Cys Glu Arg Gly Phe Ser Gln Ala Thr Ile Ala Lys Met Ala Gly Asn
    450                 455                 460

Gly Gly Gly Ala Gln Ala Leu Gln Thr Val Leu Asp Leu Glu Pro Ala
465                 470                 475                 480
```

```
Leu Arg Lys Arg Asp Phe Arg Gln Ala Asp Ile Ile Lys Ile Ala Gly
            485                 490                 495

Asn Ile Gly Gly Ala Gln Ala Leu Gln Ala Val Ile Glu His Gly Pro
        500                 505                 510

Thr Leu Arg Gln His Gly Phe Asn Leu Ala Asp Ile Val Lys Met Ala
    515                 520                 525

Gly Asn Gly Gly Ala Gln Ala Leu Gln Ala Val Leu Asp Leu Lys
530                 535                 540

Pro Val Leu Asp Glu His Gly Phe Ser Gln Pro Asp Ile Val Lys Met
545                 550                 555                 560

Ala Gly Asn Ile Gly Gly Ala Gln Ala Leu Gln Ala Val Leu Ser Leu
                565                 570                 575

Gly Pro Ala Leu Arg Glu Arg Gly Phe Ser Gln Pro Asp Ile Val Lys
                580                 585                 590

Ile Ala Gly His Asp Gly Gly Ala Gln Ala Leu Gln Ala Val Leu Asp
            595                 600                 605

Leu Glu Leu Thr Leu Val Glu His Gly Phe Ser Gln Ala Asp Ile Val
            610                 615                 620

Lys Ile Ala Gly Asn Gly Gly Thr Gln Ala Leu His Ala Val Leu
625                 630                 635                 640

Asp Leu Glu Arg Met Leu Gly Glu Arg Gly Phe Ser Arg Ala Asp Ile
                645                 650                 655

Val Asn Val Ala Gly Asn Asn Gly Gly Ala Gln Ala Leu Lys Ala Val
                660                 665                 670

Leu Glu His Glu Ala Thr Leu Asn Glu Arg Gly Phe Asn Leu Thr Asp
            675                 680                 685

Ile Val Glu Met Ala Ala Asn Asn Gly Gly Ala Gln Ala Leu Lys Ala
            690                 695                 700

Val Leu Glu His Gly Pro Thr Leu Arg Gln Arg Gly Leu Ser Leu Ile
705                 710                 715                 720

Asp Ile Val Glu Ile Ala Gly Asn Gly Gly Ala Gln Ala Leu Lys
                725                 730                 735

Ala Val Leu Lys Tyr Gly Pro Val Leu Met Gln Ala Gly Arg Ser Asn
                740                 745                 750

Glu Glu Ile Val His Val Ala Ala Arg Arg Gly Gly Ala Gly Arg Ile
            755                 760                 765

Arg Lys Met Val Ala Pro Leu Leu Glu Arg Gln Gly Arg Ser Gly Ala
            770                 775                 780

Pro Lys Lys Lys Arg Lys Val Glu Ser Pro Lys Lys Arg Lys Val
785                 790                 795                 800

Glu Ser Pro Lys Lys Arg Lys Val Glu Gly Asn Ser Tyr Pro Tyr
                805                 810                 815

Asp Val Pro Asp Tyr Ala Ala Asp
            820

<210> SEQ ID NO 442
<211> LENGTH: 785
<212> TYPE: PRT
<213> ORGANISM: artificial sequence
<220> FEATURE:
<223> OTHER INFORMATION: TevM01::b36_ SH6_T03g06_17

<400> SEQUENCE: 442

Met Ala Lys Ser Gly Ile Tyr Gln Ile Lys Asn Thr Leu Asn Asn Lys
1               5                   10                  15
```

Val Tyr Val Gly Ser Ala Lys Asp Phe Glu Lys Arg Trp Lys Arg His
               20                  25                  30

Phe Lys Asp Leu Glu Lys Gly Cys His Ser Ser Ile Lys Leu Gln Arg
           35                  40                  45

Ser Phe Asn Lys His Gly Asn Val Phe Glu Cys Ser Ile Leu Glu Glu
 50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ile Ala Ser Thr Ala Phe
    130                 135                 140

Val Asp Gln Asp Lys Gln Met Ala Asn Arg Leu Asn Leu Ser Pro Leu
145                 150                 155                 160

Glu Arg Ser Lys Ile Glu Lys Gln Tyr Gly Gly Ala Thr Thr Leu Ala
                165                 170                 175

Phe Ile Ser Asn Lys Gln Asn Glu Leu Ala Gln Ile Leu Ser Arg Ala
            180                 185                 190

Asp Ile Leu Lys Ile Ala Ser Tyr Asp Cys Ala Ala His Ala Leu Gln
        195                 200                 205

Ala Val Leu Asp Cys Gly Pro Met Leu Gly Lys Arg Gly Phe Ser Gln
    210                 215                 220

Ser Asp Ile Val Lys Ile Ala Gly Asn Asn Gly Gly Ala Gln Ala Leu
225                 230                 235                 240

Gln Ala Val Leu Asp Leu Glu Ser Met Leu Gly Lys Arg Gly Phe Ser
                245                 250                 255

Arg Asp Asp Ile Ala Lys Met Ala Gly Asn Asn Gly Gly Ala Gln Thr
            260                 265                 270

Leu Gln Ala Val Leu Asp Leu Glu Ser Ala Phe Arg Glu Arg Gly Phe
        275                 280                 285

Ser Gln Ala Asp Ile Val Lys Ile Ala Gly Asn Asn Gly Gly Ala Gln
    290                 295                 300

Ala Leu Tyr Ser Val Leu Asp Val Glu Pro Thr Leu Gly Lys Arg Gly
305                 310                 315                 320

Phe Ser Arg Ala Asp Ile Val Lys Ile Ala Gly Asn Ile Gly Gly Ala
                325                 330                 335

Gln Ala Leu His Thr Val Leu Asp Leu Glu Pro Ala Leu Gly Lys Arg
            340                 345                 350

Gly Phe Ser Arg Ile Asp Ile Val Lys Ile Ala Ala Asn Gly Gly Gly
        355                 360                 365

Ala Gln Ala Leu His Ala Val Leu Asp Leu Gly Pro Thr Leu Arg Glu
    370                 375                 380

Cys Gly Phe Ser Gln Ala Thr Ile Ala Lys Ile Ala Gly Asn Asn Gly
385                 390                 395                 400

Gly Ala Gln Ala Leu Gln Met Val Leu Asp Leu Gly Pro Ala Leu Gly
                405                 410                 415

Lys Arg Gly Phe Ser Gln Ala Thr Ile Ala Lys Ile Ala Gly His Asp
            420                 425                 430

```
Gly Gly Ala Gln Ala Leu Gln Thr Val Leu Asp Leu Glu Pro Ala Leu
            435                 440                 445

Cys Glu Arg Gly Phe Ser Gln Ala Thr Ile Ala Lys Met Ala Gly Asn
    450                 455                 460

Gly Gly Gly Ala Gln Ala Leu Gln Thr Val Leu Asp Leu Glu Pro Ala
465                 470                 475                 480

Leu Arg Lys Arg Asp Phe Arg Gln Ala Asp Ile Ile Lys Ile Ala Gly
                485                 490                 495

Asn Ile Gly Gly Ala Gln Ala Leu Ala Val Ile Glu His Gly Pro
            500                 505                 510

Thr Leu Arg Gln His Gly Phe Asn Leu Ala Asp Ile Val Lys Met Ala
            515                 520                 525

Gly Asn Gly Gly Gly Ala Gln Ala Leu Gln Ala Val Leu Asp Leu Lys
530                 535                 540

Pro Val Leu Asp Glu His Gly Phe Ser Gln Pro Asp Ile Val Lys Met
545                 550                 555                 560

Ala Gly Asn Ile Gly Gly Ala Gln Ala Leu Gln Ala Val Leu Ser Leu
                565                 570                 575

Gly Pro Ala Leu Arg Glu Arg Gly Phe Ser Gln Pro Asp Ile Val Lys
            580                 585                 590

Ile Ala Gly His Asp Gly Gly Ala Gln Ala Leu Gln Ala Val Leu Asp
        595                 600                 605

Leu Glu Leu Thr Leu Val Glu His Gly Phe Ser Gln Ala Asp Ile Val
            610                 615                 620

Lys Ile Ala Gly Asn Gly Gly Thr Gln Ala Leu His Ala Val Leu
625                 630                 635                 640

Asp Leu Glu Arg Met Leu Gly Glu Arg Gly Phe Ser Arg Ala Asp Ile
                645                 650                 655

Val Asn Val Ala Gly Asn Asn Gly Gly Ala Gln Ala Leu Lys Ala Val
            660                 665                 670

Leu Glu His Glu Ala Thr Leu Asn Glu Arg Gly Phe Asn Leu Thr Asp
            675                 680                 685

Ile Val Glu Met Ala Ala Asn Asn Gly Gly Ala Gln Ala Leu Lys Ala
        690                 695                 700

Val Leu Glu His Gly Pro Thr Leu Arg Gln Arg Gly Leu Ser Leu Ile
705                 710                 715                 720

Asp Ile Val Glu Ile Ala Gly Asn Gly Gly Ala Gln Ala Leu Lys
                725                 730                 735

Ala Val Leu Lys Tyr Gly Pro Val Leu Met Gln Ala Gly Arg Ser Asn
            740                 745                 750

Glu Glu Ile Val His Val Ala Ala Arg Arg Gly Gly Ala Gly Arg Ile
            755                 760                 765

Arg Lys Met Val Ala Pro Leu Leu Glu Arg Gln Gly Arg Ser Ser Ala
770                 775                 780

Asp
785

<210> SEQ ID NO 443
<211> LENGTH: 956
<212> TYPE: PRT
<213> ORGANISM: artificial sequence
<220> FEATURE:
<223> OTHER INFORMATION: RVD_bhSH6_T03g06_20

<400> SEQUENCE: 443
```

-continued

```
Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
            35                  40                  45

Ser Phe Asn Lys His Gly Asn Val Phe Glu Cys Ser Ile Leu Glu Glu
50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
            115                 120                 125

Gly Arg Lys Ala Leu Tyr Ser Lys Pro Gly Ile Ala Ser Thr Ala Phe
        130                 135                 140

Val Asp Gln Asp Lys Gln Met Ala Asn Arg Leu Asn Leu Ser Pro Leu
145                 150                 155                 160

Glu Arg Ser Lys Ile Glu Lys Gln Tyr Gly Ala Thr Thr Leu Ala
                165                 170                 175

Phe Ile Ser Asn Lys Gln Asn Glu Leu Ala Gln Ile Leu Ser Arg Ala
            180                 185                 190

Asp Ile Leu Lys Ile Ala Ser Tyr Asp Cys Ala Ala His Ala Leu Gln
        195                 200                 205

Ala Val Leu Asp Cys Gly Pro Met Leu Gly Lys Arg Gly Phe Ser Gln
        210                 215                 220

Ser Asp Ile Val Lys Ile Ala Gly Asn Asn Gly Gly Ala Gln Ala Leu
225                 230                 235                 240

Gln Ala Val Leu Asp Leu Glu Ser Met Leu Gly Lys Arg Gly Phe Ser
                245                 250                 255

Arg Asp Asp Ile Ala Lys Met Ala Gly Asn Asn Gly Gly Ala Gln Thr
            260                 265                 270

Leu Gln Ala Val Leu Asp Leu Glu Ser Ala Phe Arg Glu Arg Gly Phe
        275                 280                 285

Ser Gln Ala Asp Ile Val Lys Ile Ala Gly Asn Asn Gly Gly Ala Gln
        290                 295                 300

Ala Leu Tyr Ser Val Leu Asp Val Glu Pro Thr Leu Gly Lys Arg Gly
305                 310                 315                 320

Phe Ser Arg Ala Asp Ile Val Lys Ile Ala Gly Asn Ile Gly Gly Ala
            325                 330                 335

Gln Ala Leu His Thr Val Leu Asp Leu Glu Pro Ala Leu Gly Lys Arg
            340                 345                 350

Gly Phe Ser Arg Ile Asp Ile Val Lys Ile Ala Ala Asn Gly Gly Gly
        355                 360                 365

Ala Gln Ala Leu His Ala Val Leu Asp Leu Gly Pro Thr Leu Arg Glu
370                 375                 380

Cys Gly Phe Ser Gln Ala Thr Ile Ala Lys Ile Ala Gly Asn Asn Gly
385                 390                 395                 400

Gly Ala Gln Ala Leu Gln Met Val Leu Asp Leu Gly Pro Ala Leu Gly
            405                 410                 415

Lys Arg Gly Phe Ser Gln Ala Thr Ile Ala Lys Ile Ala Gly His Asp
```

```
            420                 425                 430
Gly Gly Ala Gln Ala Leu Gln Thr Val Leu Asp Leu Glu Pro Ala Leu
            435                 440                 445

Cys Glu Arg Gly Phe Ser Gln Ala Thr Ile Ala Lys Met Ala Gly Asn
450                 455                 460

Gly Gly Gly Ala Gln Ala Leu Gln Thr Val Leu Asp Leu Glu Pro Ala
465                 470                 475                 480

Leu Arg Lys Arg Asp Phe Arg Gln Ala Asp Ile Ile Lys Ile Ala Gly
                485                 490                 495

Asn Ile Gly Gly Ala Gln Ala Leu Gln Ala Val Ile Glu His Gly Pro
                500                 505                 510

Thr Leu Arg Gln His Gly Phe Asn Leu Ala Asp Ile Val Lys Met Ala
                515                 520                 525

Gly Asn Gly Gly Gly Ala Gln Ala Leu Gln Ala Val Leu Asp Leu Lys
                530                 535                 540

Pro Val Leu Asp Glu His Gly Phe Ser Gln Pro Asp Ile Val Lys Met
545                 550                 555                 560

Ala Gly Asn Ile Gly Gly Ala Gln Ala Leu Gln Ala Val Leu Ser Leu
                565                 570                 575

Gly Pro Ala Leu Arg Glu Arg Gly Phe Ser Gln Pro Asp Ile Val Lys
                580                 585                 590

Ile Ala Gly His Asp Gly Ala Gln Ala Leu Gln Ala Val Leu Asp
                595                 600                 605

Leu Glu Leu Thr Leu Val Glu His Gly Phe Ser Gln Pro Asp Ile Val
                610                 615                 620

Arg Ile Thr Gly Asn Gly Gly Ala Gln Ala Leu Gln Ala Val Leu
625                 630                 635                 640

Ala Leu Glu Leu Thr Leu Arg Glu Arg Gly Phe Ser Gln Pro Asp Ile
                645                 650                 655

Val Lys Ile Ala Gly Asn Asn Gly Gly Ala Gln Ala Leu Gln Ala Val
                660                 665                 670

Leu Asp Leu Glu Leu Thr Phe Arg Glu Arg Gly Phe Ser Gln Ala Asp
                675                 680                 685

Ile Val Lys Ile Ala Gly Asn Asn Gly Gly Thr Gln Ala Leu His Ala
                690                 695                 700

Val Leu Asp Leu Glu Arg Met Leu Gly Glu Arg Gly Phe Ser Arg Ala
705                 710                 715                 720

Asp Ile Val Asn Val Ala Gly Asn Gly Gly Gly Ala Gln Ala Leu Lys
                725                 730                 735

Ala Val Leu Glu His Glu Ala Thr Leu Asn Glu Arg Gly Phe Ser Arg
                740                 745                 750

Ala Asp Ile Val Lys Ile Ala Gly Asn Ile Gly Gly Ala Gln Ala Leu
                755                 760                 765

Lys Ala Val Leu Glu His Glu Ala Thr Leu Asp Glu Arg Gly Phe Ser
                770                 775                 780

Arg Ala Asp Ile Val Arg Ile Ala Gly Asn Asn Gly Gly Ala Gln Ala
785                 790                 795                 800

Leu Lys Ala Val Leu Glu His Gly Pro Thr Leu Asn Glu Arg Gly Phe
                805                 810                 815

Asn Leu Thr Asp Ile Val Glu Met Ala Ala Asn Ile Gly Gly Ala Gln
                820                 825                 830

Ala Leu Lys Ala Val Leu Glu His Gly Pro Thr Leu Arg Gln Arg Gly
                835                 840                 845
```

```
Leu Ser Leu Ile Asp Ile Val Glu Ile Ala Ser Asn Ile Gly Gly Ala
        850                 855                 860

Gln Ala Leu Lys Ala Val Leu Lys Tyr Gly Pro Val Leu Met Gln Ala
865                 870                 875                 880

Gly Arg Ser Asn Glu Glu Ile Val His Val Ala Ala Arg Arg Gly Gly
                885                 890                 895

Ala Gly Arg Ile Arg Lys Met Val Ala Pro Leu Leu Glu Arg Gln Gly
            900                 905                 910

Arg Ser Gly Ala Pro Lys Lys Arg Lys Val Glu Ser Pro Lys Lys
        915                 920                 925

Lys Arg Lys Val Glu Ser Pro Lys Lys Arg Lys Val Glu Gly Asn
    930                 935                 940

Ser Tyr Pro Tyr Asp Val Pro Asp Tyr Ala Ala Asp
945                 950                 955

<210> SEQ ID NO 444
<211> LENGTH: 38
<212> TYPE: DNA
<213> ORGANISM: artificial sequence
<220> FEATURE:
<223> OTHER INFORMATION: SH6_gene

<400> SEQUENCE: 444
tttcatcata ggtaaactgg gatgctatac tggtagaa                           38

<210> SEQ ID NO 445
<211> LENGTH: 956
<212> TYPE: PRT
<213> ORGANISM: artificial sequence
<220> FEATURE:
<223> OTHER INFORMATION: TevM01::b36N3H_ SH6_T03g06_20

<400> SEQUENCE: 445

Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
        35                  40                  45

Ser Phe Asn Lys His Gly Asn Val Phe Glu Cys Ser Ile Leu Glu Glu
    50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ile Ala Ser Thr Ala Phe
    130                 135                 140

Val Asp Gln Asp Lys Gln Met Ala Asn Arg Leu Asn Leu Ser Pro Leu
145                 150                 155                 160

Glu Arg Ser Lys Ile Glu Lys Gln Tyr Gly Gly Ala Thr Thr Leu Ala
                165                 170                 175

Phe Ile Ser Asn Lys Gln Asn Glu Leu Ala Gln Ile Leu Ser Arg Ala
            180                 185                 190
```

```
Asp Ile Leu Lys Ile Ala Ser Tyr Asp Cys Ala Ala His Ala Leu Gln
            195                 200                 205

Ala Val Leu Asp Cys Gly Pro Met Leu Gly Lys Arg Gly Phe Ser Gln
        210                 215                 220

Ser Asp Ile Val Lys Ile Ala Gly Asn Gly Gly Ala Gln Ala Leu
225                 230                 235                 240

Gln Ala Val Leu Asp Leu Glu Ser Met Leu Gly Lys Arg Gly Phe Ser
                245                 250                 255

Arg Asp Asp Ile Ala Lys Met Ala Gly Asn Asn Gly Gly Ala Gln Thr
                    260                 265                 270

Leu Gln Ala Val Leu Asp Leu Glu Ser Ala Phe Arg Glu Arg Gly Phe
                275                 280                 285

Ser Gln Ala Asp Ile Val Lys Ile Ala Gly Asn Asn Gly Gly Ala Gln
            290                 295                 300

Ala Leu Tyr Ser Val Leu Asp Val Glu Pro Thr Leu Gly Lys Arg Gly
305                 310                 315                 320

Phe Ser Arg Ala Asp Ile Val Lys Ile Ala Gly Asn Ile Gly Gly Ala
                    325                 330                 335

Gln Ala Leu His Thr Val Leu Asp Leu Glu Pro Ala Leu Gly Lys Arg
                340                 345                 350

Gly Phe Ser Arg Ile Asp Ile Val Lys Ile Ala Ala Asn Gly Gly Gly
            355                 360                 365

Ala Gln Ala Leu His Ala Val Leu Asp Leu Gly Pro Thr Leu Arg Glu
        370                 375                 380

Cys Gly Phe Ser Gln Ala Thr Ile Ala Lys Ile Ala Gly Asn Asn Gly
385                 390                 395                 400

Gly Ala Gln Ala Leu Gln Met Val Leu Asp Leu Gly Pro Ala Leu Gly
                    405                 410                 415

Lys Arg Gly Phe Ser Gln Ala Thr Ile Ala Lys Ile Ala Gly His Asp
                420                 425                 430

Gly Gly Ala Gln Ala Leu Gln Thr Val Leu Asp Leu Glu Pro Ala Leu
            435                 440                 445

Cys Glu Arg Gly Phe Ser Gln Ala Thr Ile Ala Lys Met Ala Gly Asn
        450                 455                 460

Gly Gly Gly Ala Gln Ala Leu Gln Thr Val Leu Asp Leu Glu Pro Ala
465                 470                 475                 480

Leu Arg Lys Arg Asp Phe Arg Gln Ala Asp Ile Ile Lys Ile Ala Gly
                    485                 490                 495

Asn Ile Gly Gly Ala Gln Ala Leu Gln Ala Val Ile Glu His Gly Pro
                500                 505                 510

Thr Leu Arg Gln His Gly Phe Asn Leu Ala Asp Ile Val Lys Met Ala
            515                 520                 525

Gly Asn Gly Gly Ala Gln Ala Leu Gln Ala Val Leu Asp Leu Lys
        530                 535                 540

Pro Val Leu Asp Glu His Gly Phe Ser Gln Pro Asp Ile Val Lys Met
545                 550                 555                 560

Ala Gly Asn Ile Gly Gly Ala Gln Ala Leu Gln Ala Val Leu Ser Leu
                    565                 570                 575

Gly Pro Ala Leu Arg Glu Arg Gly Phe Ser Gln Pro Asp Ile Val Lys
                580                 585                 590

Ile Ala Gly His Asp Gly Gly Ala Gln Ala Leu Gln Ala Val Leu Asp
            595                 600                 605
```

```
Leu Glu Leu Thr Leu Val Glu His Gly Phe Ser Gln Pro Asp Ile Val
610                 615                 620
Arg Ile Thr Gly Asn Gly Gly Ala Gln Ala Leu Gln Ala Val Leu
625                 630                 635                 640
Ala Leu Glu Leu Thr Leu Arg Glu Arg Gly Phe Ser Gln Pro Asp Ile
                645                 650                 655
Val Lys Ile Ala Gly Asn Asn Gly Gly Ala Gln Ala Leu Gln Ala Val
                660                 665                 670
Leu Asp Leu Glu Leu Thr Phe Arg Glu Arg Gly Phe Ser Gln Ala Asp
                675                 680                 685
Ile Val Lys Ile Ala Gly Asn Asn Gly Gly Thr Gln Ala Leu His Ala
690                 695                 700
Val Leu Asp Leu Glu Arg Met Leu Gly Glu Arg Gly Phe Ser Arg Ala
705                 710                 715                 720
Asp Ile Val Asn Val Ala Gly Asn Gly Gly Ala Gln Ala Leu Lys
                725                 730                 735
Ala Val Leu Glu His Glu Ala Thr Leu Asn Glu Arg Gly Phe Ser Arg
                740                 745                 750
Ala Asp Ile Val Lys Ile Ala Gly Asn Ile Gly Gly Ala Gln Ala Leu
                755                 760                 765
Lys Ala Val Leu Glu His Glu Ala Thr Leu Asp Glu Arg Gly Phe Ser
770                 775                 780
Arg Ala Asp Ile Val Arg Ile Ala Gly Asn Asn Gly Gly Ala Gln Ala
785                 790                 795                 800
Leu Lys Ala Val Leu Glu His Gly Pro Thr Leu Asn Glu Arg Gly Phe
                805                 810                 815
Asn Leu Thr Asp Ile Val Glu Met Ala Ala Asn Ile Gly Gly Ala Gln
                820                 825                 830
Ala Leu Lys Ala Val Leu Glu His Gly Pro Thr Leu Arg Gln Arg Gly
                835                 840                 845
Leu Ser Leu Ile Asp Ile Val Glu Ile Ala Ser Asn Ile Gly Gly Ala
850                 855                 860
Gln Ala Leu Lys Ala Val Leu Lys Tyr Gly Pro Val Leu Met Gln Ala
865                 870                 875                 880
Gly Arg Ser Asn Glu Glu Ile Val His Val Ala Ala Arg Arg Gly Gly
                885                 890                 895
Ala Gly Arg Ile Arg Lys Met Val Ala Pro Leu Leu Glu Arg Gln Gly
                900                 905                 910
Arg Ser Gly Ala Pro Lys Lys Lys Arg Lys Val Glu Ser Pro Lys Lys
                915                 920                 925
Lys Arg Lys Val Glu Ser Pro Lys Lys Arg Lys Val Glu Gly Asn
930                 935                 940
Ser Tyr Pro Tyr Asp Val Pro Asp Tyr Ala Ala Asp
945                 950                 955

<210> SEQ ID NO 446
<211> LENGTH: 350
<212> TYPE: DNA
<213> ORGANISM: artificial sequence
<220> FEATURE:
<223> OTHER INFORMATION: pcr_SH6

<400> SEQUENCE: 446
tctttgtgtt tccaaagagt tcctttggct ttcacattta gccttttatt gatggttaat      60 cttttttcagt ctttcatttt tgcttcccac agcattaatt gccccagca agtactgtcc     120
```

```
aataccattg cccttataat aactacttgc ctcatttacc tctaaagatt aatacccgt    180 acctaatatt gcatttcctt ctaccagtat agcatcccag tttacctatg atgaaagctt    240
tataatttcc atcttgtgtc acagaatctt tgttctctac ctcattgtcc actgaataat    300
gggtgatcca gcttcaaaat ctcatttaac ctctccattt tcagaccatt              350
```

<210> SEQ ID NO 447
<211> LENGTH: 35
<212> TYPE: DNA
<213> ORGANISM: artificial sequence
<220> FEATURE:
<223> OTHER INFORMATION: primer CMP_M009

<400> SEQUENCE: 447

```
tctttgtgtt tccaaagagt tcctttggct ttcac                              35
```

<210> SEQ ID NO 448
<211> LENGTH: 35
<212> TYPE: DNA
<213> ORGANISM: artificial sequence
<220> FEATURE:
<223> OTHER INFORMATION: primer CMP_M010

<400> SEQUENCE: 448

```
aaatctcatt taacctctcc attttcagac cattc                              35
```

<210> SEQ ID NO 449
<211> LENGTH: 5043
<212> TYPE: DNA
<213> ORGANISM: artificial sequence
<220> FEATURE:
<223> OTHER INFORMATION: pCLS 23895

<400> SEQUENCE: 449

```
gcccctgcag ccgaattata ttattttgc caaataattt ttaacaaaag ctctgaagtc    60
ttcttcattt aaattcttag atgatacttc atctggaaaa ttgtcccaat tagtagcatc    120
acgctgtgag taagttctaa accattttt tattgttgta ttatctctaa tcttactact    180
cgatgagttt tcggtattat ctctattttt aacttggagc aggttccatt cattgttttt    240
ttcatcatag tgaataaaat caactgcttt aacacttgtg cctgaacacc atatccatcc    300
ggcgtaatac gactcactat agggagagcg gccgccagat cttccggatg gctcgagttt    360
ttcagcaaga ttactgtctt atcatagaca tctcctccaa actatgactt ctttcaacat    420
aactctatct caaacatgga ttcagtgcag tctcagtact tctgaaagta aacactgaga    480
atactgttta acaaaacttt actaaaggtt tgtgagccat tgagttttcc aagcctccca    540
aagacattcc aagggcatgt tagcaccata tgttagtgtt cttgacagtg tgttaaatgc    600
tgtatcctga aaaagcatat ccataaattt tccctttcct ggctttattt cccaccccctc    660 ttaatcttcc atcctgagaa tgtaatccca atatcctatc ccatgtattt tacattctct    720
ttccagtaca tctgagctag gtcttgtatc tcaggtctcc actagtgcaa taatacactt    780
agttatttgg cttaacttta gttaattgtc ttagtggcca ggacatacgg tagacacaaa    840
tgctgagggg gacatctgct gtcttacgcg gtagtgcctc tgtgtcacct tcaagccagg    900
ctactcttaa aggagtggtg ggcacttctg caggctcaaa gggtccagga aatctgaggg    960
gaccagattt tcaaatgcat caaacaagtg tcttcatcca ataactttgg gtctcattta    1020
ttgcagccag ggccctactc ttgtcatggc agacctaact agttggggaa ttttactttc    1080
```

```
tctggaggtc tgctgtcctt agttcctgag cctgatcctc agccttttct gtcctccagc    1140
tgcaagaaat aggaatctct ctttgtgttt ccaaagagtt cctttggctt tcacatttag    1200
ccttttattg atggttaatc tttttcagtc tttcattttt gcttcccaca gcattaattg    1260
cccccagcaa gtactgtcca ataccattgc ccttataata actacttgcc tcatttacct    1320
ctaaagatta atacccgta cctaatattg catttccttc taccagtata gcctcccagt    1380
ttacctattt aaggcgcgcc ggaccgcggc cgcaattgat gaaagcttta taatttccat    1440
cttgtgtcac agaatctttg ttctctacct cattgtccac tgaataatgg gtgatccagc    1500
ttcaaaatct catttaacct ctccattttc agaccattct cagatcaact gtcaggccta    1560
cttctgtagt aagtaggctc agatgacatt tagaaaattg agggttcatt aagaaatgct    1620
cttgggatca caactgtgg gagaaggaaa caaaagcaaa ttgaggtggt gtgtgaaatc    1680
acaacaagcc ctcagccaaa tttacaggat gctctgaagc tggcaaatat cttcagaatt    1740
aaagaaaggg gtcaagcctt taatatgcca tgattaacca gtcattggtt gcaagctacc    1800
acctctccca cagggaaccc aatcccagag aaggggtatg atcttgaatg aggcagctac    1860
tgtccatcga ggacaagttt ccaaatgggt agacagctaa gaaattttaa ccctcaacct    1920
ttgggataac tgaggaataa atcctttagt cttaaagtgg agatctgagt ggcaaaggcc    1980
gccctccatt gcagaaggat taagtactga tgaggacatg tctaaaagat gcaggaacca    2040
gtttgaaaga ggctcactag ttaattttg gctaatgtaa atatcaaaaa gaataatgat    2100
gacagtgagt tttcaaatat tgaatgagaa ataatttga ctaaatatat tctgaatacg    2160
tttagtatat ccatcggtgt cctgaaaaga agagtggatg gaagctcttt tttgtagaat    2220
aatgccagtt ccttaatgtg aaatgaccaa attaaaagaa ctagatcatt ttcaaacatc    2280
aatgtatgaa ttgatttagt tatcaatagt tgcaaaaacc tttagctgat aatttgttga    2340
ggatcaggat ttcacataca ttacaaagta tcaacataca gaatacacat taatgacaaa    2400
ggggaagaaa acacctttac aatgggggggg tgttgtagat atctttctag aagatctcct    2460
acaatattct cagctgccat ggaaaatcga tgttcttctt ttattctctc aagattttca    2520
ggctgtatat taaaacttat attaagaact atgctaacca cctcatcagg aaccgttgta    2580
ggtggcgtgg gttttcttgg caatcgactc tcatgaaaac tacgagctaa atattcaata    2640
tgttcctctt gaccaacttt attctgcatt tttttgaac gaggtttaga gcaagcttca    2700
ggaaactgag acaggaattt tattaaaaat ttaaattttg aagaaagttc agggttaata    2760
gcatccattt tttgctttgc aagttcctca gcattcttaa caaagacgt ctcttttgac    2820 atgtttaaag tttaaacctc ctgtgtgaaa ttattatccg ctcataattc cacacattat    2880
acgagccgga agcataaagt gtaaagcctg gggtgcctaa tgagtgagct aactcacatt    2940
aattgcgttg cgctcactgc caattgcttt ccagtcggga aacctgtcgt gccagctgca    3000
ttaatgaatc ggccaacgcg cggggagagg cggtttgcgt attgggcgct cttccgcttc    3060
ctcgctcact gactcgctgc gctcggtcgt tcggctgcgg cgagcggtat cagctcactc    3120
aaaggcggta atacggttat ccacagaatc aggggataac gcaggaaaga acatgtgagc    3180
aaaaggccag caaaaggcca ggaaccgtaa aaaggccgcg ttgctggcgt ttttccatag    3240
gctccgcccc cctgacgagc atcacaaaaa tcgacgctca agtcagaggt ggcgaaaccc    3300
gacaggacta taaagatacc aggcgtttcc ccctggaagc tccctcgtgc gctctcctgt    3360
tccgaccctg ccgcttaccg gatacctgtc cgcctttctc ccttcgggaa gcgtggcgct    3420
ttctcatagc tcacgctgta ggtatctcag ttcggtgtag gtcgttcgct ccaagctggg    3480
```

```
ctgtgtgcac gaaccccccg ttcagcccga ccgctgcgcc ttatccggta actatcgtct    3540
tgagtccaac ccggtaagac acgacttatc gccactggca gcagccactg gtaacaggat    3600
tagcagagcg aggtatgtag gcggtgctac agagttcttg aagtggtggc ctaactacgg    3660
ctacactaga aggacagtat ttggtatctg cgctctgctg aagccagtta ccttcggaaa    3720
aagagttggt agctcttgat ccggcaaaca accaccgct ggtagcggtg gttttttgt     3780 ttgcaagcag cagattacgc gcagaaaaaa aggatctcaa gaagatcctt tgatcttttc    3840
tacggggtct gacgctcagt ggaacgaaaa ctcacgttaa gggattttgg tcatgagatt    3900
atcaaaaagg atcttcacct agatcctttt aaattaaaaa tgaagtttta aatcaatcta    3960
aagtatatat gagtaaactt ggtctgacag ttaccaatgc ttaatcagtg aggcacctat    4020
ctcagcgatc tgtctatttc gttcatccat agttgcctga ctccccgtcg tgtagataac    4080
tacgatacgg gagggcttac catctggccc cagtgctgca atgataccgc gagacccacg    4140
ctcaccggct ccagatttat cagcaataaa ccagccagcc ggaagggccg agcgcagaag    4200
tggtcctgca actttatccg cctccatcca gtctattaat tgttgccggg aagctagagt    4260
aagtagttcg ccagttaata gtttgcgcaa cgttgttgcc attgctacag gcatcgtggt    4320
gtcacgctcg tcgtttggta tggcttcatt cagctccggt tcccaacgat caaggcgagt    4380
tacatgatcc cccatgttgt gcaaaaaagc ggttagctcc ttcggtcctc cgatcgttgt    4440
cagaagtaag ttggccgcag tgttatcact catggttatg gcagcactgc ataattctct    4500
tactgtcatg ccatccgtaa gatgcttttc tgtgactggt gagtactcaa ccaagtcatt    4560
ctgagaatag tgtatgcggc gaccgagttg ctcttgcccg gcgtcaatac gggataatac    4620
cgcgccacat agcagaactt taaaagtgct catcattgga aaacgttctt cggggcgaaa    4680
actctcaagg atcttaccgc tgttgagatc cagttcgatg taacccactc gtgcacccaa    4740
ctgatcttca gcatctttta ctttcaccag cgtttctggg tgagcaaaaa caggaaggca    4800
aaatgccgca aaaaagggaa taagggcgac acggaaatgt tgaatactca tactcttcct    4860
ttttcaatat tattgaagca tttatcaggg ttattgtctc atgagcggat acatatttga    4920
atgtatttag aaaaataaac aaataggggt tccgcgcaca tttccccgaa aagtgccacc    4980
tgacgtctaa gaaaccatta ttatcatgac attaacctat aaaaataggc gtatcacgag    5040
gcc                                                                  5043
```

<210> SEQ ID NO 450
<211> LENGTH: 22
<212> TYPE: DNA
<213> ORGANISM: artificial sequence
<220> FEATURE:
<223> OTHER INFORMATION: primer CMP_M011

<400> SEQUENCE: 450
aattgcggcc gcggtccggc gc                                              22

<210> SEQ ID NO 451
<211> LENGTH: 22
<212> TYPE: DNA
<213> ORGANISM: artificial sequence
<220> FEATURE:
<223> OTHER INFORMATION: primer CMP_M012

<400> SEQUENCE: 451
gggaatgcag cccattacat ac                                              22

```
<210> SEQ ID NO 452
<211> LENGTH: 937
<212> TYPE: PRT
<213> ORGANISM: artificial sequence
<220> FEATURE:
<223> OTHER INFORMATION: TevD02-Ct11 chimeric endonuclease
<220> FEATURE:
<221> NAME/KEY: misc_feature
<222> LOCATION: (337)..(338)
<223> OTHER INFORMATION: Xaa can be any naturally occurring amino acid
<220> FEATURE:
<221> NAME/KEY: misc_feature
<222> LOCATION: (371)..(372)
<223> OTHER INFORMATION: Xaa can be any naturally occurring amino acid
<220> FEATURE:
<221> NAME/KEY: misc_feature
<222> LOCATION: (405)..(406)
<223> OTHER INFORMATION: Xaa can be any naturally occurring amino acid
<220> FEATURE:
<221> NAME/KEY: misc_feature
<222> LOCATION: (439)..(440)
<223> OTHER INFORMATION: Xaa can be any naturally occurring amino acid
<220> FEATURE:
<221> NAME/KEY: misc_feature
<222> LOCATION: (473)..(474)
<223> OTHER INFORMATION: Xaa can be any naturally occurring amino acid
<220> FEATURE:
<221> NAME/KEY: misc_feature
<222> LOCATION: (507)..(508)
<223> OTHER INFORMATION: Xaa can be any naturally occurring amino acid
<220> FEATURE:
<221> NAME/KEY: misc_feature
<222> LOCATION: (541)..(542)
<223> OTHER INFORMATION: Xaa can be any naturally occurring amino acid
<220> FEATURE:
<221> NAME/KEY: misc_feature
<222> LOCATION: (575)..(576)
<223> OTHER INFORMATION: Xaa can be any naturally occurring amino acid
<220> FEATURE:
<221> NAME/KEY: misc_feature
<222> LOCATION: (609)..(610)
<223> OTHER INFORMATION: Xaa can be any naturally occurring amino acid
<220> FEATURE:
<221> NAME/KEY: misc_feature
<222> LOCATION: (643)..(644)
<223> OTHER INFORMATION: Xaa can be any naturally occurring amino acid
<220> FEATURE:
<221> NAME/KEY: misc_feature
<222> LOCATION: (677)..(678)
<223> OTHER INFORMATION: Xaa can be any naturally occurring amino acid
<220> FEATURE:
<221> NAME/KEY: misc_feature
<222> LOCATION: (711)..(712)
<223> OTHER INFORMATION: Xaa can be any naturally occurring amino acid
<220> FEATURE:
<221> NAME/KEY: misc_feature
<222> LOCATION: (745)..(746)
<223> OTHER INFORMATION: Xaa can be any naturally occurring amino acid
<220> FEATURE:
<221> NAME/KEY: misc_feature
<222> LOCATION: (779)..(780)
<223> OTHER INFORMATION: Xaa can be any naturally occurring amino acid
<220> FEATURE:
<221> NAME/KEY: misc_feature
<222> LOCATION: (813)..(814)
<223> OTHER INFORMATION: Xaa can be any naturally occurring amino acid
<220> FEATURE:
<221> NAME/KEY: misc_feature
<222> LOCATION: (847)..(848)
<223> OTHER INFORMATION: Xaa can be any naturally occurring amino acid
<220> FEATURE:
<221> NAME/KEY: misc_feature
<222> LOCATION: (881)..(882)
<223> OTHER INFORMATION: Xaa can be any naturally occurring amino acid
<220> FEATURE:
<221> NAME/KEY: misc_feature
<222> LOCATION: (915)..(916)
<223> OTHER INFORMATION: Xaa can be any naturally occurring amino acid
```

<400> SEQUENCE: 452

```
Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
        35                  40                  45

Ser Phe Asn Lys His Gly Asn Val Phe Glu Cys Ser Ile Leu Glu Glu
    50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ser Lys Asn Gly Arg Trp
    130                 135                 140

Asn Pro Glu Thr His Lys Phe Cys Lys Cys Gly Val Arg Ile Gln Thr
145                 150                 155                 160

Ser Ala Tyr Thr Cys Ser Lys Cys Arg Asn Arg Ser Gly Glu Asn Asn
                165                 170                 175

Ser Phe Phe Asn His Lys His Ser Gln Gly Pro Ser Gly Val Asp Leu
            180                 185                 190

Arg Thr Leu Gly Tyr Ser Gln Gln Gln Glu Lys Ile Lys Pro Lys
        195                 200                 205

Val Arg Ser Thr Val Ala Gln His His Glu Ala Leu Val Gly His Gly
    210                 215                 220

Phe Thr His Ala His Ile Val Ala Leu Ser Gln His Pro Ala Ala Leu
225                 230                 235                 240

Gly Thr Val Ala Val Lys Tyr Gln Asp Met Ile Ala Ala Leu Pro Glu
                245                 250                 255

Ala Thr His Glu Ala Ile Val Gly Val Gly Lys Gln Trp Ser Gly Ala
            260                 265                 270

Arg Ala Leu Glu Ala Leu Leu Thr Val Ala Gly Glu Leu Arg Gly Pro
        275                 280                 285

Pro Leu Gln Leu Asp Thr Gly Gln Leu Leu Lys Ile Ala Lys Arg Gly
    290                 295                 300

Gly Val Thr Ala Val Glu Ala Val His Ala Trp Arg Asn Ala Leu Thr
305                 310                 315                 320

Gly Ala Pro Leu Asn Leu Thr Pro Glu Gln Val Val Ala Ile Ala Ser
                325                 330                 335

Xaa Xaa Gly Gly Lys Gln Ala Leu Glu Thr Val Gln Arg Leu Leu Pro
            340                 345                 350

Val Leu Cys Gln Ala His Gly Leu Thr Pro Gln Gln Val Val Ala Ile
        355                 360                 365

Ala Ser Xaa Xaa Gly Gly Lys Gln Ala Leu Glu Thr Val Gln Arg Leu
    370                 375                 380

Leu Pro Val Leu Cys Gln Ala His Gly Leu Thr Pro Glu Gln Val Val
385                 390                 395                 400

Ala Ile Ala Ser Xaa Xaa Gly Gly Lys Gln Ala Leu Glu Thr Val Gln
```

-continued

```
                405                 410                 415
Ala Leu Leu Pro Val Leu Cys Gln Ala His Gly Leu Thr Pro Gln Gln
            420                 425                 430

Val Val Ala Ile Ala Ser Xaa Xaa Gly Gly Lys Gln Ala Leu Glu Thr
        435                 440                 445

Val Gln Arg Leu Leu Pro Val Leu Cys Gln Ala His Gly Leu Thr Pro
    450                 455                 460

Glu Gln Val Val Ala Ile Ala Ser Xaa Xaa Gly Gly Lys Gln Ala Leu
465                 470                 475                 480

Glu Thr Val Gln Ala Leu Leu Pro Val Leu Cys Gln Ala His Gly Leu
                485                 490                 495

Thr Pro Glu Gln Val Val Ala Ile Ala Ser Xaa Xaa Gly Gly Lys Gln
            500                 505                 510

Ala Leu Glu Thr Val Gln Ala Leu Leu Pro Val Leu Cys Gln Ala His
        515                 520                 525

Gly Leu Thr Pro Glu Gln Val Val Ala Ile Ala Ser Xaa Xaa Gly Gly
    530                 535                 540

Lys Gln Ala Leu Glu Thr Val Gln Ala Leu Leu Pro Val Leu Cys Gln
545                 550                 555                 560

Ala His Gly Leu Thr Pro Glu Gln Val Val Ala Ile Ala Ser Xaa Xaa
                565                 570                 575

Gly Gly Lys Gln Ala Leu Glu Thr Val Gln Arg Leu Leu Pro Val Leu
            580                 585                 590

Cys Gln Ala His Gly Leu Thr Pro Glu Gln Val Val Ala Ile Ala Ser
        595                 600                 605

Xaa Xaa Gly Gly Lys Gln Ala Leu Glu Thr Val Gln Arg Leu Leu Pro
    610                 615                 620

Val Leu Cys Gln Ala His Gly Leu Thr Pro Gln Gln Val Val Ala Ile
625                 630                 635                 640

Ala Ser Xaa Xaa Gly Gly Lys Gln Ala Leu Glu Thr Val Gln Arg Leu
                645                 650                 655

Leu Pro Val Leu Cys Gln Ala His Gly Leu Thr Pro Glu Gln Val Val
            660                 665                 670

Ala Ile Ala Ser Xaa Xaa Gly Gly Lys Gln Ala Leu Glu Thr Val Gln
        675                 680                 685

Ala Leu Leu Pro Val Leu Cys Gln Ala His Gly Leu Thr Pro Glu Gln
    690                 695                 700

Val Val Ala Ile Ala Ser Xaa Xaa Gly Gly Lys Gln Ala Leu Glu Thr
705                 710                 715                 720

Val Gln Ala Leu Leu Pro Val Leu Cys Gln Ala His Gly Leu Thr Pro
                725                 730                 735

Glu Gln Val Val Ala Ile Ala Ser Xaa Xaa Gly Gly Lys Gln Ala Leu
            740                 745                 750

Glu Thr Val Gln Arg Leu Leu Pro Val Leu Cys Gln Ala His Gly Leu
        755                 760                 765

Thr Pro Glu Gln Val Val Ala Ile Ala Ser Xaa Xaa Gly Gly Lys Gln
    770                 775                 780

Ala Leu Glu Thr Val Gln Arg Leu Leu Pro Val Leu Cys Gln Ala His
785                 790                 795                 800

Gly Leu Thr Pro Glu Gln Val Val Ala Ile Ala Ser Xaa Xaa Gly Gly
                805                 810                 815

Lys Gln Ala Leu Glu Thr Val Gln Arg Leu Leu Pro Val Leu Cys Gln
            820                 825                 830
```

```
Ala His Gly Leu Thr Pro Gln Gln Val Val Ala Ile Ala Ser Xaa Xaa
        835                 840                 845

Gly Gly Lys Gln Ala Leu Glu Thr Val Gln Arg Leu Leu Pro Val Leu
    850                 855                 860

Cys Gln Ala His Gly Leu Thr Pro Glu Gln Val Val Ala Ile Ala Ser
865                 870                 875                 880

Xaa Xaa Gly Gly Lys Gln Ala Leu Glu Thr Val Gln Arg Leu Leu Pro
            885                 890                 895

Val Leu Cys Gln Ala His Gly Leu Thr Pro Gln Gln Val Val Ala Ile
            900                 905                 910

Ala Ser Xaa Xaa Gly Gly Arg Pro Ala Leu Glu Ser Ile Val Ala Gln
            915                 920                 925

Leu Ser Arg Pro Asp Pro Ser Ala Asp
    930                 935

<210> SEQ ID NO 453
<211> LENGTH: 897
<212> TYPE: PRT
<213> ORGANISM: artificial sequence
<220> FEATURE:
<223> OTHER INFORMATION: TevD02-b36 chimeric endonuclease
<220> FEATURE:
<221> NAME/KEY: misc_feature
<222> LOCATION: (282)..(283)
<223> OTHER INFORMATION: Xaa can be any naturally occurring amino acid
<220> FEATURE:
<221> NAME/KEY: misc_feature
<222> LOCATION: (315)..(316)
<223> OTHER INFORMATION: Xaa can be any naturally occurring amino acid
<220> FEATURE:
<221> NAME/KEY: misc_feature
<222> LOCATION: (348)..(349)
<223> OTHER INFORMATION: Xaa can be any naturally occurring amino acid
<220> FEATURE:
<221> NAME/KEY: misc_feature
<222> LOCATION: (381)..(382)
<223> OTHER INFORMATION: Xaa can be any naturally occurring amino acid
<220> FEATURE:
<221> NAME/KEY: misc_feature
<222> LOCATION: (414)..(415)
<223> OTHER INFORMATION: Xaa can be any naturally occurring amino acid
<220> FEATURE:
<221> NAME/KEY: misc_feature
<222> LOCATION: (447)..(448)
<223> OTHER INFORMATION: Xaa can be any naturally occurring amino acid
<220> FEATURE:
<221> NAME/KEY: misc_feature
<222> LOCATION: (480)..(481)
<223> OTHER INFORMATION: Xaa can be any naturally occurring amino acid
<220> FEATURE:
<221> NAME/KEY: misc_feature
<222> LOCATION: (513)..(514)
<223> OTHER INFORMATION: Xaa can be any naturally occurring amino acid
<220> FEATURE:
<221> NAME/KEY: misc_feature
<222> LOCATION: (546)..(547)
<223> OTHER INFORMATION: Xaa can be any naturally occurring amino acid
<220> FEATURE:
<221> NAME/KEY: misc_feature
<222> LOCATION: (579)..(580)
<223> OTHER INFORMATION: Xaa can be any naturally occurring amino acid
<220> FEATURE:
<221> NAME/KEY: misc_feature
<222> LOCATION: (612)..(613)
<223> OTHER INFORMATION: Xaa can be any naturally occurring amino acid
<220> FEATURE:
<221> NAME/KEY: misc_feature
<222> LOCATION: (645)..(646)
<223> OTHER INFORMATION: Xaa can be any naturally occurring amino acid
<220> FEATURE:
<221> NAME/KEY: misc_feature
```

```
<222> LOCATION: (678)..(679)
<223> OTHER INFORMATION: Xaa can be any naturally occurring amino acid
<220> FEATURE:
<221> NAME/KEY: misc_feature
<222> LOCATION: (711)..(712)
<223> OTHER INFORMATION: Xaa can be any naturally occurring amino acid
<220> FEATURE:
<221> NAME/KEY: misc_feature
<222> LOCATION: (744)..(745)
<223> OTHER INFORMATION: Xaa can be any naturally occurring amino acid
<220> FEATURE:
<221> NAME/KEY: misc_feature
<222> LOCATION: (777)..(778)
<223> OTHER INFORMATION: Xaa can be any naturally occurring amino acid
<220> FEATURE:
<221> NAME/KEY: misc_feature
<222> LOCATION: (810)..(811)
<223> OTHER INFORMATION: Xaa can be any naturally occurring amino acid
<220> FEATURE:
<221> NAME/KEY: misc_feature
<222> LOCATION: (843)..(844)
<223> OTHER INFORMATION: Xaa can be any naturally occurring amino acid

<400> SEQUENCE: 453

Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
        35                  40                  45

Ser Phe Asn Lys His Gly Asn Val Phe Glu Cys Ser Ile Leu Glu Glu
    50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ser Lys Asn Gly Arg Trp
    130                 135                 140

Asn Pro Glu Thr His Lys Phe Cys Lys Cys Gly Val Arg Ile Gln Thr
145                 150                 155                 160

Ser Ala Tyr Thr Cys Ser Lys Cys Arg Asn Arg Ser Gly Glu Asn Asn
                165                 170                 175

Ser Phe Phe Asn His Lys His Ser Gln Gly Pro Ser Gly Ser Thr Ala
            180                 185                 190

Phe Val Asp Gln Asp Lys Gln Met Ala Asn Arg Leu Asn Leu Ser Pro
        195                 200                 205

Leu Glu Arg Ser Lys Ile Glu Lys Gln Tyr Gly Gly Ala Thr Thr Leu
    210                 215                 220

Ala Phe Ile Ser Asn Lys Gln Asn Glu Leu Ala Gln Ile Leu Ser Arg
225                 230                 235                 240

Ala Asp Ile Leu Lys Ile Ala Ser Tyr Asp Cys Ala Ala His Ala Leu
                245                 250                 255

Gln Ala Val Leu Asp Cys Gly Pro Met Leu Gly Lys Arg Gly Phe Ser
            260                 265                 270

Gln Ser Asp Ile Val Lys Ile Ala Gly Xaa Xaa Gly Gly Ala Gln Ala
        275                 280                 285
```

```
Leu Gln Ala Val Leu Asp Leu Glu Ser Met Leu Gly Lys Arg Gly Phe
290                 295                 300
Ser Arg Asp Asp Ile Ala Lys Met Ala Gly Xaa Xaa Gly Gly Ala Gln
305                 310                 315                 320
Thr Leu Gln Ala Val Leu Asp Leu Glu Ser Ala Phe Arg Glu Arg Gly
            325                 330                 335
Phe Ser Gln Ala Asp Ile Val Lys Ile Ala Gly Xaa Xaa Gly Gly Ala
            340                 345                 350
Gln Ala Leu Tyr Ser Val Leu Asp Val Glu Pro Thr Leu Gly Lys Arg
            355                 360                 365
Gly Phe Ser Arg Ala Asp Ile Val Lys Ile Ala Gly Xaa Xaa Gly Gly
370                 375                 380
Ala Gln Ala Leu His Thr Val Leu Asp Leu Glu Pro Ala Leu Gly Lys
385                 390                 395                 400
Arg Gly Phe Ser Arg Ile Asp Ile Val Lys Ile Ala Ala Xaa Xaa Gly
            405                 410                 415
Gly Ala Gln Ala Leu His Ala Val Leu Asp Leu Gly Pro Thr Leu Arg
            420                 425                 430
Glu Cys Gly Phe Ser Gln Ala Thr Ile Ala Lys Ile Ala Gly Xaa Xaa
            435                 440                 445
Gly Gly Ala Gln Ala Leu Gln Met Val Leu Asp Leu Gly Pro Ala Leu
450                 455                 460
Gly Lys Arg Gly Phe Ser Gln Ala Thr Ile Ala Lys Ile Ala Gly Xaa
465                 470                 475                 480
Xaa Gly Gly Ala Gln Ala Leu Gln Thr Val Leu Asp Leu Glu Pro Ala
            485                 490                 495
Leu Cys Glu Arg Gly Phe Ser Gln Ala Thr Ile Ala Lys Met Ala Gly
            500                 505                 510
Xaa Xaa Gly Gly Ala Gln Ala Leu Gln Thr Val Leu Asp Leu Glu Pro
            515                 520                 525
Ala Leu Arg Lys Arg Asp Phe Arg Gln Ala Asp Ile Ile Lys Ile Ala
530                 535                 540
Gly Xaa Xaa Gly Gly Ala Gln Ala Leu Gln Ala Val Ile Glu His Gly
545                 550                 555                 560
Pro Thr Leu Arg Gln His Gly Phe Asn Leu Ala Asp Ile Val Lys Met
            565                 570                 575
Ala Gly Xaa Xaa Gly Gly Ala Gln Ala Leu Gln Ala Val Leu Asp Leu
            580                 585                 590
Lys Pro Val Leu Asp Glu His Gly Phe Ser Gln Pro Asp Ile Val Lys
            595                 600                 605
Met Ala Gly Xaa Xaa Gly Gly Ala Gln Ala Leu Gln Ala Val Leu Ser
610                 615                 620
Leu Gly Pro Ala Leu Arg Glu Arg Gly Phe Ser Gln Pro Asp Ile Val
625                 630                 635                 640
Lys Ile Ala Gly Xaa Xaa Gly Gly Ala Gln Ala Leu Gln Ala Val Leu
            645                 650                 655
Asp Leu Glu Leu Thr Leu Val Glu His Gly Phe Ser Gln Ala Asp Ile
            660                 665                 670
Val Lys Ile Ala Gly Xaa Xaa Gly Gly Thr Gln Ala Leu His Ala Val
            675                 680                 685
Leu Asp Leu Glu Arg Met Leu Gly Glu Arg Gly Phe Ser Arg Ala Asp
690                 695                 700
Ile Val Asn Val Ala Gly Xaa Xaa Gly Gly Ala Gln Ala Leu Lys Ala
```

```
                705                 710                 715                 720
Val Leu Glu His Glu Ala Thr Leu Asn Glu Arg Gly Phe Ser Arg Ala
                    725                 730                 735

Asp Ile Val Lys Ile Ala Gly Xaa Xaa Gly Gly Ala Gln Ala Leu Lys
                740                 745                 750

Ala Val Leu Glu His Glu Ala Thr Leu Asp Glu Arg Gly Phe Ser Arg
                755                 760                 765

Ala Asp Ile Val Asn Val Ala Gly Xaa Xaa Gly Gly Ala Gln Ala Leu
                770                 775                 780

Lys Ala Val Leu Glu His Glu Ala Thr Leu Asn Glu Arg Gly Phe Asn
785                 790                 795                 800

Leu Thr Asp Ile Val Glu Met Ala Ala Xaa Xaa Gly Gly Ala Gln Ala
                    805                 810                 815

Leu Lys Ala Val Leu Glu His Gly Pro Thr Leu Arg Gln Arg Gly Leu
                820                 825                 830

Ser Leu Ile Asp Ile Val Glu Ile Ala Gly Xaa Xaa Gly Gly Ala Gln
                835                 840                 845

Ala Leu Lys Ala Val Leu Lys Tyr Gly Pro Val Leu Met Gln Ala Gly
                850                 855                 860

Arg Ser Asn Glu Glu Ile Val His Val Ala Ala Arg Arg Gly Gly Ala
865                 870                 875                 880

Gly Arg Ile Arg Lys Met Val Ala Pro Leu Leu Glu Arg Gln Ser Ala
                    885                 890                 895

Asp

<210> SEQ ID NO 454
<211> LENGTH: 888
<212> TYPE: PRT
<213> ORGANISM: artificial sequence
<220> FEATURE:
<223> OTHER INFORMATION: TevM01-cT11 chimeric endonuclease
<220> FEATURE:
<221> NAME/KEY: misc_feature
<222> LOCATION: (288)..(289)
<223> OTHER INFORMATION: Xaa can be any naturally occurring amino acid
<220> FEATURE:
<221> NAME/KEY: misc_feature
<222> LOCATION: (322)..(323)
<223> OTHER INFORMATION: Xaa can be any naturally occurring amino acid
<220> FEATURE:
<221> NAME/KEY: misc_feature
<222> LOCATION: (356)..(357)
<223> OTHER INFORMATION: Xaa can be any naturally occurring amino acid
<220> FEATURE:
<221> NAME/KEY: misc_feature
<222> LOCATION: (390)..(391)
<223> OTHER INFORMATION: Xaa can be any naturally occurring amino acid
<220> FEATURE:
<221> NAME/KEY: misc_feature
<222> LOCATION: (424)..(425)
<223> OTHER INFORMATION: Xaa can be any naturally occurring amino acid
<220> FEATURE:
<221> NAME/KEY: misc_feature
<222> LOCATION: (458)..(459)
<223> OTHER INFORMATION: Xaa can be any naturally occurring amino acid
<220> FEATURE:
<221> NAME/KEY: misc_feature
<222> LOCATION: (492)..(493)
<223> OTHER INFORMATION: Xaa can be any naturally occurring amino acid
<220> FEATURE:
<221> NAME/KEY: misc_feature
<222> LOCATION: (526)..(527)
<223> OTHER INFORMATION: Xaa can be any naturally occurring amino acid
<220> FEATURE:
<221> NAME/KEY: misc_feature
<222> LOCATION: (560)..(561)
```

```
<223> OTHER INFORMATION: Xaa can be any naturally occurring amino acid
<220> FEATURE:
<221> NAME/KEY: misc_feature
<222> LOCATION: (594)..(595)
<223> OTHER INFORMATION: Xaa can be any naturally occurring amino acid
<220> FEATURE:
<221> NAME/KEY: misc_feature
<222> LOCATION: (628)..(629)
<223> OTHER INFORMATION: Xaa can be any naturally occurring amino acid
<220> FEATURE:
<221> NAME/KEY: misc_feature
<222> LOCATION: (662)..(663)
<223> OTHER INFORMATION: Xaa can be any naturally occurring amino acid
<220> FEATURE:
<221> NAME/KEY: misc_feature
<222> LOCATION: (696)..(697)
<223> OTHER INFORMATION: Xaa can be any naturally occurring amino acid
<220> FEATURE:
<221> NAME/KEY: misc_feature
<222> LOCATION: (730)..(731)
<223> OTHER INFORMATION: Xaa can be any naturally occurring amino acid
<220> FEATURE:
<221> NAME/KEY: misc_feature
<222> LOCATION: (764)..(765)
<223> OTHER INFORMATION: Xaa can be any naturally occurring amino acid
<220> FEATURE:
<221> NAME/KEY: misc_feature
<222> LOCATION: (798)..(799)
<223> OTHER INFORMATION: Xaa can be any naturally occurring amino acid
<220> FEATURE:
<221> NAME/KEY: misc_feature
<222> LOCATION: (832)..(833)
<223> OTHER INFORMATION: Xaa can be any naturally occurring amino acid
<220> FEATURE:
<221> NAME/KEY: misc_feature
<222> LOCATION: (866)..(867)
<223> OTHER INFORMATION: Xaa can be any naturally occurring amino acid

<400> SEQUENCE: 454
```

Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
        35                  40                  45

Ser Phe Asn Lys His Gly Asn Val Phe Glu Cys Ser Ile Leu Glu Glu
    50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ser Gly Val Asp Leu Arg
    130                 135                 140

Thr Leu Gly Tyr Ser Gln Gln Gln Glu Lys Ile Lys Pro Lys Val
145                 150                 155                 160

Arg Ser Thr Val Ala Gln His His Glu Ala Leu Val Gly His Gly Phe
                165                 170                 175

Thr His Ala His Ile Val Ala Leu Ser Gln His Pro Ala Ala Leu Gly
            180                 185                 190

Thr Val Ala Val Lys Tyr Gln Asp Met Ile Ala Ala Leu Pro Glu Ala
        195                 200                 205

```
Thr His Glu Ala Ile Val Gly Val Gly Lys Gln Trp Ser Gly Ala Arg
    210                 215                 220
Ala Leu Glu Ala Leu Leu Thr Val Ala Gly Glu Leu Arg Gly Pro Pro
225                 230                 235                 240
Leu Gln Leu Asp Thr Gly Gln Leu Leu Lys Ile Ala Lys Arg Gly Gly
                245                 250                 255
Val Thr Ala Val Glu Ala Val His Ala Trp Arg Asn Ala Leu Thr Gly
                260                 265                 270
Ala Pro Leu Asn Leu Thr Pro Glu Gln Val Val Ala Ile Ala Ser Xaa
            275                 280                 285
Xaa Gly Gly Lys Gln Ala Leu Glu Thr Val Gln Arg Leu Leu Pro Val
290                 295                 300
Leu Cys Gln Ala His Gly Leu Thr Pro Gln Gln Val Val Ala Ile Ala
305                 310                 315                 320
Ser Xaa Xaa Gly Gly Lys Gln Ala Leu Glu Thr Val Gln Arg Leu Leu
                325                 330                 335
Pro Val Leu Cys Gln Ala His Gly Leu Thr Pro Glu Gln Val Val Ala
            340                 345                 350
Ile Ala Ser Xaa Xaa Gly Gly Lys Gln Ala Leu Glu Thr Val Gln Ala
        355                 360                 365
Leu Leu Pro Val Leu Cys Gln Ala His Gly Leu Thr Pro Gln Gln Val
370                 375                 380
Val Ala Ile Ala Ser Xaa Xaa Gly Gly Lys Gln Ala Leu Glu Thr Val
385                 390                 395                 400
Gln Arg Leu Leu Pro Val Leu Cys Gln Ala His Gly Leu Thr Pro Glu
                405                 410                 415
Gln Val Val Ala Ile Ala Ser Xaa Xaa Gly Gly Lys Gln Ala Leu Glu
            420                 425                 430
Thr Val Gln Ala Leu Leu Pro Val Leu Cys Gln Ala His Gly Leu Thr
        435                 440                 445
Pro Glu Gln Val Val Ala Ile Ala Ser Xaa Xaa Gly Gly Lys Gln Ala
    450                 455                 460
Leu Glu Thr Val Gln Ala Leu Leu Pro Val Leu Cys Gln Ala His Gly
465                 470                 475                 480
Leu Thr Pro Glu Gln Val Val Ala Ile Ala Ser Xaa Xaa Gly Gly Lys
                485                 490                 495
Gln Ala Leu Glu Thr Val Gln Ala Leu Leu Pro Val Leu Cys Gln Ala
            500                 505                 510
His Gly Leu Thr Pro Glu Gln Val Val Ala Ile Ala Ser Xaa Xaa Gly
        515                 520                 525
Gly Lys Gln Ala Leu Glu Thr Val Gln Arg Leu Leu Pro Val Leu Cys
    530                 535                 540
Gln Ala His Gly Leu Thr Pro Glu Gln Val Val Ala Ile Ala Ser Xaa
545                 550                 555                 560
Xaa Gly Gly Lys Gln Ala Leu Glu Thr Val Gln Arg Leu Leu Pro Val
                565                 570                 575
Leu Cys Gln Ala His Gly Leu Thr Pro Gln Gln Val Val Ala Ile Ala
            580                 585                 590
Ser Xaa Xaa Gly Gly Lys Gln Ala Leu Glu Thr Val Gln Arg Leu Leu
        595                 600                 605
Pro Val Leu Cys Gln Ala His Gly Leu Thr Pro Glu Gln Val Val Ala
    610                 615                 620
Ile Ala Ser Xaa Xaa Gly Gly Lys Gln Ala Leu Glu Thr Val Gln Ala
```

625                 630                 635                 640
Leu Leu Pro Val Leu Cys Gln Ala His Gly Leu Thr Pro Glu Gln Val
                    645                 650                 655

Val Ala Ile Ala Ser Xaa Xaa Gly Gly Lys Gln Ala Leu Glu Thr Val
                660                 665                 670

Gln Ala Leu Leu Pro Val Leu Cys Gln Ala His Gly Leu Thr Pro Glu
            675                 680                 685

Gln Val Val Ala Ile Ala Ser Xaa Xaa Gly Gly Lys Gln Ala Leu Glu
        690                 695                 700

Thr Val Gln Arg Leu Leu Pro Val Leu Cys Gln Ala His Gly Leu Thr
705                 710                 715                 720

Pro Glu Gln Val Val Ala Ile Ala Ser Xaa Xaa Gly Gly Lys Gln Ala
                725                 730                 735

Leu Glu Thr Val Gln Arg Leu Leu Pro Val Leu Cys Gln Ala His Gly
                740                 745                 750

Leu Thr Pro Glu Gln Val Val Ala Ile Ala Ser Xaa Xaa Gly Gly Lys
                755                 760                 765

Gln Ala Leu Glu Thr Val Gln Arg Leu Leu Pro Val Leu Cys Gln Ala
            770                 775                 780

His Gly Leu Thr Pro Gln Gln Val Val Ala Ile Ala Ser Xaa Xaa Gly
785                 790                 795                 800

Gly Lys Gln Ala Leu Glu Thr Val Gln Arg Leu Leu Pro Val Leu Cys
                805                 810                 815

Gln Ala His Gly Leu Thr Pro Glu Gln Val Val Ala Ile Ala Ser Xaa
                820                 825                 830

Xaa Gly Gly Lys Gln Ala Leu Glu Thr Val Gln Arg Leu Leu Pro Val
            835                 840                 845

Leu Cys Gln Ala His Gly Leu Thr Pro Gln Gln Val Val Ala Ile Ala
        850                 855                 860

Ser Xaa Xaa Gly Gly Arg Pro Ala Leu Glu Ser Ile Val Ala Gln Leu
865                 870                 875                 880

Ser Arg Pro Asp Pro Ser Ala Asp
                885

<210> SEQ ID NO 455
<211> LENGTH: 851
<212> TYPE: PRT
<213> ORGANISM: artificial sequence
<220> FEATURE:
<223> OTHER INFORMATION: TevM01-b36 chimeric endonuclease
<220> FEATURE:
<221> NAME/KEY: misc_feature
<222> LOCATION: (266)..(267)
<223> OTHER INFORMATION: Xaa can be any naturally occurring amino acid
<220> FEATURE:
<221> NAME/KEY: misc_feature
<222> LOCATION: (299)..(300)
<223> OTHER INFORMATION: Xaa can be any naturally occurring amino acid
<220> FEATURE:
<221> NAME/KEY: misc_feature
<222> LOCATION: (332)..(333)
<223> OTHER INFORMATION: Xaa can be any naturally occurring amino acid
<220> FEATURE:
<221> NAME/KEY: misc_feature
<222> LOCATION: (365)..(366)
<223> OTHER INFORMATION: Xaa can be any naturally occurring amino acid
<220> FEATURE:
<221> NAME/KEY: misc_feature
<222> LOCATION: (398)..(399)
<223> OTHER INFORMATION: Xaa can be any naturally occurring amino acid
<220> FEATURE:
<221> NAME/KEY: misc_feature

```
<222> LOCATION: (431)..(432)
<223> OTHER INFORMATION: Xaa can be any naturally occurring amino acid
<220> FEATURE:
<221> NAME/KEY: misc_feature
<222> LOCATION: (464)..(465)
<223> OTHER INFORMATION: Xaa can be any naturally occurring amino acid
<220> FEATURE:
<221> NAME/KEY: misc_feature
<222> LOCATION: (497)..(498)
<223> OTHER INFORMATION: Xaa can be any naturally occurring amino acid
<220> FEATURE:
<221> NAME/KEY: misc_feature
<222> LOCATION: (530)..(531)
<223> OTHER INFORMATION: Xaa can be any naturally occurring amino acid
<220> FEATURE:
<221> NAME/KEY: misc_feature
<222> LOCATION: (563)..(564)
<223> OTHER INFORMATION: Xaa can be any naturally occurring amino acid
<220> FEATURE:
<221> NAME/KEY: misc_feature
<222> LOCATION: (596)..(597)
<223> OTHER INFORMATION: Xaa can be any naturally occurring amino acid
<220> FEATURE:
<221> NAME/KEY: misc_feature
<222> LOCATION: (629)..(630)
<223> OTHER INFORMATION: Xaa can be any naturally occurring amino acid
<220> FEATURE:
<221> NAME/KEY: misc_feature
<222> LOCATION: (662)..(663)
<223> OTHER INFORMATION: Xaa can be any naturally occurring amino acid
<220> FEATURE:
<221> NAME/KEY: misc_feature
<222> LOCATION: (695)..(696)
<223> OTHER INFORMATION: Xaa can be any naturally occurring amino acid
<220> FEATURE:
<221> NAME/KEY: misc_feature
<222> LOCATION: (728)..(729)
<223> OTHER INFORMATION: Xaa can be any naturally occurring amino acid
<220> FEATURE:
<221> NAME/KEY: misc_feature
<222> LOCATION: (761)..(762)
<223> OTHER INFORMATION: Xaa can be any naturally occurring amino acid
<220> FEATURE:
<221> NAME/KEY: misc_feature
<222> LOCATION: (794)..(795)
<223> OTHER INFORMATION: Xaa can be any naturally occurring amino acid

<400> SEQUENCE: 455

Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
        35                  40                  45

Ser Phe Asn Lys His Gly Asn Val Phe Glu Cys Ser Ile Leu Glu Glu
    50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ile Ala Ser Thr Ala Phe
    130                 135                 140

Val Asp Gln Asp Lys Gln Met Ala Asn Arg Leu Asn Leu Ser Pro Leu
145                 150                 155                 160
```

```
Glu Arg Ser Lys Ile Glu Lys Gln Tyr Gly Ala Thr Thr Leu Ala
            165                 170                 175

Phe Ile Ser Asn Lys Gln Asn Glu Leu Ala Gln Ile Leu Ser Arg Ala
        180                 185                 190

Asp Ile Leu Lys Ile Ala Ser Tyr Asp Cys Ala Ala His Ala Leu Gln
        195                 200                 205

Ala Val Leu Asp Cys Gly Pro Met Leu Gly Lys Arg Gly Phe Ser Gln
210                 215                 220

Ser Asp Ile Val Lys Ile Ala Gly His Asp Gly Ala Gln Ala Leu
225                 230                 235                 240

Gln Ala Val Leu Asp Leu Glu Ser Met Leu Gly Lys Arg Gly Phe Ser
                245                 250                 255

Arg Asp Asp Ile Ala Lys Met Ala Gly Xaa Xaa Gly Gly Ala Gln Thr
                260                 265                 270

Leu Gln Ala Val Leu Asp Leu Glu Ser Ala Phe Arg Glu Arg Gly Phe
        275                 280                 285

Ser Gln Ala Asp Ile Val Lys Ile Ala Gly Xaa Xaa Gly Gly Ala Gln
        290                 295                 300

Ala Leu Tyr Ser Val Leu Asp Val Glu Pro Thr Leu Gly Lys Arg Gly
305                 310                 315                 320

Phe Ser Arg Ala Asp Ile Val Lys Ile Ala Gly Xaa Xaa Gly Gly Ala
                325                 330                 335

Gln Ala Leu His Thr Val Leu Asp Leu Glu Pro Ala Leu Gly Lys Arg
                340                 345                 350

Gly Phe Ser Arg Ile Asp Ile Val Lys Ile Ala Ala Xaa Xaa Gly Gly
            355                 360                 365

Ala Gln Ala Leu His Ala Val Leu Asp Leu Gly Pro Thr Leu Arg Glu
370                 375                 380

Cys Gly Phe Ser Gln Ala Thr Ile Ala Lys Ile Ala Gly Xaa Xaa Gly
385                 390                 395                 400

Gly Ala Gln Ala Leu Gln Met Val Leu Asp Leu Gly Pro Ala Leu Gly
                405                 410                 415

Lys Arg Gly Phe Ser Gln Ala Thr Ile Ala Lys Ile Ala Gly Xaa Xaa
            420                 425                 430

Gly Gly Ala Gln Ala Leu Gln Thr Val Leu Asp Leu Glu Pro Ala Leu
            435                 440                 445

Cys Glu Arg Gly Phe Ser Gln Ala Thr Ile Ala Lys Met Ala Gly Xaa
        450                 455                 460

Xaa Gly Gly Ala Gln Ala Leu Gln Thr Val Leu Asp Leu Glu Pro Ala
465                 470                 475                 480

Leu Arg Lys Arg Asp Phe Arg Gln Ala Asp Ile Ile Lys Ile Ala Gly
                485                 490                 495

Xaa Xaa Gly Gly Ala Gln Ala Leu Gln Ala Val Ile Glu His Gly Pro
            500                 505                 510

Thr Leu Arg Gln His Gly Phe Asn Leu Ala Asp Ile Val Lys Met Ala
            515                 520                 525

Gly Xaa Xaa Gly Gly Ala Gln Ala Leu Gln Ala Val Leu Asp Leu Lys
530                 535                 540

Pro Val Leu Asp Glu His Gly Phe Ser Gln Pro Asp Ile Val Lys Met
545                 550                 555                 560

Ala Gly Xaa Xaa Gly Gly Ala Gln Ala Leu Gln Ala Val Leu Ser Leu
                565                 570                 575

Gly Pro Ala Leu Arg Glu Arg Gly Phe Ser Gln Pro Asp Ile Val Lys
```

```
                580             585             590
Ile Ala Gly Xaa Xaa Gly Gly Ala Gln Ala Leu Gln Ala Val Leu Asp
            595                 600             605
Leu Glu Leu Thr Leu Val Glu His Gly Phe Ser Gln Ala Asp Ile Val
    610                 615                 620
Lys Ile Ala Gly Xaa Xaa Gly Gly Thr Gln Ala Leu His Ala Val Leu
625                 630                 635                 640
Asp Leu Glu Arg Met Leu Gly Glu Arg Gly Phe Ser Arg Ala Asp Ile
                645                 650                 655
Val Asn Val Ala Gly Xaa Xaa Gly Gly Ala Gln Ala Leu Lys Ala Val
            660                 665                 670
Leu Glu His Glu Ala Thr Leu Asn Glu Arg Gly Phe Ser Arg Ala Asp
        675                 680                 685
Ile Val Lys Ile Ala Gly Xaa Xaa Gly Gly Ala Gln Ala Leu Lys Ala
    690                 695                 700
Val Leu Glu His Glu Ala Thr Leu Asp Glu Arg Gly Phe Ser Arg Ala
705                 710                 715                 720
Asp Ile Val Asn Val Ala Gly Xaa Xaa Gly Gly Ala Gln Ala Leu Lys
                725                 730                 735
Ala Val Leu Glu His Glu Ala Thr Leu Asn Glu Arg Gly Phe Asn Leu
            740                 745                 750
Thr Asp Ile Val Glu Met Ala Ala Xaa Xaa Gly Gly Ala Gln Ala Leu
        755                 760                 765
Lys Ala Val Leu Glu His Gly Pro Thr Leu Arg Gln Arg Gly Leu Ser
    770                 775                 780
Leu Ile Asp Ile Val Glu Ile Ala Gly Xaa Xaa Gly Gly Ala Gln Ala
785                 790                 795                 800
Leu Lys Ala Val Leu Lys Tyr Gly Pro Val Leu Met Gln Ala Gly Arg
                805                 810                 815
Ser Asn Glu Glu Ile Val His Val Ala Ala Arg Arg Gly Gly Ala Gly
            820                 825                 830
Arg Ile Arg Lys Met Val Ala Pro Leu Leu Glu Arg Gln Gly Arg Ser
        835                 840                 845
Ser Ala Asp
    850

<210> SEQ ID NO 456
<211> LENGTH: 859
<212> TYPE: PRT
<213> ORGANISM: artificial sequence
<220> FEATURE:
<223> OTHER INFORMATION: TevM01-cT11n3H chimeric endonuclease
<220> FEATURE:
<221> NAME/KEY: misc_feature
<222> LOCATION: (288)..(289)
<223> OTHER INFORMATION: Xaa can be any naturally occurring amino acid
<220> FEATURE:
<221> NAME/KEY: misc_feature
<222> LOCATION: (322)..(323)
<223> OTHER INFORMATION: Xaa can be any naturally occurring amino acid
<220> FEATURE:
<221> NAME/KEY: misc_feature
<222> LOCATION: (356)..(357)
<223> OTHER INFORMATION: Xaa can be any naturally occurring amino acid
<220> FEATURE:
<221> NAME/KEY: misc_feature
<222> LOCATION: (390)..(391)
<223> OTHER INFORMATION: Xaa can be any naturally occurring amino acid
<220> FEATURE:
<221> NAME/KEY: misc_feature
<222> LOCATION: (424)..(425)
```

```
<223> OTHER INFORMATION: Xaa can be any naturally occurring amino acid
<220> FEATURE:
<221> NAME/KEY: misc_feature
<222> LOCATION: (458)..(459)
<223> OTHER INFORMATION: Xaa can be any naturally occurring amino acid
<220> FEATURE:
<221> NAME/KEY: misc_feature
<222> LOCATION: (492)..(493)
<223> OTHER INFORMATION: Xaa can be any naturally occurring amino acid
<220> FEATURE:
<221> NAME/KEY: misc_feature
<222> LOCATION: (526)..(527)
<223> OTHER INFORMATION: Xaa can be any naturally occurring amino acid
<220> FEATURE:
<221> NAME/KEY: misc_feature
<222> LOCATION: (560)..(561)
<223> OTHER INFORMATION: Xaa can be any naturally occurring amino acid
<220> FEATURE:
<221> NAME/KEY: misc_feature
<222> LOCATION: (594)..(595)
<223> OTHER INFORMATION: Xaa can be any naturally occurring amino acid
<220> FEATURE:
<221> NAME/KEY: misc_feature
<222> LOCATION: (628)..(629)
<223> OTHER INFORMATION: Xaa can be any naturally occurring amino acid
<220> FEATURE:
<221> NAME/KEY: misc_feature
<222> LOCATION: (662)..(663)
<223> OTHER INFORMATION: Xaa can be any naturally occurring amino acid
<220> FEATURE:
<221> NAME/KEY: misc_feature
<222> LOCATION: (696)..(697)
<223> OTHER INFORMATION: Xaa can be any naturally occurring amino acid
<220> FEATURE:
<221> NAME/KEY: misc_feature
<222> LOCATION: (730)..(731)
<223> OTHER INFORMATION: Xaa can be any naturally occurring amino acid
<220> FEATURE:
<221> NAME/KEY: misc_feature
<222> LOCATION: (764)..(765)
<223> OTHER INFORMATION: Xaa can be any naturally occurring amino acid
<220> FEATURE:
<221> NAME/KEY: misc_feature
<222> LOCATION: (798)..(799)
<223> OTHER INFORMATION: Xaa can be any naturally occurring amino acid

<400> SEQUENCE: 456

Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
        35                  40                  45

Ser Phe Asn Lys His Gly Asn Val Phe Glu Cys Ser Ile Leu Glu Glu
    50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ser Gly Val Asp Leu Arg
    130                 135                 140

Thr Leu Gly Tyr Ser Gln Gln Gln Glu Lys Ile Lys Pro Lys Val
145                 150                 155                 160

Arg Ser Thr Val Ala Gln His His Glu Ala Leu Val Gly His Gly Phe
```

```
                    165                 170                 175
Thr His Ala His Ile Val Ala Leu Ser Gln His Pro Ala Ala Leu Gly
                180                 185                 190
Thr Val Ala Val Lys Tyr Gln Asp Met Ile Ala Ala Leu Pro Glu Ala
                195                 200                 205
Thr His Glu Ala Ile Val Gly Val Gly Lys Gln Trp Ser Gly Ala Arg
                210                 215                 220
Ala Leu Glu Ala Leu Leu Thr Val Ala Gly Glu Leu Arg Gly Pro Pro
225                 230                 235                 240
Leu Gln Leu Asp Thr Gly Gln Leu Leu Lys Ile Ala Lys Arg Gly Gly
                245                 250                 255
Val Thr Ala Val Glu Ala Val His Ala Trp Arg Asn Ala Leu Thr Gly
                260                 265                 270
Ala Pro Leu Asn Leu Thr Pro Gln Gln Val Val Ala Ile Ala Ser Xaa
                275                 280                 285
Xaa Gly Gly Lys Gln Ala Leu Glu Thr Val Gln Arg Leu Leu Pro Val
                290                 295                 300
Leu Cys Gln Ala His Gly Leu Thr Pro Glu Gln Val Val Ala Ile Ala
305                 310                 315                 320
Ser Xaa Xaa Gly Gly Lys Gln Ala Leu Glu Thr Val Gln Ala Leu Leu
                325                 330                 335
Pro Val Leu Cys Gln Ala His Gly Leu Thr Pro Glu Gln Val Val Ala
                340                 345                 350
Ile Ala Ser Xaa Xaa Gly Gly Lys Gln Ala Leu Glu Thr Val Gln Ala
                355                 360                 365
Leu Leu Pro Val Leu Cys Gln Ala His Gly Leu Thr Pro Gln Gln Val
                370                 375                 380
Val Ala Ile Ala Ser Xaa Xaa Gly Gly Lys Gln Ala Leu Glu Thr Val
385                 390                 395                 400
Gln Arg Leu Leu Pro Val Leu Cys Gln Ala His Gly Leu Thr Pro Gln
                405                 410                 415
Gln Val Val Ala Ile Ala Ser Xaa Xaa Gly Gly Lys Gln Ala Leu Glu
                420                 425                 430
Thr Val Gln Arg Leu Leu Pro Val Leu Cys Gln Ala His Gly Leu Thr
                435                 440                 445
Pro Gln Gln Val Val Ala Ile Ala Ser Xaa Xaa Gly Gly Lys Gln Ala
450                 455                 460
Leu Glu Thr Val Gln Arg Leu Leu Pro Val Leu Cys Gln Ala His Gly
465                 470                 475                 480
Leu Thr Pro Glu Gln Val Val Ala Ile Ala Ser Xaa Xaa Gly Gly Lys
                485                 490                 495
Gln Ala Leu Glu Thr Val Gln Arg Leu Leu Pro Val Leu Cys Gln Ala
                500                 505                 510
His Gly Leu Thr Pro Glu Gln Val Val Ala Ile Ala Ser Xaa Xaa Gly
                515                 520                 525
Gly Lys Gln Ala Leu Glu Thr Val Gln Ala Leu Leu Pro Val Leu Cys
                530                 535                 540
Gln Ala His Gly Leu Thr Pro Gln Gln Val Val Ala Ile Ala Ser Xaa
545                 550                 555                 560
Xaa Gly Gly Lys Gln Ala Leu Glu Thr Val Gln Arg Leu Leu Pro Val
                565                 570                 575
Leu Cys Gln Ala His Gly Leu Thr Pro Glu Gln Val Val Ala Ile Ala
                580                 585                 590
```

```
Ser Xaa Xaa Gly Gly Lys Gln Ala Leu Glu Thr Val Gln Arg Leu Leu
        595                 600                 605

Pro Val Leu Cys Gln Ala His Gly Leu Thr Pro Gln Gln Val Val Ala
610                 615                 620

Ile Ala Ser Xaa Xaa Gly Gly Lys Gln Ala Leu Glu Thr Val Gln Arg
625                 630                 635                 640

Leu Leu Pro Val Leu Cys Gln Ala His Gly Leu Thr Pro Gln Gln Val
                645                 650                 655

Val Ala Ile Ala Ser Xaa Xaa Gly Gly Lys Gln Ala Leu Glu Thr Val
                    660                 665                 670

Gln Arg Leu Leu Pro Val Leu Cys Gln Ala His Gly Leu Thr Pro Glu
                675                 680                 685

Gln Val Val Ala Ile Ala Ser Xaa Xaa Gly Gly Lys Gln Ala Leu Glu
                690                 695                 700

Thr Val Gln Arg Leu Leu Pro Val Leu Cys Gln Ala His Gly Leu Thr
705                 710                 715                 720

Pro Glu Gln Val Val Ala Ile Ala Ser Xaa Xaa Gly Gly Lys Gln Ala
                725                 730                 735

Leu Glu Thr Val Gln Ala Leu Leu Pro Val Leu Cys Gln Ala His Gly
                740                 745                 750

Leu Thr Pro Glu Gln Val Val Ala Ile Ala Ser Xaa Xaa Gly Gly Lys
                755                 760                 765

Gln Ala Leu Glu Thr Val Gln Arg Leu Leu Pro Val Leu Cys Gln Ala
                770                 775                 780

His Gly Leu Thr Pro Gln Gln Val Val Ala Ile Ala Ser Xaa Xaa Gly
785                 790                 795                 800

Gly Arg Pro Ala Leu Glu Ser Ile Val Ala Gln Leu Ser Arg Pro Asp
                805                 810                 815

Pro Gly Ala Pro Lys Lys Lys Arg Lys Val Glu Ser Pro Lys Lys Lys
                820                 825                 830

Arg Lys Val Glu Ser Pro Lys Lys Lys Arg Lys Val Glu Gly Asn Ser
                835                 840                 845

Tyr Pro Tyr Asp Val Pro Asp Tyr Ala Ala Asp
850                 855

<210> SEQ ID NO 457
<211> LENGTH: 888
<212> TYPE: PRT
<213> ORGANISM: artificial sequence
<220> FEATURE:
<223> OTHER INFORMATION: TevM01-cT40n3H chimeric endonuclease
<220> FEATURE:
<221> NAME/KEY: misc_feature
<222> LOCATION: (288)..(289)
<223> OTHER INFORMATION: Xaa can be any naturally occurring amino acid
<220> FEATURE:
<221> NAME/KEY: misc_feature
<222> LOCATION: (322)..(323)
<223> OTHER INFORMATION: Xaa can be any naturally occurring amino acid
<220> FEATURE:
<221> NAME/KEY: misc_feature
<222> LOCATION: (356)..(357)
<223> OTHER INFORMATION: Xaa can be any naturally occurring amino acid
<220> FEATURE:
<221> NAME/KEY: misc_feature
<222> LOCATION: (390)..(391)
<223> OTHER INFORMATION: Xaa can be any naturally occurring amino acid
<220> FEATURE:
<221> NAME/KEY: misc_feature
<222> LOCATION: (424)..(425)
<223> OTHER INFORMATION: Xaa can be any naturally occurring amino acid
```

```
<220> FEATURE:
<221> NAME/KEY: misc_feature
<222> LOCATION: (458)..(459)
<223> OTHER INFORMATION: Xaa can be any naturally occurring amino acid
<220> FEATURE:
<221> NAME/KEY: misc_feature
<222> LOCATION: (492)..(493)
<223> OTHER INFORMATION: Xaa can be any naturally occurring amino acid
<220> FEATURE:
<221> NAME/KEY: misc_feature
<222> LOCATION: (526)..(527)
<223> OTHER INFORMATION: Xaa can be any naturally occurring amino acid
<220> FEATURE:
<221> NAME/KEY: misc_feature
<222> LOCATION: (560)..(561)
<223> OTHER INFORMATION: Xaa can be any naturally occurring amino acid
<220> FEATURE:
<221> NAME/KEY: misc_feature
<222> LOCATION: (594)..(595)
<223> OTHER INFORMATION: Xaa can be any naturally occurring amino acid
<220> FEATURE:
<221> NAME/KEY: misc_feature
<222> LOCATION: (628)..(629)
<223> OTHER INFORMATION: Xaa can be any naturally occurring amino acid
<220> FEATURE:
<221> NAME/KEY: misc_feature
<222> LOCATION: (662)..(663)
<223> OTHER INFORMATION: Xaa can be any naturally occurring amino acid
<220> FEATURE:
<221> NAME/KEY: misc_feature
<222> LOCATION: (696)..(697)
<223> OTHER INFORMATION: Xaa can be any naturally occurring amino acid
<220> FEATURE:
<221> NAME/KEY: misc_feature
<222> LOCATION: (730)..(731)
<223> OTHER INFORMATION: Xaa can be any naturally occurring amino acid
<220> FEATURE:
<221> NAME/KEY: misc_feature
<222> LOCATION: (764)..(765)
<223> OTHER INFORMATION: Xaa can be any naturally occurring amino acid
<220> FEATURE:
<221> NAME/KEY: misc_feature
<222> LOCATION: (798)..(799)
<223> OTHER INFORMATION: Xaa can be any naturally occurring amino acid

<400> SEQUENCE: 457

Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
        35                  40                  45

Ser Phe Asn Lys His Gly Asn Val Phe Glu Cys Ser Ile Leu Glu Glu
    50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala Asp Ala Thr
                85                  90                  95

Phe Gly Asp Thr Cys Ser Thr His Pro Leu Lys Glu Glu Ile Ile Lys
            100                 105                 110

Lys Arg Ser Glu Thr Val Lys Ala Lys Met Leu Lys Leu Gly Pro Asp
        115                 120                 125

Gly Arg Lys Ala Leu Tyr Ser Lys Pro Gly Ser Gly Val Asp Leu Arg
    130                 135                 140

Thr Leu Gly Tyr Ser Gln Gln Gln Glu Lys Ile Lys Pro Lys Val
145                 150                 155                 160

Arg Ser Thr Val Ala Gln His His Glu Ala Leu Val Gly His Gly Phe
                165                 170                 175
```

```
Thr His Ala His Ile Val Ala Leu Ser Gln His Pro Ala Ala Leu Gly
            180                 185                 190

Thr Val Ala Val Lys Tyr Gln Asp Met Ile Ala Ala Leu Pro Glu Ala
            195                 200             205

Thr His Glu Ala Ile Val Gly Val Gly Lys Gln Trp Ser Gly Ala Arg
    210                 215                 220

Ala Leu Glu Ala Leu Leu Thr Val Ala Gly Glu Leu Arg Gly Pro Pro
225                 230                 235                 240

Leu Gln Leu Asp Thr Gly Gln Leu Leu Lys Ile Ala Lys Arg Gly Gly
                245                 250                 255

Val Thr Ala Val Glu Ala Val His Ala Trp Arg Asn Ala Leu Thr Gly
            260                 265                 270

Ala Pro Leu Asn Leu Thr Pro Gln Gln Val Val Ala Ile Ala Ser Xaa
            275                 280                 285

Xaa Gly Gly Lys Gln Ala Leu Glu Thr Val Gln Arg Leu Leu Pro Val
        290                 295                 300

Leu Cys Gln Ala His Gly Leu Thr Pro Glu Gln Val Val Ala Ile Ala
305                 310                 315                 320

Ser Xaa Xaa Gly Gly Lys Gln Ala Leu Glu Thr Val Gln Ala Leu Leu
                325                 330                 335

Pro Val Leu Cys Gln Ala His Gly Leu Thr Pro Glu Gln Val Val Ala
            340                 345                 350

Ile Ala Ser Xaa Xaa Gly Gly Lys Gln Ala Leu Glu Thr Val Gln Ala
        355                 360                 365

Leu Leu Pro Val Leu Cys Gln Ala His Gly Leu Thr Pro Gln Gln Val
        370                 375                 380

Val Ala Ile Ala Ser Xaa Xaa Gly Gly Lys Gln Ala Leu Glu Thr Val
385                 390                 395                 400

Gln Arg Leu Leu Pro Val Leu Cys Gln Ala His Gly Leu Thr Pro Gln
                405                 410                 415

Gln Val Val Ala Ile Ala Ser Xaa Xaa Gly Gly Lys Gln Ala Leu Glu
            420                 425                 430

Thr Val Gln Arg Leu Leu Pro Val Leu Cys Gln Ala His Gly Leu Thr
            435                 440                 445

Pro Gln Gln Val Val Ala Ile Ala Ser Xaa Xaa Gly Gly Lys Gln Ala
    450                 455                 460

Leu Glu Thr Val Gln Arg Leu Leu Pro Val Leu Cys Gln Ala His Gly
465                 470                 475                 480

Leu Thr Pro Glu Gln Val Val Ala Ile Ala Ser Xaa Xaa Gly Gly Lys
                485                 490                 495

Gln Ala Leu Glu Thr Val Gln Arg Leu Leu Pro Val Leu Cys Gln Ala
            500                 505                 510

His Gly Leu Thr Pro Glu Gln Val Val Ala Ile Ala Ser Xaa Xaa Gly
        515                 520                 525

Gly Lys Gln Ala Leu Glu Thr Val Gln Ala Leu Leu Pro Val Leu Cys
        530                 535                 540

Gln Ala His Gly Leu Thr Pro Gln Gln Val Val Ala Ile Ala Ser Xaa
545                 550                 555                 560

Xaa Gly Gly Lys Gln Ala Leu Glu Thr Val Gln Arg Leu Leu Pro Val
                565                 570                 575

Leu Cys Gln Ala His Gly Leu Thr Pro Glu Gln Val Val Ala Ile Ala
            580                 585                 590
```

-continued

```
Ser Xaa Xaa Gly Gly Lys Gln Ala Leu Glu Thr Val Gln Arg Leu Leu
        595                 600                 605

Pro Val Leu Cys Gln Ala His Gly Leu Thr Pro Gln Gln Val Val Ala
    610                 615                 620

Ile Ala Ser Xaa Xaa Gly Gly Lys Gln Ala Leu Glu Thr Val Gln Arg
625                 630                 635                 640

Leu Leu Pro Val Leu Cys Gln Ala His Gly Leu Thr Pro Gln Gln Val
                645                 650                 655

Val Ala Ile Ala Ser Xaa Xaa Gly Gly Lys Gln Ala Leu Glu Thr Val
            660                 665                 670

Gln Arg Leu Leu Pro Val Leu Cys Gln Ala His Gly Leu Thr Pro Glu
        675                 680                 685

Gln Val Val Ala Ile Ala Ser Xaa Xaa Gly Gly Lys Gln Ala Leu Glu
    690                 695                 700

Thr Val Gln Arg Leu Leu Pro Val Leu Cys Gln Ala His Gly Leu Thr
705                 710                 715                 720

Pro Glu Gln Val Val Ala Ile Ala Ser Xaa Xaa Gly Gly Lys Gln Ala
                725                 730                 735

Leu Glu Thr Val Gln Ala Leu Leu Pro Val Leu Cys Gln Ala His Gly
            740                 745                 750

Leu Thr Pro Glu Gln Val Val Ala Ile Ala Ser Xaa Xaa Gly Gly Lys
        755                 760                 765

Gln Ala Leu Glu Thr Val Gln Arg Leu Leu Pro Val Leu Cys Gln Ala
    770                 775                 780

His Gly Leu Thr Pro Gln Gln Val Val Ala Ile Ala Ser Xaa Xaa Gly
785                 790                 795                 800

Gly Arg Pro Ala Leu Glu Ser Ile Val Ala Gln Leu Ser Arg Pro Asp
                805                 810                 815

Pro Ala Leu Ala Ala Leu Thr Asn Asp His Leu Val Ala Leu Ala Cys
            820                 825                 830

Leu Gly Gly Arg Pro Ala Leu Asp Ala Val Lys Lys Gly Leu Gly Ala
        835                 840                 845

Pro Lys Lys Lys Arg Lys Val Glu Ser Pro Lys Lys Lys Arg Lys Val
    850                 855                 860

Glu Ser Pro Lys Lys Lys Arg Lys Val Glu Gly Asn Ser Tyr Pro Tyr
865                 870                 875                 880

Asp Val Pro Asp Tyr Ala Ala Asp
                885
```

<210> SEQ ID NO 458
<211> LENGTH: 874
<212> TYPE: PRT
<213> ORGANISM: artificial sequence
<220> FEATURE:
<223> OTHER INFORMATION: TevI:cT40n3H:scTrex2 chimeric endonuclease
<220> FEATURE:
<221> NAME/KEY: misc_feature
<222> LOCATION: (287)..(288)
<223> OTHER INFORMATION: Xaa can be any naturally occurring amino acid
<220> FEATURE:
<221> NAME/KEY: misc_feature
<222> LOCATION: (321)..(322)
<223> OTHER INFORMATION: Xaa can be any naturally occurring amino acid
<220> FEATURE:
<221> NAME/KEY: misc_feature
<222> LOCATION: (355)..(356)
<223> OTHER INFORMATION: Xaa can be any naturally occurring amino acid
<220> FEATURE:
<221> NAME/KEY: misc_feature
<222> LOCATION: (389)..(390)

```
<223> OTHER INFORMATION: Xaa can be any naturally occurring amino acid
<220> FEATURE:
<221> NAME/KEY: misc_feature
<222> LOCATION: (423)..(424)
<223> OTHER INFORMATION: Xaa can be any naturally occurring amino acid
<220> FEATURE:
<221> NAME/KEY: misc_feature
<222> LOCATION: (457)..(458)
<223> OTHER INFORMATION: Xaa can be any naturally occurring amino acid
<220> FEATURE:
<221> NAME/KEY: misc_feature
<222> LOCATION: (491)..(492)
<223> OTHER INFORMATION: Xaa can be any naturally occurring amino acid
<220> FEATURE:
<221> NAME/KEY: misc_feature
<222> LOCATION: (525)..(526)
<223> OTHER INFORMATION: Xaa can be any naturally occurring amino acid
<220> FEATURE:
<221> NAME/KEY: misc_feature
<222> LOCATION: (559)..(560)
<223> OTHER INFORMATION: Xaa can be any naturally occurring amino acid
<220> FEATURE:
<221> NAME/KEY: misc_feature
<222> LOCATION: (593)..(594)
<223> OTHER INFORMATION: Xaa can be any naturally occurring amino acid
<220> FEATURE:
<221> NAME/KEY: misc_feature
<222> LOCATION: (627)..(628)
<223> OTHER INFORMATION: Xaa can be any naturally occurring amino acid
<220> FEATURE:
<221> NAME/KEY: misc_feature
<222> LOCATION: (661)..(662)
<223> OTHER INFORMATION: Xaa can be any naturally occurring amino acid
<220> FEATURE:
<221> NAME/KEY: misc_feature
<222> LOCATION: (695)..(696)
<223> OTHER INFORMATION: Xaa can be any naturally occurring amino acid
<220> FEATURE:
<221> NAME/KEY: misc_feature
<222> LOCATION: (729)..(730)
<223> OTHER INFORMATION: Xaa can be any naturally occurring amino acid
<220> FEATURE:
<221> NAME/KEY: misc_feature
<222> LOCATION: (763)..(764)
<223> OTHER INFORMATION: Xaa can be any naturally occurring amino acid
<220> FEATURE:
<221> NAME/KEY: misc_feature
<222> LOCATION: (797)..(798)
<223> OTHER INFORMATION: Xaa can be any naturally occurring amino acid

<400> SEQUENCE: 458

Met Ala Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
            20                  25                  30

Phe Lys Asp Leu Glu Lys Gly Cys His Ser Ser Ile Lys Leu Gln Arg
        35                  40                  45

Ser Phe Asn Lys His Gly Asn Val Phe Glu Cys Ser Ile Leu Glu Glu
    50                  55                  60

Ile Pro Tyr Glu Lys Asp Leu Ile Ile Glu Arg Glu Asn Phe Trp Lys
65                  70                  75                  80

Glu Leu Asn Ser Lys Ile Asn Gly Tyr Asn Ile Ala Asp Ala Thr Phe
                85                  90                  95

Gly Asp Thr Cys Ser Thr His Pro Leu Lys Glu Ile Ile Lys Lys
            100                 105                 110

Arg Ser Glu Thr Val Lys Ala Lys Met Leu Lys Leu Gly Pro Asp Gly
        115                 120                 125

Arg Lys Ala Leu Tyr Ser Lys Pro Gly Ser Gly Val Asp Leu Arg Thr
    130                 135                 140
```

-continued

Leu Gly Tyr Ser Gln Gln Gln Glu Lys Ile Lys Pro Lys Val Arg
145                 150                 155                 160

Ser Thr Val Ala Gln His His Glu Ala Leu Val Gly His Gly Phe Thr
                165                 170                 175

His Ala His Ile Val Ala Leu Ser Gln His Pro Ala Ala Leu Gly Thr
            180                 185                 190

Val Ala Val Lys Tyr Gln Asp Met Ile Ala Ala Leu Pro Glu Ala Thr
        195                 200                 205

His Glu Ala Ile Val Gly Val Gly Lys Gln Trp Ser Gly Ala Arg Ala
    210                 215                 220

Leu Glu Ala Leu Leu Thr Val Ala Gly Glu Leu Arg Gly Pro Pro Leu
225                 230                 235                 240

Gln Leu Asp Thr Gly Gln Leu Leu Lys Ile Ala Lys Arg Gly Gly Val
                245                 250                 255

Thr Ala Val Glu Ala Val His Ala Trp Arg Asn Ala Leu Thr Gly Ala
            260                 265                 270

Pro Leu Asn Leu Thr Pro Gln Gln Val Val Ala Ile Ala Ser Xaa Xaa
        275                 280                 285

Gly Gly Lys Gln Ala Leu Glu Thr Val Gln Arg Leu Leu Pro Val Leu
    290                 295                 300

Cys Gln Ala His Gly Leu Thr Pro Glu Gln Val Val Ala Ile Ala Ser
305                 310                 315                 320

Xaa Xaa Gly Gly Lys Gln Ala Leu Glu Thr Val Gln Arg Leu Leu Pro
                325                 330                 335

Val Leu Cys Gln Ala His Gly Leu Thr Pro Gln Gln Val Val Ala Ile
            340                 345                 350

Ala Ser Xaa Xaa Gly Gly Lys Gln Ala Leu Glu Thr Val Gln Arg Leu
        355                 360                 365

Leu Pro Val Leu Cys Gln Ala His Gly Leu Thr Pro Glu Gln Val Val
370                 375                 380

Ala Ile Ala Ser Xaa Xaa Gly Gly Lys Gln Ala Leu Glu Thr Val Gln
385                 390                 395                 400

Arg Leu Leu Pro Val Leu Cys Gln Ala His Gly Leu Thr Pro Gln Gln
                405                 410                 415

Val Val Ala Ile Ala Ser Xaa Xaa Gly Gly Lys Gln Ala Leu Glu Thr
            420                 425                 430

Val Gln Arg Leu Leu Pro Val Leu Cys Gln Ala His Gly Leu Thr Pro
        435                 440                 445

Gln Gln Val Val Ala Ile Ala Ser Xaa Xaa Gly Gly Lys Gln Ala Leu
    450                 455                 460

Glu Thr Val Gln Arg Leu Leu Pro Val Leu Cys Gln Ala His Gly Leu
465                 470                 475                 480

Thr Pro Glu Gln Val Val Ala Ile Ala Ser Xaa Xaa Gly Gly Lys Gln
                485                 490                 495

Ala Leu Glu Thr Val Gln Ala Leu Leu Pro Val Leu Cys Gln Ala His
            500                 505                 510

Gly Leu Thr Pro Glu Gln Val Val Ala Ile Ala Ser Xaa Xaa Gly Gly
        515                 520                 525

Lys Gln Ala Leu Glu Thr Val Gln Arg Leu Leu Pro Val Leu Cys Gln
    530                 535                 540

Ala His Gly Leu Thr Pro Glu Gln Val Val Ala Ile Ala Ser Xaa Xaa
545                 550                 555                 560

Gly Gly Lys Gln Ala Leu Glu Thr Val Gln Arg Leu Leu Pro Val Leu

```
            565                 570                 575
Cys Gln Ala His Gly Leu Thr Pro Gln Gln Val Val Ala Ile Ala Ser
                580                 585                 590
Xaa Xaa Gly Gly Lys Gln Ala Leu Glu Thr Val Gln Arg Leu Leu Pro
            595                 600                 605
Val Leu Cys Gln Ala His Gly Leu Thr Pro Gln Gln Val Val Ala Ile
        610                 615                 620
Ala Ser Xaa Xaa Gly Gly Lys Gln Ala Leu Glu Thr Val Gln Arg Leu
625                 630                 635                 640
Leu Pro Val Leu Cys Gln Ala His Gly Leu Thr Pro Gln Gln Val Val
                645                 650                 655
Ala Ile Ala Ser Xaa Xaa Gly Gly Lys Gln Ala Leu Glu Thr Val Gln
            660                 665                 670
Arg Leu Leu Pro Val Leu Cys Gln Ala His Gly Leu Thr Pro Glu Gln
        675                 680                 685
Val Val Ala Ile Ala Ser Xaa Xaa Gly Gly Lys Gln Ala Leu Glu Thr
        690                 695                 700
Val Gln Ala Leu Leu Pro Val Leu Cys Gln Ala His Gly Leu Thr Pro
705                 710                 715                 720
Glu Gln Val Val Ala Ile Ala Ser Xaa Xaa Gly Gly Lys Gln Ala Leu
                725                 730                 735
Glu Thr Val Gln Arg Leu Leu Pro Val Leu Cys Gln Ala His Gly Leu
            740                 745                 750
Thr Pro Glu Gln Val Val Ala Ile Ala Ser Xaa Xaa Gly Gly Lys Gln
        755                 760                 765
Ala Leu Glu Thr Val Gln Arg Leu Leu Pro Val Leu Cys Gln Ala His
    770                 775                 780
Gly Leu Thr Pro Gln Gln Val Val Ala Ile Ala Ser Xaa Xaa Gly Gly
785                 790                 795                 800
Arg Pro Ala Leu Glu Ser Ile Val Ala Gln Leu Ser Arg Pro Asp Pro
                805                 810                 815
Ala Leu Ala Ala Leu Thr Asn Asp His Leu Val Ala Leu Ala Cys Leu
            820                 825                 830
Gly Gly Arg Pro Ala Leu Asp Ala Val Lys Lys Gly Leu Gly Ala Pro
        835                 840                 845
Lys Lys Lys Arg Lys Val Glu Ser Pro Lys Lys Lys Arg Lys Val Glu
    850                 855                 860
Ser Pro Lys Lys Lys Arg Lys Val Glu Gly
865                 870

<210> SEQ ID NO 459
<211> LENGTH: 448
<212> TYPE: DNA
<213> ORGANISM: artificial sequence
<220> FEATURE:
<223> OTHER INFORMATION: CD52 endogenous locus

<400> SEQUENCE: 459
tacctcaccc cgcctcctct gcctcctggt tcaaaagcag ctaaaccaaa agaagcctcc      60
agacagccct gagatcacct aaaaagctgc taccaagaca gccacgaaga tcctaccaaa     120
atgaagcgct tcctcttcct cctactcacc atcagcctcc tggttatggt acaggtaaga     180
gcaacgcctg gcaccactgc caggactccc caaagttgct tggcatggag ggagggcata     240
caggatgtga gctcccagag acccagcctt ctctcctgag agcacagcag atggactcca     300
```

```
acaggaaaac tggggacaca gcgggcctgg ccgcccagcc ttccagctct tctggctggg    360
gctgcactgc ttgcgggctg ccctgagaga aacctgtatc cacagctggg gagcacttac    420
agggtgctag gcgcgttggg gcacccaa                                        448
```

TEVI CHIMERIC ENDONUCLEASE AND THEIR PREFERENTIAL CLEAVAGE SITES

CROSS-REFERENCE TO RELATED APPLICATION(S)

This application is a divisional of U.S. application Ser. No. 14/764,933, filed on Jul. 30, 2015 (now abandoned), which is a 371 national stage entry of PCT/IB2014/058646, filed Jan. 29, 2014, which claims priority, including priority claims under 35 U.S.C. § 119(e) and § 120, to U.S. Provisional Application No. 61/759,728, filed Feb. 1, 2013.

FIELD OF THE INVENTION

The present invention relates to a method to cleave target nucleic acid sequence by the catalytic domain of a GIY-YIG homing endonucleases I-TevI. More precisely, the invention relates to the deciphering of new preferential I-TevI cleavage sites for efficient and specific cleavage activity. The invention concerns a method for the generation of TevI specific chimeric endonucleases to target nucleic acid sequence including such cleavage sites and methods of using same for gene editing.

BACKGROUND OF THE INVENTION

Genome engineering requires the consolidation of many diverse concepts (Silva, Poirot et al. 2011), the most fundamental being the need to specifically and efficiently target a DNA sequence within a complex genome. Re-engineering a DNA binding protein for this purpose has been mainly limited to few semi-modular archetypes (Pingoud and Wende 2011) such as artificial zinc-finger proteins (ZFP), the naturally occurring LAGLIDADG homing endonucleases (LHE), and the chimeric Transcription Activator Like Effectors nuclease (TALEN).

Meganucleases, also called homing endonucleases (HEs), can be divided into five families based on sequence and structure motifs: LAGLIDADG, GIY-YIG, HNH, His-Cys box and PD-(D/E)XK (Stoddard 2005; Zhao, Bonocora et al. 2007). The most well studied family is that of the LAGLIDADG proteins, with a considerable body of biochemical, genetic and structural work having established that these endonucleases could be used as molecular tools (Stoddard, Monnat et al. 2007; Arnould, Delenda et al. 2011). Although numerous engineering efforts have focused on LAGLIDADG HEs, members from two other families, GIY-YIG and HNH, are of particular interest. Biochemical and structural studies have established that in both families, member proteins can adopt a bipartite fold with distinct functional domains: (1) a catalytic domain responsible mainly for DNA cleavage, and; (2) a DNA-binding domain to provide target specificity (Stoddard 2005; Marcaida, Munoz et al. 2010).

Zinc-finger nucleases (ZFNs), generated by fusing Zinc-finger-based DNA-binding domains to an independent catalytic domain (Kim, Cha et al. 1996; Smith, Berg et al. 1999; Smith, Bibikova et al. 2000), represent another type of engineered nuclease commonly used to stimulate gene targeting and have been successfully used to induce gene correction, gene insertion, and gene deletion. The archetypal ZFNs are based on the catalytic domain of the Type IIS restriction enzyme FokI and Zinc Finger-based DNA binding domains made of strings of 3 or 4 individual Zinc Fingers, each recognizing a DNA triplet (Pabo, Peisach et al. 2001). Two Zinc Finger-FokI monomers have to bind to their respective Zinc Finger DNA-recognition sites on opposite strands in an inverted orientation in order to form a catalytically active dimer that catalyze double strand cleavage (Bitinaite, Wah et al. 1998).

Recently, a new class of chimeric nuclease using a FokI catalytic domain has been described (Christian, Cermak et al. 2010; Li, Huang et al. 2011). The DNA binding domain of these nucleases is derived from Transcription Activator Like Effectors (TALE), a family of proteins used in the infection process by plant pathogens of the *Xanthomonas* genus. In these DNA binding domains, sequence specificity is driven by a series of 33-35 amino acids repeats, differing essentially by the two positions. Each base pair in the DNA target is contacted by a single repeat, with the specificity resulting from the two variant amino acids of the repeat (the so-called repeat variable dipeptide, RVD). The apparent modularity of these DNA binding domains has been confirmed to a certain extent by modular assembly of designed TALE-derived protein with new specificities (Boch, Scholze et al. 2009; Moscou and Bogdanove 2009). As such, DNA cleavage by a TALEN requires two DNA recognition regions flanking an unspecific central region.

One notable constraint imposed by FokI nuclease domain is the requirement to function as a dimer to efficiently cleave DNA. For any given DNA target, this necessitates the design of two distinct ZFNs or two TALENs, such that each pair of zinc finger or TAL effector domains is oriented for FokI dimerization and DNA cleavage (Kleinstiver, Wolfs et al. 2012).

To overcome these drawbacks, the inventors and others have recently developed new types of monomeric chimeric endonucleases, in which DNA binding domain such as Zinc Finger, Homing Endonuclease (Kleinstiver, Wolfs et al. 2012) and TALE (International PCT application WO2012/138927) was fused to a monomeric catalytic domain.

In considering design possibilities for the monomeric chimeric endonuclease, the inventors reasoned that a low affinity cleavage domain that retained some sequence specificity would alleviate accidental off-site cleavage events resulting from DNA proximity during target-site scanning by the DNA binding domain. The inventors chose a homing endonuclease member of the GIY-YIG protein family, I-TevI (Mueller, Smith et al. 1995; Edgell, Stanger et al. 2004). By contrast to Fok1, I-TevI endonuclease do not require dimerization for DNA processing activity, thereby alleviating the need for "dual" target sites with intervening DNA "spacers" as for current TAL-nucleases and Zing-finger nucleases.

I-TevI exhibits a tripartite protein layout wherein an N-terminal catalytic domain is tethered by a long, flexible linker to a minimal C-terminal DNA binding domain. In the protein-DNA interaction the C-terminal domain is responsible for binding specificity as well as the majority of the complex affinity. However, the N-terminal I-TevI catalytic domain has been described as having its own DNA cleavage selectivity (Dean, Stanger et al. 2002), which interferes with the overall specificity of the chimeric endonuclease. This cleavage specificity reduces the number of possible nucleic acid sequences that can be targeted by the chimeric endonucleases.

I-TevI catalytic domain has been characterized biochemically in vitro as being specific to the CAACGC natural target sequence and, to a certain extend to sequences defined by the degenerate CN↑NN↓G motif, where arrows represent bottom (↑) and top (↓) strand cleavage. This general motif theoretically increases the number of potential cleavage sites.

However, the inventors have observed dramatic variation in efficacy of targeted gene disruption by TevI chimeric endonuclease using the above motif. It has appeared that targeting any sequences corresponding to this motif, often result into poor cleavage activity.

BRIEF SUMMARY OF THE INVENTION

The inventors have shown that variations in the CNNNG motif modulate I-TevI nuclease activity. These results contrast with recently published reports suggesting equivalence in cleavage for all CNNNG motif target (Kleinstiver, Wolfs et al. 2012). These data allow determining appropriate cleavage site to be efficiently cleaved by TevI chimeric endonucleases, using various types of nucleic acid binding domains.

The present invention thus concerns the characterization of new I-TevI cleavage sites that allow obtaining efficient cleavage activity using I-TevI catalytic domain. More specifically, the present invention relates to method to design an I-TevI chimeric endonuclease capable of targeting these cleavage sites, and efficiently process target nucleic acid sequence comprising said cleavage sites. Moreover, the inventors determined optimal chimeric endonuclease scaffolds to process such nucleic acid sequences. The present invention also concerns host cells, non human transgenic animal and transgenic plant obtained by using the chimeric endonucleases designed according to the invention.

BRIEF DESCRIPTION OF THE FIGURES

FIG. 1B: position 2; FIG. 1C: position 3).

BRIEF DESCRIPTION OF THE TABLES

Figure 1A:
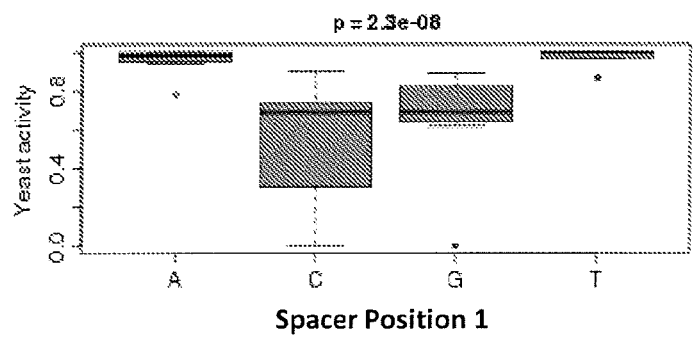
FIGS. 1A, 1B, and 1C: Statistical analysis of TevI::TALE nuclease activity in yeast on targets (SEQ ID NO: 346 to SEQ ID NO: 404) comprising the I-TevI cleavage site (SEQ ID NO: 17) separated from the T0 of the TALE recognition site by a spacer of 10 nucleotides differing by a NNN motif at the 3 first positions of their spacer (FIG. 1A: position 1.

Table 1: List of nucleic acid target sequences containing a DNA binding domain site and a I-TevI cleavage site spaced from 0 to 50 bp.

Table 2: Activity of TevI chimeric endonucleases in yeast (37° C.) on targets containing a single AvrBs3 recognition site and the I-TevI cleavage sequence CAACGC spaced from 0 to 50 bps away from the T0.

Table 3: High activity of TevI chimeric endonucleases in yeast (37° C.) on a series of I-TevI cleavage sites.

Table 4: Medium activity of TevI chimeric endonucleases in yeast (37° C.) on a series of I-TevI cleavage sites.

Table 5: Low and no activity of TevI chimeric endonucleases in yeast (37° C.) on a series of I-TevI cleavage sites.

Table 6: Activity of TevM01 TALE nuclease in yeast (37° C.) on a series of targets containing different spacer sequences.

DETAILED DESCRIPTION OF THE INVENTION

Unless specifically defined herein, all technical and scientific terms used have the same meaning as commonly understood by a skilled artisan in the fields of gene therapy, biochemistry, genetics, and molecular biology.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

I-TevI Preferential Cleavage Sites

The present invention relates to the deciphering of new preferential I-TevI cleavage sites. These cleavage sites are more appropriate to be cleaved by the catalytic domain of I-TevI, particularly when the latter is fused with a nucleic acid binding domain or a protein that specifies a target nucleic acid sequence in order to form a chimeric endonuclease. Said preferential cleavage sites are those selected from the group consisting of: SEQ ID NO: 2 to SEQ ID NO: 117 as shown in Table 3 and 4, and more preferably from SEQ ID NO: 2 to SEQ ID NO: 55 as shown in Table 3.

I-TevI cleavage sites were primarily defined in the art by the degenerate CN↑NN↓G motif, where arrows represent bottom (↑) and top (↓) strand cleavage and N represents any nucleotide bases. However, the inventors have shown that most sites characterized by this motif did not efficiently result into cleavage upon testing with different scaffolds of TevI chimeric endonucleases, in particular TAL-TevI and MBBD-TevI fusions (see examples). By contrast, the preferential I-TevI cleavage sites of the present invention have proven ability to be cleaved by different TevI chimeric endonucleases, which makes them more universal ones.

I-TevI catalytic domain corresponds to the protein domain or module of I-TevI enzyme containing the active site of said enzyme; by active site is intended the part of said enzyme at which catalysis of the substrate occurs. In the scope of the present invention, I-TevI catalytic domain can provide a nuclease activity. By "nuclease catalytic domain" is intended the protein domain comprising the active site of an endonuclease enzyme. Such nuclease catalytic domain can be, for instance, a "cleavage domain" or a "nickase domain". By "cleavage domain" is intended a protein domain whose catalytic activity generates a Double Strand Break (DSB) in a DNA target. By "nickase domain" is intended a protein domain whose catalytic activity generates a single strand break in a DNA target sequence.

Said catalytic domain is I-TevI or a variant thereof. In a preferred embodiment, said catalytic domain is a variant of catalytic domain of I-TevI designed from the N-terminal region of I-TevI. Said catalytic domain comprises a part of the protein sequence SEQ ID NO: 257. In a preferred embodiment, said I-TevI catalytic domain corresponds to the amino acid sequence of SEQ ID NO: 268 or SEQ ID NO: 284. Alternatively, amino acid sequence variants of the I-TevI catalytic domain can be prepared by mutations in the DNA which encodes the catalytic domain. Such variants include, for example, deletions from, or insertions or substitutions of, residues within the amino acid sequence. Any combination of deletions, insertions, and substitutions may also be made to arrive at the final construct, provided that the final construct possesses the desired activity. In another preferred embodiment, said catalytic domain of I-TevI according to the present invention comprises a part of the protein sequence having at least 80%, more preferably 90%, again more preferably 95% amino acid sequence identity with the protein sequence SEQ ID NO: 257. In a more preferred embodiment, said catalytic domain of I-TevI comprises a protein sequence having at least 80%, more preferably 90%, again more preferably 95% amino acid sequence identity with the protein sequence SEQ ID NO: 268 or the protein sequence SEQ ID NO: 284.

Generation of TevI Chimeric Endonuclease

By selecting the above cleavage sites, one skilled in the art is able to design TevI chimeric endonculeases to precisely target nucleotide sequences that include such cleavage sites.

This method to generate TevI chimeric endonuclease according to the invention comprises, for instance, the steps of:
a) Determining a target nucleic acid sequence comprising a I-TevI cleavage site selected from the group consisting of: SEQ ID NO: 2 to SEQ ID NO: 117, preferably SEQ ID NO: 2 to SEQ ID NO: 55;
b) Selecting or engineering at least one nucleic acid binding domain to specifically bind a recognition site adjacent to said cleavage site;

Fusing said nucleic acid binding domain with at least one catalytic domain of I-TevI. By chimeric endonuclease is meant any fusion proteins comprising at least one catalytic domain of an endonuclease and at least one nucleic acid binding domain or protein specifying a nucleic acid target sequence. Tev-I chimeric endonuclease according to the invention is a fusion protein comprising at least one I-TevI catalytic domain.

The nucleic acid binding domain is generally a RNA or DNA-binding domain formed by an independently folded polypeptide protein domain that contains at least one motif that recognizes double- or single-stranded polynucleotides. Said nucleic acid binding domain preferably recognizes a specific nucleic acid sequence named recognition site.

Many such polypeptides have been described in the art having the ability to bind specific nucleic acid sequences. Such binding domains often comprise, as non limiting examples, helix-turn helix domains, leucine zipper domains, winged helix domains, helix-loop-helix domains, HMG-box domains, Immunoglobin domains and B3 domain.

As far as nucleic acid binding domains are concerned, those from homing endonuclease also known as meganuclease (Paques and Duchateau 2007) have been widely investigated by the inventors and are well documented in the art (see e.g. (Stoddard, Monnat et al. 2007)). Homing endonucleases recognize a nucleic acid target sequence and can generate by themselves a single- or double-strand break. However, they can be engineered only to retain binding activity and not cleavage activity to form DNA binding polyopeptides. Homing endonucleases are highly specific, recognizing DNA target sites ranging from 12 to 45 base pairs (bp) in length, usually ranging from 14 to 40 bp in length.

Such homing endonuclease may for example correspond to a LAGLIDADG endonuclease, to a HNH endonuclease, or to a GIY-YIG endonuclease. Examples of such endonuclease include I-Sce I, I-Chu I, I-Cre I, I-Csm I, PI-Sce I, PI-Tli I, PI-Mtu I, I-Ceu I, I-Sce II, I-Sce III, HO, PI-Civ I, PI-Ctr I, PI-Aae I, PI-Bsu I, PI-Dha I, PI-Dra I, PI-May I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, I-Onul, PI-Pfu I, PI-Rma I, PI-Spb I, PI-Ssp I, PI-Fac I, PI-Mja I, PI-Pho I, PI-Tag I, PI-Thy I, PI-Tko I, PI-Tsp I or I-Msol.

In a preferred embodiment, the homing endonuclease is a wild type or a variant of a LAGLIDADG endonuclease such as I-Scel, I-Crel, I-Ceul, I-Msol, and I-Dmol. In a most preferred embodiment, said LAGLIDADG endonuclease is I-Crel. Wild-type I-Crel is a homodimeric homing endonuclease that is capable of cleaving a 22 to 24 bp double-stranded target sequence.

A "variant" endonuclease, i.e. an endonuclease that does not naturally exist in nature and that is obtained by genetic engineering or by random mutagenesis can bind DNA sequences different from that recognized by wild-type endonucleases (see WO2006097854).

Other binding domains can be zinc finger domains. In this case, the resulting TevI chimeric endonuclease corresponds to the fusion of engineered zinc finger domain with the I-TevI catalytic domain. According to a preferred embodiment of the invention, the nucleic acid binding domain is derived from a Transcription Activator like Effector (TALE), wherein sequence specificity is driven by a series of 33-35 amino acids repeats originating from *Xanthomonas* or *Ralstonia* bacterial proteins. These repeats differ essentially by two amino acids positions that specify an interaction with a base pair (Boch, Scholze et al. 2009; Moscou and Bogdanove 2009). Each base pair in the DNA target is contacted by a single repeat, with the specificity resulting from the two variant amino acids of the repeat (the so-called repeat variable dipeptide, RVD). TALE binding domains may further comprise a N-terminal translocation domain responsible for the requirement of a first thymine base ($T_0$) of the targeted sequence and a C-terminal domain that containing a nuclear localization signals (NLS). A TALE nucleic acid binding domain generally corresponds to an engineered core TALE scaffold comprising a plurality of TALE repeat sequence, each repeat comprising a RVD specific to each nucleotides base of a TALE recognition site. In the present invention, each TALE repeat sequence of said core scaffold is made of 30 to 42 amino acids, more preferably 33 or 34 wherein two critical amino acids (the so-called repeat variable dipeptide, RVD) located at positions 12 and 13 mediates the recognition of one nucleotide of said TALE binding site sequence; equivalent two critical amino acids can be located at positions other than 12 and 13 specially in TALE repeat sequence taller than 33 or 34 amino acids long. Preferably, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. More preferably, RVDs associated with recognition of the nucleotides C, T, A, G/A and G respectively are selected from the group consisting of NN or NK for recognizing G, HD for recognizing C, NG for recognizing T and NI for recognizing A, TL for recognizing A, VT for recognizing A or G and SW for recognizing A. In another embodiment, RVDs associated with recognition of the nucleotide C are selected from the group consisting of N* and RVDS associated with recognition of the nucleotide T are selected from the group consisting of N* and H*, where * denotes a gap in the repeat sequence that corresponds to a lack of amino acid residue at the second position of the RVD. In another embodiment, critical amino acids 12 and 13 can be mutated towards other amino acid residues in order to modulate their specificity towards nucleotides A, T, C and G and in particular to enhance this specificity. By other amino acid residues is intended any of the twenty natural amino acid residues or unnatural amino acids derivatives.

A TALE nucleic acid binding domain usually comprises between 8 and 30 TALE repeat sequences. More preferably, said core scaffold of the present invention comprises between 8 and 20 TALE repeat sequences; again more preferably 15 TALE repeat sequences. It can also comprise an additional single truncated TALE repeat sequence made of 20 amino acids located at the C-terminus of said set of TALE repeat sequences, i.e. an additional C-terminal half-TALE repeat sequence. The TALE nucleic acid binding domains according to the present invention preferably comprise the protein sequences selected from the group consisting of ST1 (SEQ ID NO: 258) and ST2 (SEQ ID NO: 259). In another embodiment, said engineered TAL binding domain comprises a protein sequence having at least 80%, more preferably 90%, again more preferably 95% amino acid sequence identity with the protein sequences selected from the group consisting of SEQ ID NO: 258 and SEQ ID NO: 259.

In another embodiment, said engineered TALE binding domain according to the present invention comprises the protein sequences selected from the group consisting of bT1-Avr (SEQ ID NO: 260), bT2-Avr (SEQ ID NO: 261), bT1-Pth (SEQ ID NO: 262) and bT2-Pth (SEQ ID NO: 263). In another embodiment, said TALE binding domain comprises a protein sequence having at least 80%, more preferably 90%, again more preferably 95% amino acid sequence identity with the protein sequences selected from the group consisting of SEQ ID NO: 260 to SEQ ID NO: 263.

In a preferred embodiment according to the method of the present invention, said additional N-terminal and C-terminal domains of engineered TALE binding domains are derived from natural TALE. In a more preferred embodiment said additional N-terminal and C-terminal domains of engineered core TALE scaffold are derived from natural TALE like AvrBs3, PthXo1, AvrHah1, PthA, Tal1c as non-limiting examples. In another more preferred embodiment, said additional N-terminal and/or said C-terminal domains are truncated forms of respective N-terminal and/or said C-terminal domains of natural TALE like AvrBs3, PthXo1, AvrHah1, PthA, Tal1c as non-limiting examples from which they are derived. In a more preferred embodiment, said additional N-terminal and C-terminal domains sequences of engineered core TALE scaffold are selected from the group consisting of ST1 SEQ ID NO: 258 and ST2 SEQ ID NO: 259 as respectively exemplified in baseline protein scaffolds bT1-Avr (SEQ ID NO: 260) or bT1-Pth (SEQ ID NO: 261) and bT2-Avr (SEQ ID NO: 262) or bT2-Pth (SEQ ID NO: 263).

Other engineered nucleic acid binding domains are modular base-per-base specific nucleic acid binding domains (MBBBD) (PCT application: PCT/US2013/051783). Said MBBBD can be engineered, for instance, from the newly identified proteins, namely EAV36_BURRH, E5AW43_BURRH, E5AW45_BURRH and E5AW46_BURRH proteins from the recently sequenced genome of the endosymbiont fungi *Burkholderia Rhizoxinica* (Lackner, Moebius et al. 2011).

MBBBD proteins comprise modules of about 31 to 33 amino acids that are base specific. These modules display less than 40% sequence identity with *Xanthomonas* TALE common repeats, whereas they present more polypeptides sequence variability. When they are assembled together, these modular polypeptides can although target specific nucleic acid sequences in a quite similar fashion as *Xanthomonas* TAL-nucleases.

According to a preferred embodiment of the present invention, an engineered MBBBD binding domain comprising between 10 and 30 modules, preferably between 16 and 20 modules, is used as a DNA binding domain in the TevI chimeric endonucleases. Such DNA binding domain can comprise at least a part of protein sequence selected from the group consisting of SEQ ID NO: 264 to SEQ ID NO: 267. In a more preferred embodiment, said DNA binding domain comprises a part of protein sequence SEQ ID NO: 267. In another embodiment, said engineered MBBBD binding domain comprises a protein sequence having at least 80%, more preferably 90%, again more preferably 95% amino acid sequence identity with the protein sequence selected from the group consisting of SEQ ID NO: 264 to SEQ ID NO: 267. The different domains from the above proteins (modules, N and C-terminals) from *Burkholderia* and *Xanthomonas* are useful to engineer new proteins or scaffolds having binding properties to specific nucleic acid sequences. In particular, additional N-terminal and C-terminal domains of engineered MBBBD can be derived from natural TALE like AvrBs3, PthXo1, AvrHah1, PthA, Tal1c as non-limiting examples.

According to the present invention, I-TevI catalytic domain might be fused at the N-terminal part or at the C-terminal part of the above nucleic acid binding domains. I-TevI catalytic domain can be fused to the nucleic acid binding domain by a peptide linker. Peptide linker acts as a communication device between the nucleic acid binding domain and I-TevI catalytic domain to act in concert for nucleic acid cleavage. Said peptide linker is a peptide sequence which allows the connection of different monomers in a fusion protein and the adoption of the correct conformation for said fusion protein activity and which does not alter the specificity of either of the monomers for their targets. Peptide linkers can be of various sizes, from 2 amino acids to 50 amino acids as a non limiting indicative range. Peptide linkers can also be structured or unstructured.

TevI chimeric endonuclease according to the invention thus interacts with at least two regions in the target nucleic acid sequence: the recognition site and the cleavage site. Optimal distances in the target nucleic acid sequence for the relative positioning of the binding and cleavage modules in the TevI chimeric endonuclease have to be determined. Thus, the present invention relates to a method further comprises determining target nucleic acid sequence that comprises a recognition site spaced away from said I-TevI cleavage site by an optimal distance to increase nucleic acid processing activity.

Increased DNA processing activity refers to an increase in the detected level of chimeric endonuclease processing activity against a target DNA sequence. In the present invention, DNA processing activity refers to a cleavage activity, either a cleavage activity or a nickase activity. By optimal distance is intended the distance between said recognition site and I-TevI cleavage site allowing an increase in DNA processing activity of the TevI chimeric endonuclease. An optimal distance is considered when it provides at least a 5% increase efficiency of DNA processing activity, more preferably 10%, again more preferably 15%, again more preferably 20%, again more preferably 25%, again more preferably 50%, again more preferably greater than 50%.

In particular embodiment, nucleic acid binding recognition site is also chosen based upon its optimal spacer between the residue preceded the first nucleic acid base of nucleic acid binding recognition site and the terminal G base of the I-TevI cleavage site. In a preferred embodiment, the optimal spacer distance is range between 1 to 50 bp, more preferably between 4 to 12 bp, again more preferably is 4, 5, 6, 7, 8, 9, 10, 11 or 12 bp.

In another embodiment, said nucleic acid binding recognition site is chosen upon the residue after the terminal G base of the I-TevI cleavage site is a nucleotide A or T.

In a particular embodiment, TALE recognition site is chosen based upon its optimal spacer distance to I-TevI cleavage site. TALE recognition site is immediately preceded by a thymine at the 5' end named $T_0$. So, TALE binding sequence is chosen based upon its optimal spacer distance between the first thymine $T_0$ and the terminal G base of the I-TevI cleavage site. In a preferred embodiment, the optimal spacer distance is ranged between 0 to 50 bp, and more preferably between 6 to 12 bp. In a more preferred embodiment, the optimal spacer distance is 10 bp.

Particular embodiment, the present invention also relates to the TevI chimeric endonuclease comprising the amino acid sequence selected from the group consisting of SEQ ID NO: 452 to 457. In another embodiment, said TevI chimeric endonuclease comprises a protein sequence having at least 80%, more preferably 90%, again more preferably 95% amino acid sequence identity with the protein sequences selected from the group consisting of SEQ ID NO: 452 to SEQ ID NO: 457.

Method to Process a Target Nucleic Acid Sequence

The present invention also relates to methods for use of said TevI chimeric endonuclease for various applications ranging from targeted nucleic acid cleavage to targeted gene regulation. In genome engineering experiments, the efficiency of chimeric endonuclease, e.g. their ability to induce a desired event (Homologous gene targeting, targeted mutagenesis, sequence removal or excision) at a locus, depends on several parameters, including the specific activity of the nuclease, probably the accessibility of the target, and the efficacy and outcome of the repair pathway(s) resulting in the desired event (homologous repair for gene targeting, NHEJ pathways for targeted mutagenesis).

A method to selectively cleave a target nucleic acid sequence by using a catalytic domain of I-TevI is encompassed in the present invention. This method comprises selecting a target nucleic acid sequence which comprises a I-TevI cleavage site selected from the group consisting of: SEQ ID NO: 2 to SEQ ID NO: 117, preferably SEQ ID NO: 2 to SEQ ID NO:55; selecting or engineering a nucleic acid binding domain to bind a recognition site adjacent to said cleavage site, fusing said nucleic acid binding domain with said catalytic domain of I-TevI to obtain a TevI chimeric endonuclease and contacting said target nucleic acid sequence with said TevI chimeric endonuclease. The TevI cleavage site may be introduced into the target nucleic acid sequence in order to be cleaved by the TevI chimeric endonuclease. In particular, the present invention relates to a method to process a target nucleic acid sequence in a cell comprising:

a) Generating a TevI chimeric endonuclease according to any one of methods previously described b) Introducing said TevI chimeric endonuclease into said cell.

Depending of the I-TevI catalytic domain position, resulting TevI chimeric endonuclease can present different enzymatic activities. For instance, the inventors have previously showed that when I-TevI catalytic domain is placed in natural position at the N-terminal of the DNA binding domain, chimeric endonuclease is more likely to display a cleavase activity. However, when I-TevI catalytic domain is placed in opposite position at the C-terminal of the DNA binding domain, chimeric endonuclease is more likely to display a nickase activity. Thus, different I-TevI conformation may be used to induce different enzymatic activities.

Any nucleic acid target sequence can be processed by the present methods. For example, the nucleic acid target sequence can be chromosomal, mitochondrial or chloroplast sequences.

The methods of the invention involve introducing TevI chimeric endonuclease into a cell. The TevI chimeric endonuclease may be synthesized in situ in the cell as a result of the introduction of polynucleotide encoding polypeptide into the cell. Alternatively, the chimeric endonuclease could be produced outside the cell and then introduced thereto. Methods for introducing a polynucleotide construct into bacteria, plants, fungi and animals are known in the art and including as non limiting examples stable transformation methods wherein the polynucleotide construct is integrated into the genome of the cell, transient transformation methods wherein the polynucleotide construct is not integrated into the genome of the cell and virus mediated methods. Said polynucleotides encoding MBBBD polypeptide may be introduced into a cell by for example, recombinant viral vectors (e.g. retroviruses, adenoviruses), liposomes and the like. For example, transient transformation methods include for example microinjection, electroporation or particle bombardment. Said polynucleotides encoding TevI chimeric endonucleases may be included in vectors, more particularly plasmids or virus, in view of being expressed in prokaryotic or eukaryotic cells.

Endonucleolytic breaks are known to stimulate the rate of homologous recombination. Therefore, as another embodiment, the present invention relates to a method to induce homologous gene targeting in the target nucleic acid sequence further comprising providing to the cell an exogeneous nucleic acid comprising at least a sequence homologous to a portion of the target nucleic acid sequence, such that homologous recombination occurs between the target nucleic acid sequence and the exogeneous nucleic acid. In a preferred embodiment, said exogeneous nucleic acid comprises a first and a second portions which are homologous to region 5' and 3' of the target nucleic acid. Said exogeneous nucleic acid may also comprise a third portion positioned between the first and the second portion which comprise no homology with the regions 5' and 3' of the target nucleic acid sequence.

Following cleavage of the target nucleic acid sequence, a homologous recombination event is stimulated between the genome containing the target nucleic acid sequence and the exogeneous nucleic acid.

Another aspect of the invention relates to a method to induce mutagenesis within target nucleic acid sequence. The double strand breaks caused by endonucleases are commonly repaired through non-homologous end joining (NHEJ). NHEJ comprises at least two different processes. Mechanisms involve rejoining of what remains of the two DNA ends through direct re-ligation (Critchlow and Jackson 1998) or via the so-called microhomology-mediated end joining (Ma, Kim et al. 2003). Repair via non-homologous end joining (NHEJ) often results in small insertions or deletions and can be used for the creation of specific gene knockouts. The present invention related to a method to induce mutagenesis by using a TevI chimeric endonuclease that allows nucleic acid cleavage that will lead to the loss of genetic information and any NHEJ pathway will produce targeted mutagenesis. In a preferred embodiment, the present invention related to a method for increasing mutagenesis at the target nucleic acid sequence to generate at least one nucleic acid cleavage and a loss of genetic information around said target nucleic acid sequence thus preventing any scarless re-ligation by NHEJ.

In a more preferred embodiment, the present invention relates to a method to process target nucleic acid sequence further comprising the step of expressing an additional catalytic domain into a host cell. It has been found that the coupling of DNA end-processing enzyme with an endonuclease ensures high frequency of targeted mutagenesis (International application WO 2012/058458). In a more preferred embodiment, the present invention relates to a method to increase mutagenesis wherein said additional catalytic domain is a DNA end-processing enzyme. Non limiting examples of DNA end-processing enzymes include 5-3' exonucleases, 3-5' exonucleases, 5-3' alkaline exonucleases, 5' flap endonucleases, helicases, hosphatase, hydrolases and template-independent DNA polymerases. Non limiting examples of such catalytic domain comprise of a protein domain or catalytically active derivate of the protein domain selected from the group consisting of hExoI (EXO1_HUMAN), Yeast ExoI (EXO1_YEAST), E. coli ExoI, Human TREX2, Mouse TREX1, Human TREX1, Bovine TREX1, Rat TREX1, TdT (terminal deoxynucleotidyl transferase) (WO 2012/13717) Human DNA2 and Yeast DNA2 (DNA2_YEAST). In a preferred embodiment, said additional catalytic domain has a 3'-5'-exonuclease activity, and in a more preferred embodiment, said additional catalytic domain has TREX exonuclease activity, more preferably TREX2 activity. In another preferred embodiment, said catalytic domain is encoded by a single chain TREX2 polypeptide (International application WO2013/009525). Said additional catalytic domain can be fused to TevI chimeric endonuclease by a peptide linker. In a more particular embodiment, the present invention relates to a TevI chimeric endonuclease fused to a single chain TREX2 comprising the amino acid sequence: SEQ ID NO: 458. In a more preferred embodiment said TevI chimeric endonuclease fused to single chain TREX2 comprises a protein sequence having at least 80%, more preferably 90%, again more preferably 95% amino acid sequence identity with the protein sequences selected from the group consisting of SEQ ID NO: 458.

Is also encompassed in the scope of the present invention related, a host cell modified by one of these methods. In another embodiment, the present invention relates to a non-human transgenic animal or a transgenic plant obtained by one of the methods.

Animals may be generated by introducing TevI chimeric endonuclease into a cell or an embryo. In particular, the present invention relates to a method for generating an animal, comprising providing an eukaryotic cell comprising a nucleic acid target sequence into which it is desired to introduce a genetic modification; generating a cleavage within or adjacent to the nucleic acid target sequence by introducing a TevI chimeric endonuclease according to the present invention; and generating an animal from the cell or progeny thereof, in which cleavage has occurred. Typically, the embryo is a fertilized one cell stage embryo. Polynucleotides encoding said TevI chimeric endonuclease may be introduced into the cell by any of the methods known in the art including micro-injection into the nucleus or cytoplasm of the embryo. In a particular embodiment, the method for generating an animal, further comprise introducing an exogenous nucleic acid as desired. Said exogenous nucleic acid comprises a sequence homologous to at least a portion of the nucleic acid target sequence, such that homologous recombination occurs between said exogenous nucleic acid and the nucleic acid target sequence in the cell or progeny thereof. The exogenous nucleic acid can include for example a nucleic acid sequence that disrupts a gene after homologous recombination, a nucleic acid sequence that replaces a gene after homologous recombination, a nucleic acid sequence that introduces a mutation into a gene after homologous recombination or a nucleic acid sequence that introduces a regulatory site after homologous recombination. The embryos are then cultures to develop an animal. In one aspect of the invention, an animal in which at least a nucleic acid target sequence of interest has been engineered is provided. For example, an engineered gene may become inactivated such that it is not transcribed or properly translated, or an alternate form of the gene is expressed. The animal may be homozygous or heterozygous for the engineered gene.

The present invention also related to a method for generating a plant comprising providing a plant cell comprising a nucleic acid target sequence into which it is desired to introduce a genetic modification; generating a cleavage in the nucleic acid target sequence by introducing a TevI chimeric endonuclease according to the present invention; and generating a plant from the cell or progeny thereof, in which cleavage has occurred. Progeny includes descendants of a particular plant or plant line. In a particular embodiment, the method for generating a plant, further comprise introducing an exogenous nucleic acid as desired. Said exogenous nucleic acid comprises a sequence homologous to at least a portion of the nucleic acid target sequence, such that homologous recombination occurs between said exogenous nucleic acid and the nucleic acid target sequence in the cell or progeny thereof. Plant cells produced using methods can be grown to generate plants having in their genome a modified nucleic acid target sequence. Seeds from such plants can be used to generate plants having a phenotype such as, for example, an altered growth characteristic, altered appearance, or altered compositions with respect to unmodified plants.

The polypeptides of the invention are useful to engineer genomes and to reprogram cells, especially iPS cells and ES cells.

The present invention also relates to kits used to implement the method according to the present invention. More preferably, is encompassed in the scope of the present invention, a kit comprising a TevI chimeric endonuclease and instructions for use said kit in processing target nucleic acid.

It is understood that, TevI chimeric endonuclease, nucleic acid binding domains, RVDs, TALE, protein domains and polypeptides according to the present invention can also comprise single or plural additional amino acid substitutions or amino acid insertion or amino acid deletion introduced by mutagenesis process well known in the art. Are also encompassed in the scope of the present invention variants, functional mutants and derivatives from TevI chimeric endonuclease, DNA binding domains, RVDs, TALE, protein domain and polypeptides according to the present invention. Are also encompassed in the scope of the present invention TevI chimeric endonuclease, DNA binding domains, RVDs, TALE, protein domain and polypeptides which present a sequence with high percentage of identity or high percentage of homology with sequences of TevI chimeric endonuclease, DNA binding domains, RVDs, TALE, protein domains and polypeptides according to the present invention, at nucleotidic or polypeptidic levels. By high percentage of identity or high percentage of homology it is intended 70%, more preferably 75%, more preferably 80%, more preferably 85%, more preferably 90%, more preferably 95, more preferably 97%, more preferably 99% or any integer comprised between 70% and 99%.

Definitions

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

By "delivery vector" or "delivery vectors" is intended any delivery vector which can be used in the present invention to put into cell contact (i.e "contacting") or deliver inside cells or subcellular compartments agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, Spumavirus (Coffin, J. M., Retroviridae: The viruses and their replication, In Fundamental Virology, Third Edition, B. N. Fields, et al., Eds., Lippincott-Raven Publishers, Philadelphia, 1996).

By cell or cells is intended any prokaryotic or eukaryotic living cells, cell lines derived from these organisms for in vitro cultures, primary cells from animal or plant origin.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines. These cells thus represent a more valuable model to the in vivo state they refer to.

In the frame of the present invention, "eukaryotic cells" refer to a fungal, plant or animal cell or a cell line derived from the organisms listed below and established for in vitro culture. More preferably, the fungus is of the genus *Aspergillus, Penicillium, Acremonium, Trichoderma, Chrysoporium, Mortierella, Kluyveromyces* or *Pichia*; More preferably, the fungus is of the species *Aspergillus niger, Aspergillus nidulans, Aspergillus oryzae, Aspergillus terreus, Penicillium chrysogenum, Penicillium citrinum, Acremonium Chrysogenum, Trichoderma reesei, Mortierella alpine, Chrysosporium lucknowense, Kluyveromyces lactic, Pichia pastoris* or *Pichia ciferrii*.

More preferably the plant is of the genus *Arabidospis, Nicotiana, Solanum, lactuca, Brassica, Oryza, Asparagus, Pisum, Medicago, Zea, Hordeum, Secale, Triticum, Capsicum, Cucumis, Cucurbita, Citrullis, Citrus, Sorghum*; More preferably, the plant is of the species *Arabidospis thaliana, Nicotiana tabaccum, Solanum lycopersicum, Solanum tuberosum, Solanum melongena, Solanum esculentum, Lactuca saliva, Brassica napus, Brassica oleracea, Brassica rapa, Oryza glaberrima, Oryza sativa, Asparagus officinalis, Pisum sativum, Medicago sativa, Zea mays, Hordeum vulgare, Secale cereal, Triticum aestivum, Triticum durum, Capsicum sativus, Cucurbita pepo, Citrullus lanatus, Cucumis melo, Citrus aurantifolia, Citrus maxima, Citrus medica, Citrus reticulata*.

More preferably the animal cell is of the genus *Homo, Rattus, Mus, Sus, Bos, Danio, Canis, Felis, Equus, Salmo, Oncorhynchus, Gallus, Meleagris, Drosophila, Caenorhabditis*; more preferably, the animal cell is of the species *Homo sapiens, Rattus norvegicus, Mus musculus, Sus scrofa, Bos taurus, Danio rerio, Canis lupus, Felis catus, Equus caballus, Salmo salar, Oncorhynchus mykiss, Gallus gallus, Meleagris gallopavo, Drosophila melanogaster, Caenorhabditis elegans*.

In the present invention, the cell can be a plant cell, a mammalian cell, a fish cell, an insect cell or cell lines derived from these organisms for in vitro cultures or primary cells taken directly from living tissue and established for in vitro culture. As non-limiting examples, cell can be protoplasts obtained from plant organisms listed above. As non limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells.

- by "homologous" is intended a sequence with enough identity to another one to lead to homologous recombination between sequences, more particularly having at least 95% identity, preferably 97% identity and more preferably 99%.
- "identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting.
- by "mutation" is intended the substitution, deletion, insertion of one or more nucleotides/amino acids in a polynucleotide (cDNA, gene) or a polypeptide sequence. Said mutation can affect the coding sequence of a gene or its regulatory sequence. It may also affect the structure of the genomic sequence or the structure/stability of the encoded mRNA.
- By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.
- As used herein, the term "transgene" refers to a sequence encoding a polypeptide. Preferably, the polypeptide encoded by the transgene is either not expressed or expressed but not biologically active, in the cell, tissue or individual in which the transgene is inserted. Most preferably, the transgene encodes a therapeutic polypeptide useful for the treatment of an individual.
- Nucleic acid processing activity refers to a particular/given enzymatic activity of said TevI chimeric endonuclease. Said nucleic acid processing activity can refer to a cleavage activity, either a cleavage activity either a nickase activity, more broadly a nuclease activity but also a polymerase activity, a kinase activity, a phosphatase activity, a methylase activity, a topoisomerase activity, an integrase activity, a transposase activity or a ligase activity as non-limiting examples. In the scope of this definition, said given nucleic acid processing activity of a particular enzymatic activity can also be described as nucleic acid processing efficiency of said particular enzymatic activity.
- Efficiency of TevI chimeric endonuclease according to the present invention is the property for said TevI chimeric endonuclease of producing a desired event. This desired event can be for example Homologous gene targeting, targeted mutagenesis, or sequence removal or excision. The efficiency of the desired event depends on several parameters, including the specific activity of the nuclease and the repair pathway(s) resulting in the desired event (efficacy of homologous repair for gene targeting, efficacy and outcome of NHEJ pathways for targeted mutagenesis). Efficiency of a rare cutting endonuclease for a locus is intended to mean its ability to produce a desired event at this locus. Efficiency of a rare cutting endonuclease for a target is intended to mean its ability to produce a desired event as a consequence of cleavage of this target.
- By "exogenous" it is intended nucleic acid or protein sequence not naturally associated with a target gene or a host cell into which it is introduced, including non-naturally occurring multiple copies of a naturally occurring nucleic acid e.g., DNA sequence, or naturally occurring nucleic acid sequence located in on-naturally occurring genome location.
- by "peptide linker", it is intended to mean a peptide sequence which allows the connection of different monomers in a fusion protein and the adoption of the correct conformation for said fusion protein activity and which does not alter the specificity of either of the monomers for their targets. Peptide linkers can be of various sizes, from 3 amino acids to 50 amino acids as a non limiting indicative range. Peptide linkers can also be structured or unstructured.
- by "TevI chimeric endonuclease variant", "I-TevI catalytic domain variant", it is intended an TevI chimeric endonuclease or "I-TevI catalytic domain", obtained by replacement of at least one residue in the amino acid sequence of the parent TevI chimeric endonuclease, with at least a different amino acid. "Variant" designation also applies for instance for TevI chimeric endonuclease comprising at least one supplementary protein domain (additional catalytic domain) in comparison to the starting TevI chimeric endonuclease. Are also encompassed in the scope of the present definition, variants and protein domains comprised in these variants which present a sequence with high percentage of identity or high percentage of homology with sequences of protein domains and polypeptides according to the present invention, at nucleotidic or polypeptidic levels. By high percentage of identity or high percentage of homology it is intended 60%, more preferably 70%, more preferably 75%, more preferably 80%, more preferably 85%, more preferably 90%, more preferably 95, more preferably 97%, more preferably 99% or any integer comprised between 60% and 99%.

The term "endonuclease" refers to any wild-type or variant enzyme capable of catalyzing the hydrolysis (cleavage) of bonds between nucleic acids within a DNA or RNA molecule, preferably a DNA molecule. Endonucleases can be classified as rare-cutting endonucleases when having typically a polynucleotide recognition greater than 12 base pairs (bp) in length, more preferably of 14-45 bp. Rare-cutting endonucleases significantly increase HR by inducing DNA double-strand breaks (DSBs) at a defined locus (Rouet, Smih et al. 1994; Rouet, Smih et al. 1994; Choulika, Perrin et al. 1995; Pingoud and Silva 2007). Rare-cutting endonucleases can for example be a homing endonuclease (Paques and Duchateau 2007), a chimeric Zinc-Finger nuclease (ZFN) resulting from the fusion of engineered zinc-finger domains with the catalytic domain of a restriction enzyme such as FokI (Porteus and Carroll 2005) or a chemical endonuclease (Eisenschmidt, Lanio et al. 2005; Arimondo, Thomas et al. 2006; Simon, Cannata et al. 2008). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish and Glazer 2005). Such chemical endonucleases are comprised in the term "endonuclease" according to the present invention.

Transcription Activator Like Effector (TALE) is a family of proteins used in the infection process by plant pathogens of the *Xanthomonas* genus (Boch, Scholze et al. 2009; Moscou and Bogdanove 2009; Christian, Cermak et al. 2010; Li, Huang et al. 2011; Li, Huang et al. 2011).

By "fusion protein" is intended the result of a well-known process in the art consisting in the joining of two or more genes which originally encode for separate proteins or part of them, the translation of said "fusion gene" resulting in a single polypeptide with functional properties derived from each of the original proteins.

By "catalytic domain" is intended the protein domain or module of an enzyme containing the active site of said enzyme; by active site is intended the part of said enzyme at which catalysis of the substrate occurs. Enzymes, but also their catalytic domains, are classified and named according to the reaction they catalyze. The Enzyme Commission number (EC number) is a numerical classification scheme for enzymes, based on the chemical reactions they catalyze (http://www.chem.qmul.ac.uk/iubmb/enzyme/).

By "nuclease catalytic domain" is intended the protein domain comprising the active site of an endonuclease or an exonuclease enzyme. Such nuclease catalytic domain can be, for instance, a "cleavase domain" or a "nickase domain". By "cleavase domain" is intended a protein domain whose catalytic activity generates a Double Strand Break (DSB) in a nucleic acid target. By "nickase domain" is intended a protein domain whose catalytic activity generates a single strand break in a nucleic acid target sequence.

In the frame of the present invention, the expression "double-strand break-induced mutagenesis" (DSB-induced mutagenesis) refers to a mutagenesis event consecutive to an NHEJ event following an endonuclease-induced DSB, leading to insertion/deletion at the cleavage site of an endonuclease.

By the expression "loss of genetic information" is understood the elimination or addition of at least one given nucleic acid fragment (at least one nucleotide) or sequence, bordering the recognition sites of the TevI chimeric endonuclease of the present invention or the intervening sequence between at least two processing sites of the TevI chimeric endonuclease of the present invention and leading to a change of the original sequence around said TevI chimeric endonuclease cleavage sites, within the genomic locus of interest.

By "scarless re-ligation" or "scarless religation" is intended the perfect re-ligation event, without loss of genetic information (no insertion/deletion events) of the DNA broken ends through NHEJ process after the creation of a double-strand break event.

By "Imprecise NHEJ" is intended the re-ligation of nucleic acid ends generated by a DSB, with insertions or deletions of nucleotides. Imprecise NHEJ is an outcome and not a repair pathway and can result from different NHEJ pathways (Ku dependent or Ku independent as non-limiting examples).

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Different variants of I-TevI catalytic domain, a member of the GIY-YIG endonuclease family (Mueller, Smith et al. 1995), was fused to the N-terminal part of a TAL backbone or BurrH-36 backbone derived from EAV36 BURRH protein to create a new class of TALEN (TevI::TALE) or MBBBD nuclease (TevI::BurrH_36). The construct names are written as CD::TALE-DBA or CD::Burrh_36-DBA (catalytic domain is fused N-terminal to the TALE domain or the MBBBD) where "-DBA" (DNA binding array) optionally designates the sequence recognized by the TALE or MBBBD and "CD" is the catalytic domain type.

I-TevI protein is a tripartite protein, composed of a C-terminal domain responsible for binding specificity, linked to N-terminal catalytic domain by a long flexible linker. The N-terminal catalytic domain contributes to specificity via nucleic acid cleavage selectivity, characterized biochemically and defined by the degenerate CNNNG motif (with CAACGC as the natural cleavage sequence). Herein we describe a novel pattern of specificity for I-TevI cleavage in the context of TevI::TALE and TevI::Burrh_36 constructs.

Example 1: Construction of Different TevI Chimeric Endonucleases

Construction of TevD02::cT11-AvrBs3

A variant of the I-TevI catalytic domain named TevD02 (SEQ ID NO: 268) consisting of the N-terminal 183 residues of the wild-type catalytic domain of I-TevI (SEQ ID NO: 257) was amplified by the PCR on template TevCreD02 (SEQ ID NO: 269 protein in plasmid pCLS6615 (SEQ ID NO: 270)) using the primer pair CMP_G001 (SEQ ID NO: 271) and CMP_G068 (SEQ ID NO: 272).

The sT2 (SEQ ID NO: 259) core TALE scaffold was selected to generate pCLS7865-cTAL11_NFS1 (pCLS9008, SEQ ID NO: 273), where NFS1 designates the amino acid sequence-GSSG- (with underlying restriction sites BamHI and Kpn21 in the coding DNA to facilitate cloning).

TevD02 was subcloned into the pCLS9008 backbone by restriction and ligation using NcoI and Kpn21 restriction sites, yielding pCLS7865-TevD02::cT11 (pCLS12730, SEQ ID NO: 274). The fusion contains the sequence-QGPSG-linking the TALE-derived DNA binding domain and I-TevI derived catalytic domain.

The DNA sequence coding for the DNA binding array to target the AvrBs3 site (SEQ ID NO: 275) was subcloned into plasmid pCLS12730 (SEQ ID NO: 274) using Type IIS restriction enzymes BsmBI for the receiving plasmid and BbvI and SfaNI for the inserted RVD sequence to create the subsequent TevD02::cT11-AvrBs3 construct (pCLS12731, SEQ ID NO: 276). The TevD02::cT11-AvrBs3 construct was sequenced and the insert transferred to additional vectors as needed (see below).

The final TevD02::cT11-AvrBs3 yeast expression plasmid pCLS8522 (SEQ ID NO: 277) encoding TevD02-TALE chimeric endonuclease (SEQ ID NO: 279) was prepared by yeast in vivo cloning using plasmid pCLS12731. To generate an intact coding sequence by in vivo homologous recombination, approximately 40 ng of pCLS12731 plasmid linearized by digestion with BssHII and 1 ng of the pCLS0542 (SEQ ID NO: 278) plasmid linearized by digestion with NcoI and EagI were used to transform the yeast S. cerevisiae strain FYC2-6A (MATα, trp1Δ63, leu2Δ1, his3Δ200) using a high efficiency LiAc transformation protocol (Arnould, Perez et al. 2007).

Construction of TevD02::b36-AvrBs3

The BurrH_36 core scaffold (SEQ ID NO: 280) derived from EAV36 BURRH protein was composed of a N-terminal domain and a C-terminal domain separated by a small DNA sequence containing two BsmBI sites allowing further cloning of the DNA coding for the DNA binding array. Short sequences were added between the different pieces for cloning purpose or to create linkers at the protein level. The BurrH_36 scaffold was then cloned into vector pCLS7865 (SEQ ID NO: 281) to generate pCLS7865-BurrH_36.

TevD02 (SEQ ID NO: 268) was fused to the N-terminal part of the BurrH_36 scaffold into the pCLS7865-BurrH_36 by restriction and ligation using standard biological tools, yielding pCLS7865-TevD002::b36. The fusion contains the sequence-QGPSG-linking the BurrH_36-derived DNA binding domain and I-TevI-derived catalytic domain.

The DNA sequence coding for the DNA binding array to target the AvrBs3 site (SEQ ID NO: 282) was subcloned into plasmid pCLS7865-TevD02::b36 using Type IIS restriction enzymes BsmBI for the receiving plasmid and for the inserted DNA binding array sequence to create the subsequent TevD02::b36-AvrBs3 construct. The TevD02::b36-AvrBs3 construct was sequenced and the insert transferred to additional vectors as needed (see below).

The final TevD02::b36-AvrBs3 yeast expression plasmid encoding TevD02-BurrH chimeric endonuclease (SEQ ID NO: 283) was prepared by yeast in vivo cloning using TevD02::b36-AvrBs3 construct. To generate an intact coding sequence by in vivo homologous recombination, approximately 40 ng of TevD02::b36-AvrBs3 plasmid linearized and 1 ng of the pCLS0542 (SEQ ID NO: 278) plasmid linearized were used to transform the yeast S. cerevisiae strain FYC2-6A (MATα, trp1Δ63, leu2Δ1, his3Δ200) using a high efficiency LiAc transformation protocol (Arnould, Perez et al. 2007).

Construction of TevM01::cT11-AvrBs3

Another variant of the I-TevI catalytic domain named TevM01 (SEQ ID NO: 284) consisting of the N-terminal 137 residues of the wild-type I-TevI (SEQ ID NO: 257) was amplified by the PCR on template TevCreD02 [SEQ ID NO: 269 protein in plasmid pCLS6615 (SEQ ID NO: 270].

The sT2 (SEQ ID NO: 259) core TALE scaffold was selected to generate pCLS7865-cTAL11_NFS1 (pCLS9008, SEQ ID NO: 273), where NFS1 designates the amino acid sequence-GSSG- (with underlying restriction sites BamHI and Kpn21 in the coding DNA to facilitate cloning).

TevM01 was subcloned into the pCLS9008 backbone, yielding pCLS7865-TevM01::cT11. The fusion contains the sequence-SG-linking the TALE-derived DNA binding domain and I-TevI-derived catalytic domain.

The DNA sequence coding for the DNA binding array to target the AvrBs3 site (SEQ ID NO: 275) was subcloned into pCLS7865-TevM01::cT11 plasmid to create the subsequent TevM01::cT11-AvrBs3 constructs. The TevM01::cT11-AvrBs3 construct was sequenced and the insert transferred to additional vectors as needed (see below).

The final TevM01::cT11-AvrBs3 yeast expression plasmid encoding TevM01-TALE chimeric endonuclease (SEQ ID NO: 285) was prepared by yeast in vivo cloning using TevM01::cT11-AvrBs3 construct. To generate an intact coding sequence by in vivo homologous recombination, approximately 40 ng of TevM01::cT11-AvrBs3 construct linearized and 1 ng of the pCLS0542 (SEQ ID NO: 278) plasmid linearized were used to transform the yeast S. cerevisiae strain FYC2-6A (MATα, trp1Δ63, leu2Δ1, his3Δ200) using a high efficiency LiAc transformation protocol (Arnould, Perez et al. 2007).

Construction of TevM01::b36-AvrBs3

TevM01 was fused to the N-terminal part of the Burrh_36 scaffold into the pCLS7865-Burrh_36 by restriction and ligation using standard biological tools, yielding pCLS7865-TevM01::b36. The fusion contains the dipeptide-IA-linking the BurrH_36-derived DNA binding domain and I-TevI-derived catalytic domain.

The DNA sequence coding for the DNA binding array to target the AvrBs3 site (SEQ ID NO: 282) was subcloned into plasmid pCLS7865-TevM01::b36 to create the subsequent TevM01::b36-AvrBs3 construct. The TevM01::b36-AvrBs3 construct was sequenced and the insert transferred to additional vectors as needed (see below).

The final TevM01::b36-AvrBs3 yeast expression plasmid encoding TevM01-BurrH-AvrBs3 chimeric endonuclease (SEQ ID NO: 286) was prepared by yeast in vivo cloning using plasmid pCLS12731. To generate an intact coding sequence by in vivo homologous recombination, approximately 40 ng of TevM01::b36-AvrBs3 construct linearized and 1 ng of the pCLS0542 (SEQ ID NO: 278) plasmid linearized were used to transform the yeast S. cerevisiae strain FYC2-6A (MATα, trp1Δ63, leu2Δ1, his3Δ200) using a high efficiency LiAc transformation protocol (Arnould, Perez et al. 2007).

Example 2: Distance Requirement for TevI::TALE Cleavage in an In Vivo Yeast Assay All the yeast target reporter plasmids containing the TALE nucleic acid target sequences were constructed as previously described (International PCT Applications WO 2004/067736 and in (Epinat, Arnould et al. 2003; Chames, Epinat et al. 2005; Arnould, Chames et al. 2006; Smith, Grizot et al. 2006)).

As the natural I-TevI linker can act as a distance determinant for nucleic acid cleavage by the catalytic domain, we asked whether a similar relationship exists in the context of a TALE fusion. The TevD02::cT11-AvrBs3 construct was tested in a yeast SSA assay as previously described (International PCT Applications WO 2004/067736 and in (Epinat, Arnould et al. 2003; Chames, Epinat et al. 2005; Arnould, Chames et al. 2006; Smith, Grizot et al. 2006)) on targets containing a single AvrBs3 recognition site and the I-TevI cleavage sequence CAACGC (SEQ ID NO:1) spaced from 0 to 50 bps away from the T1 of the AvrBS3 TALE binding site, with spacing reported as the distance between the G base of the cleavage sequence and the T0 (SEQ ID NO: 288 to 342, Table 1). The TevD02::cT11-AvrBs3 activity levels on single AvrBs3 site targets in yeast cells are shown in table 2. TevD02::cT11-AvrBs3 construct presents an optimal activity for a spacing of 10 bp between the cleavage sequence and the T0 of the TALE binding site.

TABLE 1

List of nucleic acid target sequences containing a DNA binding domain site and an I-Tevl cleavage site spaced from 0 to 50 bp. The target numbers correspond to the distance between the G of the I-Tevl cleavage sequence CAACGC (SEQ ID NO: 1) (uppercase bold) and the T0 of the TALE DNA binding site (uppercase). The "a" targets correspond to duplicate targets where a cryptic CNNNG I-Tevl cleavage site (underlined) has been removed.

| Spacer | Nucleic acid Target Sequence | SEQ ID |
|---|---|---|
| 01 | actagatcaatcagtcatctaatacaagctactgtacttacgatactaatCAACGCTATATAAACCTAACCCTCT | 288 |
| 02 | actagatcaatcagtcatctaatacaagctactgtacttacgatactaaCAACGCtTATATAAACCTAACCCTCT | 289 |
| 03 | actagatcaatcagtcatctaatacaagctactgtacttacgatactaCAACGCatTATATAAACCTAACCCTCT | 290 |
| 04 | actagatcaatcagtcatctaatacaagctactgtacttacgatactCAACGCaatTATATAAACCTAACCCTCT | 291 |
| 05 | actagatcaatcagtcatctaatacaagctactgtacttacgatacCAACGCatatTATATAAACCTAACCCTCT | 292 |
| 06 | actagatcaatcagtcatctaatacaagctactgtacttacgataCAACGCatgatTATATAAACCTAACCCTCT | 293 |
| 07 | actagatcaatcagtcatctaatacaagctactgtacttacgatCAACGCatgcatTATATAAACCTAACCCTCT | 294 |
| 08 | actagatcaatcagtcatctaatacaagctactgtacttacgaCAACGCatgctatTATATAAACCTAACCCTCT | 295 |
| 09 | actagatcaatcagtcatctaatacaagctactgtacttacgCAACGCatgcgtatTATATAAACCTAACCCTCT | 296 |
| 10 | actagatcaatcagtcatctaatacaagctactgtacttacCAACGCatgccgtatTATATAAACCTAACCCTCT | 297 |
| 11 | actagatcaatcagtcatctaatacaagctactgtacttaCAACGCatgctcgtatTATATAAACCTAACCCTCT | 298 |
| 12 | actagatcaatcagtcatctaatacaagctactgtacttCAACGCatg<u>cttcg</u>tatTATATAAACCTAACCCTCT | 299 |
| 12a | actagatcaatcagtcatctaatacaagctactgtacttCAACGCatgcttcAtatTATATAAACCTAACCCTCT | 300 |
| 13 | actagatcaatcagtcatctaatacaagctactgtactCAACGCatgcattcgtatTATATAAACCTAACCCTCT | 301 |
| 14 | actagatcaatcagtcatctaatacaagctactgtacCAACGCatgcaattcgtatTATATAAACCTAACCCTCT | 302 |
| 15 | actagatcaatcagtcatctaatacaagctactgtaCAACGCatgctaattcgtatTATATAAACCTAACCCTCT | 303 |

TABLE 1-continued

List of nucleic acid target sequences containing a DNA binding domain site and an I-TevI cleavage site spaced from 0 to 50 bp. The target numbers correspond to the distance between the G of the I-TevI cleavage sequence CAACGC (SEQ ID NO: 1) (uppercase bold) and the T0 of the TALE DNA binding site (uppercase). The "a" targets correspond to duplicate targets where a cryptic CNNNG I-TevI cleavage site (underlined) has been removed.

| Spacer | Nucleic acid Target Sequence | SEQ ID |
|---|---|---|
| 16 | actagatcaatcagtcatctaatacaagctactgtCAACGCatgcctaattcgtatTATATAAACCTAACCCTCT | 304 |
| 17 | actagatcaatcagtcatctaatacaagctactgCAACGCatgcactaattcgtatTATATAAACCTAACCCTCT | 305 |
| 18 | actagatcaatcagtcatctaatacaagctactCAACGCatgctactaattcgtatTATATAAACCTAACCCTCT | 306 |
| 19 | actagatcaatcagtcatctaatacaagctacCAACGCatgcatactaattcgtatTATATAAACCTAACCCTCT | 307 |
| 20 | actagatcaatcagtcatctaatacaagctCAACGCatgccgatactaattcgtatTATATAAACCTAACCCTCT | 308 |
| 21 | actagatcaatcagtcatctaatacaagcCAACGCatgcacgatactaattcgtatTATATAAACCTAACCCTCT | 309 |
| 21a | actagatcaatcagtcatctaatacaagCAACGCatgctacgatactaattcgtatTATATAAACCTAACCCTCT | 310 |
| 22 | actagatcaatcagtcatctaatacaagCAACGCatgctacAatactaattcgtatTATATAAACCTAACCCTCT | 311 |
| 23 | actagatcaatcagtcatctaatacaaCAACGCatgcttacgatactaattcgtatTATATAAACCTAACCCTCT | 312 |
| 24 | actagatcaatcagtcatctaatacaCAACGCatgccttacgatactaattcgtatTATATAAACCTAACCCTCT | 313 |
| 25 | actagatcaatcagtcatctaatacCAACGCatgcacttacgatactaattcgtatTATATAAACCTAACCCTCT | 314 |
| 26 | actagatcaatcagtcatctaataCAACGCatgctacttacgatactaattcgtatTATATAAACCTAACCCTCT | 315 |
| 27 | actagatcaatcagtcatctaatCAACGCatgcgtacttacgatactaattcgtatTATATAAACCTAACCCTCT | 316 |
| 28 | actagatcaatcagtcatctaaCAACGCatgctgtacttacgatactaattcgtatTATATAAACCTAACCCTCT | 317 |
| 29 | actagatcaatcagtcatctaCAACGCatgcctgtacttacgatactaattcgtatTATATAAACCTAACCCTCT | 318 |
| 29a | actagatcaatcagtcatctCAACGCatgcactgtacttacgatactaattcgtatTATATAAACCTAACCCTCT | 319 |
| 30 | actagatcaatcagtcatctCAACGCatgcactAtacttacgatactaattcgtatTATATAAACCTAACCCTCT | 320 |
| 31 | actagatcaatcagtcatcCAACGCatgctactgtacttacgatactaattcgtatTATATAAACCTAACCCTCT | 321 |
| 32 | actagatcaatcagtcatCAACGCatgcgtactgtacttacgatactaattcgtatTATATAAACCTAACCCTCT | 322 |
| 33 | actagatcaatcagtcaCAACGCatgcgctactgtacttacgatactaattcgtatTATATAAACCTAACCCTCT | 323 |
| 34 | actagatcaatcagtcCAACGCatgcagctactgtacttacgatactaattcgtatTATATAAACCTAACCCTCT | 324 |
| 35 | actagatcaatcagtCAACGCatgcaagctactgtacttacgatactaattcgtatTATATAAACCTAACCCTCT | 325 |
| 36 | actagatcaatcagCAACGCatgccaagctactgtacttacgatactaattcgtatTATATAAACCTAACCCTCT | 326 |
| 37 | actagatcaatcagCAACGCatgccaaActactgtacttacgatactaattcgtatTATATAAACCTAACCCTCT | 327 |
| 38 | actagatcaatcaCAACGCatgcacaagctactgtacttacgatactaattcgtatTATATAAACCTAACCCTCT | 328 |
| 39 | actagatcaatcCAACGCatgctacaagctactgtacttacgatactaattcgtatTATATAAACCTAACCCTCT | 329 |
| 40 | ActagatcaatCAACGCatgcatacaagctactgtacttacgatactaattcgtatTATATAAACCTAACCCTCT | 330 |
| 41 | actagatcaaCAACGCatgcaatacaagctactgtacttacgatactaattcgtatTATATAAACCTAACCCTCT | 331 |
| 42 | actagatcaCAACGCatgctaatacaagctactgtacttacgatactaattcgtatTATATAAACCTAACCCTCT | 332 |
| 43 | actagatcCAACGCatgcctaatacaagctactgtacttacgatactaattcgtatTATATAAACCTAACCCTCT | 333 |
| 44 | actagatCAACGCatgctctaatacaagctactgtacttacgatactaattcgtatTATATAAACCTAACCCTCT | 334 |
| 45 | actagaCAACGCatgcatctaatacaagctactgtacttacgatactaattcgtatTATATAAACCTAACCCTCT | 335 |
| 46 | actagCAACGCatgccatctaatacaagctactgtacttacgatactaattcgtatTATATAAACCTAACCCTCT | 336 |
| 47 | actaCAACGCatgctcatctaatacaagctactgtacttacgatactaattcgtatTATATAAACCTAACCCTCT | 337 |
| 48 | actCAACGCatgcgtcatctaatacaagctactgtacttacgatactaattcgtatTATATAAACCTAACCCTCT | 338 |

TABLE 1-continued

List of nucleic acid target sequences containing a DNA binding domain site and an I-TevI cleavage site spaced from 0 to 50 bp. The target numbers correspond to the distance between the G of the I-TevI cleavage sequence CAACGC (SEQ ID NO: 1) (uppercase bold) and the T0 of the TALE DNA binding site (uppercase). The "a" targets correspond to duplicate targets where a cryptic CNNNG I-TevI cleavage site (underlined) has been removed.

| Spacer | Nucleic acid Target Sequence | SEQ ID |
|---|---|---|
| 49 | acCAACGCatgcagtcatctaatacaagctactgtacttacgatactaattcgtatTATATAAACCTAACCCTCT | 339 |
| 50 | aCAACGCatgccagtcatctaatacaagctactgtacttacgatactaattcgtatTATATAAACCTAACCCTCT | 340 |
| 51 | CAACGCatg<u>ctcagt</u>catctaatacaagctactgtacttacgatactaattcgtatTATATAAACCTAACCCTCT | 341 |
| 51a | CAACGCatgctcaAtcatctaatacaagctactgtacttacgatactaattcgtatTATATAAACCTAACCCTCT | 342 |

TABLE 2

Activity of TevI chimeric endonucleases in yeast (37° C.) on targets containing a single AvrBs3 recognition site and the I-TevI cleavage sequence CAACGC spaced from 0 to 50 bp away from the T0. The TevD02::cT11-AvrBs3 construct was tested in a yeast SSA assay as previously described (International PCT Applications WO 2004/067736 and in (Epinat, Arnould et al. 2003; Chames, Epinat et al. 2005; Arnould, Chames et al. 2006; Smith, Grizot et al. 2006)) on targets containing a single AvrBs3 recognition site and the terminal G base of the I-TevI cleavage sequence CAACGC (SEQ ID NO1) spaced from 0 to 50 bps listed in table1.

| Spacer | Neg. Control | TevD02::cT11-AvrBs3 |
|---|---|---|
| Spacer-01 | n.d. | n.d. |
| Spacer-02 | n.d. | n.d. |
| Spacer-03 | n.d. | n.d. |
| Spacer-04 | n.d. | n.d. |
| Spacer-05 | n.d. | + |
| Spacer-06 | n.d. | ++ |
| Spacer-07 | n.d. | ++ |
| Spacer-08 | n.d. | ++ |
| Spacer-09 | n.d. | ++ |
| Spacer-10 | n.d. | +++ |
| Spacer-11 | n.d. | ++ |
| Spacer-12 | n.d. | ++ |
| Spacer-12a | n.d. | ++ |
| Spacer-13 | n.d. | + |
| Spacer-14 | n.d. | n.d. |
| Spacer-15 | n.d. | n.d. |
| Spacer-16 | n.d. | n.d. |
| Spacer-17 | n.d. | n.d. |
| Spacer-18 | n.d. | n.d. |
| Spacer-19 | n.d. | n.d. |
| Spacer-20 | n.d. | n.d. |
| Spacer-21 | n.d. | n.d. |
| Spacer-21a | n.d. | n.d. |
| Spacer-22 | n.d. | n.d. |
| Spacer-23 | n.d. | n.d. |
| Spacer-24 | n.d. | n.d. |
| Spacer-25 | n.d. | n.d. |
| Spacer-26 | n.d. | n.d. |
| Spacer-27 | n.d. | n.d. |
| Spacer-28 | n.d. | n.d. |
| Spacer-29 | n.d. | n.d. |
| Spacer-29a | n.d. | n.d. |
| Spacer-30 | n.d. | n.d. |
| Spacer-31 | n.d. | n.d. |
| Spacer-32 | n.d. | n.d. |
| Spacer-33 | n.d. | n.d. |
| Spacer-34 | n.d. | n.d. |
| Spacer-35 | n.d. | n.d. |
| Spacer-36 | n.d. | n.d. |
| Spacer-37 | n.d. | n.d. |
| Spacer-38 | n.d. | n.d. |
| Spacer-39 | n.d. | n.d. |
| Spacer-40 | n.d. | n.d. |
| Spacer-41 | n.d. | n.d. |
| Spacer-42 | n.d. | n.d. |
| Spacer-43 | n.d. | n.d. |
| Spacer-44 | n.d. | n.d. |
| Spacer-45 | n.d. | n.d. |
| Spacer-46 | n.d. | n.d. |
| Spacer-47 | n.d. | n.d. |
| Spacer-48 | n.d. | n.d. |
| Spacer-49 | n.d. | n.d. |
| Spacer-50 | n.d. | n.d. |
| Spacer-51 | n.d. | n.d. |
| Spacer-51a | n.d. | n.d. |

Example 3: Target Sequence Specificity for TevI::TALE and TevI::BurrH_36 Cleavage

Example 3a: Sequence Specificity for TevI::TALE and TevI::BurrH_36 Cleavage in an In Vivo Yeast Assay In order to address whether all CNNNG motifs were equivalently cut by I-TevI in the context of a TALE or BurrH_36 fusion, we tested TevD02::cT11-AvrBs3, TevD02::b36-AvrBs3, TevM01::cT11-AvrBs3 and TevM01::b36-AvrBs3 cleavage activity on a series of targets (TG10RGAr_CNNGN) containing a CNNNGN motif (with N=A, C, G or T) (SEQ ID NO:2 to SEQ ID NO:256) spaced at the optimal distance of 10 bp from the T0 of a single AvrBs3 recognition site (SEQ ID NO: 287) (CNNNGN-10N-AvrBs3 recognition site; with N=A, C, G or T) (SEQ ID NO: 343). The results show that variations in the CNNNGN motif modulate TevD02::TALE-AvrBs3, TevD02::BurrH_36-AvrBs3, TevM01::cT11-AvrBs3 and TevM01::b36-AvrBs3 activities. TevD02::TALE-AvrBs3, TevD02::BurrH_36-AvrBs3, TevM01::cT11-AvrBs3 and TevM01::b36-AvrBs3 activity levels on their respective targets in yeast cells are shown respectively in Tables 3 to 5.

TABLE 3

High activity of TevI chimeric endonucleases in yeast (37° C.) on a series of I-TevI cleavage sites. Activity of TevD02::cT11-AvrBs3, TevD02::b36-AvrBs3, TevM01::cT11-AvrBs3 and TevM01::b36-AvrBs3 on a series of targets (TG10RGAr_CNNNGN; SEQ ID NO: 343) containing a CNNNGN motif (SEQ ID NO: 2 to SEQ ID NO: 55). The negative control consists in a TALE scaffold without any DNA binding domain. n.d. indicates no detectable activity, +++ indicates an activity over 0.7 and ++ indicates an activity between 0.5 and 0.7 in our assay (International PCT Applications WO 2004/067736 and in Epinat, Arnould et al. 2003; Chames, Epinat et al. 2005; Arnould, Chames et al. 2006; Smith, Grizot et al. 2006).

| I-TevI cleavage site | SEQ ID | Neg. Control | TevD02::cT11-AvrBs3 | TevD02::b36-AvrBs3 | TevM01::cT11-AvrBs3 | TevM01::b36-AvrBs3 |
|---|---|---|---|---|---|---|
| CAAAGG | 2 | n.d. | +++ | +++ | +++ | +++ |
| CAACGG | 3 | n.d. | +++ | +++ | +++ | +++ |
| CAATGG | 4 | n.d. | +++ | +++ | +++ | +++ |
| CACAGG | 5 | n.d. | +++ | +++ | +++ | +++ |
| CACCGG | 6 | n.d. | +++ | +++ | +++ | +++ |
| CAGAGG | 7 | n.d. | +++ | +++ | +++ | +++ |
| CAGCGC | 8 | n.d. | +++ | +++ | +++ | +++ |
| CAGCGG | 9 | n.d. | +++ | +++ | +++ | +++ |
| CAGTGG | 10 | n.d. | +++ | +++ | +++ | +++ |
| CATAGC | 11 | n.d. | +++ | +++ | +++ | +++ |
| CATAGG | 12 | n.d. | +++ | +++ | +++ | +++ |
| CATCGG | 13 | n.d. | +++ | +++ | +++ | +++ |
| CATGGG | 14 | n.d. | +++ | +++ | +++ | +++ |
| CATTGG | 15 | n.d. | +++ | +++ | +++ | +++ |
| CCACGG | 16 | n.d. | +++ | +++ | +++ | +++ |
| CGACGG | 17 | n.d. | +++ | +++ | +++ | +++ |
| CTACGG | 18 | n.d. | +++ | +++ | +++ | +++ |
| CTATGG | 19 | n.d. | +++ | +++ | +++ | +++ |
| CTGAGG | 20 | n.d. | +++ | +++ | +++ | +++ |
| CTGCGG | 21 | n.d. | +++ | +++ | +++ | +++ |
| CTTAGG | 22 | n.d. | +++ | +++ | +++ | +++ |
| CAACGT | 23 | n.d. | +++ | ++ | +++ | +++ |
| CAAGGG | 24 | n.d. | +++ | ++ | +++ | +++ |
| CAATGC | 25 | n.d. | +++ | ++ | +++ | +++ |
| CAATGT | 26 | n.d. | +++ | ++ | +++ | +++ |
| CACTGG | 27 | n.d. | +++ | ++ | +++ | +++ |
| CAGAGC | 28 | n.d. | +++ | ++ | +++ | +++ |
| CAGCGA | 29 | n.d. | +++ | ++ | +++ | +++ |
| CAGGGG | 30 | n.d. | +++ | ++ | +++ | +++ |
| CAGTGT | 31 | n.d. | +++ | ++ | +++ | +++ |
| CATAGA | 32 | n.d. | +++ | ++ | +++ | +++ |
| CATAGT | 33 | n.d. | +++ | ++ | +++ | +++ |
| CATCGC | 34 | n.d. | +++ | ++ | +++ | +++ |
| CATTGC | 35 | n.d. | +++ | ++ | +++ | +++ |
| CCAAGG | 36 | n.d. | +++ | ++ | +++ | +++ |
| CCATGG | 37 | n.d. | +++ | ++ | +++ | +++ |
| CCGCGG | 38 | n.d. | +++ | ++ | +++ | +++ |
| CCTAGG | 39 | n.d. | +++ | ++ | +++ | +++ |
| CCTCGG | 40 | n.d. | +++ | ++ | +++ | +++ |
| CGAAGG | 41 | n.d. | +++ | ++ | +++ | +++ |
| CGATGG | 42 | n.d. | +++ | ++ | +++ | +++ |
| CTAAGG | 43 | n.d. | +++ | ++ | +++ | +++ |
| CTACGA | 44 | n.d. | +++ | ++ | +++ | +++ |
| CTACGC | 45 | n.d. | +++ | ++ | +++ | +++ |
| CTACGT | 46 | n.d. | +++ | ++ | +++ | +++ |
| CTATGC | 47 | n.d. | +++ | ++ | +++ | +++ |
| CTCAGG | 48 | n.d. | +++ | ++ | +++ | +++ |
| CTGTGG | 49 | n.d. | +++ | ++ | +++ | +++ |
| CTTCGG | 50 | n.d. | +++ | ++ | +++ | +++ |
| CTTTGG | 51 | n.d. | +++ | ++ | +++ | +++ |
| CTGCGC | 52 | n.d. | ++ | ++ | +++ | +++ |
| CAGTGC | 53 | n.d. | ++ | ++ | ++ | +++ |
| CGTAGG | 54 | n.d. | +++ | ++ | ++ | +++ |
| CACGGG | 55 | n.d. | +++ | ++ | ++ | +++ |

TABLE 4

Medium activity of TevI chimeric endonucleases in yeast (37° C.) on a series of I-TevI cleavage sites. Activity of TevD02::cT11-AvrBs3, TevD02::b36-AvrBs3, TevM01::cT11-AvrBs3 and TevM01::b36-AvrBs3 on a series of targets (TG10RGAr_CNNGN; SEQ ID NO: 343) containing a CNNNGN motif (SEQ ID NO: 56 to SEQ ID NO: 117). The negative control consists in a TALE scaffold without any DNA binding domain. n.d. indicates no detectable activity, +++ indicates an activity over 0.7 and ++ indicates an activity between 0.5 and 0.7, + indicates an activity between 03 and 0.5 in our assay (International PCT Applications WO 2004/067736 and in Epinat, Arnould et al. 2003; Chames, Epinat et al. 2005; Arnould, Chames et al. 2006; Smith, Grizot et al. 2006).

| I-TevI cleavage site | SEQ ID NO | Neg. Control | TevD02::cT11-AvrBs3 | TevD02::b36-AvrBs3 | TevM01::cT11-AvrBs3 | TevM01::b36-AvrBs3 |
|---|---|---|---|---|---|---|
| CAATGA | 56 | n.d. | +++ | + | +++ | +++ |
| CAGAGT | 57 | n.d. | +++ | + | +++ | +++ |
| CATTGA | 58 | n.d. | +++ | + | +++ | +++ |
| CATTGT | 59 | n.d. | +++ | + | +++ | +++ |
| CCACGT | 60 | n.d. | +++ | + | +++ | +++ |
| CCGAGG | 61 | n.d. | +++ | + | +++ | +++ |
| CCGTGG | 62 | n.d. | +++ | + | +++ | +++ |
| CCTTGG | 63 | n.d. | +++ | + | +++ | +++ |
| CGACGC | 64 | n.d. | +++ | + | +++ | +++ |
| CGTCGG | 65 | n.d. | +++ | + | +++ | +++ |
| CTATGT | 66 | n.d. | +++ | + | +++ | +++ |
| CTCCGG | 67 | n.d. | +++ | + | +++ | +++ |
| CTTCGC | 68 | n.d. | +++ | + | +++ | +++ |
| CAAAGC | 69 | n.d. | +++ | + | ++ | +++ |
| CATGGC | 70 | n.d. | +++ | + | ++ | +++ |
| CACCGT | 71 | n.d. | ++ | + | +++ | +++ |
| CAGCGT | 72 | n.d. | ++ | + | +++ | +++ |
| CAGTGA | 73 | n.d. | ++ | + | +++ | +++ |
| CCACGC | 74 | n.d. | ++ | + | +++ | +++ |
| CGGAGG | 75 | n.d. | ++ | + | +++ | +++ |
| CGTTGG | 76 | n.d. | ++ | + | +++ | +++ |
| CTCTGG | 77 | n.d. | ++ | + | +++ | +++ |
| CTGTGT | 78 | n.d. | ++ | + | +++ | +++ |
| CTTCGT | 79 | n.d. | ++ | + | +++ | +++ |
| CTTGGG | 80 | n.d. | ++ | + | +++ | +++ |
| CAAAGA | 81 | n.d. | ++ | + | ++ | +++ |
| CAACGA | 82 | n.d. | ++ | + | ++ | +++ |
| CACAGC | 83 | n.d. | ++ | + | ++ | +++ |
| CACAGT | 84 | n.d. | ++ | + | ++ | +++ |
| CACCGC | 85 | n.d. | ++ | + | ++ | +++ |
| CAGAGA | 86 | n.d. | ++ | + | ++ | +++ |
| CATCGA | 87 | n.d. | ++ | + | ++ | +++ |
| CCAGGG | 88 | n.d. | ++ | + | ++ | +++ |
| CCATGC | 89 | n.d. | ++ | + | ++ | +++ |
| CCATGT | 90 | n.d. | ++ | + | ++ | +++ |
| CCCAGG | 91 | n.d. | ++ | + | ++ | +++ |
| CCCCGG | 92 | n.d. | ++ | + | ++ | +++ |
| CCCTGG | 93 | n.d. | ++ | + | ++ | +++ |
| CCTGGG | 94 | n.d. | ++ | + | ++ | +++ |
| CGACGA | 95 | n.d. | ++ | + | ++ | +++ |
| CGACGT | 96 | n.d. | ++ | + | ++ | +++ |
| CGCAGG | 97 | n.d. | ++ | + | ++ | +++ |
| CGCCGG | 98 | n.d. | ++ | + | ++ | +++ |
| CGCTGG | 99 | n.d. | ++ | + | ++ | +++ |
| CGGCGG | 100 | n.d. | ++ | + | ++ | +++ |
| CGGTGG | 101 | n.d. | ++ | + | ++ | +++ |
| CGTGGG | 102 | n.d. | ++ | + | ++ | +++ |
| CTAAGC | 103 | n.d. | ++ | + | ++ | +++ |
| CTAGGG | 104 | n.d. | ++ | + | ++ | +++ |
| CTATGA | 105 | n.d. | ++ | + | ++ | +++ |
| CTGAGC | 106 | n.d. | ++ | + | ++ | +++ |
| CTGCGA | 107 | n.d. | ++ | + | ++ | +++ |
| CTGCGT | 108 | n.d. | ++ | + | ++ | +++ |
| CTGGGG | 109 | n.d. | ++ | + | ++ | +++ |
| CTGTGC | 110 | n.d. | ++ | + | ++ | +++ |
| CTTAGC | 111 | n.d. | ++ | + | ++ | +++ |
| CTTTGC | 112 | n.d. | ++ | + | ++ | +++ |
| CACTGC | 113 | n.d. | ++ | + | + | +++ |

TABLE 4-continued

Medium activity of Tev1 chimeric endonucleases in yeast (37° C.) on a series of I-TevI cleavage sites. Activity of TevD02::cT11-AvrBs3, TevD02::b36-AvrBs3, TevM01::cT11-AvrBs3 and TevM01::b36-AvrBs3 on a series of targets (TG10RGAr_CNNGN; SEQ ID NO: 343) containing a CNNNGN motif (SEQ ID NO: 56 to SEQ ID NO: 117). The negative control consists in a TALE scaffold without any DNA binding domain. n.d. indicates no detectable activity, +++ indicates an activity over 0.7 and ++ indicates an activity between 0.5 and 0.7, + indicates an activity between 03 and 0.5 in our assay (International PCT Applications WO 2004/067736 and in Epinat, Arnould et al. 2003; Chames, Epinat et al. 2005; Arnould, Chames et al. 2006; Smith, Grizot et al. 2006).

| I-Tev1 cleavage site | SEQ ID NO | Neg. Control | TevD02:: cT11-AvrBs3 | TevD02:: b36-AvrBs3 | TevM01:: cT11-AvrBs3 | TevM01:: b36-AvrBs3 |
|---|---|---|---|---|---|---|
| CATGGA | 114 | n.d. | ++ | + | + | +++ |
| CGAGGG | 115 | n.d. | ++ | + | + | +++ |
| CGTAGC | 116 | n.d. | ++ | + | + | +++ |
| CATCGT | 117 | n.d. | ++ | n.d. | +++ | +++ |

TABLE 5

Low and no activity of Tev1 chimeric endonucleases in yeast (37° C.) on a series of I-TevI cleavage sites. Activity of TevD02::cT11-AvrBs3, TevD02::b36-AvrBs3, TevM01::cT11-AvrBs3 and TevM01::b36-AvrBs3 on a series of targets (TG10RGAr_CNNGN; SEQ ID NO: 343) containing a CNNNGN motif (SEQ ID NO: 117 to SEQ ID NO: 256). The negative control consists in a TALE scaffold without any DNA binding domain. n.d. indicates no detectable activity, +++ indicates an activity over 0.7 and ++ indicates an activity between 0.5 and 0.7, + indicates an activity between 03 and 0.5 in our assay (International PCT Applications WO 2004/067736 and in Epinat, Arnould et al. 2003; Chames, Epinat et al. 2005; Arnould, Chames et al. 2006; Smith, Grizot et al. 2006).

| I-Tev1 cleavage site | SEQ ID NO | Neg. Control | TevD02:: cT11-AvrBs3 | TevD02:: b36-AvrBs3 | TevM01:: cT11-AvrBs3 | TevM01:: b36-AvrBs3 |
|---|---|---|---|---|---|---|
| CAAAGT | 118 | n.d. | + | + | ++ | +++ |
| CACTGT | 119 | n.d. | + | + | ++ | +++ |
| CCTTGT | 120 | n.d. | + | + | ++ | +++ |
| CGATGT | 121 | n.d. | + | + | ++ | +++ |
| CGTTGT | 122 | n.d. | + | + | ++ | ++ |
| CTAAGT | 123 | n.d. | + | + | ++ | ++ |
| CTGTGA | 124 | n.d. | + | + | ++ | +++ |
| CTTAGT | 125 | n.d. | + | + | ++ | +++ |
| CTTTGT | 126 | n.d. | + | + | ++ | +++ |
| CAAGGT | 127 | n.d. | + | + | + | ++ |
| CAGGGC | 128 | n.d. | + | + | + | +++ |
| CATGGT | 129 | n.d. | + | + | + | +++ |
| CCAAGC | 130 | n.d. | + | + | + | +++ |
| CCATGA | 131 | n.d. | + | + | + | +++ |
| CCGCGC | 132 | n.d. | + | + | + | +++ |
| CCGCGT | 133 | n.d. | + | + | + | +++ |
| CCGTGC | 134 | n.d. | + | + | + | +++ |
| CCGTGT | 135 | n.d. | + | + | + | ++ |
| CCTAGC | 136 | n.d. | + | + | + | +++ |
| CCTCGC | 137 | n.d. | + | + | + | +++ |
| CCTCGT | 138 | n.d. | + | + | + | ++ |
| CCTTGC | 139 | n.d. | + | + | + | +++ |
| CGAAGC | 140 | n.d. | + | + | + | +++ |
| CGATGC | 141 | n.d. | + | + | + | +++ |
| CGGTGC | 142 | n.d. | + | + | + | +++ |
| CGGTGT | 143 | n.d. | + | + | + | ++ |
| CGTAGT | 144 | n.d. | + | + | + | ++ |
| CGTCGC | 145 | n.d. | + | + | + | +++ |
| CGTTGC | 146 | n.d. | + | + | + | +++ |
| CTCCGC | 147 | n.d. | + | + | + | +++ |
| CTCGGG | 148 | n.d. | + | + | + | +++ |
| CTCTGC | 149 | n.d. | + | + | + | ++ |
| CTGAGT | 150 | n.d. | + | + | + | ++ |
| CTTTGA | 151 | n.d. | + | + | + | ++ |
| CACGGC | 152 | n.d. | + | + | n.d. | ++ |
| CGCTGC | 153 | n.d. | + | + | n.d. | ++ |
| CTTAGA | 154 | n.d. | + | n.d. | ++ | +++ |
| CACCGA | 155 | n.d. | + | n.d. | + | +++ |
| CACGGT | 156 | n.d. | + | n.d. | + | + |
| CACTGA | 157 | n.d. | + | n.d. | + | +++ |

TABLE 5-continued

Low and no activity of TevI chimeric endonucleases in yeast (37° C.) on a series of I-TevI cleavage sites. Activity of TevD02::cT11-AvrBs3, TevD02::b36-AvrBs3, TevM01::cT11-AvrBs3 and TevM01::b36-AvrBs3 on a series of targets (TG10RGAr_CNNGN; SEQ ID NO: 343) containing a CNNNGN motif (SEQ ID NO: 117 to SEQ ID NO: 256). The negative control consists in a TALE scaffold without any DNA binding domain. n.d. indicates no detectable activity, +++ indicates an activity over 0.7 and ++ indicates an activity between 0.5 and 0.7, + indicates an activity between 03 and 0.5 in our assay (International PCT Applications WO 2004/067736 and in Epinat, Arnould et al. 2003; Chames, Epinat et al. 2005; Arnould, Chames et al. 2006; Smith, Grizot et al. 2006).

| I-TevI cleavage site | SEQ ID NO | Neg. Control | TevD02::cT11-AvrBs3 | TevD02::b36-AvrBs3 | TevM01::cT11-AvrBs3 | TevM01::b36-AvrBs3 |
|---|---|---|---|---|---|---|
| CAGGGT | 158 | n.d. | + | n.d. | + | +++ |
| CCAAGT | 159 | n.d. | + | n.d. | + | +++ |
| CCACGA | 160 | n.d. | + | n.d. | + | +++ |
| CCGGGG | 161 | n.d. | + | n.d. | + | ++ |
| CCTAGT | 162 | n.d. | + | n.d. | + | ++ |
| CCTTGA | 163 | n.d. | + | n.d. | + | ++ |
| CGAAGA | 164 | n.d. | + | n.d. | + | ++ |
| CGATGA | 165 | n.d. | + | n.d. | + | ++ |
| CGGAGC | 166 | n.d. | + | n.d. | + | ++ |
| CGGCGT | 167 | n.d. | + | n.d. | + | ++ |
| CGGTGA | 168 | n.d. | + | n.d. | + | + |
| CGTAGA | 169 | n.d. | + | n.d. | + | +++ |
| CGTCGA | 170 | n.d. | + | n.d. | + | ++ |
| CGTCGT | 171 | n.d. | + | n.d. | + | ++ |
| CGTTGA | 172 | n.d. | + | n.d. | + | + |
| CTAAGA | 173 | n.d. | + | n.d. | + | +++ |
| CTCAGC | 174 | n.d. | + | n.d. | + | +++ |
| CTCAGT | 175 | n.d. | + | n.d. | + | ++ |
| CTCCGT | 176 | n.d. | + | n.d. | + | ++ |
| CTCTGT | 177 | n.d. | + | n.d. | + | + |
| CTGAGA | 178 | n.d. | + | n.d. | + | +++ |
| CTTCGA | 179 | n.d. | + | n.d. | + | +++ |
| CTTGGC | 180 | n.d. | + | n.d. | + | ++ |
| CAAGGC | 181 | n.d. | + | n.d. | n.d. | +++ |
| CGGCGC | 182 | n.d. | + | n.d. | n.d. | +++ |
| CACGGA | 183 | n.d. | + | n.d. | n.d. | ++ |
| CCAAGA | 184 | n.d. | + | n.d. | n.d. | + |
| CCCGGG | 185 | n.d. | + | n.d. | n.d. | ++ |
| CCCGGT | 186 | n.d. | + | n.d. | n.d. | n.d. |
| CCGAGC | 187 | n.d. | + | n.d. | n.d. | +++ |
| CGCAGC | 188 | n.d. | + | n.d. | n.d. | ++ |
| CGCGGG | 189 | n.d. | + | n.d. | n.d. | ++ |
| CGGAGA | 190 | n.d. | + | n.d. | n.d. | + |
| CGGAGT | 191 | n.d. | + | n.d. | n.d. | + |
| CTAGGC | 192 | n.d. | + | n.d. | n.d. | +++ |
| CTCAGA | 193 | n.d. | + | n.d. | n.d. | ++ |
| CAGGGA | 194 | n.d. | n.d. | + | n.d. | ++ |
| CCAGGT | 195 | n.d. | n.d. | + | n.d. | + |
| CCCCGC | 196 | n.d. | n.d. | + | n.d. | ++ |
| CCCTGC | 197 | n.d. | n.d. | + | n.d. | + |
| CGCAGT | 198 | n.d. | n.d. | + | n.d. | + |
| CACAGA | 199 | n.d. | n.d. | n.d. | + | ++ |
| CCGTGA | 200 | n.d. | n.d. | n.d. | + | ++ |
| CCTCGA | 201 | n.d. | n.d. | n.d. | + | ++ |
| CAAGGA | 202 | n.d. | n.d. | n.d. | n.d. | +++ |
| CCAGGA | 203 | n.d. | n.d. | n.d. | n.d. | + |
| CCAGGC | 204 | n.d. | n.d. | n.d. | n.d. | ++ |
| CCCAGA | 205 | n.d. | n.d. | n.d. | n.d. | + |
| CCCAGC | 206 | n.d. | n.d. | n.d. | n.d. | + |
| CCCAGT | 207 | n.d. | n.d. | n.d. | n.d. | + |
| CCCCGA | 208 | n.d. | n.d. | n.d. | n.d. | + |
| CCCCGT | 209 | n.d. | n.d. | n.d. | n.d. | ++ |
| CCCGGA | 210 | n.d. | n.d. | n.d. | n.d. | n.d. |
| CCCGGC | 211 | n.d. | n.d. | n.d. | n.d. | + |
| CCCTGA | 212 | n.d. | n.d. | n.d. | n.d. | + |
| CCCTGT | 213 | n.d. | n.d. | n.d. | n.d. | + |
| CCGAGA | 214 | n.d. | n.d. | n.d. | n.d. | + |

TABLE 5-continued

Low and no activity of TevI chimeric endonucleases in yeast (37° C.) on a series of I-TevI cleavage sites. Activity of TevD02::cT11-AvrBs3, TevD02::b36-AvrBs3, TevM01::cT11-AvrBs3 and TevM01::b36-AvrBs3 on a series of targets (TG10RGAr_CNNGN; SEQ ID NO: 343) containing a CNNNGN motif (SEQ ID NO: 117 to SEQ ID NO: 256). The negative control consists in a TALE scaffold without any DNA binding domain. n.d. indicates no detectable activity, +++ indicates an activity over 0.7 and ++ indicates an activity between 0.5 and 0.7, + indicates an activity between 03 and 0.5 in our assay (International PCT Applications WO 2004/067736 and in Epinat, Arnould et al. 2003; Chames, Epinat et al. 2005; Arnould, Chames et al. 2006; Smith, Grizot et al. 2006).

| I-TevI cleavage site | SEQ ID NO | Neg. Control | TevD02::cT11-AvrBs3 | TevD02::b36-AvrBs3 | TevM01::cT11-AvrBs3 | TevM01::b36-AvrBs3 |
|---|---|---|---|---|---|---|
| CCGAGT | 215 | n.d. | n.d. | n.d. | n.d. | + |
| CCGCGA | 216 | n.d. | n.d. | n.d. | n.d. | ++ |
| CCGGGA | 217 | n.d. | n.d. | n.d. | n.d. | + |
| CCGGGC | 218 | n.d. | n.d. | n.d. | n.d. | + |
| CCGGGT | 219 | n.d. | n.d. | n.d. | n.d. | + |
| CCTAGA | 220 | n.d. | n.d. | n.d. | n.d. | + |
| CCTGGA | 221 | n.d. | n.d. | n.d. | n.d. | + |
| CCTGGC | 222 | n.d. | n.d. | n.d. | n.d. | ++ |
| CCTGGT | 223 | n.d. | n.d. | n.d. | n.d. | + |
| CGAAGT | 224 | n.d. | n.d. | n.d. | n.d. | + |
| CGAGGA | 225 | n.d. | n.d. | n.d. | n.d. | + |
| CGAGGC | 226 | n.d. | n.d. | n.d. | n.d. | ++ |
| CGAGGT | 227 | n.d. | n.d. | n.d. | n.d. | + |
| CGCAGA | 228 | n.d. | n.d. | n.d. | n.d. | + |
| CGCCGA | 229 | n.d. | n.d. | n.d. | n.d. | + |
| CGCCGC | 230 | n.d. | n.d. | n.d. | n.d. | ++ |
| CGCCGT | 231 | n.d. | n.d. | n.d. | n.d. | + |
| CGCGGA | 232 | n.d. | n.d. | n.d. | n.d. | n.d. |
| CGCGGC | 233 | n.d. | n.d. | n.d. | n.d. | + |
| CGCGGT | 234 | n.d. | n.d. | n.d. | n.d. | + |
| CGCTGA | 235 | n.d. | n.d. | n.d. | n.d. | + |
| CGCTGT | 236 | n.d. | n.d. | n.d. | n.d. | + |
| CGGCGA | 237 | n.d. | n.d. | n.d. | n.d. | ++ |
| CGGGGA | 238 | n.d. | n.d. | n.d. | n.d. | + |
| CGGGGC | 239 | n.d. | n.d. | n.d. | n.d. | + |
| CGGGGG | 240 | n.d. | n.d. | n.d. | n.d. | + |
| CGGGGT | 241 | n.d. | n.d. | n.d. | n.d. | + |
| CGTGGA | 242 | n.d. | n.d. | n.d. | n.d. | + |
| CGTGGC | 243 | n.d. | n.d. | n.d. | n.d. | ++ |
| CGTGGT | 244 | n.d. | n.d. | n.d. | n.d. | + |
| CTAGGA | 245 | n.d. | n.d. | n.d. | n.d. | + |
| CTAGGT | 246 | n.d. | n.d. | n.d. | n.d. | + |
| CTCCGA | 247 | n.d. | n.d. | n.d. | n.d. | + |
| CTCGGA | 248 | n.d. | n.d. | n.d. | n.d. | + |
| CTCGGC | 249 | n.d. | n.d. | n.d. | n.d. | + |
| CTCGGT | 250 | n.d. | n.d. | n.d. | n.d. | + |
| CTCTGA | 251 | n.d. | n.d. | n.d. | n.d. | + |
| CTGGGA | 252 | n.d. | n.d. | n.d. | n.d. | + |
| CTGGGC | 253 | n.d. | n.d. | n.d. | n.d. | ++ |
| CTGGGT | 254 | n.d. | n.d. | n.d. | n.d. | + |
| CTTGGA | 255 | n.d. | n.d. | n.d. | n.d. | ++ |
| CTTGGT | 256 | n.d. | n.d. | n.d. | n.d. | + |

Example 3b: Spacer Specificity for Tev::TALE Cleavage in an In Vivo Yeast Assay In order to address whether the sequence of the spacer between the TevI cleavage motif and the TALE binding domain site could impact the activity of the Tev::TALE nuclease, we tested the TevM01::cT11 construct against a series of targets (TG10_CGACGG_NNN) containing a highly cut cleavage motif (CGACGG, SEQID NO: 17) separated from the T0 of the TALE recognition site TTG-TATGCCAATCGAAT (SEQ ID NO: 344) by a spacer of 10 bp and differing by a NNN motif (with N=A, C, G or T) (SEQ ID NO: 346 to SEQ ID NO: 404) at the 3 first positions of their spacer (CGACGG_NNNGAAACT_TTGTATGC-CAATCGAAT recognition site; with N=A, C, G or T; SEQ ID NO: 345). On the 64 theoretical targets, 59 were available and tested in our yeast assay (Table 6). A DNA binding array RVD_NNNT01g10 (SEQ ID NO: 405), targeting the TTG-TATGCCAATCGAAT sequence, was synthesized and subcloned into TevM01::cT11 yeast expression plasmid (pCLS 20649, SEQ ID NO: 406) yielding plasmid pCLS 23422. The final pCLS23422 vector contains the coding sequence for TevM01::cT11-NNNT01g10 construct (SEQ ID NO: 407), which targets the TTGTATGCCAATCGAAT motif. The results of TevM01::cT11-NNNT01g10 activity on the series of TG10_CGACGG_NNN targets are presented in Table 6 and show that variations in the NNN three first bases of the spacer modulate the level of TevI::TALE nuclease activity.

TABLE 6

Activity of TevM01 TALE nuclease in yeast (37° C.) on a serie of targets containing different spacer sequences. Activity of TevM01::cT11-NNNT01g10 on a serie of targets (TG10_CGACGG_NNN, SEQ ID NO: 346 to 404) containing the motif NNN at the three first positions of their 10 bp spacer. The negative control consists in an empty pCLS0542 plasmid (SEQ ID NO: 278). n.d. indicates no detectable activity, +++ indicates an activity over 0.7, ++ an activity between 0.5 and 0.7 in our assay (International PCT Applictaions WO 2004/067736 and in Epinat, arnould et al. 2003; Chames, Epinat et al. 2005; Arnould, Chames et al. 2006; Smith, Grizot et al. 2006).

| Spacer (3 first bases) | SEQ ID NO: | Neg. Control | TevM01:: cT11- NNNT01g10 |
|---|---|---|---|
| GCT | 346 | n.d. | n.d. |
| GAT | 347 | n.d. | n.d. |
| CGG | 348 | n.d. | n.d. |
| CAT | 349 | n.d. | n.d. |
| CCC | 350 | n.d. | n.d. |
| CCT | 351 | n.d. | n.d. |
| CGT | 352 | n.d. | n.d. |
| GGT | 353 | n.d. | ++ |
| GCG | 354 | n.d. | ++ |
| GGG | 355 | n.d. | ++ |
| CTC | 356 | n.d. | ++ |
| GTT | 357 | n.d. | ++ |
| CAG | 358 | n.d. | ++ |
| GAG | 359 | n.d. | ++ |
| CAC | 360 | n.d. | ++ |
| CTA | 361 | n.d. | ++ |
| GAC | 362 | n.d. | ++ |
| CTG | 363 | n.d. | ++ |
| CGC | 364 | n.d. | ++ |
| CCA | 365 | n.d. | ++ |
| CCG | 366 | n.d. | ++ |
| GCA | 367 | n.d. | ++ |
| CGA | 368 | n.d. | ++ |
| GGA | 369 | n.d. | ++ |
| ATT | 370 | n.d. | ++ |
| GTC | 371 | n.d. | ++ |
| GTG | 372 | n.d. | ++ |
| GTA | 373 | n.d. | ++ |
| TAT | 374 | n.d. | ++ |
| TTT | 375 | n.d. | ++ |
| GAA | 376 | n.d. | +++ |
| CAA | 377 | n.d. | +++ |
| ATC | 378 | n.d. | +++ |
| AAT | 379 | n.d. | +++ |
| ATA | 380 | n.d. | +++ |
| ACT | 381 | n.d. | +++ |
| TTA | 382 | n.d. | +++ |
| TAC | 383 | n.d. | +++ |
| ATG | 384 | n.d. | +++ |
| TTG | 385 | n.d. | +++ |
| ACC | 386 | n.d. | +++ |
| ACG | 387 | n.d. | +++ |
| TTC | 388 | n.d. | +++ |
| TAG | 389 | n.d. | +++ |
| TGT | 390 | n.d. | +++ |
| AGT | 391 | n.d. | +++ |
| TGG | 392 | n.d. | +++ |
| AAG | 393 | n.d. | +++ |
| TCA | 394 | n.d. | +++ |
| AAA | 395 | n.d. | +++ |
| AAC | 396 | n.d. | +++ |
| TGT | 397 | n.d. | +++ |
| TCG | 398 | n.d. | +++ |
| TCC | 399 | n.d. | +++ |

TABLE 6-continued

Activity of TevM01 TALE nuclease in yeast (37° C.) on a serie of targets containing different spacer sequences. Activity of TevM01::cT11-NNNT01g10 on a serie of targets (TG10_CGACGG_NNN, SEQ ID NO: 346 to 404) containing the motif NNN at the three first positions of their 10 bp spacer. The negative control consists in an empty pCLS0542 plasmid (SEQ ID NO: 278). n.d. indicates no detectable activity, +++ indicates an activity over 0.7, ++ an activity between 0.5 and 0.7 in our assay (International PCT Applictaions WO 2004/067736 and in Epinat, arnould et al. 2003; Chames, Epinat et al. 2005; Arnould, Chames et al. 2006; Smith, Grizot et al. 2006).

| Spacer (3 first bases) | SEQ ID NO: | Neg. Control | TevM01:: cT11- NNNT01g10 |
|---|---|---|---|
| TAA | 400 | n.d. | +++ |
| TGA | 401 | n.d. | +++ |
| AGA | 402 | n.d. | +++ |
| AGC | 403 | n.d. | +++ |
| TGC | 404 | n.d. | +++ |

Figure 1B:
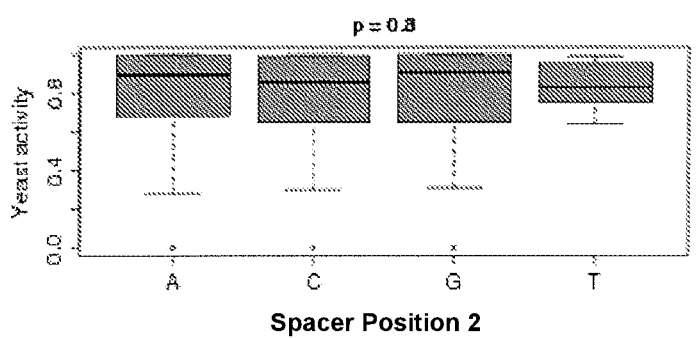
Figure 1C:
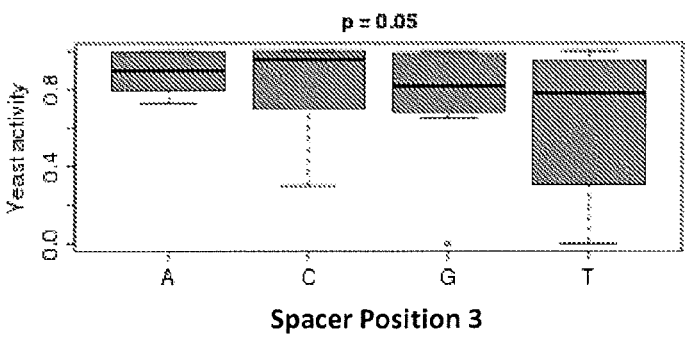

A statistical analysis of these results was then performed, showing that the nature of the first base of the target spacer has a significant impact on TevI::TALE nuclease activity, with the bases A and T being the more favorable for cleavage activity (FIG. 1A, ANOVA, p=2.3 $e^{10-8}$) whereas no significant impact of the nature of bases 2 and 3 of the spacer was observed (FIGS. 1B and 1C respectively, ANOVA, p=0.8 and p=0.05).

Example 4: Activity of TevI:TALE in Mammalian Cells

Example 4a: Activity of TevI::cT11 in Mammalian Cells (CHO-K1) on a Chromosomal Target The ability of TevI::cT11 based nucleases to induce targeted mutagenesis on a chromosomal target was monitored using an engineered cell line (CHOpi-10, ref: patent US20120272348 A1) having a single integrated copy of a GFP-encoding sequence under the control of a CMV promoter. A DNA binding array was synthesized (RVD_ctEGFP_T03g12-L1; SEQ ID NO: 408) to target a unique sequence within the encoded GFP gene TGCCAC-CTACGGCAAGCTGACCCTGAAGTTCATCTGCACC [(SEQ ID NO: 409) comprising a preferential I-TevI cleavage site (in bold SEQ ID NO: 18) spaced away from the TALE recognition site (in italic) thus allowing for measuring in vivo mutagenic activity via a reduction in GFP-positive cells as determined by flow cytometry.

To prepare a suitable vector for expression in mammalian cells, the core TevM01::cT11 scaffold insert was first transferred from pCLS7865-TevM01::cT11 to pCLS1853 (SEQ ID NO: 410) to create plasmid pCLS20650 (SEQ ID NO: 411). The DNA binding array insert from RVD_ctEGFP_T03g12-L1 was subcloned into pCLS20650, yielding plasmid pCLS20790. The final pCLS20790 vector contains the coding sequence for the TevI::cT11EGfpT3g12 construct (SEQ ID NO: 412), which targets GFP and whose expression is controlled by a CMV promoter.

Transfection into the CHOpi-10 cell line was carried out using the Amaxa Nucleofector Kit T (Lonza) with a slightly modified protocol: 1 µg of sample plasmid was used in $1 \times 10^6$ cells, in total of 7.25 µg DNA, complemented with pCLS0003 (SEQ ID NO: 413). Samples were additionally assayed with 2 µg of the enhancer reagent scTrex2 (pCLS8982; SEQ ID NO: 414) (WO2012138927). For baseline controls, plasmids pCLS0003 and pCLS8982 were individually tested in the absence of pCLS20790. Plasmid pCLS2198 containing blue fluorescent protein (BFP) (pCLS2198 (SEQ ID NO: 415)) was added (250 ng) to all samples to monitor uniformity of transfection. Upon transfection, cells were grown for three days ("Day3" samples) at 37° C. (5% $CO_2$) before being harvested in a volume of 5 ml each. A sample volume (150 µl) was transferred to a 96-well assay block and measured via flow cytometry using a MACSQuant Analyzer (Miltenyi Biotec).

Figure 2A:
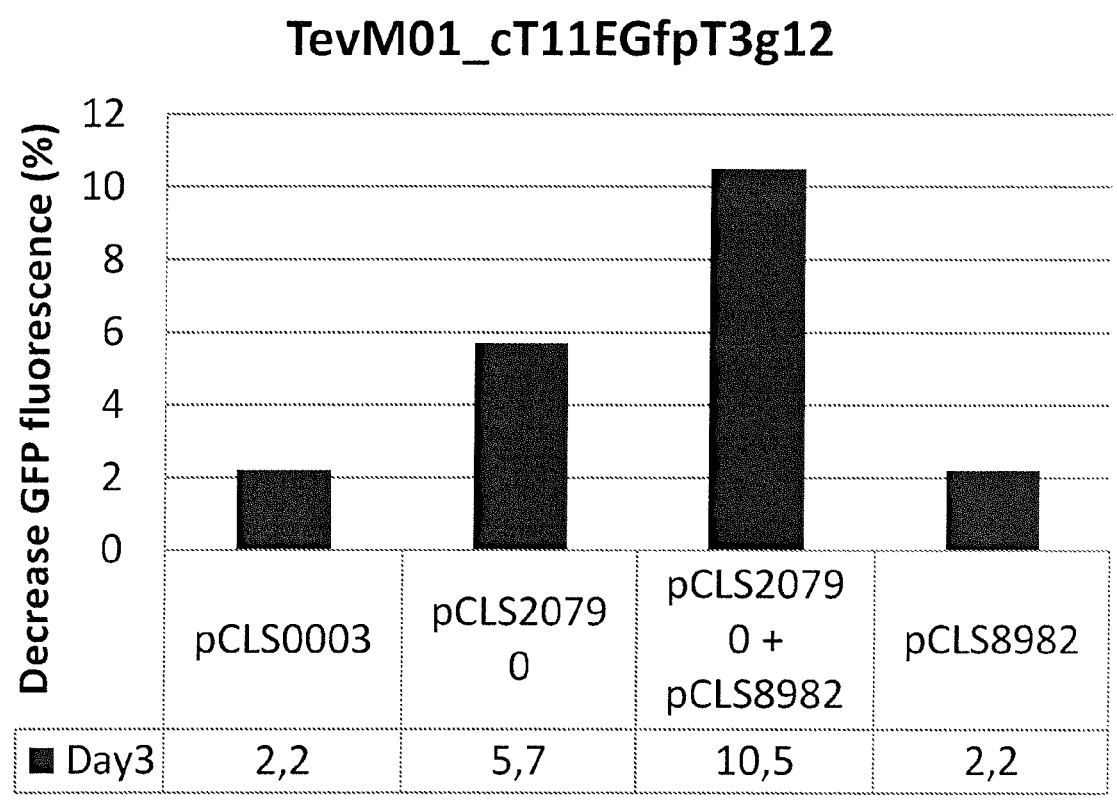
FIG. 2A: Activity of the TevM01::cT11 construct in mammalian cells (CHO-K1) on a chromosomal target measured as a reduction in GFP fluorescence.

FIG. 2A illustrates the activity of the TevM01::cT11 construct measured as a reduction in GFP fluorescence.

Example 4b: Optimization of the TALE Core Scaffold for Improvement of TevI::TALE Activity on a Chromosomal Target in Mammalian Cells (CHO-K1)

In order to further improve TevI::TALE activity in mammalian cells, several optimizations of the TAL core scaffold were tested. Three Nuclear localization Signals (NLS) and a HA tag allowing for protein detection, were added to the existing core scaffold TevM01::cT11 and to a new core scaffold TevM01::cT40, bearing a C40 truncation at its C-terminal part, leading respectively to TevM01::cT11N3H (SEQID NO: 418) and TevM01::cT40N3H (SEQ ID NO: 419) obtained from a provider in the puc57 plasmid (Genecust).

To prepare suitable vectors for expression in mammalian cells, the core TevM01::cT11N3H and TevM01::cT40N3H scaffolds were transferred from plasmid puc57 to pCLS 14975 (SEQ ID NO: 420) to create respectively pCLS 21563 and pCLS 21565. The DNA binding array RVD_ctEGFP_T03g12-L1 (SEQID NO: 408) was then subcloned into pCLS 21563 and pCLS21565 in order to monitor the targeted mutagenesis induced on the GFP integrated sequence in the CHOpi-10 cells described above. The subcloning of the GFP RVD into pCLS21563 and pCLS21565 yielded respectively to plasmids pCLS 22330 and pCLS 22332. The final pCLS 22330 and pCLS 22332 plasmids contain the coding sequences for the TevM01:: cT11N3H_EGfpT3g12 construct (SEQ ID NO: 421) and for the TevM01::cT40N3H_EGfpT3g12 construct (SEQ ID NO: 422), which target GFP and whose expression is controlled by a CMV promoter.

Transfection into the CHOpi-10 cell-line was carried out using the amaxa Nucleofector kit T (Lonza) with 0.5 µg TevI::TALE plasmids, complemented with pCLS003 (SEQ ID NO: 413). For baseline controls, plasmids pCLS003 (SEQ ID NO: 413) and pCLS20790 (SEQ ID NO: 412) were individually tested. Plasmid pCLS2198 containing blue fluorescent protein (BFP) (SEQ ID NO: 415) was added (500 ng) to all samples to monitor uniformity of transfection. Upon transfection, cells were grown for three days ("Day3" samples) at 37° C. (5% C02) before being harvested in a volume of 5 ml each. A sample volume (150 µl) was transferred to a 96-well assay block and measured via flow cytometry using a MACSQuant analyser (Miltenyi Biotec).

Figure 2B:
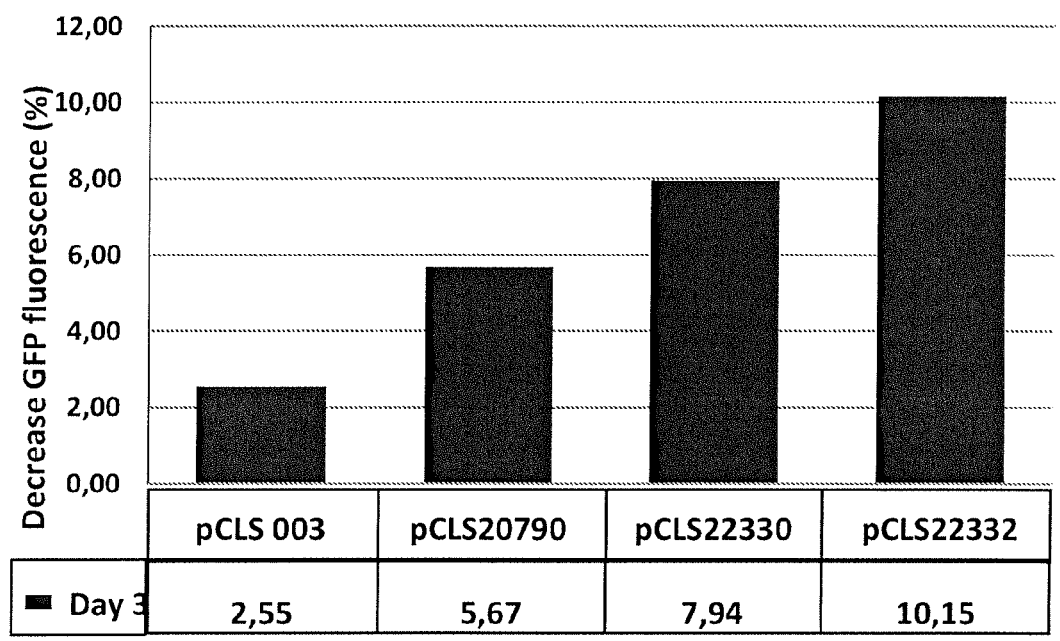
FIG. 2B: Activity of the TevM01::cT11N3H and TevM01::cT40N3H constructs compared to TevM01::cT11 construct in mammalian cells (CHO-K1) on a chromosomal target measured as a reduction in GFP fluorescence.

FIG. 2B illustrates the activity of the TevM01::cT11N3H and TevM01::cT40N3H constructs compared to TevM01::

cT11 construct measured as a reduction in GFP fluorescence. It shows an improvement of mutagenic activity for TevM01::cT11N3H and TevM01::cT40N3H with optimal activity detected for TevM01::cT40N3H construct.

Example 4c: Activity of TevI::TALE Fused to the Enhancer Reagent scTrex2 in Mammalian Cells (HEK-293)

As the targeted mutagenesis activity of TevI::TALE in mammalian cells was shown to be improved by scTrex2 reagent (pCSL8982; SEQ ID NO: 414) (see Example 4a), a single-chain TevI::TALE::scTrex2 fusion was designed and tested in Human 293H cells (HEK-293). The first monomer of the scTrex2 was amplified by PCR on template pCLS8982 with the primer pair CMP_M001 (SEQ ID NO: 423) and CMP_M002 (SEQ ID NO: 424) containing respectively EcoRI and AgeI restriction sites. The second monomer of the scTrex2 was amplified by PCR on template pCLS8982 with the primer pair CMP_M003 (SEQ ID NO: 425) and CMP_M004 (SEQ ID NO: 426) containing respectively restriction sites AgeI and EagI. The two PCR inserts were then cloned into pCLS21565 by restriction and ligation using EcoRI and EagI restriction sites, yielding TevM01::cT40N3::scTrex2, pCLS 25202 (SEQ ID NO: 427). A DNA binding array (RVD_cTCD52_T02g10, SEQ ID NO: 428) was synthesized to target a unique sequence within the CAMPATH-1 antigen (CD52) gene in human cells TCCTG-GCAGTGGTGCCAGGCGTTGCTCTTACCTGTACCA (SEQ ID NO: 429) comprising a preferential I-TevI cleavage site (in bold (SEQ ID NO: 10)) spaced away from the TALE recognition site (in italic, SEQ ID NO: 430) allowing for measuring in vivo mutagenic activity via a PCR surrounding the targeted endogenous locus followed by an EndoT7 assay (Reyon, Tsai et al. 2012).

To prepare a suitable vector for expression in mammalian cells, the DNA binding array insert from RVD_cTCD52_T02g10 was subcloned into pCLS21565 and pCLS25202, yielding respectively plasmids pCLS24059 and pCLS25203. The final pCLS24059 vector contains the coding sequence for the TevI::cT40n3HCD52T02g10 construct (SEQ ID NO: 431) and the final pCLS 25203 vector contains the coding sequence for the TevI::cT40n3H::sc-Trex2CD52T02g10 construct (SEQ ID NO: 432), which target CD52 and whose expression is controlled by a CMV promoter. HEK-293 cells (Life Technologies) were cultured at 37° C. with 5% $CO_2$ in DMEM complete medium supplemented with 2 mM I-glutamine, penicillin (100 IU/ml), streptomycin (100 µg/ml), amphotericin B (Fongizone: 0.25 µg/ml, Life Technologies,) and 10% FBS. 293H cells were seeded at 1.2 $10^6$ cells in 10 cm Petri dishes one day before transfection. Cell transfection was performed using the Lipofectamine 2000 reagent according to the manufacturer's instructions (Invitrogen). 0.5 µg of the plasmids TevI::cT40n3H::sc-Trex2CD52T02g10 and 500 ng of GFP expression vector (to monitor transfection efficiencies) were mixed with 0.3 ml of DMEM without FBS (5 µg final DNA amount). In another tube 25 µL of Lipofectamine were mixed with 0.3 ml of DMEM without FBS. After 5 minutes incubation, both DNA and Lipofectamine mixes were combined and incubated for 25 min at RT. The mixture was transferred to a Petri dish containing the 293H cells in 9 ml of complete and then cultured at 37° C. under 5% $CO_2$. Three days post-transfection, the cells were washed twice with phosphate-buffered saline (PBS), trypsinized, resuspended in 5 ml complete medium and the percentage of GFP positive cells was measured by flow cytometry (Guava EasyCyte) in order to monitor transfection efficacy. For baseline controls, pCLS 24059 with or without the addition of pCLS8982 (SEQID NO: 414) and pCLS003 were individually tested. Cells were pelleted by centrifugation and genomic DNA was extracted using DNeasy Blood & Tissue Kit (Qiagen) according to the manufacturer's instructions. PCR of the CD52 endogenous locus (393 bp, SEQ ID NO: 459) was performed using the oligonucleotide sequences CMP_M005 (SEQ ID NO: 433) and CMP_M006 (SEQ ID NO: 434) and purified using the AMPure kit (Invitrogen). To detect mutagenic events, amplicons were further digested with an Endo T7 endonuclease as described in (Reyon, Tsai et al. 2012).

Figure 2C:
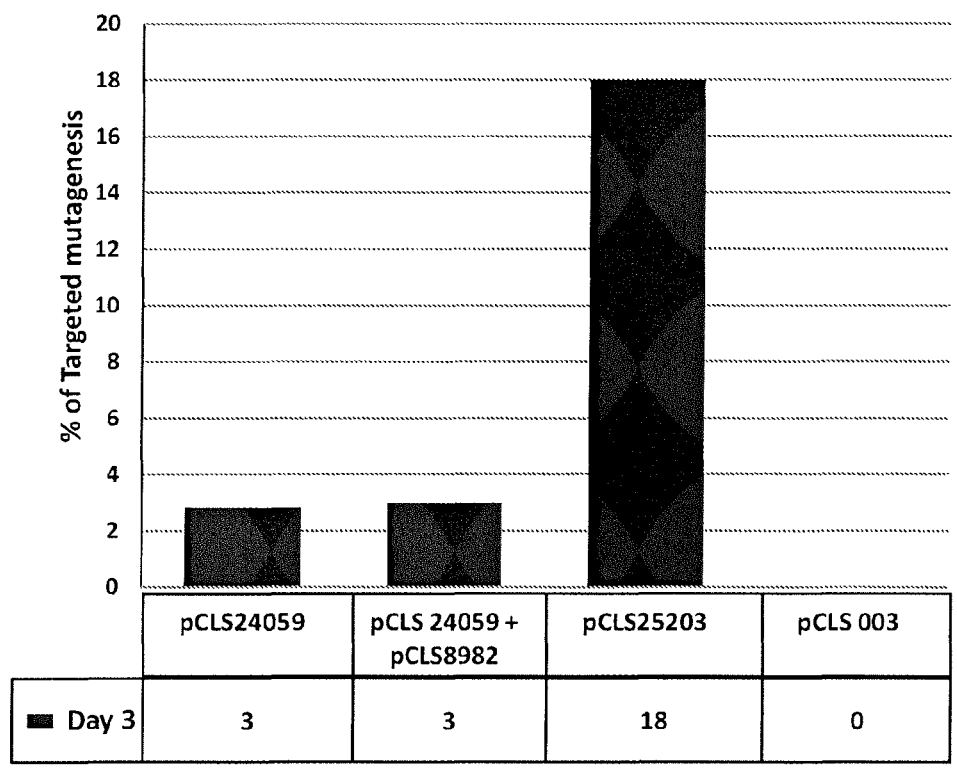
FIG. 2C: Target mutagenesis induced by the TevI::TALE::scTrex2 fusion measured by EndoT7 assay.

FIG. 2C illustrates the target mutagenesis induced by the TevI::TALE::scTrex2 fusion Example 4d: Targeted Gene Correction Induced by Optimized TevI::TALE in Mammalian Cells (HEK-293)

In order to evaluate if TevI::TALE could promote targeted gene insertion (TGI) at the CD52 endogenous locus by inducing homology-directed repair via double-strand break, a repair matrix consisting in a single-stranded oligonucleotide composed of two homologous arms (50 bp each) separated by 29 bp of an exogenous sequence was designed (SEQ ID NO: 435). Using a homologous recombination (HR) based strategy (Daboussi, Zaslayskiy et al. 2012), specific insertions induced by the TevI::TALE CD52T02g10 were monitored. In our experimental setup, the cells were reseeded three days post transfection at a density of 10 cells/well in a 96-well plate, a strategy that was previously validated for designer nucleases (Daboussi, Zaslayskiy et al. 2012). Human 293H cells (Life Technologies) were cultured at 37° C. with 5% $CO_2$ in DMEM complete medium supplemented with 2 mM I-glutamine, penicillin (100 IU/ml), streptomycin (100 µg/ml), amphotericin B (Fongizone: 0.25 µg/ml, Life Technologies,) and 10% FBS. 293H cells were seeded at 1.2 $10^6$ cells in 10 cm Petri dishes one day before transfection. Cell transfection was performed using the Lipofectamine 2000 reagent according to the manufacturer's instructions (Invitrogen). 0.5 µg of TevI::TALE nuclease expression vector with 2 µg of single-stranded oligo donor matrix, and 500 ng of GFP expression vector (to monitor transfection efficiencies) were mixed with 0.3 ml of DMEM without FBS (3 µg final DNA amount). In another tube 25 µL of Lipofectamine were mixed with 0.3 ml of DMEM without FBS. After 5 minutes incubation, both DNA and Lipofectamine mixes were combined and incubated for 25 min at RT. The mixture was transferred to a Petri dish containing the 293H cells in 9 ml of complete and then cultured at 37° C. under 5% $CO_2$. We monitored targeted integration by performing, eighteen days post-transfection, for each well (288 wells in total), a locus specific PCR amplification using the Herculase II Fusion kit (Agilent), with one primer CMP_M007 (SEQ ID NO: 436) located within the heterologous insert of the donor DNA and the other CMP_008 (SEQ ID NO: 437) located in the genomic sequence outside of the homology arms. To evaluate the targeted gene insertion (TGI) frequency, we took into account the transfection efficiency (as monitored via GFP positive cells percentage) and plating efficiency (estimated at 30%).

Figure 2D:
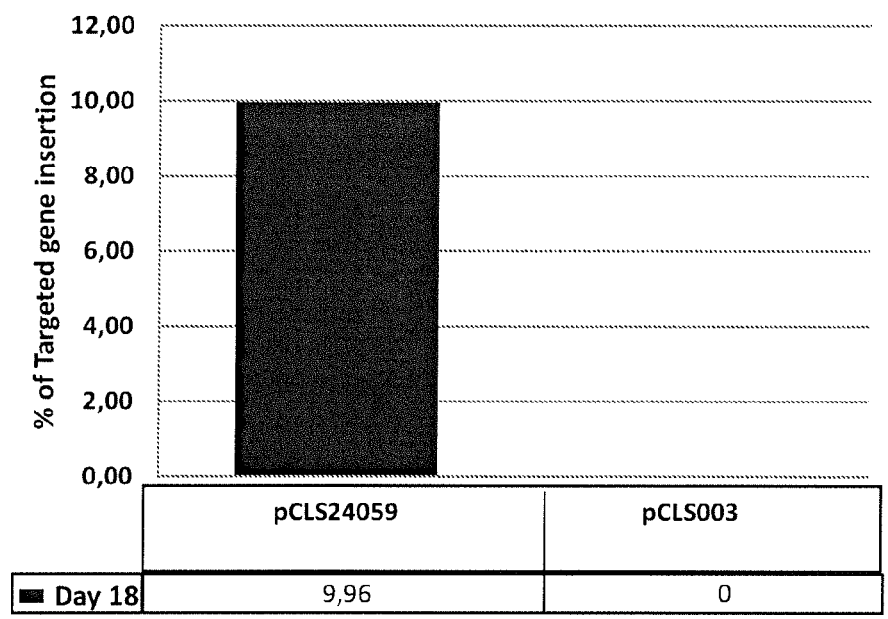
FIG. 2D: Target gene insertion frequency of the TevI::TALE on the endogenous target CD52 in HEK-293 cells

FIG. 2D illustrates the TGI activity of the TevI::TALE on the endogenous target CD52 in HEK-293 cells.

Example 5: Activity of TevI::b36 in Mammalian Cells

Example 5a: Activity of TevI::b36 in Mammalian Cells (CHO-K1) on a Chromosomal Target The ability of TevI::b36 based nucleases to induce targeted mutagenesis on a chromosomal target was monitored using an engineered cell line (CHOpi-10, ref: patent US20120272348 A1) having a single integrated copy of a GFP-encoding sequence under the control of a CMV promoter. A DNA binding array was synthesized (RVD_bhEGFP_T03g06; SEQ ID NO: 416) to target a unique sequence within the encoded GFP gene [(TGCCACCTACGGCAAGCTGACCCTGAAGTTCATCTGCACC (SEQ ID NO: 409) comprising a preferential I-TevI cleavage site (in bold SEQ ID NO: 18)) spaced away from the MBBBD recognition site (in italic), thus allowing for measuring in vivo mutagenic activity via a reduction in GFP-positive cells as determined by flow cytometry.

To prepare a suitable vector for expression in mammalian cells, the core TevM01::b36 scaffold insert was first transferred from pCLS7865-TevM01::b36 to pCLS1853 (SEQ ID NO: 410) to create plasmid pCLS21536. The DNA binding array insert from pCLS19333 was subcloned into pCLS21536, yielding plasmid pCLS20293. The final pCLS20293 vector contains the coding sequence for the TevI::b36EGfpT3g6 construct (SEQ ID NO: 417), which targets GFP and whose expression is controlled by a CMV promoter.

Figure 3A:
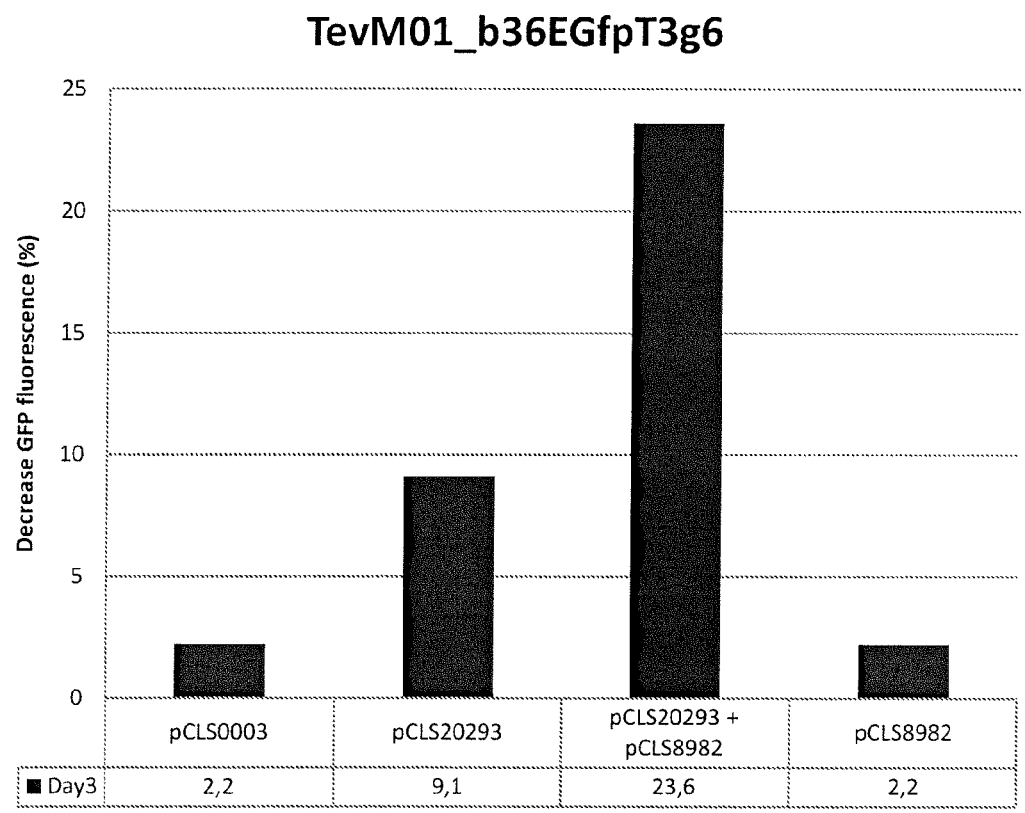
FIG. 3A: Activity of the TevM01::b36 construct in mammalian cells (CHO-K1) on a chromosomal target measured as a reduction in GFP fluorescence.

Transfection into the CHOpi-10 cell line was carried out using the Amaxa Nucleofector Kit T (Lonza) with a slightly modified protocol: 1 µg of sample plasmid was used in 1×10$^6$ cells, in total of 7.25 µg DNA, complemented with pCLS0003 (SEQ ID NO: 413). Samples were additionally assayed with 2 µg of the enhancer reagent scTrex2 (pCLS8982; SEQ ID NO: 414) (WO2012138927). For baseline controls, plasmids pCLS0003 and pCLS8982 were individually tested in the absence of pCLS20293. Plasmid pCLS2198 containing blue fluorescent protein (BFP) (pCLS2198 (SEQ ID NO: 415)) was added (250 ng) to all samples to monitor uniformity of transfection. Upon transfection, cells were grown for three days ("Day3" samples) at 37° C. (5% CO$_2$) before being harvested in a volume of 5 ml each. A sample volume (150 µl) was transferred to a 96-well assay block and measured via flow cytometry using a MACSQuant Analyzer (Miltenyi Biotec). FIG. 3A illustrates the activity of the TevM01::b36 construct measured as a reduction in GFP fluorescence.

Example 5b: Optimization of TevI::b36 Activity in Mammalian Cells (HEK-293)

In order to further improve TevI::b36 activity in mammalian cells, several optimizations of the BurrH core scaffold were tested. To increase the nuclear addressing of the BurrH nuclease, three Nuclear localization Signals (NLS) and a HA tag allowing for protein detection were added to the TevI::b36 core scaffold leading to TevI::b36N3H scaffold. To prepare suitable vectors for expression in mammalian cells, the core TevI::b36N3H scaffold (SEQ ID NO: 438) was transferred from puc57 to pCLS 14975 (SEQ ID NO: 420) to create pCLS 25472. In order to monitor the targeted mutagenesis induced on SH6 endogenous sequence in HEK-293 cells, a DNA binding array RVD_bhSH6_T03g06_16 containing 16 BurrH modules (SEQ ID NO: 439) targeting a unique sequence in the SH6 gene TTTCATCATAGGTAAACTGGGATGCTATACTGGT [(SEQ ID NO: 440) comprising a preferential I-TevI cleavage site (in bold SEQ ID NO: 12)) spaced away from the BurrH recognition site (in italic) was then subcloned into TevI::b36N3H plasmid (pCLS 25472) yielding to pCLS24674 and into TevI::36-pCLS21536) yielding to pCLS24670 for internal control. The final pCLS 24674 plasmid contains the coding sequence for the TevM01::b36N3H_SH6T03g06_16 construct (SEQ ID NO: 441) and the final pCLS24670 contains the coding sequence for TevM01::b36_SH6T03g06_16 (SEQ ID NO: 442) which both target SH6 gene and whose expression is controlled by a CMV promoter. Another DNA binding array RVD_bhSH6_T03g06_20 (SEQ ID NO: 443) composed, as in the natural BurrH protein, of 20 modules, and targeting a unique sequence in the SH6 gene TTTCATCATAGGTAAACTGGGATGCTATACTGGTAGAA (SEQ ID NO: 444) comprising a preferential I-TevI cleavage site (in bold (SEQID NO: 12)) spaced away from the BurrH recognition site (in italic) was also synthetised and subcloned into pCLS25472 yielding to pCLS24677. The final pCLS24677 plasmid contains the coding sequence for the TevM01::b36N3H_SH6T03g06_20 construct (SEQ ID NO: 445) which targets SH6 gene and whose expression is controlled by a CMV promoter.

In our experimental set up to monitor Targeted Mutagenesis (TM), Human 293H cells (Life Technologies) were cultured at 37° C. with 5% CO$_2$ in DMEM complete medium supplemented with 2 mM I-glutamine, penicillin (100 IU/ml), streptomycin (100 µg/ml), amphotericin B (Fongizone: 0.25 µg/ml, Life Technologies,) and 10% FBS. 293H cells were seeded at 1.2 10$^6$ cells in 10 cm Petri dishes one day before transfection. Cell transfection was performed using the Lipofectamine 2000 reagent according to the manufacturer's instructions (Invitrogen). 0.5 µg of TevI::b36 nuclease expression vectors and 500 ng of GFP expression vector (to monitor transfection efficiencies) completed with 3 µg of pCLS003 were mixed with 0.3 ml of DMEM without FBS (5 µg final DNA amount). In another tube, 25 µL of Lipofectamine were mixed with 0.3 ml of DMEM without FBS. After 5 minutes incubation, both DNA and Lipofectamine mixes were combined and incubated for 25 min at RT. The mixture was transferred to a Petri dish containing the 293H cells in 9 ml of complete and then cultured at 37° C. under 5% CO$_2$. Three days post-transfection, cells were pelleted by centrifugation and genomic DNA was extracted using DNeasy Blood & Tissue Kit (Qiagen) according to the manufacturer's instructions. A PCR of the SH6 endogenous locus (351 bp, SEQ ID NO: 446) was performed using the oligonucleotides CMP_009 (SEQID NO: 447) and CMP_010 (SEQ ID NO: 448) and purified using the AMPure kit (Invitrogen). Amplicons were further analyzed by an EndoT7 assay to monitor the percentage of induced TM events.

Figure 3B:
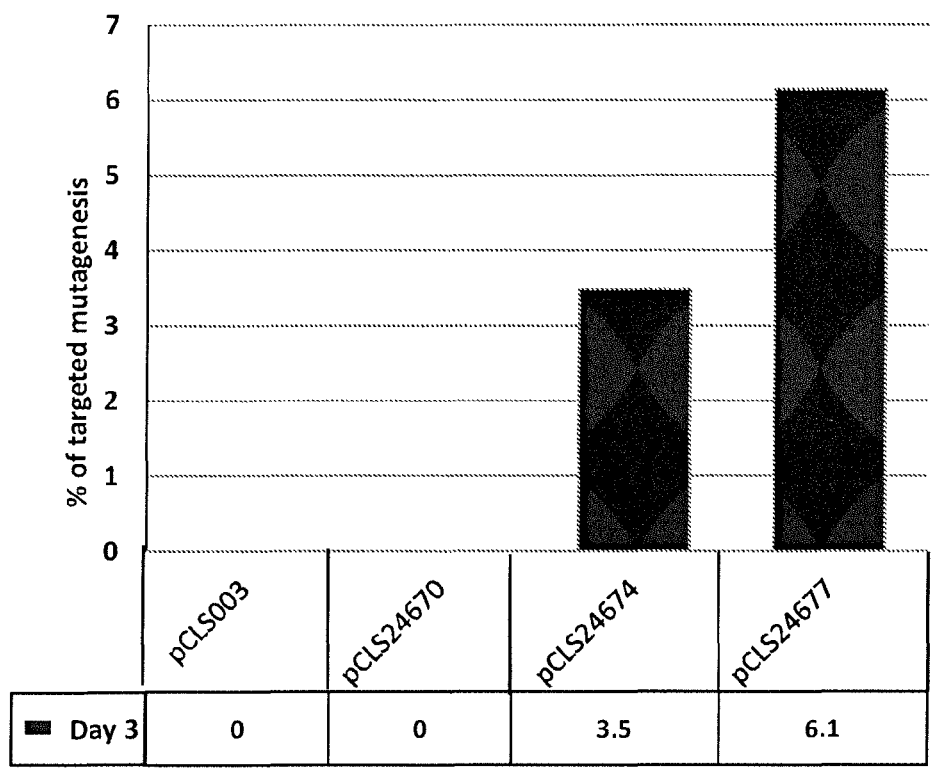
FIG. 3B: Targeted mutagenesis activity of different scaffolds for TevI::b36 at the SH6 locus.
Figure 3C:
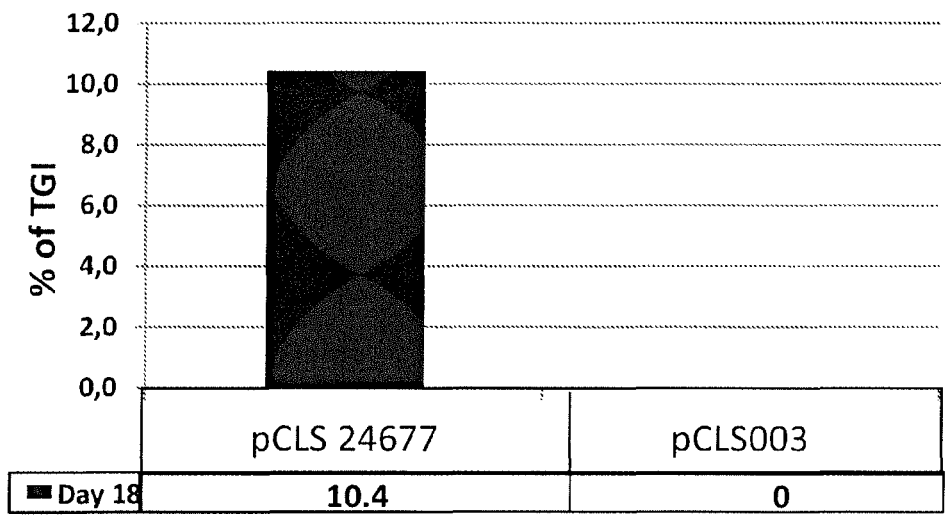
FIG. 3C: Targeted gene insertion activity for TevI::b36 on SH6 endogenous target in HEK-293 cells.

FIG. 3B illustrates the targeted mutagenesis activity of different scaffolds for TevI::b36 showing an optimal activity for TevI::b36N3H containing 20 modules for DNA targeting.

Example 5c: Targeted Gene Insertion Induced by Optimized TevI::b36 in Mammalian Cells (HEK-293)

In order to evaluate if TevI::b36 could promote targeted gene insertion (TGI) at the SH6 endogenous locus by inducing homology-directed repair via double-strand break, a repair matrix consisting in a donor DNA, cloned in a plasmid, and composed of two homologous arms (1 kb each) separated by 29 bp of an exogenous sequence was designed (pCLS 23895 SEQ ID NO: 449). Using a homologous recombination (HR) based strategy (Daboussi, Zaslayskiy et al. 2012), specific insertions induced by the TevM01:: b36N3H_SH6T03g06_20 were monitored using for baseline controls, the pCLS003 transfected with donor matrix pCLS 23895. In our experimental setup, the cells were reseeded three days post transfection at a density of 10 cells/well in a 96-well plate, a strategy that was previously validated for designer nucleases (Daboussi, Zaslayskiy et al. 2012). Human 293H cells (Life Technologies) were cultured at 37° C. with 5% $CO_2$ in DMEM complete medium supplemented with 2 mM I-glutamine, penicillin (100 IU/ml), streptomycin (100 µg/ml), amphotericin B (Fongizone: 0.25 µg/ml, Life Technologies,) and 10% FBS. 293H cells were seeded at 1.2 $10^6$ cells in 10 cm Petri dishes one day before transfection. Cell transfection was performed using the Lipofectamine 2000 reagent according to the manufacturer's instructions (Invitrogen). 0.5 µg of TevI::BurrH nuclease expression vector with 2 µg of plasmidic donor matrix, and 500 ng of GFP expression vector (to monitor transfection efficiencies) were mixed with 0.3 ml of DMEM without FBS (3 µg final DNA amount). In another tube 25 µL of Lipofectamine were mixed with 0.3 ml of DMEM without FBS. After 5 minutes incubation, both DNA and Lipofectamine mixes were combined and incubated for 25 min at RT. The mixture was transferred to a Petri dish containing the 293H cells in 9 ml of complete and then cultured at 37° C. under 5% $CO_2$. We monitored targeted integration by performing, eighteen days post-transfection, for each well (288 wells in total), a locus specific PCR amplification using the Herculase II Fusion kit (Agilent), with one primer CMP_M011 (SEQ ID NO: 450) located within the heterologous insert of the donor DNA and the other CMP_012 (SEQ ID NO: 451) located on the genomic sequence outside of the homology arms. To evaluate the targeted gene insertion (TGI) frequency, we took into account the transfection efficiency (as monitored via GFP positive cells percentage) and plating efficiency (estimated at 30%).

FIG. 2C illustrates the targeted gene insertion activity for TevI::b36 on SH6 endogenous target in HEK-293 cells.

REFERENCES

Arimondo, P. B., C. J. Thomas, et al. (2006). "Exploring the cellular activity of camptothecin-triple-helix-forming oligonucleotide conjugates." *Mol Cell Biol* 26(1): 324-33.

Arnould, S., P. Chames, et al. (2006). "Engineering of large numbers of highly specific homing endonucleases that induce recombination on novel DNA targets." *J Mol Biol* 355(3): 443-58.

Arnould, S., C. Delenda, et al. (2011). "The I-CreI meganuclease and its engineered derivatives: applications from cell modification to gene therapy." *Protein Eng Des Sel* 24(1-2): 27-31.

Arnould, S., C. Perez, et al. (2007). "Engineered I-CreI derivatives cleaving sequences from the human XPC gene can induce highly efficient gene correction in mammalian cells." *J Mol Biol* 371(1): 49-65.

Bitinaite, J., D. A. Wah, et al. (1998). "FokI dimerization is required for DNA cleavage." *Proc Natl Acad Sci USA* 95(18): 10570-5.

Boch, J., H. Scholze, et al. (2009). "Breaking the code of DNA binding specificity of TAL-type III effectors." *Science* 326(5959): 1509-12.

Chames, P., J. C. Epinat, et al. (2005). "In vivo selection of engineered homing endonucleases using double-strand break induced homologous recombination." *Nucleic Acids Res* 33(20): e178.

Choulika, A., A. Perrin, et al. (1995). "Induction of homologous recombination in mammalian chromosomes by using the I-Scel system of Saccharomyces cerevisiae." *Mol Cell Biol* 15(4): 1968-73.

Christian, M., T. Cermak, et al. (2010). "Targeting DNA double-strand breaks with TAL effector nucleases." *Genetics* 186(2): 757-61.

Critchlow, S. E. and S. P. Jackson (1998). "DNA end-joining: from yeast to man." *Trends Biochem Sci* 23(10): 394-8.

Daboussi, F., M. Zaslayskiy, et al. (2012). "Chromosomal context and epigenetic mechanisms control the efficacy of genome editing by rare-cutting designer endonucleases." *Nucleic Acids Res*.

Dean, A. B., M. J. Stanger, et al. (2002). "Zinc finger as distance determinant in the flexible linker of intron endonuclease I-TevI." *Proc Natl Acad Sci USA* 99(13): 8554-61.

Edgell, D. R., M. J. Stanger, et al. (2004). "Coincidence of cleavage sites of intron endonuclease I-TevI and critical sequences of the host thymidylate synthase gene." *J Mol Biol* 343(5): 1231-41.

Eisenschmidt, K., T. Lanio, et al. (2005). "Developing a programmed restriction endonuclease for highly specific DNA cleavage." *Nucleic Acids Res* 33(22): 7039-47.

Epinat, J. C., S. Arnould, et al. (2003). "A novel engineered meganuclease induces homologous recombination in yeast and mammalian cells." *Nucleic Acids Res* 31(11): 2952-62.

Kalish, J. M. and P. M. Glazer (2005). "Targeted genome modification via triple helix formation." *Ann NY Acad Sci* 1058: 151-61.

Kim, Y. G., J. Cha, et al. (1996). "Hybrid restriction enzymes: zinc finger fusions to Fok I cleavage domain." *Proc Natl Acad Sci USA* 93(3): 1156-60.

Kleinstiver, B. P., J. M. Wolfs, et al. (2012). "Monomeric site-specific nucleases for genome editing." *Proc Natl Acad Sci USA* 109(21): 8061-6.

Lackner, G., N. Moebius, et al. (2011). "Complete genome sequence of Burkholderia rhizoxinica, an Endosymbiont of Rhizopus microsporus." *J Bacteriol* 193(3): 783-4.

Li, T., S. Huang, et al. (2011). "TAL nucleases (TALNs): hybrid proteins composed of TAL effectors and FokI DNA-cleavage domain." *Nucleic Acids Res* 39(1): 359-72.

Li, T., S. Huang, et al. (2011). "Modularly assembled designer TAL effector nucleases for targeted gene knockout and gene replacement in eukaryotes." *Nucleic Acids Res* 39(14): 6315-25.

Ma, J. L., E. M. Kim, et al. (2003). "Yeast Mre11 and Rad1 proteins define a Ku-independent mechanism to repair double-strand breaks lacking overlapping end sequences." *Mol Cell Biol* 23(23): 8820-8.

Marcaida, M. J., I. G. Munoz, et al. (2010). "Homing endonucleases: from basics to therapeutic applications." *Cell Mol Life Sci* 67(5): 727-48.

Moscou, M. J. and A. J. Bogdanove (2009). "A simple cipher governs DNA recognition by TAL effectors." *Science* 326(5959): 1501.

Mueller, J. E., D. Smith, et al. (1995). "Intron-encoded endonuclease I-TevI binds as a monomer to effect sequential cleavage via conformational changes in the td homing site." *Embo J* 14(22): 5724-35.

Pabo, C. O., E. Peisach, et al. (2001). "Design and selection of novel Cys2His2 zinc finger proteins." *Annu Rev Biochem* 70: 313-40.

Paques, F. and P. Duchateau (2007). "Meganucleases and DNA double-strand break-induced recombination: perspectives for gene therapy." *Curr Gene Ther* 7(1): 49-66.

Pingoud, A. and G. H. Silva (2007). "Precision genome surgery." *Nat Biotechnol* 25(7): 743-4.

Pingoud, A. and W. Wende (2011). "Generation of novel nucleases with extended specificity by rational and combinatorial strategies." *Chembiochem* 12(10): 1495-500.

Porteus, M. H. and D. Carroll (2005). "Gene targeting using zinc finger nucleases." *Nat Biotechnol* 23(8): 967-73.

Reyon, D., S. Q. Tsai, et al. (2012). "FLASH assembly of TALENs for high-throughput genome editing." *Nat Biotechnol* 30(5): 460-5.

Rouet, P., F. Smih, et al. (1994). "Expression of a site-specific endonuclease stimulates homologous recombination in mammalian cells." *Proc Natl Acad Sci USA* 91(13): 6064-8.

Rouet, P., F. Smih, et al. (1994). "Introduction of double-strand breaks into the genome of mouse cells by expression of a rare-cutting endonuclease." *Mol Cell Biol* 14(12): 8096-106.

Silva, G., L. Poirot, et al. (2011). "Meganucleases and other tools for targeted genome engineering: perspectives and challenges for gene therapy." *Curr Gene Ther* 11(1): 11-27.

Simon, P., F. Cannata, et al. (2008). "Sequence-specific DNA cleavage mediated by bipyridine polyamide conjugates." *Nucleic Acids Res* 36(11): 3531-8.

Smith, J., J. M. Berg, et al. (1999). "A detailed study of the substrate specificity of a chimeric restriction enzyme." *Nucleic Acids Res* 27(2): 674-81.

Smith, J., M. Bibikova, et al. (2000). "Requirements for double-strand cleavage by chimeric restriction enzymes with zinc finger DNA-recognition domains." *Nucleic Acids Res* 28(17): 3361-9.

Smith, J., S. Grizot, et al. (2006). "A combinatorial approach to create artificial homing endonucleases cleaving chosen sequences." *Nucleic Acids Res* 34(22): e149.

Stoddard, B. L. (2005). "Homing endonuclease structure and function." *Q Rev Biophys* 38(1): 49-95.

Stoddard, B. L., R. J. Monnat, et al. (2007). "Advances in engineering homing endonucleases for gene targeting: ten years after structures." *Progress in Gene Therapy: AUtologous*: 135-167.

Zhao, L., R. P. Bonocora, et al. (2007). "The restriction fold turns to the dark side: a bacterial homing endonuclease with a PD-(D/E)-XK motif." *Embo J* 26(9): 2432-42.

The invention claimed is:

1. A method to selectively cleave a target nucleic acid in a mammalian cell using a catalytic domain of I-TevI, said method comprising:
   a) selecting a target nucleic acid sequence in a mammalian cell comprising a cleavage site having the motif CNNNGN selected from the group consisting of: SEQ ID NO: 2 to 55;
   b) selecting or engineering a nucleic acid binding domain to specifically bind a recognition site adjacent to said cleavage site; wherein the engineered nucleic acid binding domain is an engineered Transcription Activator Like Effectors (TALE) binding domain comprising a plurality of TALE like repeat sequences, each repeat comprising a repeat variable dipeptide (RVD) specific to each nucleotide base of a TALE DNA binding site;
   c) fusing said nucleic acid binding domain with said catalytic domain of I-TevI to obtain a TevI chimeric endonuclease,
   wherein said TevI chimeric endonuclease is selected from the group consisting of: SEQ ID NO: 452 to 458; and
   d) contacting said target nucleic acid with said chimeric endonuclease in said mammalian cell,
      wherein said catalytic domain of I-TevI cleaves the target nucleic acid in the mammalian cell at said cleavage site.

2. The method of claim 1, further comprising a step of introducing said cleavage site selected in step a) into said target nucleic acid in order to be cleaved by said TevI chimeric endonuclease.

3. The method of claim 1, wherein said catalytic domain of I-TevI has the protein sequence of SEQ ID NO: 257.

4. The method of claim 1, wherein said catalytic domain of I-TevI is selected from the group consisting of: SEQ ID NO: 268 and SEQ ID NO: 284.

5. The method of claim 1, wherein said catalytic domain of I-TevI shares at least 80% protein sequence identity with a protein sequence selected from the group consisting of: SEQ ID NO: 268 and SEQ ID NO: 284.

6. The method of claim 1, wherein said catalytic domain of I-TevI is fused to the N-terminal part of said nucleic acid binding domain.

7. The method of claim 1, wherein said catalytic domain of I-TevI is fused to the C-terminal part of said nucleic acid binding domain.

8. The method of claim 1, wherein said catalytic domain of I-TevI is fused to said nucleic acid binding domain by a peptide linker.

9. The method of claim 1, wherein the TALE nucleic acid recognition site comprises a T nucleotide ($T_0$) located between 5 to 20 bp away from the G base in the motif CNNNGN of said I-TevI cleavage site.

10. The method of claim 1, wherein the TALE nucleic acid recognition site comprises a T nucleotide ($T_0$) located between 6 to 12 bp away from the G base in the motif CNNNGN of said I-TevI cleavage site.

11. The method of claim 1, wherein the TALE nucleic acid recognition site comprises a T nucleotide ($T_0$) located 10 bp away from the G base in the motif CNNNGN of said I-TevI cleavage site.

12. The method according to claim 1, wherein said target nucleic acid sequence comprises a nucleotide A or T after the G base in the motif CNNNGN of said I-TevI cleavage site.

13. The method according to claim 1, further comprising providing to the mammalian cell an exogenous nucleic acid comprising a sequence homologous to at least a portion of the target nucleic acid sequence, such that homologous recombination occurs between the target DNA sequence and the exogenous nucleic acid.

14. The method according to claim 1, further comprising a step of providing and contacting an additional catalytic domain with the target nucleic acid sequence.

15. The method of claim 14, wherein said additional catalytic domain is a DNA end-processing enzyme.

16. The method of claim 15, wherein said DNA end-processing enzyme is Trex2.

17. The method of claim 15, wherein said DNA processing enzyme is a single chain Trex2.

* * * * *